(12) United States Patent
Branstetter et al.

(10) Patent No.: US 9,533,996 B2
(45) Date of Patent: *Jan. 3, 2017

(54) THERAPEUTIC THIOPHENE-, FURAN-, AND PYRIDINE-FUSED AZOLOPYRIMIDIN-5-(6H)-ONES

(71) Applicant: Dart Neuroscience (Cayman) Ltd., Grand Cayman (KY)

(72) Inventors: Bryan Branstetter, Carlsbad, CA (US); James Breitenbucher, Escondido, CA (US); Brian Dyck, San Diego, CA (US); Laurent Gomez, San Diego, CA (US); Andrew Richard Hudson, San Diego, CA (US); Tami Jo Marrone, Carlsbad, CA (US); Marco Peters, San Diego, CA (US); Troy Vickers, San Diego, CA (US); Michael Weinhouse, Escondido, CA (US)

(73) Assignee: Dart Neuroscience (Cayman) Ltd., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,856

(22) Filed: Sep. 14, 2015

(65) Prior Publication Data

US 2016/0075719 A1    Mar. 17, 2016

Related U.S. Application Data

(62) Division of application No. 13/920,974, filed on Jun. 18, 2013, now Pat. No. 9,175,010.

(60) Provisional application No. 61/661,091, filed on Jun. 18, 2012.

(51) Int. Cl.

| | | |
|---|---|---|
| C07D 495/14 | (2006.01) |
| C07D 495/22 | (2006.01) |
| C07D 471/14 | (2006.01) |
| C07D 471/22 | (2006.01) |
| C07D 487/14 | (2006.01) |
| C07D 487/22 | (2006.01) |
| C07D 491/22 | (2006.01) |
| C07D 498/08 | (2006.01) |
| C07D 491/147 | (2006.01) |
| C07D 491/107 | (2006.01) |
| C07D 519/00 | (2006.01) |
| C07D 495/12 | (2006.01) |

(52) U.S. Cl.
CPC ........... *C07D 495/14* (2013.01); *C07D 471/14* (2013.01); *C07D 487/14* (2013.01); *C07D 491/107* (2013.01); *C07D 491/147* (2013.01); *C07D 491/22* (2013.01); *C07D 495/12* (2013.01); *C07D 495/22* (2013.01); *C07D 498/08* (2013.01); *C07D 519/00* (2013.01)

(58) Field of Classification Search
CPC ... C07D 495/14; C07D 495/22; C07D 471/14; C07D 471/22; C07D 487/14; C07D 487/22; C07D 491/22
See application file for complete search history.

(56) References Cited

U.S. PATENT DOCUMENTS

| | | |
|---|---|---|
| 4,585,772 A | 4/1986 | Junge et al. |
| 4,938,949 A | 7/1990 | Borch et al. |
| 5,128,338 A | 7/1992 | Bourguignon et al. |
| 6,277,887 B1 * | 8/2001 | Young ................. A61K 31/137 514/649 |
| 7,868,015 B2 | 1/2011 | Tully et al. |
| 7,947,731 B2 | 5/2011 | Tully et al. |
| 9,175,010 B2 | 11/2015 | Branstetter et al. |
| 2008/0051437 A1 | 2/2008 | Hallam et al. |
| 2009/0053140 A1 | 2/2009 | Scott et al. |
| 2009/0163545 A1 | 6/2009 | Goldfarb |
| 2010/0029697 A1 | 2/2010 | Debenham et al. |
| 2013/0338139 A1 | 12/2013 | Branstetter et al. |
| 2015/0158885 A1 | 6/2015 | Allan et al. |

FOREIGN PATENT DOCUMENTS

| | | |
|---|---|---|
| EP | 217 748 A2 | 4/1987 |
| WO | WO 2007/143705 A1 | 12/2007 |
| WO | WO 2009/075784 A1 | 6/2009 |
| WO | WO 2010/065149 A1 | 6/2010 |
| WO | WO 2010/065153 A1 | 6/2010 |
| WO | WO 2010/098839 A1 | 9/2010 |
| WO | WO 2010/132127 A1 | 11/2010 |
| WO | WO 2011/153129 A1 | 12/2011 |
| WO | WO 2011/153135 A1 | 12/2011 |
| WO | WO 2011/153136 A1 | 12/2011 |
| WO | WO 2011/153138 A1 | 12/2011 |
| WO | WO 2012/171016 A1 | 12/2012 |

OTHER PUBLICATIONS

Database Registry Chemical Abstracts Service, Columbus Ohio, Accession No. RN 838843-34-8, Entered STN: Feb. 28, 2005.
International Search Report and Written Opinion mailed on Oct. 30, 2013 in International Application No. PCT/US2013/046403, filed Jun. 18, 2013.
International Search Report and Written Opinion mailed on Oct. 23, 2013 in International Application No. PCT/US2013/046415, filed Jun. 18, 2013.
Hackam, D.G. et al., Translation of Research Evidence From Animals to Humans, JAMA, Oct. 2006, 296(14): 1731; 5 pages.
Jordan, V. Craig; Tamozifen: A most unlikely pioneering medicine, Nature Review, Mar. 2003; 2: 205-213.

* cited by examiner

*Primary Examiner* — Sahar Javanmard
(74) *Attorney, Agent, or Firm* — Knobbe, Martens, Olson & Bear LLP

(57) ABSTRACT

Described herein are compounds of Formula I and Formula II, methods of their synthesis, compositions comprising the compounds, and use of the compounds and compositions in treating numerous diseases and disorders, including cognitive deficits associated with CNS diseases and disorders.

20 Claims, 2 Drawing Sheets

THERAPEUTIC THIOPHENE-, FURAN-, AND PYRIDINE-FUSED AZOLOPYRIMIDIN-5-(6H)-ONES

RELATED APPLICATIONS

Any and all priority claims identified in the Application Data Sheet, or any correction thereto, are hereby incorporated by reference under 37 CFR 1.57. For example, this application is a divisional of U.S. patent application Ser. No. 13/920,974, filed Jun. 18, 2013, which claims priority under 35 U.S.C. §119(e) to U.S. Provisional Application No. 61/661,091, filed on Jun. 18, 2012; the disclosures of which are incorporated herein by reference in their entireties.

FIELD OF THE INVENTION

The present invention relates to novel compounds, e.g., thiophene-, furan-, and pyridine-fused azolopyrimidin-5-(6h)-one compounds, useful, e.g., as PDE1 inhibitors; methods of preparing such compounds; pharmaceutical compositions comprising such compounds; and the use of these compounds and compositions to treat one or more disorders, including neurological disorders, cardiovascular disorders, renal disorders, and other conditions and diseases involving PDE1 or cyclic nucleotide signaling.

BACKGROUND

The cyclic nucleotides 5'-3' cyclic adenosine monophosphate (cAMP) and 5'-3' cyclic guanosine monophosphate (cGMP) are second messenger molecules, relaying signals from receptors on the cell surface to target molecules inside the cell. The cyclic nucleotide phosphodiesterases (PDEs) are a group of enzymes (which can be localized to different cellular compartments) that hydrolyze the phosphodiester bond of cyclic nucleotides and thereby inactivate their function. PDEs can therefore play important roles in signal transduction by modulating the localization, amplitude, and duration of cyclic nucleotide signaling within the cell.

PDEs comprise at least eleven families: PDE1-PDE11, each categorized by distinct molecular, kinetic, regulatory, and inhibitory properties. PDE family members are differentially expressed in various tissues and can localize to distinct sub-cellular domains. This diversity enables PDEs to modulate local intracellular cAMP and cGMP gradients in response to discrete external stimuli. For review, see Conti and Beavo, 2007, Annu. Rev. Biochem. 76, 481-511.

Among the PDE families, PDE1 is unique in its requirement for full activation by calcium ($Ca^{2+}$) and calmodulin (CaM). Calcium enters the cell and forms a complex with CaM. Binding of the $Ca^{2+}$/CaM complexes to multiple domains near the N-terminus of PDE1 can result in full phosphodiesterase activity. PDE1 is therefore a point of convergence and integration for multiple signaling pathways that regulate numerous downstream targets and cellular events. For review, see Sharma et al., 2006, Int. J. Mol. Med. 18, 95-105.

The PDE1 family comprises three genes, pde1a, pde1b, and pde1c, and each encodes multiple isoforms via alternative splicing and differential transcription. All PDE1 enzymes appear to hydrolyze both cAMP and cGMP, although they can differ in their relative affinities for each. For review, see Bender and Beavo, 2006, Pharmacol. Rev. 58, 488-520.

PDE1 is expressed in many tissues, underscoring a role in many physiological processes. Regions of PDE1 expression include, but are not limited to, the heart, lungs, veins and arteries, smooth muscle, skeletal muscle, skin, adrenal gland, thyroid, pancreas, esophagus, stomach, small intestine, colon, liver, leukocytes, testis, ovary, bladder, kidney, and the nervous system. In the brain, PDE1 isoforms are expressed in the cerebral cortex, frontal lobe, hippocampus, cerebellum, and amygdala, regions involved in memory formation and other cognitive processes. PDE1B expression, in particular, correlates closely with brain regions showing high levels of dopaminergic innervation. In the cardiovascular system, PDE1 appears to play a central role in organizing cAMP microdomains and mediating hormonal specificity in cardiac cells. See Maurice et al., 2003, Mol. Pharm. 64, 533-546. Indeed, human PDE1B is highly expressed in numerous cardiovascular regions, including the pericardium, heart atrium (left), heart apex, Purkinje fibers, and pulmonic valve.

More generally, cyclic nucleotide signaling pathways, including those involving PDE1, are implicated in numerous pathological processes. See, e.g., Keravis and Lugnier, 2012, Br. J. Pharmacol. 165, 1288-1305. For example, alterations in these pathways have been implicated in various disorders of the brain, including depression, schizophrenia and cognitive disorders. Inhibiting PDE1 activity in the nervous system, for example, can increase cAMP or cGMP levels and consequently induce expression of neuronal plasticity-related genes, neurotrophic factors, and neuroprotective molecules. Based on such properties, PDE1 inhibitors are promising therapeutic candidates in treating many CNS disorders and associated cognitive impairments. Similarly, PDE1 enzymes and cyclic nucleotides are emerging as key mediators of pathological processes that underlie many vascular disorders, including hypertension, myocardial infarction, and heart failure. See, e.g., Miller et al., 2011, Basic Res. Cardiol. 106, 1023-1039; Miller et al, 2009, Circ. Res. 105, 956-964. In addition, PDE1 is implicated in the development and progression of renal disease, where cAMP and cGMP regulate a variety of signaling pathways, including those that modulate mitogenesis, inflammation, and extracellular matrix synthesis. See, e.g., Wang et al., 2010, Kidney Int. 77. 129-140; Cheng et al., 2007, Soc. Exp. Biol. Med. 232, 38-51; Dousa, 1999, Kidney Int. 55, 29-62.

Accordingly, there is a need to develop treatments for CNS and other disorders, as well as disorders that are due, at least in part, to an aberration or dysregulation of an intracellular signaling pathway regulated by PDE1. The present invention meets these and other needs in the art by providing compounds that inhibit PDE1, and more particularly, can inhibit PDE1B.

SUMMARY

In its many embodiments, the present invention provides novel compounds of Formula I and II for use as PDE1 inhibitors; methods of preparing such compounds; pharmaceutical compositions comprising one or more of such compounds; and methods of treating one or more diseases associated with PDE1 by administering such compounds or pharmaceutical compositions.

Accordingly, in a first embodiment, the invention provides a compound of Formula I:

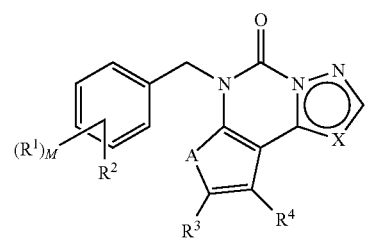

I or a pharmaceutically acceptable salt thereof, wherein
A is oxygen or sulfur;
X is CH or N;
M is 0-4;
each occurrence of $R^1$ and $R^2$ is independently selected from H, halo, aryl, heteroaryl, —($C_1$-$C_6$ alkyl) aryl, —($C_1$-$C_6$ alkyl) heteroaryl, heterocycle, —CN, $C_1$-$C_6$ alkyl, $C_1$-$C_6$ thioalkyl, $C_1$-$C_6$ thiohaloalkyl, $C_1$-$C_6$ haloalkyl, $C_2$-$C_6$ alkenyl, $C_2$-$C_6$ alkynyl, —OH, $C_1$-$C_6$ alkoxy, $C_1$-$C_6$ haloalkoxy, —$NO_2$, —$SO_2C_1$-$C_6$ alkyl, —$SOC_1$-$C_6$ alkyl, —$SO_2NH(C_1$-$C_6$ alkyl), —$SO_2N(C_1$-$C_6$ alkyl$)_2$, —CONH($C_1$-$C_6$ alkyl), —CON($C_1$-$C_6$ alkyl$)_2$, —C(O)O($C_1$-$C_6$ alkyl), —C(O)O($C_1$-$C_6$ alkyl)aryl, —OC(O)($C_1$-$C_6$ alkyl), —OC(O)($C_1$-$C_6$ alkyl)aryl, —$SO_2NH_2$, —$CONH_2$, —$CO_2H$, —COH, —$NH_2$, $C_1$-$C_6$ alkylamino, di-$C_1$-$C_6$ alkylamino, —$N_3$, cyanate, isocyanate, thiocyanate, isothiocyanate, ($C_2$-$C_6$ alkenyl)O($C_1$-$C_6$ alkyl), ($C_1$-$C_6$ alkyl)O($C_1$-$C_6$ alkyl), ($C_1$-$C_6$ alkyl)O($C_1$-$C_6$ alkyl)O($C_1$-$C_6$ alkyl), aryloxy, arylthio, —CO($C_1$-$C_6$ alkyl), —CO(aryl), —CO(heteroaryl), and —CO(heterocycle);
or $R^1$ and $R^2$ are on adjacent carbons and are taken together with the carbons to which they are attached to form an optionally substituted 5-6 member saturated or unsaturated monocylic ring system, optionally comprising one or more oxygen, sulfur, or nitrogen atoms, wherein the ring system;
$R^3$ and $R^4$ are independently selected from H, halo, —CN, $C_1$-$C_6$ alkyl, $C_1$-$C_6$ haloalkyl, OH, $C_1$-$C_6$ alkoxy, $C_1$-$C_6$ haloalkoxy, aryl, heteroaryl, —($C_1$-$C_6$ alkyl) aryl, —($C_1$-$C_6$ alkyl) heteroaryl, —$NO_2$, —$SO_2C_1$-$C_6$ alkyl, —$SO_2N(C_1$-$C_6$ alkyl$)_2$, —CONH($C_1$-$C_6$ alkyl), —CON($C_1$-$C_6$ alkyl$)_2$, and —$(CR^{10}R^{11})_{0-3}NR^{12}R^{13}$;
or $R^3$ and $R^4$ taken together with the carbons to which they are attached form a saturated or unsaturated monocylic ring system, having the following structure:

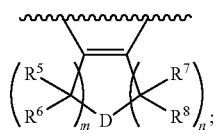

D is —O, —S, —SO, —$SO_2$, —N—$R^9$, or a bond;
m and n are independently 0-4, with the proviso that the sum of m and n is 1-5 when D is —O, —S, —SO, —$SO_2$, —N—$R^9$, or is 2-6 when D is a bond;
$R^5$, $R^6$, $R^7$, $R^8$, $R^{10}$ and $R^{11}$ are independently selected from H, —F, —$C_1$-$C_6$ alkyl, —$C_1$-$C_6$ haloalkyl, —OH, —$C_1$-$C_6$ alkoxy, —$C_1$-$C_6$haloalkoxy, —$SO_2C_1$-$C_6$ alkyl, —$SO_2N(C_1$-$C_6$ alkyl$)_2$, CONH($C_1$-$C_6$ alkyl), and CON($C_1$-$C_6$ alkyl$)_2$; and
$R^9$, $R^{12}$, and $R^{13}$ are independently selected from H, $C_1$-$C_6$ alkyl, aryl, heteroaryl, —$SO_2C_1$-$C_6$ alkyl, —$SO_2N(C_1$-$C_6$ alkyl$)_2$, —CONH($C_1$-$C_6$ alkyl), —CON($C_1$-$C_6$ alkyl$)_2$, —CO($C_1$-$C_6$ alkyl), —CO(aryl), —CO(heteroaryl), and —CO(heterocycle); or $R^{12}$ and $R^{13}$ taken together with the nitrogen to which they are attached form an optionally substituted heterocycle.

In a specific aspect, a compound of Formula I, corresponding to the first embodiment, may include one or more of the following: M=1 or 2; one or more of $R^1$, $R^2$, $R^3$, and $R^4$ is halo, more particularly, halomethyl; $R^1$ is H and $R^2$ is $C_1$-$C_6$ alkoxy, more specifically $OCH_3$; A is sulfur, and X is N; $R^1$ is halo, more specifically F, Cl, or Br, and $R^2$ is $C_1$-$C_6$ alkoxy, more specifically, $CF_3$ or $CHF_2$; $R^3$ is $C_1$-$C_6$ alkyl, more specifically methyl, and $R^4$ is H; $R^3$ is $C_1$-$C_6$ alkyl, more specifically $C_1$-$C_3$ alkyl, and $R^4$ is $(CR^{10}R^{11})_{0-3}NR^{12}R^{13}$; and $R^3$ and $R^4$ taken together with the carbons to which they are attached form a six member monocyclic ring system, wherein D is a nitrogen atom.

In a second embodiment, the invention provides a compound of Formula I, or a pharmaceutically acceptable salt thereof, wherein:
A is oxygen or sulfur;
X is CH or N;
M is 0-4;
D is O, S, SO, $SO_2$, N—$R^9$ or a bond;
each occurrence of $R^1$ and $R^2$ is independently selected from H, halo, CN, $C_1$-$C_3$ alkyl, $C_1$-$C_3$ haloalkyl, —OH, $C_1$-$C_3$ haloalkoxy, $NO_2$, $SO_2C_1$-$C_3$ alkyl, $SO_2N(C_1$-$C_3$ alkyl$)_2$, CONH($C_1$-$C_3$ alkyl), and CON($C_1$-$C_3$ alkyl$)_2$; or $R^1$ and $R^2$ are on adjacent carbons and taken together with the carbons to which they are attached form a 5-6 member monocylic ring system comprising one or more oxygen atoms, wherein the ring system is optionally substituted with one or more F;
$R^3$ and $R^4$ are independently selected from H, F, Cl, Br, CN, $C_1$-$C_3$ alkyl, $C_1$-$C_6$ $CF_3$, $CHF_2$, OH, $C_1$-$C_3$ alkoxy, $OCF_3$, $NO_2$, $SO_2C_1$-$C_3$ alkyl, $SO_2N(C_1$-$C_3$ alkyl$)_2$, CONH ($C_1$-$C_3$ alkyl), CON($C_1$-$C_3$ alkyl$)_2$, and $(CR^{10}R^{11})_{0-3}NR^{12}R^{13}$; and
$R^{12}$, and $R^{13}$ are independently selected from H, $C_1$-$C_6$ alkyl, aryl, heteroaryl, $SO_2C_1$-$C_6$ alkyl, $SO_2N(C_1$-$C_6$ alkyl$)_2$, CONH($C_1$-$C_6$ alkyl), and CON($C_1$-$C_6$ alkyl$)_2$ In a specific aspect, a compound of Formula I, corresponding to the second embodiment, may include one or more of the following: M=1 or 2; one or more of $R^1$, $R^2$, $R^3$, and $R^4$ is halo, more particularly, halomethyl; $R^1$ is H and $R^2$ is $C_1$-$C_3$ alkoxy, more specifically $OCH_3$; A is sulfur, and X is N; $R^1$ is halo, more specifically F, Cl, or Br, and $R^2$ is $C_1$-$C_3$ alkoxy; $R^1$ is F, Cl, or Br, and $R^2$ is $CF_3$ or $CHF_2$; $R^3$ is $C_1$-$C_3$ alkyl, more specifically methyl, and $R^4$ is H; $R^3$ is $C_1$-$C_3$ alkyl, more specifically methyl, and $R^4$ is $(CR^{10}R^{11})_{0-3}NR^{12}R^{13}$.

In a third embodiment, the invention provides a compound of Formula I, or a pharmaceutically acceptable salt thereof, wherein
A is oxygen or sulfur;
X is CH or N;
M is 0-4;
D is O, S, SO, $SO_2$, N—$R^9$ or a bond;
each occurrence of $R^1$ and $R^2$ is independently selected from H, halo, —CN, $C_1$-$C_6$ alkyl, $C_1$-$C_6$ haloalkyl, —OH, $C_1$-$C_6$ alkoxy, $C_1$-$C_6$ haloalkoxy, —$NO_2$, —$SO_2C_1$-$C_6$ alkyl, —$SO_2N(C_1$-$C_6$ alkyl$)_2$, —CONH($C_1$-$C_6$ alkyl), and —CON($C_1$-$C_6$ alkyl$)_2$;
or $R^1$ and $R^2$ are on adjacent carbons and taken together with the carbons to which they are attached form a 5-6 member monocylic ring system comprising one or more oxygen atoms, wherein the ring system is optionally substituted with one or more F;
$R^3$ and $R^4$ taken together with the carbons to which they are attached form a monocylic ring system, having the following structure:

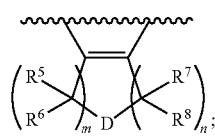

D is O, S, —SO, —SO$_2$, —N—R$^9$, or a bond;

m and n are independently 0-4, with the proviso that the sum of m and n is 1-5 when D is O, S, —SO, —SO$_2$, —N—R$^9$, or is 2-6 when D is a bond;

R$^5$, R$^6$, R$^7$, R$^8$, R$^{10}$ and R$^{11}$ are independently selected from H, F, —C$_1$-C$_6$ alkyl, —C$_1$-C$_6$ haloalkyl, —OH, —C$_1$-C$_6$ alkoxy, —C$_1$-C$_6$ haloalkoxy, —SO$_2$C$_1$-C$_6$ alkyl, —SO$_2$N(C$_1$-C$_6$ alkyl)$_2$, —CONH(C$_1$-C$_6$ alkyl), and —CON(C$_1$-C$_6$ alkyl)$_2$; and R$^9$, R$^{12}$, and R$^{13}$ are independently selected from H, —C$_1$-C$_6$ alkyl, aryl, heteroaryl, —SO$_2$C$_1$-C$_6$ alkyl, —SO$_2$N(C$_1$-C$_6$ alkyl)$_2$, —CONH(C$_1$-C$_6$ alkyl), and —CON(C$_1$-C$_6$ alkyl)$_2$.

In a specific aspect, a compound of Formula I, corresponding to the third embodiment, may include one or more of the following: M=1 or 2; one or more of R$^1$, R$^2$, R$^3$, and R$^4$ is halo, more particularly, halomethyl; R$^1$ is H and R$^2$ is C$_1$-C$_6$ alkoxy, more specifically OCH$_3$; A is sulfur, and X is N; R$^1$ is F, Cl, or Br, and R$^2$ is —CF$_3$ or —CHF$_2$; R$^3$ is C$_1$-C$_6$ alkyl, more specifically C$_1$-C$_3$ alkyl, and R$^4$ is —(CR$^{10}$R$^{11}$)$_{0-3}$NR$^{12}$R$^{13}$.

In a fourth embodiment, the invention provides a compound of Formula I, or a pharmaceutically acceptable salt thereof, wherein A is oxygen or sulfur;

X is CH or N;

M is 0-4;

each occurrence of R$^1$ and R$^2$ is independently selected from H, halo, aryl, heteroaryl, heterocycle, —CN, C$_1$-C$_3$ alkyl, C$_1$-C$_3$ thioalkyl, C$_1$-C$_3$ thiohaloalkyl, C$_1$-C$_3$ haloalkyl, C$_2$-C$_6$ alkenyl, C$_2$-C$_6$ alkynyl, —OH, C$_1$-C$_3$ alkoxy, C$_1$-C$_3$ haloalkoxy, —NO$_2$, —SO$_2$C$_1$-C$_6$ alkyl, —SOC$_1$-C$_3$ alkyl, —SO$_2$NH(C$_1$-C$_3$ alkyl), —SO$_2$N(C$_1$-C$_3$ alkyl)$_2$, —CONH(C$_1$-C$_3$ alkyl), —CON(C$_1$-C$_3$ alkyl)$_2$, —C(O)O(C$_1$-C$_3$ alkyl), —C(O)O(C$_1$-C$_3$ alkyl)aryl, —OC(O)(C$_1$-C$_3$ alkyl), —OC(O)(C$_1$-C$_3$ alkyl)aryl, —SO$_2$NH$_2$, —CONH$_2$, —CO$_2$H, —COH, —NH$_2$, C$_1$-C$_3$ alkylamino, di-C$_1$-C$_3$ alkylamino, —N$_3$, cyanate, isocyanate, thiocyanate, isothiocyanate, (C$_2$-C$_6$ alkenyl)O(C$_1$-C$_3$ alkyl), (C$_1$-C$_3$ alkyl)O(C$_1$-C$_3$ alkyl), (C$_1$-C$_3$ alkyl)O(C$_1$-C$_3$ alkyl)O(C$_1$-C$_3$ alkyl), aryloxy, arylthio, —CO(C$_1$-C$_3$ alkyl), —CO(aryl), —CO(heteroaryl), and —CO(heterocycle);

or R$^1$ and R$^2$ are on adjacent carbons and taken together with the carbons to which they are attached form a 5-6 member monocylic ring system comprising one or more oxygen atoms, preferably 1-2 oxygens, wherein the ring system is optionally substituted with one or more F;

R$^3$ and R$^4$ taken together with the carbons to which they are attached form a monocylic ring system, having the following structure:

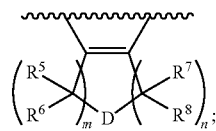

D is O, S, SO, SO$_2$, N—R$^9$, or a bond;

m and n are independently 0-4, with the proviso that the sum of m and n is 1-5 when D is O, S, SO, SO$_2$, N—R$^9$, or is 2-6 when D is a bond;

R$^5$, R$^6$, R$^7$, R$^8$, R$^{10}$ and R$^{11}$ are independently selected from H, F, C$_1$-C$_3$ alkyl, C$_1$-C$_3$ haloalkyl, OH, C$_1$-C$_3$ alkoxy, C$_1$-C$_3$ haloalkoxy, —SO$_2$C$_1$-C$_6$ alkyl, —SO$_2$N(C$_1$-C$_3$ alkyl)$_2$, —CONH(C$_1$-C$_3$ alkyl), and —CON(C$_1$-C$_3$ alkyl)$_2$; and R$^9$, R$^{12}$, and R$^{13}$ are independently selected from H, C$_1$-C$_3$ alkyl, aryl, heteroaryl, —SO$_2$C$_1$-C$_3$ alkyl, —SO$_2$N(C$_1$-C$_3$ alkyl)$_2$, —CONH(C$_1$-C$_3$ alkyl), and —CON(C$_1$-C$_3$ alkyl)$_2$.

In a specific aspect, a compound of Formula I, corresponding to the fourth embodiment, may include one or more of the following: M=1 or 2; one or more of R$^1$, R$^2$, R$^3$, and R$^4$ is halo, more particularly, halomethyl; R$^1$ is H and R$^2$ is C$_1$-C$_3$ alkoxy, more specifically OCH$_3$; A is sulfur, and X is N; R$^1$ is F, Cl, or Br, and R$^2$ is —CF$_3$ or —CHF$_2$; and R$^3$ is C$_1$-C$_3$ alkyl and R$^4$ is —(CR$^{10}$R$^{11}$)$_{0-3}$NR$^{12}$R$^{13}$.

In a fifth embodiment, the invention provides a compound of Formula II:

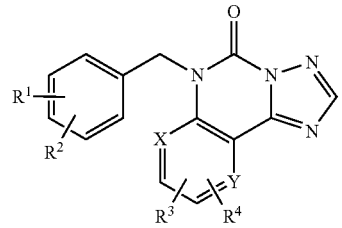

or a pharmaceutically acceptable salt thereof, wherein

X and Y are independently nitrogen or carbon, but at least one is nitrogen;

M=0-4;

each occurrence of R$^1$ and R$^2$ is independently selected from H, halo, aryl, heteroaryl, heterocycle, —(C$_1$-C$_6$ alkyl)aryl, —(C$_1$-C$_6$ alkyl) heteroaryl, —CN, C$_1$-C$_6$ alkyl, C$_1$-C$_6$ thioalkyl, C$_1$-C$_6$ thiohaloalkyl, C$_1$-C$_6$ haloalkyl, C$_2$-C$_6$ alkenyl, C$_2$-C$_6$ alkynyl, —OH, C$_1$-C$_6$ alkoxy, C$_1$-C$_6$ haloalkoxy, —NO$_2$, —SO$_2$C$_1$-C$_6$ alkyl, —SOC$_1$-C$_6$ alkyl, —SO$_2$NH(C$_1$-C$_6$ alkyl), —SO$_2$N(C$_1$-C$_6$ alkyl)$_2$, —CONH(C$_1$-C$_6$ alkyl), —CON(C$_1$-C$_6$ alkyl)$_2$, —C(O)O(C$_1$-C$_6$ alkyl), —C(O)O(C$_1$-C$_6$ alkyl)aryl, —OC(O)(C$_1$-C$_6$ alkyl), —OC(O)(C$_1$-C$_6$ alkyl)aryl, —SO$_2$NH$_2$, —CONH$_2$, —CO$_2$H, —COH, —NH$_2$, C$_1$-C$_6$ alkylamino, di-C$_1$-C$_6$ alkylamino, —N$_3$, cyanate, isocyanate, thiocyanate, isothiocyanate, —(C$_2$-C$_6$ alkenyl)O(C$_1$-C$_6$ alkyl), —(C$_1$-C$_6$ alkyl)O(C$_1$-C$_6$ alkyl), —(C$_1$-C$_6$ alkyl)O(C$_1$-C$_6$ alkyl)O(C$_1$-C$_6$ alkyl), aryloxy, arylthio, —CO(C$_1$-C$_6$ alkyl), —CO(aryl), —CO(heteroaryl), and —CO(heterocycle);

or R$^1$ and R$^2$ are on adjacent carbons and taken together with the carbons to which they are attached form a 5-6 member saturated or unsaturated monocylic ring system comprising one or more oxygen or nitrogen atoms, preferably 1-2 oxygens, wherein the ring system is optionally substituted with one or more groups selected from halo, C$_1$-C$_6$ alkyl; C$_1$-C$_6$ alkoxy; and C$_1$-C$_6$ haloalkoxy;

R$^3$ and R$^4$ are independently selected from H, halo, —CN, C$_1$-C$_6$ alkyl, C$_1$-C$_6$ haloalkyl, —OH, C$_1$-C$_6$ alkoxy, C$_1$-C$_6$ haloalkoxy, aryl, heteroaryl, —(C$_1$-C$_6$ alkyl) aryl, —(C$_1$-C$_6$ alkyl) heteroaryl, —NO$_2$, —SO$_2$C$_1$-C$_6$ alkyl, —SO$_2$N(C$_1$-C$_6$ alkyl)$_2$, —CONH(C$_1$-C$_6$ alkyl), —CON(C$_1$-C$_6$ alkyl)$_2$; —(CR$^7$R$^8$)$_{0-3}$NR$^5$R$^6$ in which R$^5$ and R$^6$ and the nitrogen to which they are attached may form a ring taken from azetidine, pyrollidine, piperidine, homopiperidine, morpholine, morpholinone, homomorpholine, homomorpholinone, piperazine, piperazinone, homopiperazine and homopiperazinone with the ring optionally substituted with up to three independent occurrences of R$^1$, and more specifically with aryl or heteroaryl, either optionally substituted with one or more halo, —CN, $C_1$-$C_6$ alkyl, OH, $C_1$-$C_6$ alkoxy, $C_1$-$C_6$ haloalkoxy, —$NO_2$, —$SO_2C_1$-$C_6$ alkyl;

or $R^3$ and $R^4$ taken together with the carbons to which they are attached form a 5-6 member monocylic ring system comprising one or more oxygen atoms;

$R^5$, $R^6$, $R^7$, and $R^8$ are independently selected from H, F, $C_1$-$C_6$ alkyl, $C_1$-$C_6$ haloalkyl, OH, $C_1$-$C_6$ alkoxy, —$C_1$-$C_6$ haloalkoxy, —$SO_2C_1$-$C_6$ alkyl, —$SO_2N(C_1$-$C_6$ alkyl$)_2$, —$CO_2(C_1$-$C_6$ alkyl), —$CO_2CH_2C_6H_5$, —$CONH(C_1$-$C_6$ alkyl), and —$CON(C_1$-$C_6$ alkyl$)_2$;

or any two of $R^5$, $R^6$, $R^7$, and $R^8$ taken together with the atoms to which they are attached form a 3-7 member monocyclic ring containing up to two heteroatoms selected from nitrogen, oxygen, and sulfur.

In a specific aspect, a compound of Formula II, corresponding to the fifth embodiment, may include one or more of the following: M=1 or 2; one or more of $R^1$, $R^2$, $R^3$, and $R^4$ is halo, more particularly, halomethyl; X is N and Y is CH; one or more of $R^1$, $R^2$, $R^3$, and $R^4$ is halo, more particularly, halomethyl; $R^1$ is H and $R^2$ is —$C_1$-$C_6$ alkoxy, more specifically —$OCH_3$; $R^1$ is halo, more specifically F, Cl, or Br, and $R^2$ is $C_1$-$C_6$ alkoxy; $R^1$ is F, Cl, or Br and $R^2$ is —$CF_3$ or —$CHF_2$; $R^3$ is $C_1$-$C_6$ alkyl, more specifically methyl, and $R^4$ is H.

In a sixth embodiment, the invention provides a compound of Formula II, or a pharmaceutically acceptable salt thereof, wherein:

X and Y are independently nitrogen or carbon, but at least one is nitrogen;

M=0-4;

each occurrence of $R^1$ and $R^2$ is independently selected from H, halo, —CN, $C_1$-$C_3$ alkyl, $C_1$-$C_3$ haloalkyl, OH, $C_1$-$C_3$ alkoxy, $C_1$-$C_3$ haloalkoxy, —$NO_2$, —$SO_2C_1$-$C_3$ alkyl, —$SO_2N(C_1$-$C_3$ alkyl$)_2$, —$CONH(C_1$-$C_3$ alkyl). —$CON(C_1$-$C_3$ alkyl$)_2$, aryl, and heteroaryl;

or $R^1$ and $R^2$ are on adjacent carbons and taken together with the carbons to which they are attached form a 5-6 member monocyclic ring system comprising one or more oxygen atoms, preferably 1-2 oxygens, wherein the ring system is optionally substituted with one or more groups selected from halo, preferably F; $C_1$-$C_3$ alkyl; $C_1$-$C_3$ alkoxy; and $C_1$-$C_3$ haloalkoxy;

$R^3$ and $R^4$ are independently selected from H, halo, —CN, $C_1$-$C_3$ alkyl, $C_1$-$C_3$ haloalkyl, OH, $C_1$-$C_3$ alkoxy, $C_1$-$C_3$ haloalkoxy, —$NO_2$, —$SO_2C_1$-$C_3$ alkyl, —$SO_2N(C_1$-$C_3$ alkyl$)_2$, —$CONH(C_1$-$C_3$ alkyl), —$CON(C_1$-$C_3$ alkyl$)_2$, —$(CR^7R^8)_{0-3}NR^5R^6$; and aryl or heteroaryl, either optionally substituted with one or more groups selected from halo, CN, $C_1$-$C_3$ alkyl, OH, $C_1$-$C_3$ alkoxy, —$C_1$-$C_3$ haloalkoxy, —$NO_2$, and —$SO_2C_1$-$C_3$ alkyl;

or $R^3$ and $R^4$ taken together with the carbons to which they are attached form a 5-6 member monocylic ring system comprising one or more oxygen atoms;

$R^5$, $R^6$, $R^7$, and $R^8$ are independently selected from H, F, $C_1$-$C_3$ alkyl, $C_1$-$C_3$ haloalkyl, OH, $C_1$-$C_3$ alkoxy, $C_1$-$C_3$ haloalkoxy, —$SO_2C_1$-$C_3$ alkyl, —$SO_2N(C_1$-$C_3$ alkyl$)_2$, —$CONH(C_1$-$C_3$ alkyl), and —$CON(C_1$-$C_3$ alkyl$)_2$;

or any two of $R^5$, $R^6$, $R^7$, and $R^8$ taken together with the atoms to which they are attached form a 3-7 member monocyclic ring containing up to two heteroatoms selected from nitrogen, oxygen, and sulfur.

In a specific aspect, a compound of Formula II, corresponding to the sixth embodiment, may include one or more of the following: M=1 or 2; one or more of $R^1$, $R^2$, $R^3$, and $R^4$ is halo, more particularly, halomethyl; X is N and Y is CH; one or more of $R^1$, $R^2$, $R^3$, and $R^4$ is halo, more particularly, halomethyl; $R^1$ is H and $R^2$ is $C_1$-$C_3$ alkoxy; $R^1$ is halo, more specifically F, Cl, or Br, and $R^2$ is $C_1$-$C_3$ alkoxy; $R^1$ is F, Cl, or Br and $R^2$ is —$CF_3$ or —$CHF_2$; $R^3$ is $C_1$-$C_3$ alkyl, more specifically methyl, and $R^4$ is H.

In other embodiments, the invention provides a compound of Formula I or II (or pharmaceutical composition thereof) wherein any of $R^1$ through $R^{11}$ is independently selected from H, halo, aryl, heteroaryl, heterocycle, —CN, $C_1$-$C_6$ alkyl, $C_1$-$C_6$ thioalkyl, $C_1$-$C_6$ thiohaloalkyl, $C_1$-$C_6$ haloalkyl, $C_2$-$C_6$ alkenyl, $C_2$-$C_6$ alkynyl, —OH, $C_1$-$C_6$ alkoxy, $C_1$-$C_6$ haloalkoxy, —$NO_2$, —$SO_2C_1$-$C_6$ alkyl, —$SOC_1$-$C_6$ alkyl, —$SO_2NH(C_1$-$C_6$ alkyl), —$SO_2N(C_1$-$C_6$ alkyl$)_2$, —$CONH(C_1$-$C_6$ alkyl), —$CON(C_1$-$C_6$ alkyl$)_2$, —$C(O)O(C_1$-$C_6$ alkyl), —$C(O)O(C_1$-$C_6$ alkyl)aryl, —$OC(O)(C_1$-$C_6$ alkyl), —$OC(O)(C_1$-$C_6$ alkyl)aryl, —$SO_2NH_2$, —$CONH_2$, —$CO_2H$, —COH, —$NH_2$, $C_1$-$C_6$ alkylamino, di-$C_1$-$C_6$ alkylamino, —$N_3$, cyanate, isocyanate, thiocyanate, isothiocyanate, —$(C_2$-$C_6$ alkenyl)O($C_1$-$C_6$ alkyl), —$(C_1$-$C_6$ alkyl)O($C_1$-$C_6$ alkyl), —$(C_1$-$C_6$ alkyl)O($C_1$-$C_6$ alkyl)O($C_1$-$C_6$ alkyl), aryloxy, arylthio, —$CO(C_1$-$C_6$ alkyl), —CO(aryl), —CO(heteroaryl), and —CO(heterocycle).

More particularly, the invention provides a compound of Formula I or II (or pharmaceutical compositions thereof) wherein any of $R^1$ through $R^{11}$ is independently selected from H, halo, aryl, heteroaryl, heterocycle, —CN, $C_1$-$C_3$ alkyl, $C_1$-$C_6$ thioalkyl, $C_1$-$C_{63}$ thiohaloalkyl, $C_1$-$C_3$ haloalkyl, $C_2$-$C_6$ alkenyl, $C_2$-$C_6$ alkynyl, —OH, $C_1$-$C_3$ alkoxy, $C_1$-$C_3$ haloalkoxy, —$NO_2$, —$SO_2C_1$-$C_3$ alkyl, —$SOC_1$-$C_3$ alkyl, —$SO_2NH(C_1$-$C_3$ alkyl), —$SO_2N(C_1$-$C_3$ alkyl$)_2$, —$CONH(C_1$-$C_3$ alkyl), —$CON(C_1$-$C_3$ alkyl$)_2$, —$C(O)O(C_1$-$C_3$ alkyl), —$C(O)O(C_1$-$C_3$ alkyl)aryl, —$OC(O)(C_1$-$C_3$ alkyl), —$OC(O)(C_1$-$C_3$ alkyl)aryl, —$SO_2NH_2$, —$CONH_2$, —$CO_2H$, —COH, —$NH_2$, $C_1$-$C_3$ alkylamino, di-$C_1$-$C_3$ alkylamino, —$N_3$, cyanate, isocyanate, thiocyanate, isothiocyanate, —$(C_2$-$C_6$ alkenyl)O($C_1$-$C_3$ alkyl), —$(C_1$-$C_3$alkyl)O($C_1$-$C_3$ alkyl), —$(C_1$-$C_3$ alkyl)O($C_1$-$C_3$ alkyl)O($C_1$-$C_3$ alkyl), aryloxy, arylthio, —$CO(C_1$-$C_3$ alkyl), —CO(aryl), —CO(heteroaryl), and —CO(heterocycle).

In specific embodiments, the invention provides a compound of Formula I selected from the following group: Preparative Examples 1, 33, 34, 35, 36, 38, 39, 44, 51, 55, 61, 62, 63, 69, 105, 109, 135 and 141.

In another embodiment, the invention provides a compound of Formula II selected from the following group: Preparative Examples 220, 222, 223, 225, 229, 247, 248, 266, 267, 268, 270, 272, 277, 290, 294 and 295.

The invention also provides methods for synthesizing the compounds of Formula I and Formula II.

The invention further provides a pharmaceutical composition comprising a compound corresponding to any of the embodiments and examples disclosed herein; and a pharmaceutically acceptable carrier.

The invention further relates to the use of a compound or composition of the instant invention in a method of treating disorders that include an aberrant or dysregulated signaling pathway mediated by PDE1, and more specifically, PDE1B. Such PDE1-related signaling pathways, preferably in the nervous system, include, but are not limited to, those involving nitric oxide, natriuretic peptides, dopamine, noradrenalin, neurotensin, cholecystokinin, vasoactive intestinal peptide, serotonin, glutamate, GABA, acetylcholine, adenosine, cannabinoids, natriuretic peptides, and endorphins. In a specific aspect, the compounds and compositions are useful in treating disorders characterized by alterations in dopamine signaling.

The invention further relates to the use of a compound or composition of the instant invention in a method of treating neurological disorders, cognitive disorders, cardiovascular disorders, renal disorders, hematological disorders, gastrointestinal and liver diseases, cancer disorders, or neurodegenerative disorders in a mammal.

In a specific embodiment, the invention provides a method for treating a CNS disorder, comprising administration of an effective amount of a compound or composition of the instant invention to a patient in need thereof. In one aspect, the CNS disorder is selected from one or more of the group comprising dementias and neurodegenerative disorders, cognitive disorders, psychiatric disorders, developmental and genetic conditions (including progressive CNS diseases), age-associated memory impairments, and learning disabilities.

In particular embodiments, the CNS disorder is selected from one or more of the group comprising Huntington's disease, Parkinson's disease, Alzheimer's disease, schizophrenia, mild-cognitive impairment, and attention deficit hyperactivity disorder (ADHD. In another embodiment, the CNS disorder is a cognitive disorder associated with a progressive nervous system disease, and more particularly, is a cognitive disorder associated with multiple sclerosis.

The invention further provides a method for treating a cognitive impairment, comprising:
(a) providing cognitive training to an animal in need of treatment of a cognitive impairment under conditions sufficient to produce an improvement in performance by said animal of a cognitive function whose deficit is associated with said cognitive impairment;
(b) administering a compound (or pharmaceutically acceptable salt thereof) or composition comprising such a compound to said animal in conjunction with cognitive training;
(c) repeating the providing and administering steps one or more times; and
(d) reducing the number of training sessions sufficient to produce said improvement in performance, relative to the improvement in performance produced by cognitive training alone.

In another embodiment, the invention provides a method for treating a vascular disorder, comprising administration of a compound (or pharmaceutically acceptable salt thereof) or composition of the present invention to a patient in need thereof. In one aspect, the vascular disorder is selected from one or more of the group comprising atherosclerosis, postangioplasty restenosis, allograft vasculopathy, and pulmonary hypertension. In another aspect, the vascular disorder is heart failure or congestive heart failure, the cause of which may be, but is not limited to, myocardial infarction and other forms of ischemic heart disease, hypertension, valvular heart disease, and cardiomyopathy.

In a further embodiment, the invention provides a method for treating a renal disorder, comprising administration a compound (or pharmaceutically acceptable salt thereof) or composition of the present invention to a patient in need thereof. In one aspect, the renal disorder is selected from one or more of the group comprising renal artery stenosis, pyelonephritis, glomerulonephritis, kidney tumors, polycystic kidney disease, injury to the kidney, and damage resulting from radiation of the kidney.

The present invention also provides methods for treating and injury or disease that results in neuronal degeneration; and methods for promoting neurogenesis, by administering a compound or composition of the instant invention. In certain embodiments, the injury is a primary nervous system injury, which includes, but is not limited to, closed head injuries and blunt trauma, such as those resulting from playing sports; penetrating trauma, including gunshot wounds; hemorrhagic stroke; ischemic stroke; glaucoma; cerebral ischemia; or damage cause by surgical procedures such as tumor excision. In other embodiments, the injury is secondary degeneration that can result from a primary nervous system injury.

DETAILED DESCRIPTION

Figure 1:
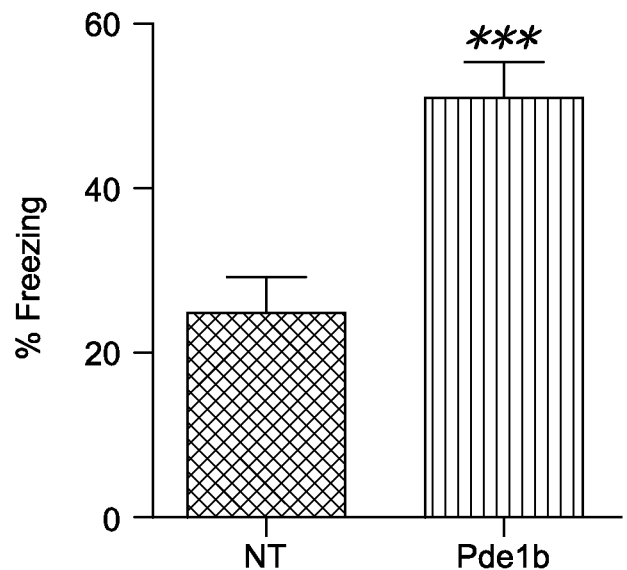
FIG. 1 is bar graph showing the effect of siRNA-mediated knockdown of PDE1b in mouse hippocampal tissue on one-day memory in a contextual fear-conditioning assay.

The present invention may be understood even more readily by reference to the following detailed description of exemplary embodiments of the invention and the examples included therein.

Unless otherwise defined, all technical and scientific terms used herein have the same meaning as commonly understood by one of ordinary skill in the pharmaceutical arts. It is also to be understood that the terminology used herein is for the purpose of describing particular embodiments only and is not intended to be limiting. The plural and singular should be treated as interchangeable, other than the indication of number:

Although methods and materials similar or equivalent to those described herein can be used in the practice or testing of the present invention, suitable methods and materials are described herein. All publications, patent applications, patents, and other references, including product descriptions, clinical studies, and protocols, mentioned in this Application are incorporated by reference in their entirety. In addition, the materials, methods, and examples are illustrative only and are not intended to be limiting.

Reference is made to standard textbooks of molecular biology and pharmaceutics that contain definitions and methods and means for carrying out basic techniques, which may be encompassed by the present invention. See, e.g., Current Protocols in Pharmacology, Enna et al. (eds.), John Wiley and Sons, Inc., Hoboken, N.J. (2011), Current Protocols in Molecular Biology, Ausubel et al. (eds.), John Wiley & Sons, Inc., Hoboken, N.J. (2011), Current Protocols in Cell Biology, Bonifacino et al. (eds.), John Wiley & Sons, Inc.: Hoboken, N.J. (2011); Current Protocols in Neuroscience, Gerfen et al. (eds.), John Wiley & Sons, Inc., Hoboken, N.J. (2011); and the various references cited therein.

General Terms

The terms "comprising" and "including" are used herein in their open, non-limiting sense. Other terms and phrases used in this document, and variations thereof, unless otherwise expressly stated, should be construed as open ended as opposed to limiting. As examples of the foregoing: the term "example" is used to provide exemplary instances of the item in discussion, not an exhaustive or limiting list thereof; adjectives such as "conventional," "traditional," "normal,"

"criterion," "known" and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

As used herein, the terms "a," "an," and "the" are to be understood as meaning both singular and plural, unless explicitly stated otherwise. Thus, "a," "an," and "the" (and grammatical variations thereof where appropriate) refer to one or more.

As used herein, the term "about" or "approximately" means within an acceptable range for a particular value as determined by one skilled in the art, and may depend in part on how the value is measured or determined, e.g., the limitations of the measurement system or technique.

As used herein, the term "about," when located before a dosage amount or dosage range of a specific ingredient, refers to an amount or range closely above or closely below the stated amount or range that does not manifestly alter the therapeutic effect of the specific ingredient from the stated amount or range and is meant to encompass at least all equivalents of that amount. For example, "about" can mean a range of up to 20%, up to 10%, up to 5%, or up to 1% or less of a given value. Alternatively, with respect to biological systems or processes, the term "about" can mean within an order of magnitude, within 5-fold, or within 2-fold of a value. Numerical quantities given herein are approximate unless stated otherwise, meaning that the term "about" or "approximately" can be inferred when not expressly stated.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Compounds

Definitions

As used herein, common organic abbreviations are defined as follows:

Ac: Acetyl; aq: Aqueous
Bu: n-Butyl
cat: Catalytic
CDI: 1,1'-carbonyldiimidazole
° C.: Temperature in degrees Centigrade
DBU: 1,8-Diazabicyclo[5.4.0]undec-7-ene
DIEA: Diisopropylethylamine
DMA: Dimethylacetamide
DMF: N,N'-Dimethylformamide
DMSO Dimethylsulfoxide
Et: Ethyl
g: Gram(s)
h: Hour (hours)
HPLC: High performance liquid chromatography
iPr or isopr: Isopropyl
LCMS Liquid chromatography-mass spectrometry
Me: Methyl
MeOH: Methanol
ml: Milliliter(s)
Pd/C: Palladium on activated carbon
rt: Room temperature
TEA: Triethylamine
Tert; t: tertiary Unless specifically limited otherwise, the term "halogen", as well as derivative terms such as "halo", as used herein, refer to fluorine, chlorine, bromine, and iodine. Preferred halogens are fluorine and chlorine.

The terms "halomethyl" and "haloalkyl" refer to methyl and alkyl groups substituted with from one up to the maximum possible number of halo atoms. The terms "halomethoxy" and "haloalkoxy" refer to methoxy and alkoxy groups substituted with from one up to the maximum possible number of halo atoms.

As used herein, the term "alkyl" refers to an aliphatic hydrocarbon group. The alkyl moiety may be a "saturated alkyl" group, which means that it does not contain any alkene or alkyne moieties. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety may be branched, straight chain, or cyclic. Examples of branched alkyl groups include, but are not limited to, isopropy, sec-butyl, t-butyl and the like. Examples of straight chain alkyl groups include, but are not limited to, methyl, ethyl, propyl, butyl, pentyl, hexyl, heptyl, and the like. Examples of cyclic alkyl groups include, but are not limited to, cyclopropyl, cyclopentyl, cyclohexyl, cycloheptyl, and the like. In some embodiments alkyl is $C_1$-$C_6$ alkyl, and more specifically, is $C_1$-$C_3$ alkyl. Alkyl groups are optionally substituted as defined herein.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like. In some embodiments alkoxy is $C_1$-$C_6$ alkoxy, and more specifically, is $C_1$-$C_3$ alkoxy. Alkyoxy groups are optionally substituted as defined herein.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like. Alkenyl groups are optionally substituted as defined herein.

The term "alkynyl" used herein refers to a monovalent straight or branched chain radical of from two to twenty carbon atoms containing a carbon triple bond including, but not limited to, 1-propynyl, 1-butynyl, 2-butynyl, and the like. Alkynyl groups are optionally substituted as defined herein.

The term "aryl" used herein refers to an optionally substituted homocyclic aromatic radical whether one ring or multiple fused rings. Moreover, the term "aryl" includes optionally substituted fused ring systems wherein at least two aryl rings, or at least one aryl and an ortho-fused bicyclic carbocyclic radical having about nine to ten ring atoms in which at least one ring is aromatic share at least one chemical bond. Examples of "aryl" rings include, but are not limited to, optionally substituted phenyl, biphenyl, naphthalenyl, phenanthrenyl, anthracenyl, tetralinyl, fluorenyl, indenyl, and indanyl. Aryl groups are optionally substituted as defined herein.

The term, "heterocycle," "heterocycle group," or "heterocyclic group" used herein refers to a monocyclic or polycyclic ring system comprising at least one heteroatom in the ring system backbone. The heteroatoms are independently selected from oxygen, sulfur, and nitrogen. The term "heterocycle" includes multiple fused ring systems. Moreover, the term "heterocycle" includes fused ring systems that may have any degree of saturation provided that at least one ring in the ring system is not aromatic. The heterocycle can be attached to other groups via any available valence, preferably any available carbon or nitrogen. Preferred monocyclic ring systems are of 4, 5, 6, 7, or 8 members. Six membered monocyclic rings contain from up to three heteroatoms wherein each heteroatom is individually selected from oxygen, sulfur, and nitrogen, and wherein when the ring is five membered, preferably it has one or two heteroatoms wherein each heteroatom is individually selected from oxygen, sulfur, and nitrogen. Preferred bicyclic cyclic ring systems are of 8 to 12 members and include spirocycles. In some embodiments, an optional substituent includes, but is not limited to, oxo (=O). Heterocycles include, but are not limited to, azetidine, pyrrolidine, piperidine, homopiperidine, morpholine, morpholinone, homomorpholine, homomorpholinone, piperazine, piperazinone, homopiperazine homopiperazinone, tetrahydrofuran, dihydrofuran, tetrahydrothiene, oxazolidinone, tetrahydropyran, dihydropyran, tetrahydrothiopyran, thiomorpholin, thioxene, aziridine, oxetane, thietane, oxepane, thiepane, oxazepine, diazepine, thiazepine, 1,2,3,6-tetrahydropyridine, indoline, 2H-pyrane, 4H-pyrane, dioxane, 1,3-dioxolane, pyrazoline, dithiane, dithiolane, dihydropyrane, dihydrothiene, dihydrofuran, pyrazolidine, imidazoline, imidazolidine, 3-azabicyclo[3.1.0]hexane, 3-azabicyclo[4.1.0]heptane, 3H-indole and quinolizine. Heterocycles are optionally substituted as defined herein.

The term "heteroaryl" used herein refers to an optionally substituted heterocyclic group, whether one ring or multiple fused rings. In fused ring systems, the one or more heteroatoms may be present in only one of the rings. Examples of heteroaryl groups include, but are not limited to, quinazolinyl, quinolinyl, isoquinolinyl, quinoxalinyl, pyridyl, pyrrolyl, oxazolyl, indolyl, thienyl, imidazolyl, pyrimidinyl, pyrazolyl, triazolyl, pyrazinyl, tetrazolyl, furyl, isoxazolyl, thiazolyl, isothiazolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The term "heterocycle" encompasses heteroaryl fused to a non-aromatic ring system. Heteroaryls are optionally substituted as defined herein.

The term "heteroatom" used herein refers to an atom other than carbon and hydrogen, for example, oxygen, sulfur, or nitrogen.

The term "amino" used herein refers to a nitrogen radical substituted with hydrogen, alkyl, aryl, heteroaryl, heterocycle, or combinations thereof. Examples of amino groups include, but are not limited to, —NHMethyl, —NH$_2$, —NMethyl$_2$, —NPhenylMethyl, —NHPhenyl, —NEthylMethyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage.

The term "carbonyl" used herein refers to C=O (i.e. carbon double bonded to oxygen).

The term "oxo" used herein refers to =O (i.e. double bond to oxygen). For example, cyclohexane substituted with "oxo" is cyclohexanone.

As used herein, a "radical" indicates a species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

"Optionally substituted" as used herein means that the referenced group may be chemically substituted with one or more additional groups(s) individually and independently selected from the group comprising halo, aryl, heteroaryl, —(C$_1$-C$_6$ alkyl) aryl, —(C$_1$-C$_6$ alkyl) heteroaryl, heterocycle, —CN, C$_1$-C$_6$ alkyl, C$_1$-C$_6$ thioalkyl, C$_1$-C$_6$ thiohaloalkyl, C$_1$-C$_6$ haloalkyl, C$_2$-C$_6$ alkenyl, C$_2$-C$_6$ alkynyl, —OH, C$_1$-C$_6$ alkoxy, C$_1$-C$_6$ haloalkoxy, —NO$_2$, —SO$_2$C$_1$-C$_6$ alkyl, —SOC$_1$-C$_6$ alkyl, —SO$_2$NH(C$_1$-C$_6$ alkyl), —SO$_2$N(C$_1$-C$_6$ alkyl)$_2$, —CONH(C$_1$-C$_6$ alkyl), —CON(C$_1$-C$_6$ alkyl)$_2$, —C(O)O(C$_1$-C$_6$ alkyl), —C(O)O(C$_1$-C$_6$ alkyl) aryl, —OC(O)(C$_1$-C$_6$ alkyl), —OC(O)(C$_1$-C$_6$ alkyl)aryl, —SO$_2$NH$_2$, —CONH$_2$, —CO$_2$H, —COH, —NH2, C$_1$-C$_6$ alkylamino, di-C$_1$-C$_6$ alkylamino, —N3, cyanate, isocyanate, thiocyanate, isothiocyanate, (C$_2$-C$_6$ alkenyl)O(C$_1$-C$_6$ alkyl), (C$_1$-C$_6$ alkyl)O(C$_1$-C$_6$ alkyl), (C$_1$-C$_6$ alkyl)O(C$_1$-C$_6$ alkyl)O(C$_1$-C$_6$ alkyl), aryloxy, arylthio, —CO(C$_1$-C$_6$ alkyl), —CO(aryl), —CO(heteroaryl), and —CO(heterocycle).

As used herein, a "substituted group" is derived from the unsubstituted parent structure in which there has been an exchange of one or more hydrogen atoms for another atom or group.

Asymmetric carbon atoms may be present in the compounds described herein. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

Compounds of Formula I

In a first embodiment, the invention provides a compound of Formula I:

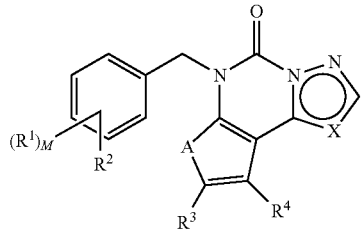

I or a pharmaceutically acceptable salt thereof, wherein
A is oxygen or sulfur;
X is CH or N;
M is 0-4;
each occurrence of $R^1$ and $R^2$ is independently selected from H, halo, aryl, heteroaryl, —($C_1$-$C_6$ alkyl) aryl, —($C_1$-$C_6$ alkyl) heteroaryl, heterocycle, —CN, $C_1$-$C_6$ alkyl, $C_1$-$C_6$ thioalkyl, $C_1$-$C_6$ thiohaloalkyl, $C_1$-$C_6$ haloalkyl, $C_2$-$C_6$ alkenyl, $C_2$-$C_6$ alkynyl, —OH, $C_1$-$C_6$ alkoxy, $C_1$-$C_6$ haloalkoxy, —$NO_2$, —$SO_2C_1$-$C_6$ alkyl, —$SOC_1$-$C_6$ alkyl, —$SO_2NH(C_1$-$C_6$ alkyl), —$SO_2N(C_1$-$C_6$ alkyl)$_2$, —CONH($C_1$-$C_6$ alkyl), —CON($C_1$-$C_6$ alkyl)$_2$, —C(O)O($C_1$-$C_6$ alkyl), —C(O)O($C_1$-$C_6$ alkyl)aryl, —OC(O)($C_1$-$C_6$ alkyl), —OC(O)($C_1$-$C_6$ alkyl)aryl, —$SO_2NH_2$, —$CONH_2$, —$CO_2H$, —COH, —$NH_2$, $C_1$-$C_6$ alkylamino, di-$C_1$-$C_6$ alkylamino, —$N_3$, cyanate, isocyanate, thiocyanate, isothiocyanate, ($C_2$-$C_6$ alkenyl)O($C_1$-$C_6$ alkyl), ($C_1$-$C_6$ alkyl)O($C_1$-$C_6$ alkyl), ($C_1$-$C_6$ alkyl)O($C_1$-$C_6$ alkyl)O($C_1$-$C_6$ alkyl), aryloxy, arylthio, —CO($C_1$-$C_6$ alkyl), —CO(aryl), —CO(heteroaryl), and —CO(heterocycle);
or $R^1$ and $R^2$ are on adjacent carbons and are taken together with the carbons to which they are attached to form an optionally substituted 5-6 member saturated or unsaturated monocylic ring system, optionally comprising one or more oxygen, sulfur, or nitrogen atoms, wherein the ring system;
$R^3$ and $R^4$ are independently selected from H, halo, —CN, $C_1$-$C_6$ alkyl, $C_1$-$C_6$ haloalkyl, OH, $C_1$-$C_6$ alkoxy, $C_1$-$C_6$ haloalkoxy, aryl, heteroaryl, —($C_1$-$C_6$ alkyl) aryl, —($C_1$-$C_6$ alkyl) heteroaryl, —$NO_2$, —$SO_2C_1$-$C_6$ alkyl, —$SO_2N(C_1$-$C_6$ alkyl)$_2$, —CONH($C_1$-$C_6$ alkyl), —CON($C_1$-$C_6$ alkyl)$_2$, and —($CR^{10}R^{11})_{0-3}NR^{12}R^{13}$;
or $R^3$ and $R^4$ taken together with the carbons to which they are attached form a saturated or unsaturated monocylic ring system, having the following structure:

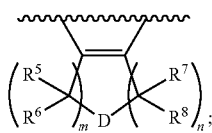

D is —O, —S, —SO, —$SO_2$, —N—$R^9$, or a bond;
m and n are independently 0-4, with the proviso that the sum of m and n is 1-5 when D is —O, —S, —SO, —$SO_2$, —N—$R^9$, or is 2-6 when D is a bond;
$R^5$, $R^6$, $R^7$, $R^8$, $R^{10}$ and $R^{11}$ are independently selected from H, —F, —$C_1$-$C_6$ alkyl, —$C_1$-$C_6$ haloalkyl, —OH, —$C_1$-$C_6$ alkoxy, —$C_1$-$C_6$haloalkoxy, —$SO_2C_1$-$C_6$ alkyl, —$SO_2N(C_1$-$C_6$ alkyl)$_2$, CONH($C_1$-$C_6$ alkyl), and CON($C_1$-$C_6$ alkyl)$_2$; and
$R^9$, $R^{12}$, and $R^{13}$ are independently selected from H, $C_1$-$C_6$ alkyl, aryl, heteroaryl, —$SO_2C_1$-$C_6$ alkyl, —$SO_2N(C_1$-$C_6$ alkyl)$_2$, —CONH($C_1$-$C_6$ alkyl), —CON($C_1$-$C_6$ alkyl)$_2$, —CO($C_1$-$C_6$ alkyl), —CO(aryl), —CO(heteroaryl), and —CO(heterocycle); or $R^{12}$ and $R^{13}$ taken together with the nitrogen to which they are attached form an optionally substituted heterocycle.

In a specific aspect, a compound of Formula I, corresponding to the first embodiment, may include one or more of the following: M=1 or 2; one or more of $R^1$, $R^2$, $R^3$, and $R^4$ is halo, more particularly, halomethyl; $R^1$ is H and $R^2$ is $C_1$-$C_6$ alkoxy, more specifically $OCH_3$; A is sulfur, and X is N; $R^1$ is halo, more specifically F, Cl, or Br, and $R^2$ is $C_1$-$C_6$ alkoxy, more specifically, $CF_3$ or $CHF_2$; $R^3$ is $C_1$-$C_6$ alkyl, more specifically methyl, and $R^4$ is H; $R^3$ is $C_1$-$C_6$ alkyl, more specifically $C_1$-$C_3$ alkyl, and $R^4$ is $(CR^{10}R^{11})_{0-3}NR^{12}R^{13}$; and $R^3$ and $R^4$ taken together with the carbons to which they are attached form a six member monocyclic ring system, wherein D is a nitrogen atom.

In a second embodiment, the invention provides a compound of Formula I, or a pharmaceutically acceptable salt thereof, wherein:
A is oxygen or sulfur;
X is CH or N;
M is 0-4;
D is O, S, SO, $SO_2$, N—$R^9$ or a bond;
each occurrence of $R^1$ and $R^2$ is independently selected from H, halo, CN, $C_1$-$C_3$ alkyl, $C_1$-$C_3$ haloalkyl, —OH, $C_1$-$C_3$ haloalkoxy, $NO_2$, $SO_2C_1$-$C_3$ alkyl, $SO_2N(C_1$-$C_3$ alkyl)$_2$, CONH($C_1$-$C_3$ alkyl), and CON($C_1$-$C_3$ alkyl)$_2$; or $R^1$ and $R^2$ are on adjacent carbons and taken together with the carbons to which they are attached form a 5-6 member monocylic ring system comprising one or more oxygen atoms, wherein the ring system is optionally substituted with one or more F;
$R^3$ and $R^4$ are independently selected from H, F, Cl, Br, CN, $C_1$-$C_3$ alkyl, $C_1$-$C_6$ $CF_3$, $CHF_2$, OH, $C_1$-$C_3$ alkoxy, $OCF_3$, $NO_2$, $SO_2C_1$-$C_3$ alkyl, $SO_2N(C_1$-$C_3$ alkyl)$_2$, CONH($C_1$-$C_3$ alkyl), CON($C_1$-$C_3$ alkyl)$_2$, and $(CR^{10}R^{11})_{0-3}NR^{12}R^{13}$; and
$R^{12}$, and $R^{13}$ are independently selected from H, $C_1$-$C_6$ alkyl, aryl, heteroaryl, $SO_2C_1$-$C_6$ alkyl, $SO_2N(C_1$-$C_6$ alkyl)$_2$, CONH($C_1$-$C_6$ alkyl), and CON($C_1$-$C_6$ alkyl)$_2$ In a specific aspect, a compound of Formula I, corresponding to the second embodiment, may include one or more of the following: M=1 or 2; one or more of $R^1$, $R^2$, $R^3$, and $R^4$ is halo, more particularly, halomethyl; $R^1$ is H and $R^2$ is $C_1$-$C_3$ alkoxy, more specifically $OCH_3$; A is sulfur, and X is N; $R^1$ is halo, more specifically F, Cl, or Br, and $R^2$ is $C_1$-$C_3$ alkoxy; $R^1$ is F, Cl, or Br, and $R^2$ is $CF_3$ or $CHF_2$; $R^3$ is $C_1$-$C_3$ alkyl, more specifically methyl, and $R^4$ is H; $R^3$ is $C_1$-$C_3$ alkyl, more specifically methyl, and $R^4$ is $(CR^{10}R^{11})_{0-3}NR^{12}R^{13}$.

In a third embodiment, the invention provides a compound of Formula I, or a pharmaceutically acceptable salt thereof, wherein A is oxygen or sulfur;

X is CH or N;

M is 0-4;

D is O, S, SO, $SO_2$, N—$R^9$ or a bond;

each occurrence of $R^1$ and $R^2$ is independently selected from H, halo, —CN, $C_1$-$C_6$ alkyl, $C_1$-$C_6$ haloalkyl, —OH, $C_1$-$C_6$ alkoxy, $C_1$-$C_6$ haloalkoxy, —$NO_2$, —$SO_2C_1$-$C_6$ alkyl, —$SO_2N(C_1$-$C_6$ alkyl$)_2$, —CONH($C_1$-$C_6$ alkyl), and —CON($C_1$-$C_6$ alkyl$)_2$;

or $R^1$ and $R^2$ are on adjacent carbons and taken together with the carbons to which they are attached form a 5-6 member monocylic ring system comprising one or more oxygen atoms, wherein the ring system is optionally substituted with one or more F;

$R^3$ and $R^4$ taken together with the carbons to which they are attached form a monocylic ring system, having the following structure:

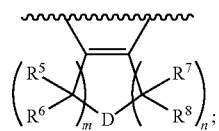

D is O, S, —SO, —$SO_2$, —N—$R^9$, or a bond;

m and n are independently 0-4, with the proviso that the sum of m and n is 1-5 when D is O, S, —SO, —$SO_2$, —N—$R^9$, or is 2-6 when D is a bond;

$R^5$, $R^6$, $R^7$, $R^8$, $R^{10}$ and $R^{11}$ are independently selected from H, F, —$C_1$-$C_6$ alkyl, —$C_1$-$C_6$ haloalkyl, —OH, —$C_1$-$C_6$ alkoxy, —$C_1$-$C_6$ haloalkoxy, —$SO_2C_1$-$C_6$ alkyl, —$SO_2N(C_1$-$C_6$ alkyl$)_2$, —CONH($C_1$-$C_6$ alkyl), and —CON($C_1$-$C_6$ alkyl$)_2$; and $R^9$, $R^{12}$, and $R^{13}$ are independently selected from H, —$C_1$-$C_6$ alkyl, aryl, heteroaryl, —$SO_2C_1$-$C_6$ alkyl, —$SO_2N(C_1$-$C_6$ alkyl$)_2$, —CONH($C_1$-$C_6$ alkyl), and —CON($C_1$-$C_6$ alkyl$)_2$.

In a specific aspect, a compound of Formula I, corresponding to the third embodiment, may include one or more of the following: M=1 or 2; one or more of $R^1$, $R^2$, $R^3$, and $R^4$ is halo, more particularly, halomethyl; $R^1$ is H and $R^2$ is $C_1$-$C_6$ alkoxy, more specifically $OCH_3$; A is sulfur, and X is N; $R^1$ is F, Cl, or Br, and $R^2$ is —$CF_3$ or —$CHF_2$; $R^3$ is $C_1$-$C_6$ alkyl, more specifically $C_1$-$C_3$ alkyl, and $R^4$ is —$(CR^{10}R^{11})_{0-3}NR^{12}R^{13}$.

In a fourth embodiment, the invention provides a compound of Formula I, or a pharmaceutically acceptable salt thereof, wherein A is oxygen or sulfur;

X is CH or N;

M is 0-4;

each occurrence of $R^1$ and $R^2$ is independently selected from H, halo, aryl, heteroaryl, heterocycle, —CN, $C_1$-$C_3$ alkyl, $C_1$-$C_3$ thioalkyl, $C_1$-$C_3$ thiohaloalkyl, $C_1$-$C_3$ haloalkyl, $C_2$-$C_6$ alkenyl, $C_2$-$C_6$ alkynyl, —OH, $C_1$-$C_3$ alkoxy, $C_1$-$C_3$ haloalkoxy, —$NO_2$, —$SO_2C_1$-$C_3$ alkyl, —$SOC_1$-$C_3$ alkyl, —$SO_2NH(C_1$-$C_3$ alkyl), —$SO_2N(C_1$-$C_3$ alkyl$)_2$, —CONH($C_1$-$C_3$ alkyl), —CON($C_1$-$C_3$ alkyl$)_2$, —C(O)O($C_1$-$C_3$ alkyl), —C(O)O($C_1$-$C_3$ alkyl)aryl, —OC(O)($C_1$-$C_3$ alkyl), —OC(O)($C_1$-$C_3$ alkyl)aryl, —$SO_2NH_2$, —$CONH_2$, —$CO_2H$, —COH, —$NH_2$, $C_1$-$C_3$ alkylamino, di-$C_1$-$C_3$ alkylamino, —$N_3$, cyanate, isocyanate, thiocyanate, isothiocyanate, ($C_2$-$C_6$ alkenyl)O($C_1$-$C_3$ alkyl), ($C_1$-$C_3$ alkyl)O ($C_1$-$C_3$ alkyl), ($C_1$-$C_3$ alkyl)O($C_1$-$C_3$ alkyl)O($C_1$-$C_3$ alkyl), aryloxy, arylthio, —CO($C_1$-$C_3$ alkyl), —CO(aryl), —CO (heteroaryl), and —CO(heterocycle);

or $R^1$ and $R^2$ are on adjacent carbons and taken together with the carbons to which they are attached form a 5-6 member monocylic ring system comprising one or more oxygen atoms, preferably 1-2 oxygens, wherein the ring system is optionally substituted with one or more F;

$R^3$ and $R^4$ taken together with the carbons to which they are attached form a monocylic ring system, having the following structure:

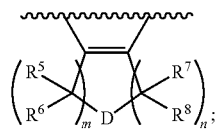

D is O, S, SO, $SO_2$, N—$R^9$, or a bond;

m and n are independently 0-4, with the proviso that the sum of m and n is 1-5 when D is O, S, SO, $SO_2$, N—$R^9$, or is 2-6 when D is a bond;

$R^5$, $R^6$, $R^7$, $R^8$, $R^{10}$ and $R^{11}$ are independently selected from H, F, $C_1$-$C_3$ alkyl, $C_1$-$C_3$ haloalkyl, OH, $C_1$-$C_3$ alkoxy, $C_1$-$C_3$ haloalkoxy, —$SO_2C_1$-$C_6$ alkyl, —$SO_2N(C_1$-$C_3$ alkyl$)_2$, —CONH($C_1$-$C_3$ alkyl), and —CON($C_1$-$C_3$ alkyl$)_2$; and $R^9$, $R^{12}$, and $R^{13}$ are independently selected from H, $C_1$-$C_3$ alkyl, aryl, heteroaryl, —$SO_2C_1$-$C_3$ alkyl, —$SO_2N$ ($C_1$-$C_3$ alkyl$)_2$, —CONH($C_1$-$C_3$ alkyl), and —CON($C_1$-$C_3$ alkyl$)_2$.

In a specific aspect, a compound of Formula I, corresponding to the fourth embodiment, may include one or more of the following: M=1 or 2; one or more of $R^1$, $R^2$, $R^3$, and $R^4$ is halo, more particularly, halomethyl; $R^1$ is H and $R^2$ is $C_1$-$C_3$ alkoxy, more specifically $OCH_3$; A is sulfur, and X is N; $R^1$ is F, Cl, or Br, and $R^2$ is —$CF_3$ or —$CHF_2$; and $R^3$ is $C_1$-$C_3$ alkyl and $R^4$ is —$(CR^{10}R^{11})_{0-3}NR^{12}R^{13}$.

In other embodiments, the invention provides a compound of Formula I (or pharmaceutical composition thereof), wherein any of $R^1$ through $R^{11}$ is independently selected from H, halo, aryl, heteroaryl, heterocycle, —CN, $C_1$-$C_6$ alkyl, $C_1$-$C_6$ thioalkyl, $C_1$-$C_6$ thiohaloalkyl, $C_1$-$C_6$ haloalkyl, $C_2$-$C_6$ alkenyl, $C_2$-$C_6$ alkynyl, —OH, $C_1$-$C_6$ alkoxy, $C_1$-$C_6$ haloalkoxy, —$NO_2$, —$SO_2C_1$-$C_6$ alkyl, —$SOC_1$-$C_6$ alkyl, —$SO_2NH(C_1$-$C_6$ alkyl), —$SO_2N(C_1$-$C_6$ alkyl$)_2$, —CONH($C_1$-$C_6$ alkyl), —CON($C_1$-$C_6$ alkyl$)_2$, —C(O)O($C_1$-$C_6$ alkyl), —C(O)O($C_1$-$C_6$ alkyl)aryl, —OC (O)($C_1$-$C_6$ alkyl), —OC(O)($C_1$-$C_6$ alkyl)aryl, —$SO_2NH_2$, —$CONH_2$, —$CO_2H$, —COH, —$NH_2$, $C_1$-$C_6$ alkylamino, di-$C_1$-$C_6$ alkylamino, —$N_3$, cyanate, isocyanate, thiocyanate, isothiocyanate, —($C_2$-$C_6$ alkenyl)O($C_1$-$C_6$ alkyl), —($C_1$-$C_6$ alkyl)O($C_1$-$C_6$ alkyl), —($C_1$-$C_6$ alkyl)O($C_1$-$C_6$ alkyl)O($C_1$-$C_6$ alkyl), aryloxy, arylthio, —CO($C_1$-$C_6$ alkyl), —CO(aryl), —CO(heteroaryl), and —CO(heterocycle).

In other embodiments, the invention provides a compound of Formula I (or pharmaceutical composition thereof) wherein any of $R^1$ through $R^{11}$ is independently selected from H, halo, aryl, heteroaryl, heterocycle, —CN, $C_1$-$C_6$ alkyl, $C_1$-$C_6$ thioalkyl, $C_1$-$C_6$ thiohaloalkyl, $C_1$-$C_6$ haloalkyl, $C_2$-$C_6$ alkenyl, $C_2$-$C_6$ alkynyl, —OH, $C_1$-$C_6$ alkoxy, $C_1$-$C_6$ haloalkoxy, —$NO_2$, —$SO_2C_1$-$C_6$ alkyl, —$SOC_1$-$C_6$ alkyl, —SO$_2$NH(C$_1$-C$_6$ alkyl), —SO$_2$N(C$_1$-C$_6$ alkyl)$_2$, —CONH (C$_1$-C$_6$ alkyl), —CON(C$_1$-C$_6$ alkyl)$_2$, —C(O)O(C$_1$-C$_6$ alkyl), —C(O)O(C$_1$-C$_6$ alkyl)aryl, —OC(O)(C$_1$-C$_6$ alkyl), —OC(O)(C$_1$-C$_6$ alkyl)aryl, —SO$_2$NH$_2$, —CONH$_2$, —CO$_2$H, —COH, —NH$_2$, C$_1$-C$_6$ alkylamino, di-C$_1$-C$_6$ alkylamino, —N$_3$, cyanate, isocyanate, thiocyanate, isothiocyanate, —(C$_2$-C$_6$ alkenyl)O(C$_1$-C$_6$ alkyl), —(C$_1$-C$_6$ alkyl)O(C$_1$-C$_6$ alkyl), —(C$_1$-C$_6$ alkyl)O(C$_1$-C$_6$ alkyl)O(C$_1$-C$_6$ alkyl), aryloxy, arylthio, —CO(C$_1$-C$_6$ alkyl), —CO(aryl), —CO(heteroaryl), and —CO(heterocycle).

More particularly, the invention provides a compound of Formula I (or pharmaceutical compositions thereof) wherein any of R$^1$ through R$^{11}$ is independently selected from H, halo, aryl, heteroaryl, heterocycle, —CN, C$_1$-C$_3$ alkyl, C$_1$-C$_6$ thioalkyl, C$_1$-C$_{63}$ thiohaloalkyl, C$_1$-C$_3$ haloalkyl, C$_2$-C$_6$ alkenyl, C$_2$-C$_6$ alkynyl, —OH, C$_1$-C$_3$ alkoxy, C$_1$-C$_3$ haloalkoxy, —NO$_2$, —SO$_2$C$_1$-C$_3$ alkyl, —SOC$_1$-C$_3$ alkyl, —SO$_2$NH(C$_1$-C$_3$ alkyl), —SO$_2$N(C$_1$-C$_3$ alkyl)$_2$, —CONH (C$_1$-C$_3$ alkyl), —CON(C$_1$-C$_3$ alkyl)$_2$, —C(O)O(C$_1$-C$_3$ alkyl), —C(O)O(C$_1$-C$_3$ alkyl)aryl, —OC(O)(C$_1$-C$_3$ alkyl), —OC(O)(C$_1$-C$_3$ alkyl)aryl, —SO$_2$NH$_2$, —CONH$_2$, —CO$_2$H, —COH, —NH$_2$, C$_1$-C$_3$ alkylamino, di-C$_1$-C$_3$ alkylamino, —N$_3$, cyanate, isocyanate, thiocyanate, isothiocyanate, —(C$_2$-C$_6$ alkenyl)O(C$_1$-C$_3$ alkyl), —(C$_1$-C$_3$alkyl)O(C$_1$-C$_3$ alkyl), —(C$_1$-C$_3$ alkyl)O(C$_1$-C$_3$ alkyl)O (C$_1$-C$_3$ alkyl), aryloxy, arylthio, —CO(C$_1$-C$_3$ alkyl), —CO (aryl), —CO(heteroaryl), and —CO(heterocycle).

SYNTHETIC EXAMPLES

Compounds of Formula I can be prepared using the general synthetic schemes illustrated below. Amino-cyanothiophenes can be prepared from ketones and aldehydes by heating in the presence of elemental sulfur and malononitrile with an organic base as a catalyst (Scheme 1). In some cases, regioisomeric thiophenes may form. The amino-cyanothiophene can be alkoxyformylated with ethyl or methyl chloroformate and the resulting carbonate, when heated with formylhydrazine affords the triazolopyrimidinone. This compound can be treated with a suitable electrophile ArCH2L in which L is a leaving group such as chloride, bromide, methanesulfonate, etc. to afford target compounds.

Scheme 1

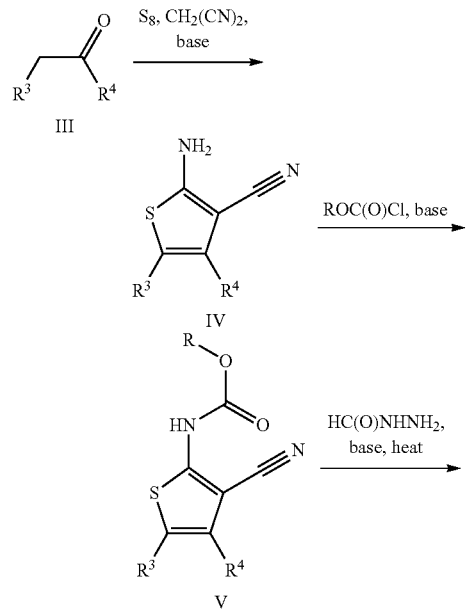

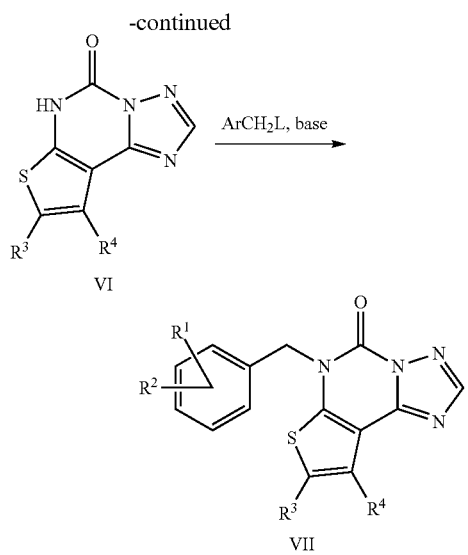

In cases where R$^3$ and R$^4$ form a nitrogen-containing ring, the compounds are prepared from a cyclic starting material in which the nitrogen is blocked by a suitable protecting group PG such as tert-butyloxycarbonyl, benzyl, benzyloxycarbonyl, etc. (Scheme 2). This starting material can be elaborated as described above and the resulting protecting group can be removed to provide a secondary amine. This can be alkylated with electrophiles R$^9$-L, in which L is a leaving group as described above. Alternatively, substitution can be introduced by treating the secondary amine with an aldehyde or ketone in the presence of sodium cyanoborohydride or sodium triacetoxyborohydride.

Scheme 2

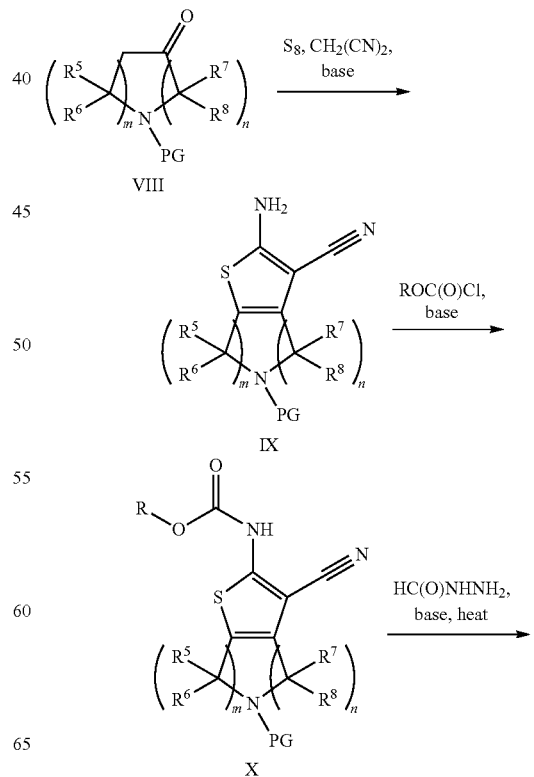

Scheme (continued)

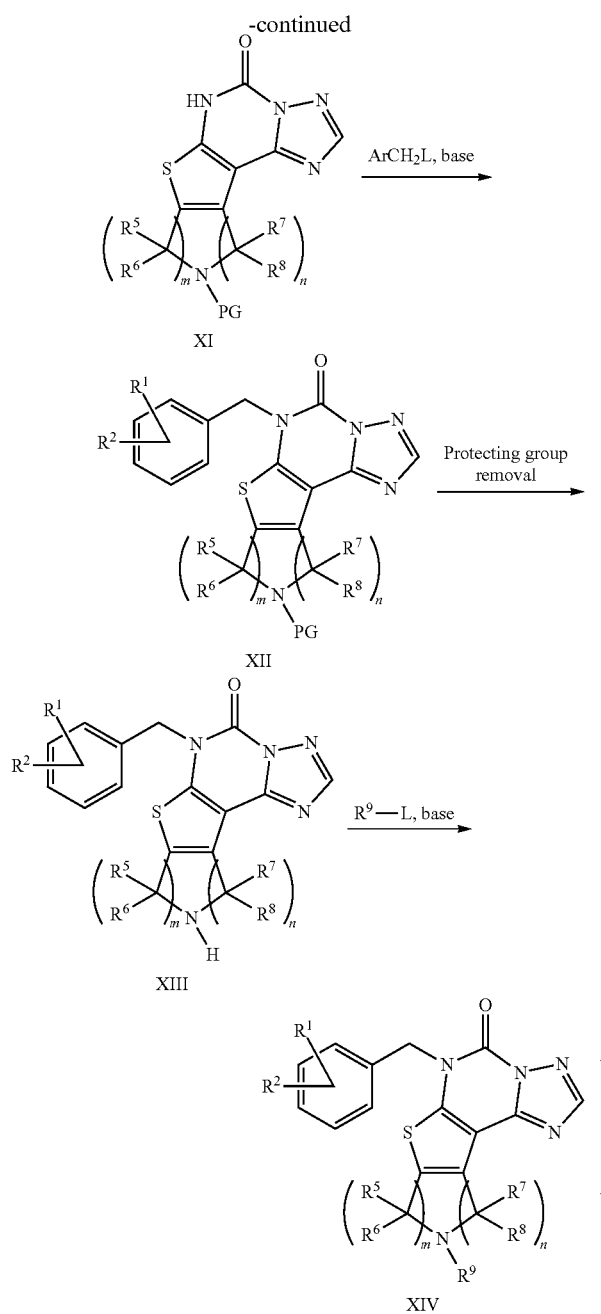

In some instances it is preferable to brominate the 2-position of the thiophene. The resulting bromothiophene can be elaborated to the pyrimidinone as described above. The bromine group can then be replaced by various side chains by treating it with an organometallic compound such as an organozinc, organotin, organoboron or organomagnesium reagent, in the presence of a palladium catalyst.

The bromothiophenes from above can be converted to 2-thiophenecarbaldehydes by the action of potassium vinyltrifluoroborate in the presence of palladium and base, followed by oxidative cleavage of the resulting vinylthiophene using catalytic osmium tetroxide or ozonolysis. The 2-thienocarbaldehyde can then be reductively aminated by treating with a primary or secondary amine and a reducing agent such as sodium cyanoborohydride or sodium triacetoxyborohydride.

The 2-thiophenecarbaldehydes can also be prepared directly by subjecting the thiophene to phosphorous oxychloride and dimethylformamide (Scheme 4). The resulting aldehyde can be similarly elaborated to aminomethyl-substituted compounds.

Scheme 3

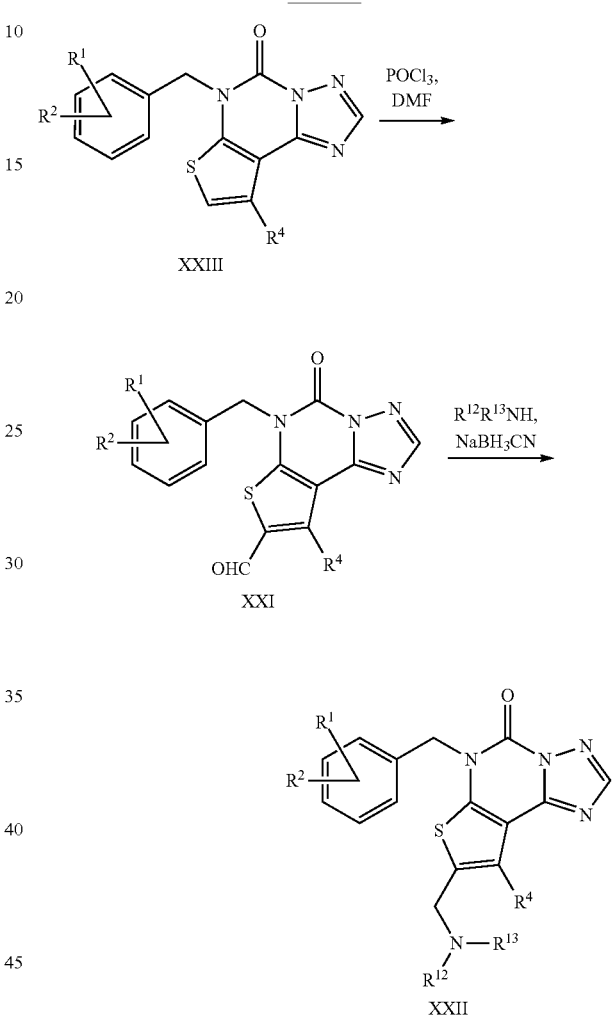

Furan-fused derivatives can be prepared in a similar manner to their thiophene counterparts (Scheme 5). Aminofurancaronitriles can be alkoxyformylated and treated with formyl hydrazide to give triazolopyrimidinone. Substituted benzyl groups can then be introduced by the action of a suitable benzylating reagent ArCH$_2$L as described above.

Scheme 4

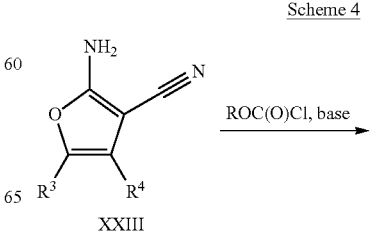

-continued

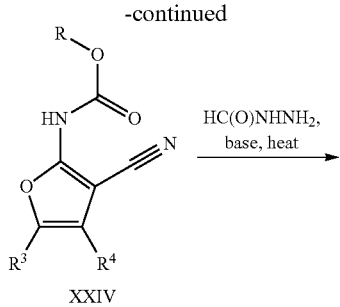

XXIV

XXV

XXVI

Preparative Examples

Instrumentation

1H NMR spectra were obtained on a Bruker Ultrashield 400 Plus instrument at 400 MHz and referenced relative to residual protonated material in the deuterated solvent. Preparative HPLC was performed on a Shimadzu SIL-10AP system using a Waters SunFire OBD 30 mm×100 mm×2.5 m (particle size) C18 column with a 15 minute gradient of 10-100% acetonitrile in water and 0.05% trifluoroacetic acid added as a modifier to both phases. Elution profiles were monitored by UV at 254 and 220 nm. LC-MS analyses were performed on an Agilent LC-1200 system employing a Waters SunFire 2.1 mm×50 mm×2.5 m (particle size) C18 column with a 4.5 minute gradient of 0-100% acetonitrile in water and 0.1% formic acid added as a modifier to both phases. Elution profiles were monitored by UV at 254 and 220 nm. TIC chromatograms were monitored using APCI in positive mode.

Preparative Example 1

6-(2-Chlorobenzyl)thieno[3,2-e][1,2,4]triazolo[1,5-c]pyrimidin-5(6H)-one (1)

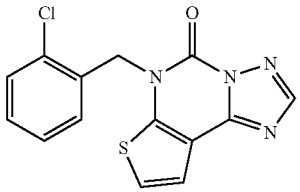

Step 1.1: methyl 3-cyanothiophen-2-ylcarbamate

Methyl chloroformate (7.61 g, 80.5 mmol) was added drop-wise to a stirred of 2-amino-3-cyanothiophene (10 g, 80.5 mmol) and pyridine (19.1 g, 242 mmol) in dichloromethane (250 mL) at 0° C. After addition, the mixture was warmed to room temperature and stirred overnight. The reaction was treated with water (50 mL) and extracted with dichloromethane (3×150 mL). The combined organic phase was washed with 1 N hydrochloric acid (2×150 mL), saturated aqueous sodium bicarbonate (100 mL), brine (100 mL), and dried over sodium sulfate. It was filtered and concentrated to give a crude product, which was triturated with a solution of methyl tert-butyl ether and petroleum ether (1:1, 50 mL) to give 11 g (75%) of methyl 3-cyanothiophen-2-ylcarbamate as a pale white solid. 1H NMR (400 MHz, CDCl3) δ 3.90 (s, 3H), 6.63-6.65 (d, 1H), 6.94-6.96 (d, 1H), 7.94 (s, 1H).

Step 1.2: thieno[3,2-e][1,2,4]triazolo[1,5-c]pyrimidin-5(6H)-one

Formylhydrazine (2.08 g, 34.6 mmol) and tri-n-propylamine (3 mL) was added to a suspension of methyl 3-cyanothiophen-2-ylcarbamate (6 g, 32.9 mmol) in 2-methoxyethanol (70 mL) at room temperature. The mixture was heated at reflux overnight under nitrogen. The mixture was concentrated under vacuum to give a crude product, which was purified by preparative HPLC to give 1.8 g (26%) of thieno[3,2-e][1,2,4]triazolo[1,5-c]pyrimidin-5(6H)-one as a solid. 1H NMR (400 MHz, DMSO) δ 7.28-7.30 (d, 1H), 7.39-7.41 (d, 1H), 8.34 (s, 1H).

Step 1.3: 6-(2-chlorobenzyl)thieno[3,2-e][1,2,4]triazolo[1,5-c]pyrimidin-5(6H)-one (1)

Potassium carbonate (302 mg, 2.19 mmol) was added to a suspension of 1c (140 mg, 0.73 mmol) in dimethylformamide (3 mL) and the mixture was stirred for 10 minutes. 1-Bromomethyl-2-chloro-benzene (180 mg, 0.87 mmol) was added and the mixture was stirred overnight at 40° C. The mixture was concentrated in vacuum and the residue was diluted with water (10 mL) and extracted with dichloromethane (3×30 mL). The combined organic extracts were washed with brine (30 mL), dried over sodium sulfate, filtered, and concentrated to give a crude product. This material was triturated with a solution of methyl tert-butyl ether-dichloromethane (20:1) to afford 63 mg (22%) 1 as a white powder.

Numerous compounds were made using the above general procedure, as exemplified in Table 1:

TABLE 1

| Example | Structure | LC-MS (MH+) | 1H-NMR |
|---|---|---|---|
| 1 | C₁₄H₉ClN₄OS | 317.0 | 1H NMR (400 MHz, CDCl3) δ 5.64 (s, 2H), 7.08 (d, 1H), 7.13 (d, 1H), 7.20 (t, 1H), 7.25 (t, 1H), 7.48 (d, 1H), 7.61 (d, 1H), 8.35 (s, 1H) |
| 2 | C₁₄H₉ClN₄OS | 317.0 | 1H NMR (400 MHz, CDCl3) δ 5.64 (s, 2H), 7.16 (d, 1H), 7.35-7.25 (m, 3H), 7.48 (s, 1H), 7.62 (d, 1H), 8.33 (s, 1H) |
| 3 | C₁₅H₁₁ClN₄OS | 331.0 | 1H NMR (400 MHz, CDCl3) δ 2.67 (s, 3H), 5.40 (s, 2H), 6.74 (s, 1H), 7.33 (d, 2H), 7.43 (d, 2H), 8.33 (s, 1H) |
| 4 | C₂₀H₁₄N₄OS | 359.0 | 1H NMR (400 MHz, CDCl3) δ 5.49 (s, 2H), 7.14 (d, 1H), 7.35 (m, 1H), 7.42 (t, 2H), 7.57 (m, 7H), 8.31 (s, 1H) |

TABLE 1-continued

| Example | Structure | LC-MS (MH+) | 1H-NMR |
|---|---|---|---|
| 5 | C₁₄H₉ClN₄OS | 317.0 | 1H NMR (400 MHz, CDCl3) δ 5.34 (s, 2H), 7.06 (d, 1H), 7.27 (d, 2H), 7.37 (d, 2H), 7.53 (d, 1H), 8.24 (s, 1H) |
| 6 | C₁₅H₁₂N₄OS | 297.0 | 1H NMR (400 MHz, CDCl3) δ 2.64 (s, 3H), 5.42 (s, 2H), 6.70 (s, 1H), 7.34 (m, 3H), 7.46 (d, 1H), 8.31 (s, 1H) |
| 7 | C₂₁H₁₆N₄OS | 373.0 | 1H NMR (400 MHz, CDCl3) δ 2.66 (s, 3H), 5.46 (s, 2H), 6.72 (s, 1H), 7.35 (t, 1H), 7.42 (t, 2H), 7.54 (m, 6H), 8.32 (s, 1H) |
| 8 | C₂₁H₁₅ClN₄OS | 407.0 | 1H NMR (400 MHz, CDCl3) δ 4.03 (s, 2H), 5.45 (s, 2H), 6.93 (m, 1H), 7.3-7.1 (m, 8H), 7.37 (m, 1H), 8.22 (s, 1H) |
| 9 | C₂₁H₁₅ClN₄OS | 407.0 | 1H NMR (400 MHz, CDCl3) δ 4.07 (s, 2H), 5.25 (s, 2H), 7.3-7.1 (m, 10H), 8.20 (s, 1H) |

TABLE 1-continued

| Example | Structure | LC-MS (MH+) | 1H-NMR |
|---|---|---|---|
| 10 | C₁₅H₁₁ClN₄OS | 331.0 | 1H NMR (400 MHz, CDCl3) δ 2.67 (s, 2H), 5.59 (s, 2H), 6.70 (s, 1H), 7.02 (d, 1H), 7.17 (t, 1H), 7.25 (t, 1H), 7.45 (d, 1H), 8.34 (s, 1H) |
| 11 | C₁₅H₁₁ClN₄OS | 331.0 | 1H NMR (400 MHz, CDCl3) δ 2.66 (s, 3H), 5.39 (s, 2H), 6.72 (s, 1H), 7.29 (m, 3H), 7.44 (s, 1H), 8.32 (s, 1H) |
| 12 | C₁₅H₁₂N₄OS | 297.0 | 1H NMR (400 MHz, MeOD) δ 2.50 (s, 3H), 5.43 (s, 2H), 7.21 (s, 1H), 7.32 (m, 3H), 7.43 (m, 2H), 8.37 (s, 1H) |
| 13 | C₁₅H₁₁ClN₄OS | 331.0 | 1H NMR (400 MHz, CDCl3) δ 2.67 (s, 3H), 5.59 (s, 2H), 6.70 (s, 1H), 7.02 (d, 1H), 7.16 (t, 1H), 7.25 (t, 1H), 7.45 (d, 1H), 8.34 (s, 1H) |
| 14 | C₁₂H₁₆N₄OS | 373.0 | 1H NMR (400 MHz, CDCl3) δ 2.52 (s, 3H), 5.43 (s, 2H), 7.21 (s, 1H), 7.35 (t, 1H), 7.44 (t, 2H), 7.56 (m, 6H), 8.27 (s, 1H) |

TABLE 1-continued

| Example | Structure | LC-MS (MH+) | 1H-NMR |
|---|---|---|---|
| 15 | C$_{15}$H$_{11}$ClN$_4$OS | 331.0 | 1H NMR (400 MHz, CDCl3) δ 2.52 (s, 3H), 5.35 (s, 2H), 7.21 (s, 1H), 7.33 (d, 2H), 7.40 (d, 2H), 8.27 (s, 1H) |
| 16 | C$_{15}$H$_{11}$ClN$_4$OS | 331.0 | 1H NMR (400 MHz, CDCl3) δ 2.46 (s, 3H), 5.29 (s, 2H), 7.15 (s, 1H), 7.25 (m, 3H), 7.37 (s, 1H), 8.21 (s, 1H). |
| 17 | C$_{21}$H$_{16}$N$_4$OS | 373.0 | 1H NMR (400 MHz, CDCl3) δ 4.13 (s, 2H), 5.36 (s, 2H), 7.22 (s, 1H), 7.30 (m, 8H), 7.43 (m, 2H), 8.26 (s, 1H). |
| 18 | C$_{27}$H$_{20}$N$_4$OS | 449.0 | 1H NMR (400 MHz, CDCl3) δ 4.13 (s, 2H), 5.39 (s, 2H), 7.28 (m, 7H), 7.42 (t, 2H), 7.55 (m, 6H), 8.26 (s, 1H) |

TABLE 1-continued

| Example | Structure | LC-MS (MH+) | 1H-NMR |
|---|---|---|---|
| 19 | C₁₉H₁₉ClN₄OS (2-chlorobenzyl derivative) | 387.0 | 1H NMR (400 MHz, CDCl3) δ 0.92 (d, 6H), 1.56 (m, 3H), 2.79 (m, 2H), 5.56 (s, 2H), 7.01 (d, 1H), 7.20 (t, 1H), 7.26 (m, 2H), 7.45 (d, 1H), 8.30 (s, 1H) |
| 20 | C₁₉H₁₉ClN₄OS (3-chlorobenzyl derivative) | 387.0 | 1H NMR (400 MHz, CDCl3) δ 0.87 (d, 6H), 1.52 (m, 3H), 2.76 (m, 2H), 5.29 (s, 2H), 7.22 (m, 4H), 7.38 (s, 1H), 8.21 (s, 1H) |
| 21 | C₂₅H₂₄N₄OS (biphenylmethyl derivative) | 429.0 | 1H NMR (400 MHz, CDCl3) δ 0.95 (d, 6H), 1.59 (m, 3H), 2.82 (m, 2H), 5.44 (s, 2H), 7.24 (s, 1H), 7.34 (m, 1H), 7.42 (t, 2H), 7.57 (m, 6H), 8.28 (s, 1H) |
| 22 | C₂₁H₁₅ClN₄OS (4-chlorobenzyl, benzyl derivative) | 407.0 | 1H NMR (400 MHz, CDCl3) δ 4.15 (s, 2H), 5.33 (s, 2H), 7.4-7.2 (m, 10H), 8.28 (s, 1H) |

TABLE 1-continued

| Example | Structure | LC-MS (MH+) | 1H-NMR |
|---|---|---|---|
| 23 | C₁₉H₁₉ClN₄OS | 387.0 | 1H NMR (400 MHz, CDCl3) δ 0.88 (d, 6H), 1.55 (m, 3H), 2.75 (t, 2H), 5.28 (s, 2H), 7.18 (s, 1H), 7.26 (d, 2H), 7.34 (d, 2H), 8.20 (s, 1H) |
| 24 | C₁₄H₁₀N₄OS | 283.0 | 1H NMR (400 MHz, CDCl3) δ 5.44 (s, 2H), 7.11 (d, 1H), 7.35 (m, 3H), 7.46 (m, 2H), 7.57 (d, 1H), 8.29 (s, 1H) |
| 25 | C₁₉H₂₀N₄OS | 353.0 | 1H NMR (400 MHz, CDCl3) δ 0.95 (d, 6H), 1.60 (m, 3H), 2.83 (m, 2H), 5.41 (s, 2H), 7.24 (s, 1H), 7.37 (m, 3H), 7.48 (d, 2H), 8.28 (s, 1H) |
| 26 | C₁₆H₁₃ClN₄OS | 345.0 | 1H NMR (400 MHz, DMSO-d6) δ 2.35 (s, 3H), 2.48 (s, 3H), 5.35 (s, 2H), 7.41-7.42 (m, 4H), 8.49 (s, 1H) |

TABLE 1-continued

| Example | Structure | LC-MS (MH+) | 1H-NMR |
|---|---|---|---|
| 27 | C₁₅H₁₂N₄O₂S | 313.1 | 1H NMR (400 MHz, CDCl3) δ 3.78 (s, 3H), 5.39 (s, 3H), 6.86-6.88 (m, 2H), 7.12 (d, J = 4.8 Hz, 1H), 7.44-7.45 (m, 2H), 7.57 (d, J = 4.3 Hz, 1H), 8.29 (s, 1H) |
| 28 | C₁₆H₁₄N₄O₂S | 327.1 | 1H NMR (400 MHz, CDCl3) δ 2.65 (s, 3H), 3.78 (s, 3H), 5.36 (s, 2H), 6.71 (d, J = 1.1 Hz, 1H), 6.87-6.85 (m, 1H), 7.44-7.43 (m, 2H), 8.31 (s, 1H) |

Preparative Example 29

8-((1,4-Oxazepan-4-yl)methyl)-6-(4-methoxybenzyl)thieno[32-e][1,2,4]triazolo[1,5-c]pyrimidin-5(6H)-one

29

Step 2.1: methyl 5-bromo-3-cyanothiophen-2-ylcarbamate

To a solution of compound methyl 3-cyanothiophen-2-ylcarbamate (11.5 g, 63 mmol) in acetic acid (500 mL) was added bromine (12 g, 75 mmol) at room temperature. The solution was heated at 60° C. with stirring for 1 hour and then concentrated and treated with water (500 mL). It was extracted with ethyl acetate (3×300 mL) and the combined extracts were dried over sodium sulfate and concentrated to give 14 g (89%) of methyl 5-bromo-3-cyanothiophen-2-ylcarbamate as a solid. 1H NMR 400 MHz CDCl3 δ 3.89 (s, 3H), 6.90 (s, 1H), 8.05 (s, 1H).

Step 2.2: 8-bromo-6-(4-methoxybenzyl)thieno[3,2-e][1,2,4]triazolo[1,5-c]pyrimidin-5(6H)-one Prepared as described in Step 1.2. 1H NMR (400 MHz, DMSO-d6) δ 7.66 (s, 1H), 8.42 (s, 1H), 13.1 (br, 1H). LCMS (MH+, 270.9).

Step 2.4: 6-(4-methoxybenzyl)-8-vinylthieno[3,2-e][1,2,4]triazolo[1,5-c]pyrimidin-5(6H)-one To mixture of 8-bromo-6-(4-methoxybenzyl)thieno[3,2-e][1,2,4]triazolo[1,5-c]pyrimidin-5(6H)-one (4.00 g, 10.2 mmol), potassium trifluoro(vinyl)borate (2.05 g, 15.3 mmol), and [1,1'-bis(diphenylphosphino)ferrocene]dichloropalladium(II), complex with dichloromethane (417.5 mg, 0.51 mmol) in butan-1-ol (30 ml) was added triethylamine (1.43 ml, 0.01 mol). The resulting mixture was heated to 100 OC. Next morning the crude mixture was cooled to room temperature at which time the solvent was removed under reduced pressure. The residue was purified over silica gel eluting with 0-20% IPA in ethyl acetate to yield 6-(4-methoxybenzyl)-8-vinylthieno[3,2-e][1,2,4]triazolo[1,5-c]pyrimidin-5(6H)-one as a brown solid (2.90 g, 84%). 1H NMR (400 MHz, DMSO-d6) δ 3.74 (s, 3H), 5.24-5.30 (m, 1H), 5.34 (s, 2H), 5.52-5.63 (m, 1H), 6.94 (d, J=8.66 Hz, 2H), 7.41 (d, J=8.53 Hz, 2H), 7.60 (s, 1H), 8.51 (s, 1H). LCMS (MH+, 339.2).

Step 2.5: 6-(4-methoxybenzyl)-5-oxo-5,6-dihydrothieno[3,2-e][1,2,4]triazolo[1,5-c]pyrimidine-8-carbaldehyde 6-(4-Methoxybenzyl)-8-vinylthieno[3,2-e][1,2,4]triazolo[1,5-c]pyrimidin-5(6H)-one (2.85 g; 8.42 mmol) was suspended in tetrahydrofuran (40 ml) and heated with a heat gun to effect dissolution. Similarly sodium periodate (4.14 g; 19.4 mmol) was heated in water (20 ml) to effect dissolution. The above solutions were combined with vigorous stirring. While the stirred mixture was still about 40° C., osmium (VIII) oxide (2.06 ml, 2.50% w/w, 0.21 mmol) was added and the mixture was stirred vigorously for 4 hours. The crude mixture was diluted with water (300 mL) and extracted with DCM (4×100). The organic layers were combined, dried over $Na_2SO_4$, filtered and concentrated. The crude material was purified over silica gel (120 g) eluting with 0-30% IPA in ethyl acetate over 25 minutes. Product fractions were combined and concentrated to yield the aldehyde as a brown solid (1.82 g, 63%). 1H NMR (400 MHz, DMSO-d6) δ 3.75 (s, 3H), 5.40 (s, 2H), 6.94 (d, J=8.66 Hz, 2H), 7.45 (d, J=8.53 Hz, 2H), 8.58 (d, J=4.77 Hz, 2H), 9.95 (s, 1H). LCMS (MH+, 341.2).

Step 2.6: 8-((1,4-oxazepan-4-yl)methyl)-6-(4-methoxybenzyl)thieno[3,2-e][1,2,4]triazolo[1,5-c]pyrimidin-5(6H)-one (29)

To a mixture of 6-(4-methoxybenzyl)-5-oxo-5,6-dihydrothieno[3,2-e][1,2,4]triazolo[1,5-c]pyrimidine-8-carbaldehyde (50 mg, 0.15 mmol) and 1,4-oxazepane hydrochloride (30 mg, 0.22 mmol) in dichloromethane (2 ml) was added triethylamine (25 µl, 0.18 mmol). After 5 minutes of stirring, sodium triacetoxyhydroborate (47 mg, 0.22 mmol) was added. The resulting mixture was stirred at room temperature. After 4 hours, the mixture was concentrated under reduced pressure. The resulting residue was taken up in DMSO (2 mL), filtered and purified directly by reverse phase chromatography to yield the above product (33 mg, 41%) as a white solid.

Numerous compounds were made using the above general procedure, as exemplified in Table 2:

TABLE 2

| Example | Structure | LC-MS (MH+) | 1H-NMR |
|---|---|---|---|
| 29 | 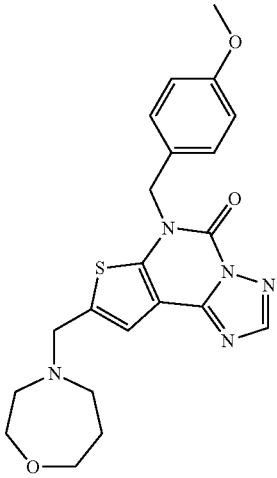 $C_{21}H_{23}N_5O_3S$ | 426.1 | 1H NMR (400 MHz, DMSO-d6) δ 1.98-2.16 (m, 2H), 3.14-3.60 (m, 4H), 3.66-3.90 (m, 7H), 4.58-4.80 (m, 2H), 5.36 (s, 2H), 6.94 (d, J = 8.53 Hz, 2H), 7.41 (d, J = 8.53 Hz, 2H), 7.84 (br s, 1H), 8.55 (s, 1H) |
| 30 | 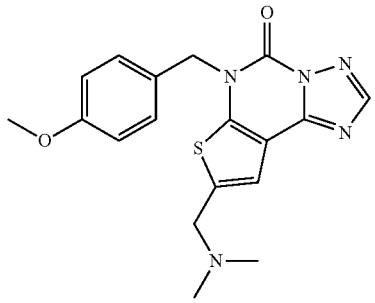 $C_{18}H_{19}N_5O_2S$ | 370.1 | 1H NMR (400 MHz, CDl3) δ 2.84 (s, 6H), 3.78 (s, 3H), 4.42 (s, 2H), 5.35 (s, 2H), 6.87-6.88 (m, 2H), 7.44-7.46 (m, 2H), 7.65 (s, 1H), 8.30 (s, 1H) |

TABLE 2-continued

| Example | Structure | LC-MS (MH+) | 1H-NMR |
|---|---|---|---|
| 31 | C<sub>20</sub>H<sub>21</sub>N<sub>5</sub>O<sub>3</sub>S | 412.2 | 1H NMR (400 MHz, DMSO-d6) δ 3.06-3.11 (m, 4H), 3.73 (s, 3H), 3.86-4.01 (m, 4H), 4.56-4.59 (m, 2H), 5.34 (s, 2H), 6.92-6.94 (d, J = 6.8 Hz, 2H), 7.40-7.38 (d, J = 6.8 Hz, 2H), 7.75 (s, 1H), 8.53 (s, 1H) |
| 32 | C<sub>21</sub>H<sub>24</sub>N<sub>6</sub>O<sub>2</sub>S | 425.2 | 1H NMR (400 MHz, DMSO-d6) δ 2.28-2.38 (m, 2H), 2.79 (s, 3H), 2.98-3.11 (m, 4H), 3.38-3.43 (m, 2H), 3.77 (s, 3H), 3.88 (s, 2H), 5.32 (s, 2H), 6.90-6.92 (m, 2H), 7.34-7.36 (m, 2H), 7.55 (s, 1H), 8.55 (s, 1H) |
| 33 | C<sub>22</sub>H<sub>25</sub>N<sub>5</sub>O<sub>3</sub>S | 440.2 | 1H NMR (400 MHz, CDCl3) δ 1.19-1.28 (m, 6H), 2.38-2.48 (m, 2H), 3.32-3.42 (m, 2H), 3.77 (s, 3H), 4.01-4.09 (m, 2H), 4.32 (s, 2H), 4.78 (s, 2H), 6.75-6.78 (m, 2H), 7.12-7.16 (m, 2H), 7.68 (s, 1H), 8.55 (s, 1H) |

TABLE 2-continued

| Example | Structure | LC-MS (MH+) | 1H-NMR |
|---|---|---|---|
| 34 | C22H24N6O3S | 453.2 | 1H NMR (400 MHz, CDCl3) δ 1.22 (t, J = 7.22 Hz, 3H), 3.11-3.20 (m, 2H), 3.48-3.63 (m, 6H), 3.82 (s, 3H), 4.15-4.22 (m, 2H), 5.40 (s, 2H), 6.92 (d, J = 8.66 Hz, 2H), 7.48 (d, J = 8.53 Hz, 2H), 7.63 (s, 1H), 8.37 (s, 1H) |
| 35 | C21H24N6O4S2 | 489.2 | 1H NMR (400 MHz, CDCl) δ 2.92 (s, 3H), 3.19-3.30 (m, 4H), 3.63-3.72 (m, 4H), 3.82 (s, 3H), 4.36 (s, 2H), 5.39 (s, 2H), 6.91 (d, J = 8.53 Hz, 2H), 7.48 (d, J = 8.53 Hz, 2H), 7.68 (s, 1H), 8.35 (s, 1H) |
| 36 | C22H25N5O3S | 440.2 | 1H NMR (400 MHz, CDCl3) δ 1.43 (s, 6H), 3.37-3.51 (m, 2H), 3.82 (s, 3H), 3.86-4.01 (m, 2H), 4.02-4.15 (m, 2H), 4.38-4.51 (m, 2H), 5.41 (s, 2H), 6.91 (d, J = 8.66 Hz, 2H), 7.51 (d, J = 8.53 Hz, 2H), 7.68 (s, 1H), 8.34 (s, 1H) |

TABLE 2-continued
| Example | Structure | LC-MS (MH+) | 1H-NMR |
|---|---|---|---|
| 37 | 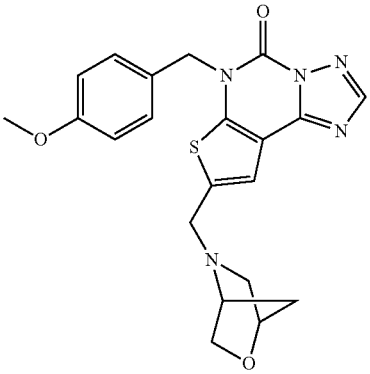 C₂₁H₂₁N₅O₃S | 424.2 | 1H NMR (400 MHz, CDCl3) δ 2.19-2.32 (m, 1H), 2.34-2.55 (m, 1H), 3.47-3.62 (m, 2H), 3.82 (s, 3H), 3.88-3.96 (m, 1H), 4.31-4.80 (m, 5H), 5.31-5.48 (m, 2H), 6.91 (d, J = 7.91 Hz, 2H), 7.50 (d, J = 8.03 Hz, 2H), 7.72 (s, 1H), 8.34 (s, 1H) |
| 38 | 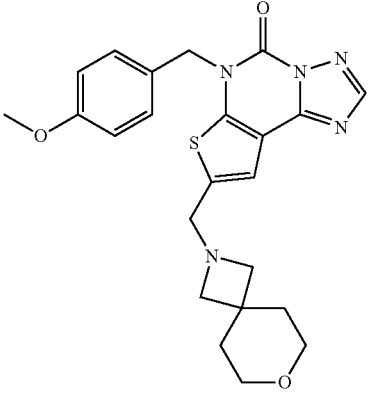 C₂₃H₂₅N₅O₃S | 452.1 | 1H NMR (400 MHz, CDCl3) δ 1.75-1.93 (m, 2H), 1.96-2.16 (m, 2H), 2.94-3.20 (m, 4H), 3.58-3.68 (m, 4H), 3.82 (s, 3H), 4.50 (br s, 2H), 5.38 (s, 2H), 6.91 (d, J = 8.41 Hz, 2H), 7.48 (d, J = 8.41 Hz, 2H), 7.75 (s, 1H), 8.36 (s, 1H) |
| 39 | 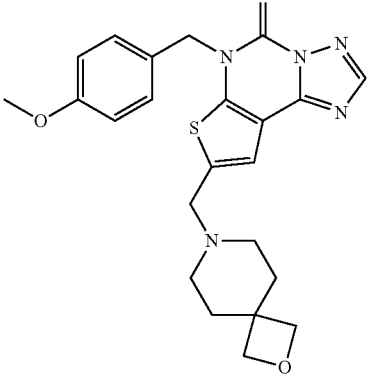 C₂₃H₂₅N₅O₃S | 452.1 | 1H NMR (400 MHz, CDCl3) δ 2.30-2.41 (m, 4H), 2.56-2.73 (m, 2H), 3.46-3.71 (m, 4H), 3.82 (s, 3H), 4.37-4.54 (m, 4H), 5.39 (s, 2H), 6.91 (d, J = 8.66 Hz, 2H), 7.49 (d, J = 8.66 Hz, 2H), 7.68 (s, 1H), 8.35 (s, 1H) |

TABLE 2-continued

| Example | Structure | LC-MS (MH+) | 1H-NMR |
|---|---|---|---|
| 40 | (structure shown) C$_{22}$H$_{22}$N$_6$O$_4$S | 467.2 | 1H NMR (400 MHz, DMSO-d6) δ 1.89-2.09 (m, 2H), 2.79-2.86 (m, 1H), 2.94-3.04 (m, 2H), 3.55-3.63 (m, 1H), 3.74 (s, 3H), 3.82 (d, J = 5.27 Hz, 3H), 3.88-3.95 (m, 1H), 4.32 (t, J = 8.47 Hz, 1H), 5.34 (s, 2H), 6.94 (d, J = 8.53 Hz, 2H), 7.39 (d, J = 8.66 Hz, 2H), 7.48 (s, 1H), 8.50 (s, 1H) |

Preparative Example 41

6-(4-Methoxybenzyl)-8-(1-methyl-3-(trifluoromethyl)-1H-pyrazol-5-yl)thieno[3,2-e][1,2,4]triazolo[1,5-c]pyrimidin-5(6H)-one

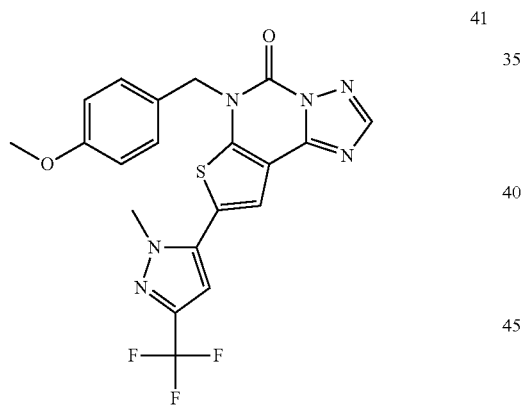

41

Step 3.1: 6-(4-methoxybenzyl)-8-vinylthieno[3,2-e][1,2,4]triazolo[1,5-c]pyrimidin-5(6H)-one (41)

To a mixture of 8-bromo-6-(4-methoxybenzyl)thieno[3,2-e][1,2,4]triazolo[1,5-c]pyrimidin-5(6H)-one (80 mg, 0.20 mmol) in toluene (2 ml) was added 1-methyl-5-(tributylstannyl)-3-(trifluoromethyl)-1H-pyrazole (135 mg, 0.31 mmol). The resulting mixture was heated to 100° C. for 16 hours and cooled to room temperature. It was filtered through a pad of celite with DCM washing. The resulting filtrate was concentrated under reduced pressure, diluted in methanol, filtered and purified directly via reverse-phase HPLC to afford the title compound.

Numerous compounds were made using the above general procedure, as exemplified in Table 3:

TABLE 3

| Example | Structure | LC-MS (MH+) | 1H-NMR |
|---|---|---|---|
| 41 | C₂₀H₁₅F₃N₆O₂S | 461.1 | 1H NMR (400 MHz, CDCl3) δ 3.83 (s, 3H), 4.07 (s, 3H), 5.43 (s, 2H), 6.70 (s, 1H), 6.93 (d, J = 8.66 Hz, 2H), 7.48 (d, J = 8.66 Hz, 2H), 7.68 (s, 1H), 8.37 (s, 1H) |
| 42 | C₂₀H₁₇N₅O₃S | 408.0 | 1H NMR (400 MHz, CDCl3) δ 2.28 (s, 3H), 2.43 (s, 3H), 3.72 (s, 3H), 5.32 (s, 2H), 6.82 (d, J = 8.66 Hz, 2H), 7.38 (d, J = 8.91 Hz, 3H), 8.25 (s, 1H) |

Preparative Example 43

6-(4-Methoxybenzyl)-9-methyl-8-(pyrrolidin-1-ylmethyl)thieno[3,2-e][1,2,4]triazolo[1,5-c]pyrimidin-5(6H)-one

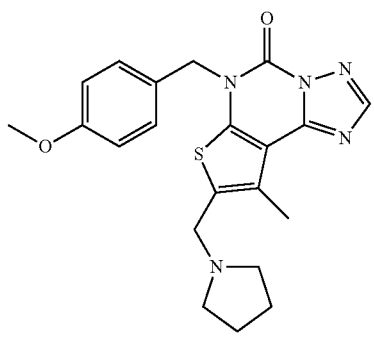

43

Step 4.1: 6-(4-methoxybenzyl)-9-methyl-5-oxo-5,6-dihydrothieno[3,2-e][1,2,4]triazolo[1,5-c]pyrimidine-8-carbaldehyde Phosphorus oxychloride (1.47 ml, 15.8 mmol) was added to N,N-dimethylformamide (13 ml) and the mixture was stirred for 20 minutes. 6-(4-Methoxybenzyl)-9-methylthieno[3,2-e][1,2,4]triazolo[1,5-c]pyrimidin-5(6H)-one (1.29 g, 3.94 mmol) was added as a solid and the mixture was heated at 90° C. for 45 minutes. The mixture was cooled to room temperature and poured into a mixture of ice (30 mL) and potassium carbonate (5 g). After the ice had melted the pH was 8-9. The mixture was extracted with dichloromethane (3×30 mL) and the combined extracts were washed with brine (30 mL), dried (MgSO₄) and concentrated under vacuum. The residue was purified by flash LC (20-100% ethyl acetate in hexanes) to afford the aldehyde (0.87 g, 62%) as a yellow powder. 1H NMR (400 MHz, CDCl3) δ 3.01 (s, 3H), 3.78 (s, 3H), 5.38 (s, 2H), 6.86-6.88 (m, 2H), 7.44-7.46 (m, 2H), 8.33 (s, 1H), 10.12 (s, 1H). LCMS (MH+, 355.0).

Step 4.2: 6-(4-Methoxybenzyl)-9-methyl-8-(pyrrolidin-1-ylmethyl)thieno[3,2-e][1,2,4]triazolo[1,5-c]pyrimidin-5(6H)-one (43)

6-(4-Methoxybenzyl)-9-methyl-5-oxo-5,6-dihydrothieno[3,2-e][1,2,4]triazolo[1,5-c]pyrimidine-8-carbaldehyde (48 mg, 0.14 mmol) was suspended in N,N-dimethylformamide (0.5 ml) and methanol (0.2 ml) and treated with pyrrolidine (0.075 ml, 0.90 mmol). The mixture was stirred for 30 minutes and sodium cyanoborohydride (20 mg, 0.32 mmol) and acetic acid (0.050 ml) were added and stirring was continued for 18 hours. The mixture was diluted with DMF and purified by HPLC (0-75% ACN in water) to afford 18 mg (25%) of 4 as a white solid.

Numerous compounds were made using the above general procedure, as exemplified in Table 4:

TABLE 4

| Example | Structure | LC-MS (MH+) | 1H-NMR |
|---|---|---|---|
| 43 | $C_{21}H_{23}N_5O_2S$ | 410.1 | 1H NMR (400 MHz, DMSO-d6) δ 1.84-1.86 (m, 2H), 2.03-2.05 (m, 2H), 2.67 (s, 3H), 3.10-3.12 (m, 2H), 3.41-3.43 (m, 2H), 3.73 (s, 3H), 4.64 (d, J = 4.7 Hz, 2H), 5.32 (s, 2H), 6.91-6.93 (m, 2H), 7.36-7.38 (m, 2H), 8.56 (s, 1H), 9.93 (br s, 1H) |
| 44 | $C_{21}H_{23}N_5O_3S$ | 426.1 | 1H NMR (400 MHz, CDCl3) δ 2.70 (s, 3H), 3.50-3.00 (m, 4H), 3.78 (s, 3H), 3.98-3.96 (m, 4H), 4.36 (s, 2H), 5.32 (s, 2H), 6.88-6.86 (m, 2H), 7.46-7.44 (m, 2H), 8.31 (s, 1H) |
| 45 | $C_{19}H_{21}N_5O_2S$ | 384.1 | 1H NMR (400 MHz, CDCl3) δ 2.71 (s, 3H), 2.85 (s, 6H), 3.78 (s, 3H), 4.42 (s, 2H), 5.33 (s, 2H), 6.86-6.87 (m, 2H), 7.43-7.45 (m, 2H), 8.32 (s, 1H) |
| 46 | $C_{21}H_{23}N_5O_2S$ | 410.1 | 1H NMR (400 MHz, CDCl3) δ 0.85-0.90 (m, 2H), 1.35-1.45 (m, 2H), 2.40-2.48 (m, 1H), 2.74 (s, 3H), 2.88 (s, 3H), 3.78 (s, 3H), 4.54 (s, 2H), 6.85-6.90 (m, 2H), 6.40-7.45 (m, 2H), 8.33 (s, 1H) |

TABLE 4-continued
| Example | Structure | LC-MS (MH+) | 1H-NMR |
|---|---|---|---|
| 47 | 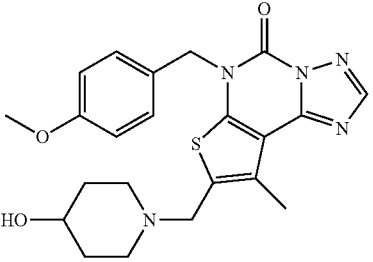 C₂₂H₂₅N₅O₃S | 440.2 | 1H NMR (400 MHz, DMSO-d6) δ 1.50-1.53 (m, 1H), 1.77-1.80 (m, 2H), 1.95-1.98 (m, 1H), 2.65-2.67 (m, 3H), 3.03-3.05 (m, 1H), 3.20-3.59 (m, 5H), 3.73 (s, 3H), 4.54-4.61 (m, 2H), 5.33 (s, 2H), 6.92-6.93 (m, 2H), 7.36-7.38 (m, 2H), 8.56 (s, 1H), 9.48 (br s, |
| 48 | 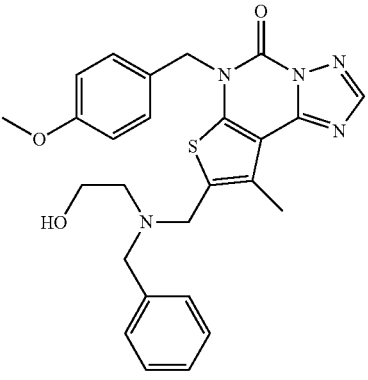 C₂₆H₂₇N₅O₃S | 490.2 | 1H NMR (400 MHz, DMSO-d6) δ 2.57 (s, 3H), 3.63-3.65 (m, 4H), 3.72 (s, 3H), 4.20-4.60 (m, 4H), 5.32 (s, 2H), 6.90-6.93 (m, 2H), 7.36-7.40 (m, 7H), 8.53 (s, 1H) |
| 49 | 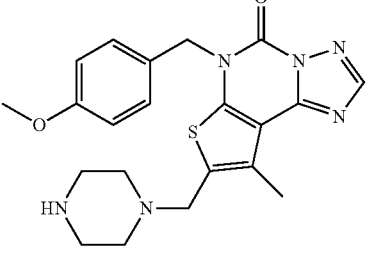 C₂₁H₂₄N₆O₂S | 425.1 | 1H NMR (400 MHz, DMSO-d6) δ 2.55 (s, 3H), 2.67 (br s, 4H), 3.09 (br s, 4H), 3.73 (s, 3H), 3.80 (br s, 2H), 5.30 (s, 2H), 6.90-6.93 (m, 2H), 7.34-7.36 (m, 2H), 8.51 (s, 1H), 8.61 (br s, 2H) |
| 50 | 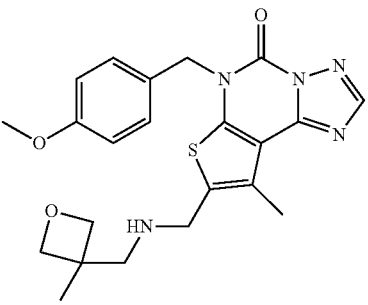 C₂₂H₂₅N₅O₃S | 440.1 | 1H NMR (400 MHz, DMSO-d6) δ 1.31 (s, 3H), 2.67 (s, 3H), 3.73 (s, 3H), 4.22 (d, J = 5.1 Hz, 2H), 4.38 (d, J = 5.0 Hz, 2H), 4.60 (br s, 2H), 5.34 (s, 2H), 6.90-6.93 (m, 2H), 7.34-7.36 (m, 2H), 8.56 (s, 1H), 8.83 (br s, 2H) |

TABLE 4-continued
| Example | Structure | LC-MS (MH+) | 1H-NMR |
|---|---|---|---|
| 51 | 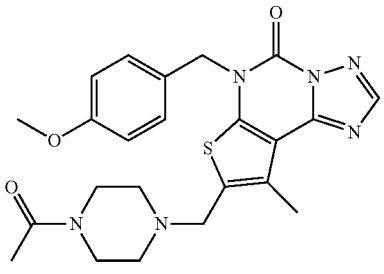 C₂₃H₂₆N₆O₃S | 467.2 | 1H NMR (400 MHz, DMSO-d6) δ 2.03 (s, 3H), 2.63 (s, 3H), 2.85-3.15 (m, 4H), 3.56 (br s, 4H), 3.73 (s, 3H), 4.45-4.65 (m, 2H), 5.32 (s, 2H), 6.91-6.93 (m, 2H), 7.36-7.38 (m, 2H), 8.55 (s, 1H) |
| 52 | 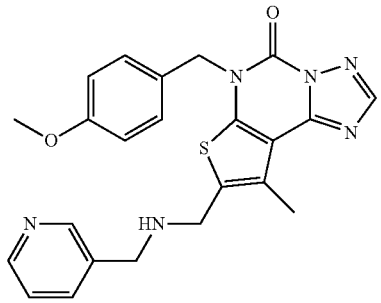 C₂₃H₂₂N₆O₂S | 447.1 | 1H NMR (400 MHz, DMSO-d6) δ 2.63 (s, 3H), 3.72 (s, 3H), 4.30 (s, 2H), 4.47 (s, 2H), 5.32 (s, 2H), 6.90-6.93 (m, 2H), 7.34-7.36 (m, 2H), 7.52 (dd, J = 6.3, 3.9 Hz, 1H), 7.94-7.96 (m, 1H), 8.55 (s, 1H), 8.63 (dd, J = 3.9, 1.2 Hz, 1H), 8.68 (d, J = 1.5 Hz, 1H), 9.34 (br s, 2H) |
| 53 | 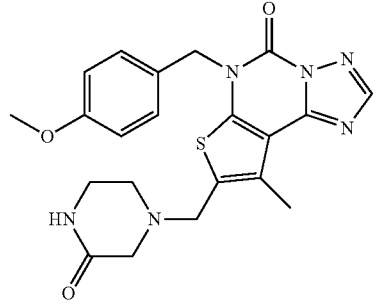 C₂₁H₂₂N₆O₃S | 439.1 | 1H NMR (400 MHz, DMSO-d6) δ 2.59 (s, 3H), 2.95 (br s, 2H), 3.72 (s, 3H), 3.24 (br s, 4H), 3.33 (br s, 2H), 5.32 (s, 2H), 6.90-6.92 (m, 2H), 7.35-7.37 (m, 2H), 8.07 (br s, 1H), 8.53 (s, 1H) |
| 54 | 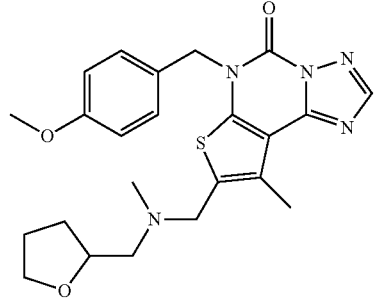 C₂₃H₂₇N₅O₃S | 454.1 | 1H NMR (400 MHz, DMSO-d6) δ 1.45-1.52 (m, 1H), 1.78-1.87 (m, 2H), 1.98-2.04 (m, 1H), 2.65 (s, 3H), 2.79 (s, 3H), 2.96-3.00 (m, 1H), 3.12-3.16 (m, 1H), 3.28-3.32 (m, 1H), 3.66-3.72 (m, 2H), 3.73 (s, 3H), 3.78-3.82 (m, 1H), 4.22-4.25 (m, 1H), 4.50-4.66 (m, 2H), 5.30-5.38 (m, 2H), 6.90-6.93 (m, 2H), 7.36-7.37 (m, 2H), 8.56 (s, 1H), 9.70-9.90 (m, 1H) |

TABLE 4-continued
| Example | Structure | LC-MS (MH+) | 1H-NMR |
|---|---|---|---|
| 55 | 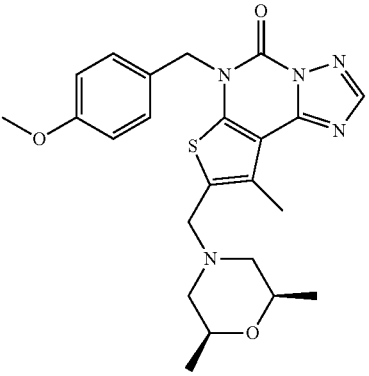 C₂₃H₂₇N₅O₃S | 454.1 | 1H NMR (400 MHz, DMSO-d6) δ 1.10 (d, J = 4.4 Hz, 6H), 2.63 (s, 3H), 2.64-2.68 (m, 2H), 3.30-3.52 (m, 4H), 3.72 (s, 3H), 4.55 (br s, 2H), 5.30 (s, 2H), 6.91-6.93 (m, 2H), 7.36-7.38 (m, 2H), 8.55 (s, 1H), 10.18 (br s, 1H) |
| 56 | 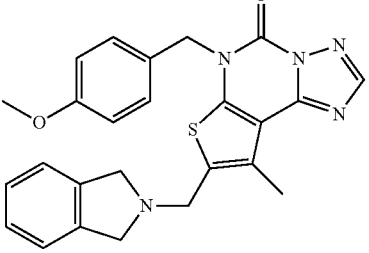 C₂₅H₂₃N₅O₂S | 458.1 | 1H NMR (400 MHz, DMSO-d6) δ 2.69 (s, 3H), 3.73 (s, 3H), 4.60 (br s, 4H), 4.87 (br s, 2H), 5.34 (s, 2H), 6.92-6.93 (m, 2H), 7.37-7.39 (m, 6H), 8.57 (s, 1H), 11.05 (br s, 1H) |
| 57 | 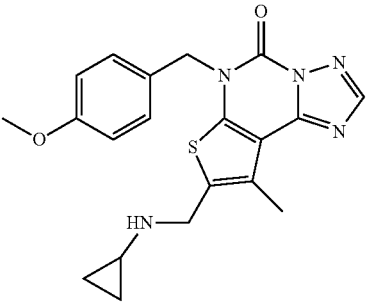 C₂₀H₂₁N₅O₂S | 396.1 | 1H NMR (400 MHz, DMSO-d6) δ 0.75-0.80 (m, 4H), 2.65 (s, 3H), 2.71-2.73 (m, 1H), 3.73 (s, 3H), 4.49 (s, 2H), 5.32 (s, 2H), 6.90-6.93 (m, 2H), 7.34-7.36 (m, 2H), 8.54 (s, 1H), 9.05 (br s, 1H) |
| 58 | 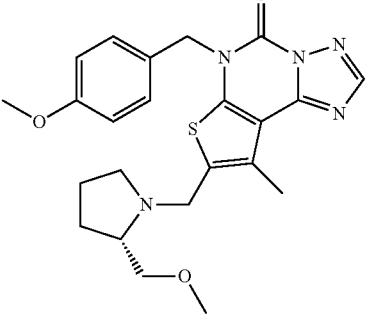 C₂₃H₂₇N₅O₃S | 454.2 | 1H NMR (400 MHz, DMSO-d6) δ 1.68-1.70 (m, 1H), 1.80-1.83 (m, 1H), 2.00-2.02 (m, 1H), 2.14-2.16 (m, 1H), 2.66 (s, 3H), 3.26 (s, 3H), 3.46-3.48 (m, 3H), 3.72 (s, 3H), 3.75 (br s, 1H), 4.55 (d, J = 11.1 Hz, 1H), 4.77 (d, J = 11.3 Hz, 1H), 5.30 (d, J = 12.9 Hz, |

TABLE 4-continued
| Example | Structure | LC-MS (MH+) | 1H-NMR |
|---|---|---|---|
| 59 | 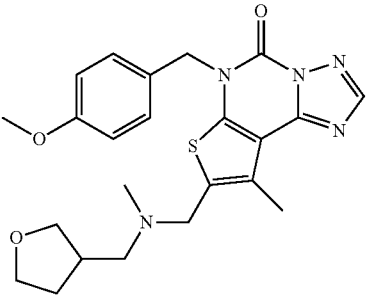 C23H27N5O3S | 454.3 | 1H NMR (400 MHz, DMSO-d6) δ 1.51-1.54 (m, 1H), 2.02-2.05 (m, 1H), 2.66 (s, 3H), 2.75 (s, 3H), 3.14-3.16 (m, 1H), 3.32-3.37 (m, 1H), 3.60-3.71 (m, 3H), 3.73 (s, 3H), 3.74-3.86 (m, 2H), 4.56-4.64 (m, 2H), 5.32-5.34 (m, 2H), 5.90-5.92 (m, 2H), 7.36-7.37 (m, 2H), 8.56 (s, 1H), 9.56 (br s, 1H) |
| 60 | 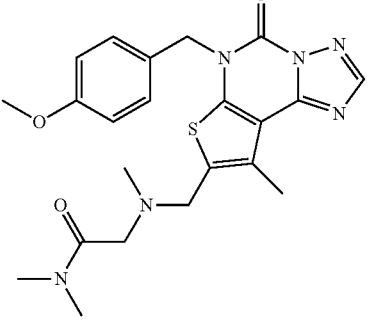 C22H26N6O3S | 339.1 (M + —C5H8N2O) | 1H NMR (400 MHz, DMSO-d6) δ 2.66 (s, 3H), 2.78 (s, 3H), 2.880 (s, 3H), 2.885 (s, 3H), 3.73 (s, 3H), 4.19 (br s, 2H), 4.52 (br s, 2H), 5.34 (s, 2H), 6.92-6.94 (m, 2H), 7.37-7.38 (m, 2H), 8.56 (s, 1H), 9.70 (br s, 1H) |
| 61 | 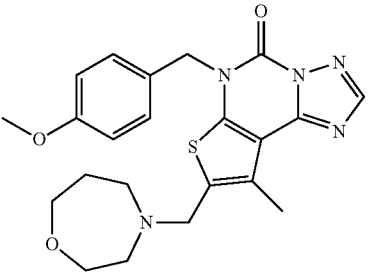 C22H25N5O3S | 440.2 | 1H NMR (400 MHz, DMSO-d6) δ 3.13 (s, 3H), 3.24-3.72 (m, 6H), 3.73 (s, 3H), 3.85-3.87 (m, 2H), 4.66 (br s, 2H), 5.33 (s, 2H), 6.91-6.94 (m, 2H), 7.36-7.38 (m, 2H), 8.56 (s, 1H), 9.83 (br s, 1H) |
| 62 | 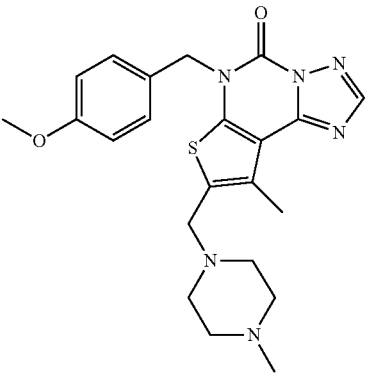 C22H26N6O2S | 440.2 | 1H NMR (400 MHz, DMSO-d6) δ 2.58 (s, 4H), 2.81 (s, 4H), 3.03 (br s, 5H), 3.39 (br s, 3H), 3.75 (s, 7H), 3.80 (s, 5H), 5.31 (s, 2H), 6.93 (d, J = 8.66 Hz, 2H), 7.36 (d, J = 8.53 Hz, 2H), 8.50 (s, 1H) |

TABLE 4-continued
| Example | Structure | LC-MS (MH+) | 1H-NMR |
|---|---|---|---|
| 63 | 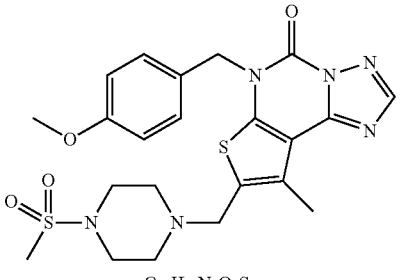 $C_{22}H_{26}N_6O_4S_2$ | 503.2 | 1H NMR (400 MHz, CDCl3 and methanol-d4) δ 2.45 (s, 3H), 2.69 (s, 3H), 2.76 (br s, 4H), 3.23 (br s, 4H), 3.60 (s, 3H), 3.88 (s, 2H), 5.17 (s, 2H), 6.59-6.79 (m, 2H), 7.25 (d, J = 8.78 Hz, 2H), 8.13 (s, 1H) |
| 64 | 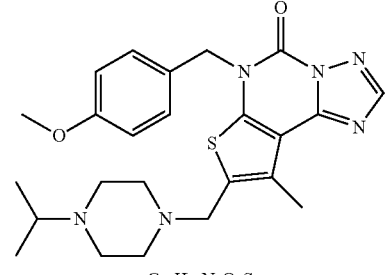 $C_{24}H_{30}N_6O_2S$ | 467.3 | 1H NMR (400 MHz, CDCl3) δ 1.41 (d, J = 5.77 Hz, 6H), 2.50-2.73 (m, 3H), 3.37 (br s, 6H), 3.53 (d, J = 5.27 Hz, 3H), 3.79 (br s, 3H), 4.07 (br s, 2H), 5.31 (br s, 2H), 6.87 (d, J = 7.15 Hz, 2H), 7.41 (d, J = 7.53 Hz, 2H), 8.31 (br s, 1H) |
| 65 | 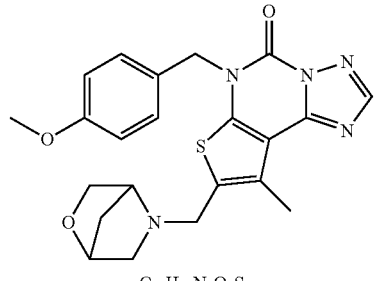 $C_{22}H_{23}N_5O_3S$ | 438.2 | 1H NMR (400 MHz, CDCl3) δ 2.24 (d, J = 11.54 Hz, 1H), 2.40 (br s, 1H), 2.73 (s, 3H), 3.79 (s, 3H), 3.80 (s, 1H), 3.89 (d, J = 10.04 Hz, 1H), 4.39 (br s, 2H), 4.46-4.54 (m, 1H), 4.56-4.64 (m, 1H), 4.73 (br s, 1H), 5.34 (s, 2H), 6.85-6.90 (m, 2H), 7.46 (d, J = 8.66 Hz, 2H), 8.32 (s, 1H) |
| 66 | 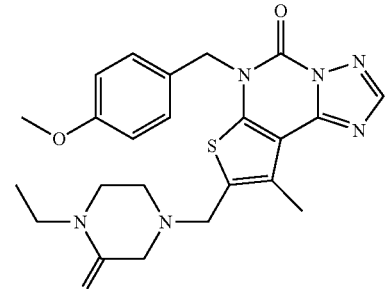 $C_{23}H_{26}N_6O_3S$ | 467.2 | 1H NMR (400 MHz, CDCl3) δ 1.10 (t, J = 7.22 Hz, 3H), 2.59 (s, 3H), 3.12 (br s, 2H), 3.34-3.47 (m, 3H), 3.52 (s, 3H), 3.70 (s, 3H), 4.11 (s, 2H), 5.26 (s, 2H), 6.79 (d, J = 8.66 Hz, 2H), 7.36 (d, J = 8.66 Hz, 2H), 8.25 (s, 1H) |

TABLE 4-continued

| Example | Structure | LC-MS (MH+) | 1H-NMR |
|---|---|---|---|
| 67 | 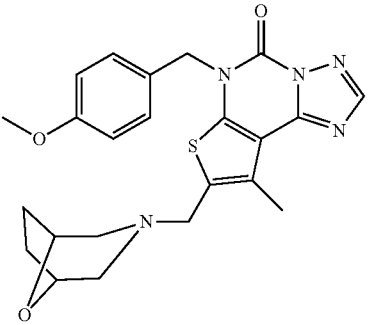<br>C₂₃H₂₅N₅O₃S | 452.2 | 1H NMR (400 MHz, CDCl3) δ 2.08-2.21 (m, 2H), 2.32-2.41 (m, 2H), 2.70 (s, 3H), 3.06 (dd, J = 11.98, 2.57 Hz, 2H), 3.46 (d, J = 11.92 Hz, 2H), 3.79 (s, 3H), 4.43 (s, 2H), 4.52 (br s, 2H), 5.36 (s, 2H), 6.86-6.91 (m, 2H), 7.46 (d, J = 8.66 Hz, 2H), 8.33 (s, 1H) |
| 68 | 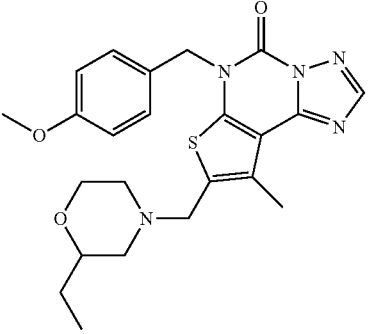 [SMILES: COc1ccc(Cn2c(=O)n3ncnc3c3c(C)c(CN4CCOC(C)C4)sc32)cc1 ; "C22H25N5O3S"]<br>C₂₃H₂₇N₅O₃S | 454.2 | 1H NMR (400 MHz, CDCl3) δ 0.98 (t, J = 7.47 Hz, 3H), 1.46-1.60 (m, 2H), 2.53 (t, J = 10.85 Hz, 1H), 2.71 (s, 3H), 2.86 (d, J = 9.29 Hz, 1H), 3.48 (dd, J = 18.89, 11.86 Hz, 2H), 3.79 (s, 3H), 3.87 (dt, J = 10.29, 5.40 Hz, 1H), 4.03-4.12 (m, 2H), 4.41 (s, 2H), 5.35 (s, 2H), 6.88 (d, J = 8.66 Hz, 2H), 7.45 (d, J = 8.66 Hz, 2H), 8.32 (s, 1H) |
| 69 | 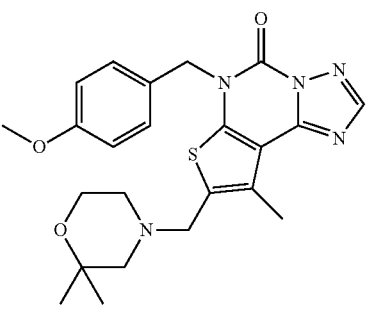<br>C₂₃H₂₇N₅O₃S | 454.2 | 1H NMR (400 MHz, CDCl3) δ 1.40 (br s, 5H), 2.71 (s, 3H), 2.79-3.36 (m, 4H), 3.79 (3, 3H), 3.93-4.13 (m, 2H), 4.44 (br s, 2H), 5.35 (s, 2H), 6.80-6.94 (m, 2H), 7.46 (d, J = 8.66 Hz, 2H), 8.32 (s, 1H) |
| 70 | 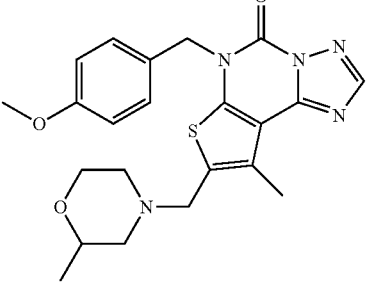<br>C₂₂H₂₅N₅O₃S | 440.2 | 1H NMR (400 MHz, CDCl3) δ 1.24 (d, J = 6.27 Hz, 3H), 2.51 (t, J = 11.11 Hz, 1H), 2.71 (s, 3H), 2.78-2.93 (m, 1H), 3.48 (dd, J = 18.01, 11.73 Hz, 2H), 3.79 (s, 3H), 3.95-4.19 (m, 3H), 4.40 (s, 2H), 5.34 (s, 2H), 6.82-6.97 (m, 2H), 7.45 (d, J = 8.66 Hz, 2H), 8.32 (s, 1H) |

TABLE 4-continued

| Example | Structure | LC-MS (MH+) | 1H-NMR |
|---|---|---|---|
| 71 | 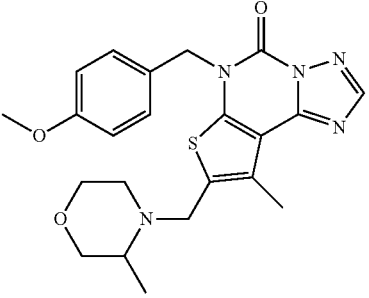<br>C22H25N5O3S | 440.2 | 1H NMR (400 MHz, CDCl3) δ 1.57 (d, J = 6.65 Hz, 3H), 2.72 (s, 3H), 2.88 (br s, 1H), 3.28 (br s, 2H), 3.44-3.61 (m, 1H), 3.79 (s, 3H), 3.82-3.92 (m, 1H), 3.92-4.02 (m, 2H), 4.04-4.14 (m, 1H), 4.23 (d, J = 12.17 Hz, 1H), 5.21-5.33 (m, 1H), 5.35-5.54 (m, 1H), 6.83-6.97 (m, 2H), 7.45 (d, J = 8.66 Hz, 2H), 8.33 (s, 1H) |
| 72 | 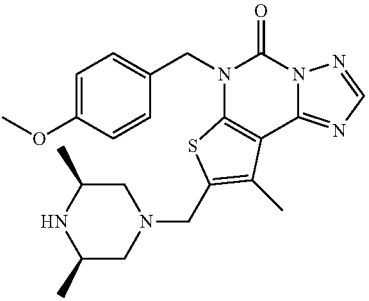<br>C23H28N6O2S | 453.2 | 1H NMR (400 MHz, CDCl3) δ 1.02 (br s, 6H), 2.00 (t, J = 11.61 Hz, 2H), 2.25 (br s, 3H), 2.61 (d, J = 11.92 Hz, 2H), 2.96 (br s, 2H), 3.40 (br s, 2H), 3.45 (br s, 3H), 5.01 (br s, 2H), 6.46-6.60 (m, 2H), 7.08 (d, J = 8.03 Hz, 2H), 7.94 (br s, 1H), 8.58 (br s, 1H), 9.83 (br s, 1H) |
| 73 | 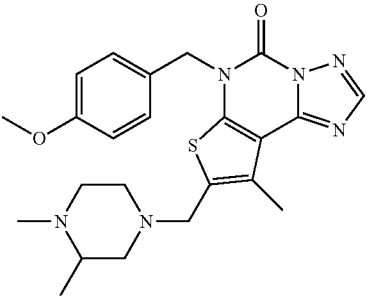<br>C23H28N6O2S | 453.3 | 1H NMR (400 MHz, CDCl3) δ 1.51 (d, J = 5.40 Hz, 3H), 2.66 (s, 3H), 2.90 (br s, 3H), 3.17-3.70 (m, 7H), 3.79 (s, 3H), 4.17 (br s, 2H), 5.23-5.31 (m, 1H), 5.32-5.42 (m, 1H), 6.87 (d, J = 8.66 Hz, 2H), 7.41 (d, J = 8.53 Hz, 2H), 8.32 (s, 1H) |
| 74 | 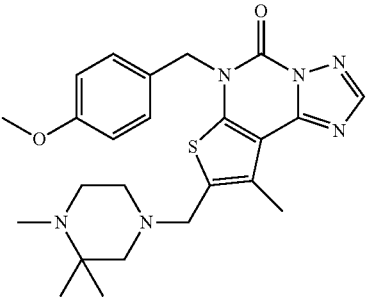<br>C24H30N6O2S | 467.3 | 1H NMR (400 MHz, CDCl3) δ 1.36 (br s, 3H), 1.44 (br s, 3H), 2.60 (s, 3H), 2.74 (s, 3H), 2.76-2.83 (m, 2H), 2.97-3.08 (m, 2H), 3.15 (br s, 1H), 3.46 (d, J = 11.54 Hz, 1H), 3.79 (s, 3H), 3.80 (br s, 2H), 5.17-5.27 (m, 1H), 5.41-5.57 (m, 1H), 6.86 (d, J = 8.66 Hz, 2H), 7.42 (d, J = 8.66 Hz, 2H), 8.32 (s, 1H) |

TABLE 4-continued

| Example | Structure | LC-MS (MH+) | 1H-NMR |
|---|---|---|---|
| 75 | 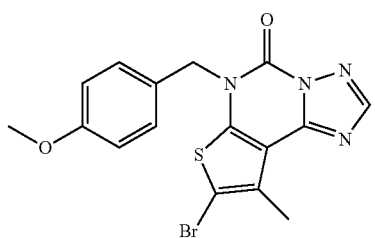<br>C24H28N6O2S | 465.3 | 1H NMR (400 MHz, CDCl3) δ 2.00-2.30 (m, 4H), 2.66 (s, 3H), 3.31-3.68 (m, 9H), 3.79 (s, 3H), 4.03-4.37 (m, 2H), 5.30 (d, J = 15.18 Hz, 1H), 5.36 (d, J = 15.43 Hz, 1H), 6.84-6.93 (m, 2H), 7.42 (d, J = 8.66 Hz, 2H), 8.32 (s, 1H) |

Preparative Example 76

8-Bromo-6-(4-methoxybenzyl)-9-methylthieno[3,2-e][1,2,4]triazolo[1,5-c]pyrimidin-5(6H)-one

Preparative Example 77

8-(Hydroxymethyl)-6-(4-methoxybenzyl)-9-methylthieno[3,2-e][1,2,4]triazolo[1,5-c]pyrimidin-5(6H)-one

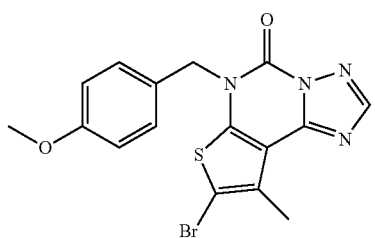

76

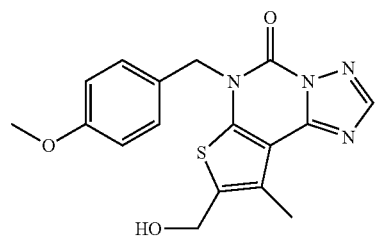

77

Step 5.1: 8-bromo-6-(4-methoxybenzyl)-9-methylthieno[3,2-e][1,2,4]triazolo[1,5-c]pyrimidin-5(6H)-one N-Bromopyrrolidine-2,5-dione (0.57 g, 3.2 mmol) was added to a stirred suspension of 6-(4-methoxybenzyl)-9-methylthieno[3,2-e][1,2,4]triazolo[1,5-c]pyrimidin-5(6H)-one (1.01 g, 3.09 mmol) in acetonitrile (20 ml) and the mixture was stirred for 14 hours. It was concentrated under vacuum, taken up in dichloromethane, and purified by flash chromatography (elution with 10-100% ethyl acetate in hexanes) to afford 1.31 g (100%) of 76 as a white solid.

Numerous compounds were made using the above general procedure, as exemplified in Table 5:

Step 6.1: 8-(hydroxymethyl)-6-(4-methoxybenzyl)-9-methylthieno[3,2-e][1,2,4]triazolo[1,5-c]pyrimidin-5(6H)-one Sodium borohydride (25 mg, 0.66 mmol) was added to a stirred suspension of 6-(4-methoxybenzyl)-9-methyl-5-oxo-5,6-dihydrothieno[3,2-e][1,2,4]triazolo[1,5-c]pyrimidine-8-carbaldehyde (65 mg, 0.18 mmol) in methanol (3 ml) and the mixture was stirred for 2 hours. Saturated sodium bicarbonate (0.2 mL) was added and the mixture was stirred for 20 minutes, concentrated under vacuum, taken up in dichlo-

TABLE 5

| Example | Structure | LC-MS (MH+) | 1H-NMR |
|---|---|---|---|
| 76 | <br>C16H13BrN4O2S | 404.9 | 1H NMR (400 MHz, CDCl3) δ 2.60 (s, 3H), 3.79 (s, 3H), 5.31 (s, 2H), 6.87-6.89 (m, 2H), 7.40-7.41 (m, 2H), 8.31 (s, 1H) | romethane, filtered and purified by preparative HPLC to afford 44 mg (68%) of 77 as a white solid.

Numerous compounds were made using the above general procedure, as exemplified in Table 6:

TABLE 6

| Example | Structure | LC-MS (MH+) | 1H-NMR |
|---|---|---|---|
| 77 | $C_{17}H_{16}N_4O_3S$ | 357.0 | 1H NMR (400 MHz, CDCl3) δ 2.62 (s, 3H), 3.78 (s, 3H), 4.84 (s, 2H), 5.33 (s, 2H), 6.85-6.87 (m, 2H), 7.42-7.44 (m, 2H), 8.30 (s, 1H) |

Preparative Example 78

9-(((2S,6R)-2,6-Dimethylmorpholino)methyl)-6-(4-methoxybenzyl)thieno[3,2-e][1,2,4]triazolo[1,5-c]pyrimidin-5(6H)-one

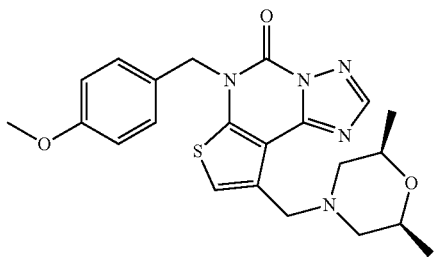

78

Step 7.1: methyl 3-cyano-4-methylthiophen-2-ylcarbamate

Methyl chloroformate (55 g, 0.58 mol) was added to a stirred solution of 2-amino-4-oxo-4,5-dihydrothiophene-3-carbonitrile (68 g, 0.49 mol) and triethylamine (147 g, 1.45 mol) in dichloromethane (1000 ml) at 0° C. After the addition, the mixture was warmed to 25° C. and stirred overnight. The reaction was treated with dichloromethane-methanol (20:1, 2000 mL) and 2N hydrochloric acid (1500 mL). The resulting mixture was filtered and the resulting solid was further extracted with dichloromethane-methanol (20:1, 1500 mL×3). The combined organic extracts were dried over sodium sulfate and concentrated to give a brown solid. The solid was washed with tert-butyl methyl ether (1500 mL) and dried under vacuum to give crude methyl 3-cyano-4-methylthiophen-2-ylcarbamate (160 g) as a brown solid, which was used in next step without purification.

Step 7.2: 4-cyano-5-((methoxycarbonyl)amino)thiophen-3-yl trifluoromethanesulfonate Triethylamine (329 mL, 2.36 mmol) was added to a suspension of methyl 3-cyano-4-methylthiophen-2-ylcarbamate (156 g, 0.788 mol) in dichloromethane (1500 mL). Trifluoroacetic anhydride (267 g, 0.945 mol) was added drop-wise at 0° C. After addition, the mixture was warmed to room temperature and stirred overnight. The mixture was concentrated under vacuum and the residue was purified by flash LC (elution with 5-50% ethyl acetate in petroleum ether) to give 100 g (38%) of the sulfonate as a yellow solid. 1H NMR (400 MHz, CDCl3) δ 3.86 (s, 3H), 6.7 (s, 1H).

Step 7.3: 5-oxo-5,6-dihydrothieno[3,2-e][1,2,4]triazolo[1,5-c]pyrimidin-9-yl trifluoromethanesulfonate A solution of 4-cyano-5-((methoxycarbonyl)amino)thiophen-3-yl trifluoromethanesulfonate (2.0 g, 6.1 mmol), formic acid hydrazide (0.73 g, 12 mmol), tri-n-propylamine (1 mL) and 2-methoxyethanol (15 mL) was heated at 160° C. for 10 minutes via microwave. The mixture was combined, concentrated, and the residue was purified by HPLC to give the triazole (0.31 g, 15%) as a pale solid. 1H NMR (400 MHz, DMSO-d6) δ 7.32 (s, 1H), 8.31 (s 1H). LCMS (MH+, 340.9).

Step 7.4: 6-(4-methoxybenzyl)-5-oxo-5,6-dihydrothieno[3,2-e][1,2,4]triazolo[1,5-c]pyrimidin-9-yl trifluoromethanesulfonate To a solution of 5-oxo-5,6-dihydrothieno[3,2-e][1,2,4]triazolo[1,5-c]pyrimidin-9-yl trifluoromethanesulfonate (3.00 g, 8.82 mmol) in DMF (60.0 mL) was added 1-(chloromethyl)-4-methoxybenzene (2.39 ml, 17.6 mmol), potassium iodide (0.73 g, 4.41 mmol) and potassium carbonate (3.66 g, 26.5 mmol). The resulting mixture was heated to 60° C. After 16 hours the crude mixture was allowed to cool to room temperature at which time water was added (100 mL) and the organics were extracted with ethyl acetate (75 mL×3). The organic layers were combined, dried, filtered and concentrated. Crude residue was purified over silica gel (120 g) eluting with 10-80% ethyl acetate in hexanes over 20 minutes. Product fractions were combined and concentrated under reduced pressure to yield the sulfonate (3.25 g, 80%) as a yellow solid. 1H NMR (400 MHz, CDCl$_3$) δ 3.83 (s, 3H), 5.40 (s, 2H), 6.93 (d, J=8.66 Hz, 2H), 7.05 (s, 1H), 7.46 (d, J=8.78 Hz, 2H), 8.41 (s, 1H). LCMS (MH+, 461.0).

Step 7.5: 6-(4-methoxybenzyl)-9-vinylthieno[3,2-e][1,2,4]triazolo[1,5-c]pyrimidin-5(6H)-one To mixture of 6-(4-methoxybenzyl)-5-oxo-5,6-dihydrothieno[3,2-e][1,2,4]triazolo[1,5-c]pyrimidin-9-yl trifluoromethanesulfonate (1.68 g, 3.65 mmol), potassium trifluoro(vinyl)borate (0.73 g, 5.47 mmol), and [1,1'-bis(diphenylphosphino)ferrocene]dichloropalladium(II), complex with dichloromethane (149 mg, 0.18 mmol) in butan-1-ol (15 ml) was added triethylamine (0.51 ml, 3.65 mmol). The resulting mixture was heated to 100 OC. After 16 hours, the mixture was cooled to room temperature at which time the solvent was removed under reduced pressure. Crude residue was purified over silica gel (120 g) eluting with 0-30% IPA in ethyl acetate over 25 minutes. Product fractions were combined then concentrated under reduced pressure to yield the vinyl thiophene (0.85 g, 69%) as a tan solid. 1H NMR (400 MHz, DMSO-d6) δ 3.74 (s, 3H), 5.35 (s, 2H), 5.45 (d, J=11.29 Hz, 1H), 6.05 (d, J=17.69 Hz, 1H), 6.93 (d, J=8.53 Hz, 2H), 7.39 (d, J=8.66 Hz, 2H), 7.41-7.50 (m, 1H), 7.64 (s, 1H), 8.53 (s, 1H). LCMS (MH+, 339.2).

Step 7.6: 6-(4-methoxybenzyl)-5-oxo-5,6-dihydrothieno[3,2-e][1,2,4]triazolo[1,5-c]pyrimidine-9-carbaldehyde 6-(4-Methoxybenzyl)-9-vinylthieno[3,2-e][1,2,4]triazolo[1,5-c]pyrimidin-5(6H)-one (850 mg, 2.51 mmol) was suspended in tetrahydrofuran (17 ml) and heated with a heat gun to effect dissolution. Similarly sodium periodate (1.24 g, 5.78 mmol) was heated in water (8.5 ml) to effect dissolution. The above solutions were combined with vigorous stirring. While the stirred mixture was at 40 OC, osmium (VIII) oxide (737 µl, 2.50% w/w, 0.08 mmol) was added and the mixture was stirred vigorously for 4 hours. It was diluted with water (300 mL) and the resulting solids were collected via vacuum filtration to yield the aldehyde (0.58 g, 68%) as pale yellow solid. 1H NMR (400 MHz, DMSO-d6) δ 3.74 (s, 3H), 5.42 (s, 2H), 6.94 (d, J=8.66 Hz, 2H), 7.42 (d, J=8.53 Hz, 2H), 8.29 (s, 1H), 8.61 (s, 1H), 10.58 (s, 1H). LCMS (MH+, 341.1).

Step 7.7: 9-(((2S,6R)-2,6-dimethylmorpholino)methyl)-6-(4-methoxybenzyl)thieno[3,2-e][1,2,4]triazolo[1,5-c]pyrimidin-5(6H)-one (78)

To a mixture of 6-(4-methoxybenzyl)-5-oxo-5,6-dihydrothieno[3,2-e][1,2,4]triazolo[1,5-c]pyrimidine-9-carbaldehyde (35 mg, 0.10 mmol) and (2S,6R)-2,6-dimethylmorpholine (24 mg, 0.21 mmol) in DMF was added sodium cyanoborohydride (9.7 mg, 0.15 mmol). The resulting mixture was stirred at room temperature. After 16 hours, the crude mixture was filtered and purified directly via reverse-phase HPLC. Product fractions were concentrated under reduced pressure to yield 78 (56 mg, 47%) as a white solid.

Numerous compounds were made using the above general procedure, as exemplified in Table 7:

TABLE 7

| Example | Structure | LC-MS (MH+) | 1H-NMR |
|---|---|---|---|
| 78 | 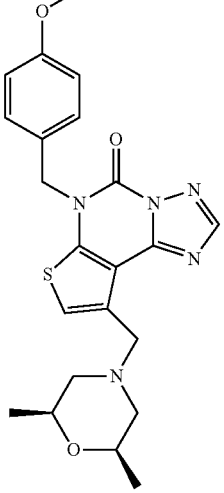 $C_{22}H_{25}N_5O_3S$ | 440.2 | 1H NMR (400 MHz, CDCl3) δ 1.21 (d, J = 6.27 Hz, 6H), 2.69-2.78 (m, 2H), 3.36-3.41 (m, 2H), 3.83 (s, 3H), 4.04-4.15 (m, 2H), 4.82 (s, 2H), 5.41 (s, 2H), 6.92 (d, J = 8.66 Hz, 2H), 7.49 (d, J = 8.66 Hz, 2H), 7.83-7.92 (m, 1H), 8.33 (s, 1H) |

Preparative Example 79

6-(4-Chlorobenzyl)-8,9-dimethylfuro[3,2-e][1,2,4]triazolo[1,5-c]pyrimidin-5(6H)-one

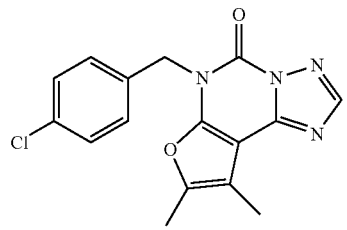

79

Step 8.1: methyl (3-cyano-4,5-dimethylfuran-2-yl)carbamate

Prepared as described in Step 1.1. 1H NMR (400 MHz, DMSO-d6) δ 1.94 (s, 3H), 2.15 (s, 3H), 3.70 (s, 3H), 10.78 (s, 1H). LCMS (MH+, 195.1).

Step 8.2: 8,9-dimethylfuro[3,2-e][1,2,4]triazolo[1,5-c]pyrimidin-5(6H)-one

Prepared as described in Step 1.2. 1H NMR (400 MHz, DMSO-d6) δ 2.21 (s, 3H), 2.29 (s, 3H), 8.31 (s, 1H). LCMS (MH+, 205.1).

Step 8.3: 6-(4-chlorobenzyl)-8,9-dimethylfuro[3,2-e][1,2,4]triazolo[1,5-c]pyrimidin-5(6H)-one (79)

Prepared as described in Step 1.3.

Numerous compounds were made using the above general procedure, as exemplified in Table 8:

TABLE 8

| Example | Structure | LC-MS (MH+) | 1H-NMR |
|---|---|---|---|
| 79 | 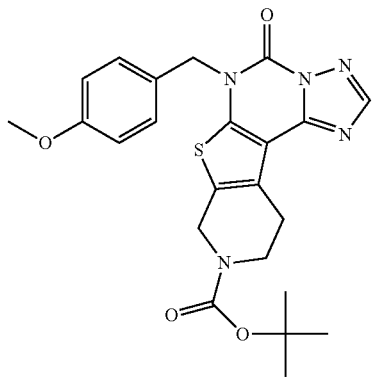 $C_{16}H_{13}ClN_4O_2$ | 329.0 | 1H NMR (400 MHz, DMSO-d6) δ 2.24 (s, 3H), 2.32 (s, 3H), 5.32 (s, 2H), 7.40-7.44 (m, 4H), 8.40 (s, 1H) |

Preparative Example 80 tert-Butyl 6-(4-methoxybenzyl)-5-oxo-5,6,10,11-tetrahydropyrido[4',3':4,5]thieno[3,2-e][1,2,4]triazolo[1,5-c]pyrimidine-9(8H)-carboxylate

Step 9.1: tert-butyl 2-amino-3-cyano-4,5-dihydrothieno[2,3-c]pyridine-6(7H)-carboxylate Prepared from tert-butyl 4-oxo-1-piperidinecarboxylate as previously described (Wang et al., Synlett 2010, 9, 1351-1354).

Step 9.2: tert-butyl 3-cyano-2-((methoxycarbonyl)amino)-4,5-dihydrothieno[2,3-c]pyridine-6(7H)-carboxylate Prepared as described for in Step 1.1. 1H NMR (400 MHz, DMSO-d6) δ 1.27 (t, J=7.09 Hz, 3H), 1.43 (s, 9H), 2.53-2.61 (m, 2H), 3.61 (t, J=5.65 Hz, 2H), 4.21 (q, J=7.15 Hz, 2H), 4.44 (s, 2H), 11.32 (br s, 1H). LCMS (MH+, 251.2).

Step 9.3: tert-butyl 5-oxo-5,6,10,11-tetrahydropyrido[4',3':4,5]thieno[3,2-e][1,2,4]triazolo[1,5-c]pyrimidine-9(8H)-carboxylate Prepared as described in Step 1.2. 1H NMR (400 MHz, DMSO-d6) δ 1.45 (s, 9H), 2.93-3.02 (m, 2H), 3.70 (t, J=5.65 Hz, 2H), 4.59 (s, 2H), 8.44 (s, 1H). LCMS (MH+, 348.2).

Step 9.4: tert-butyl 6-(4-methoxybenzyl)-5-oxo-5,6,10,11-tetrahydropyrido[4',3': 4,5]thieno[3,2-e][1,2,4]triazolo[1,5-c]pyrimidine-9(8h)-carboxylate Prepared as described in Step 1.3.

Numerous compounds were made using the above general procedure, as exemplified in Table 9:

TABLE 9

| Example | Structure | LC-MS (MH+) | 1H-NMR |
|---|---|---|---|
| 80 | 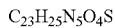 $C_{23}H_{25}N_5O_4S$ | 468.2 | 1H NMR (400 MHz, DMSO-d6) δ 1.43 (s, 9H), 2.99 (br s, 2H), 3.68 (t, J = 5.40 Hz, 2H), 3.74 (s, 3H), 4.57 (br s, 2H), 5.31 (s, 2H), 6.92 (d, J = 8.53 Hz, 2H), 7.36 (d, J = 8.53 Hz, 2H), 8.43-8.54 (m, 1H) |

TABLE 9-continued

| Example | Structure | LC-MS (MH+) | 1H-NMR |
|---|---|---|---|
| 81 | C₁₈H₁₅ClN₄OS | 371.0 | 1H NMR (400 MHz, CDCl3) δ 1.83 (m, 4H), 2.64 (m, 2H), 2.99 (m, 2H), 5.49 (s, 2H), 6.92 (d, 1H), 7.21 (t, 1H), 7.10 (t, 1H), 7.37 (d, 1H), 8.25 (s, 1H) |
| 82 | C₁₈H₁₅ClN₄OS | 371.0 | 1H NMR (400 MHz, CDCl3) δ 1.91 (m, 4H), 2.76 (m, 2H), 3.05 (m, 2H), 5.36 (s, 2H), 7.32 (d, 2H), 7.42 (d, 2H), 8.29 (s, 1H) |
| 83 | C₁₉H₁₇ClN₄O₂S | 401.0 | 1H NMR (400 MHz, DMSO-d6) δ 1.27 (s, 6H), 2.91 (s, 2H), 4.70 (s, 2H), 5.37 (s, 2H), 7.41-7.47 (m, 4H), 8.49 (s, 1H) |
| 84 | C₁₈H₁₆N₄OS | 337.0 | 1H NMR (400 MHz, CDCl3) δ 1.91 (m, 4H), 2.75 (m, 2H), 3.05 (m, 2H), 5.41 (s, 2H), 7.34 (m, 3H), 7.45 (d, 2H), 8.29 (s, 1H) |

TABLE 9-continued
| Example | Structure | LC-MS (MH+) | 1H-NMR |
|---|---|---|---|
| 85 | 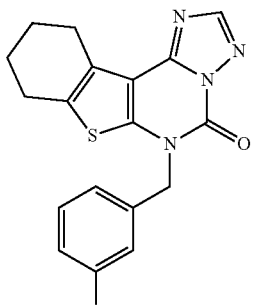 C₁₈H₁₅ClN₄OS | 371.0 | 1H NMR (400 MHz, CDCl3) δ 1.83 (m, 4H), 2.68 (m, 2H), 2.93 (m, 2H), 5.28 (s, 2H), 7.24 (m, 3H), 7.35 (s, 1H), 8.31 (s, 1H) |
| 86 | 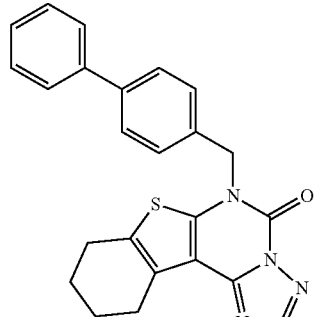 C₂₄H₂₀N₄OS | 413.0 | 1H NMR (400 MHz, CDCl3) δ 1.91 (m, 4H), 2.76 (m, 2H), 3.06 (m, 2H), 5.44 (s, 2H), 7.26 (m, 1H), 7.45 (m, 2H), 7.55 (m, 6H), 8.30 (s, 1H) |
| 87 | 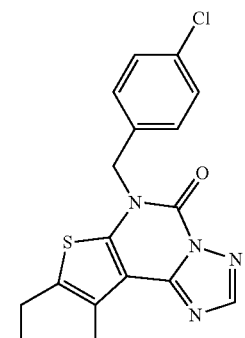 C₁₇H₁₃ClN₄O₂S | 373.0 | 1H NMR (400 MHz, DMSO-d6) δ 2.98-3.01 (m, 2H), 3.93-3.95 (m, 2H), 4.71 (s, 2H), 5.38 (s, 2H), 7.40-7.45 (m, 4H), 8.50 (s, 1H) |
| 88 | 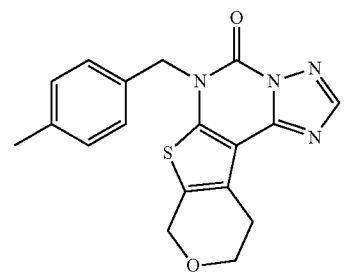 C₁₈H₁₆N₄O₂S | 353.1 | 1H NMR (400 MHz, DMSO-d6) δ 2.26 (s, 3H), 2.98-3.00 (m, 2H), 3.93-3.95 (m, 2H), 4.70 (s, 2H), 5.33 (s, 2H), 7.15-7.16 (d, J = 4 Hz, 2H), 7.27-7.28 (d, J = 4 HZ, 2H), 8.50 (s, 1H) |

TABLE 9-continued

| Example | Structure | LC-MS (MH+) | 1H-NMR |
|---|---|---|---|
| 89 | C₁₈H₁₃F₃N₄O₂S | 407.1 | 1H NMR (400 MHz, DMSO-d6) δ 2.99-3.01 (m, 2H), 3.93-3.96 (m, 2H), 4.70 (s, 2H), 5.49 (s, 2H), 7.62-7.64 (d, J = 8 Hz, 2H), 7.71-7.73 (d, J = 8 Hz, 2H), 8.51 (s, 1H) |
| 90 | C₁₈H₁₆N₄O₃S | 369.1 | 1H NMR (400 MHz, DMSO-d6) δ 2.98-3.00 (m, 2H), 3.93-3.95 (m, 2H), 4.71 (s, 2H), 5.30 (s, 2H), 6.89-6.91 (d, J = 6.9 Hz, 2H), 7.33-7.35 (d, J = 6.9 Hz, 2H), 8.49 (s, 1H) |
| 91 | C₁₇H₁₂Cl₂N₄O₂S | 408.1 | 1H NMR (400 MHz, DMSO-d6) δ 2.99-3.01 (m, 2H), 3.94-3.96 (m, 2H), 4.71 (s, 2H), 5.39 (s, 2H), 7.40-7.42 (m, 1H), 7.61-7.62 (m, 1H), 7.76-7.77 (m, 1H), 8.49 (s, 1H) |
| 92 | C₁₇H₁₃FN₄O₂S | 357.1 | 1H NMR (400 MHz, DMSO-d6) δ 2.98-3.01 (m, 2H), 3.93-3.95 (m, 2H), 4.71 (s, 2H), 5.37 (s, 2H), 7.16-7.00 (m, 2H), 7.45-7.48 (m, 2H), 8.50 (s, 1H) |
| 93 | C₁₇H₁₂ClFN₄O₂S | 391.1 | 1H NMR (400 MHz, DMSO-d6) δ 2.99-3.01 (m, 2H), 3.93-3.96 (m, 2H), 4.70 (s, 2H), 5.40 (s, 2H), 7.28-7.30 (m, 1H), 7.53-7.59 (m, 2H), 8.50 (s, 1H) |

US 9,533,996 B2
TABLE 9-continued
| Example | Structure | LC-MS (MH+) | 1H-NMR |
|---|---|---|---|
| 94 | 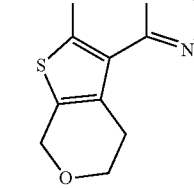<br>C₁₇H₁₂ClFN₄O₂S | 391.1 | 1H NMR (400 MHz, DMSO-d6) δ 2.99-3.01 (m, 2H), 3.94-3.96 (m, 2H), 4.71 (s, 2H), 5.39 (s, 2H), 7.23-7.25 (m, 1H), 7.40-7.43 (m, 1H), 7.52-7.54 (m, 1H), 8.51 (s, 1H) |
| 95 | 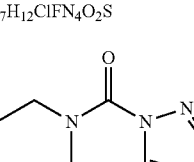<br>C₁₈H₁₅FN₄O₃S | 387.1 | 1H NMR (400 MHz, DMSO-d6) δ 2.98-3.00 (m, 2H), 3.80 (s, 3H), 3.93-3.95 (m, 2H), 4.71 (s, 2H), 5.31 (s, 2H), 7.11-7.15 (m, 1H), 7.18-7.20 (m, 1H), 7.31-7.34 (m, 1H), 8.49 (s, 1H) |
| 96 | 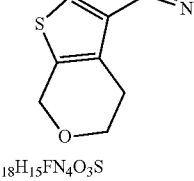<br>C₁₈H₁₃F₃N₄O₃S | 423.1 | 1H NMR (400 MHz, DMSO-d6) δ 2.99-3.01 (m, 2H), 3.94-3.96 (m, 2H), 4.71 (s, 2H), 5.41 (m, 2H), 7.34-7.36 (d, J = 8 Hz, 2H), 7.53-7.55 (d, J = 8 Hz, 2H), 8.50 (s, 1H) |
| 97 | 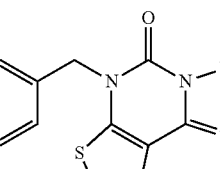<br>C₁₉H₁₈N₄O₃S | 383.1 | 1H NMR (400 MHz, DMSO-d6) δ 1.27-1.30 (t, J = 5.6 Hz, 3H), 2.98-3.00 (m, 2H), 3.93-4.00 (m, 4H), 4.71 (s, 2H), 5.30 (s, 2H), 6.88-6.90 (d, J = 6.8 Hz, 2H), 7.32-7.34 (d, J = 6.8 Hz, 2H), 8.49 (s, 1H) |
| 98 | 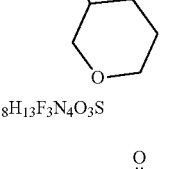<br>C₁₈H₁₄F₂N₄O₃S | 405.1 | 1H NMR (400 MHz, DMSO-d6) δ 1.23 (s, 2H), 3.08-3.10 (m, 2H), 3.94 (s, 3H), 4.01-4.03 (m, 2H), 4.85 (s, 2H), 5.67 (s, 2H), 7.39-7.41 (m, 2H), 8.61 (s, 1H) |

Preparative Example 99

6-(4-Chlorobenzyl)-8,9,10,11-tetrahydropyrido[4',3':4,5]thieno[3,2-e][1,2,4]triazolo[1,5-c]pyrimidin-5(6H)-one

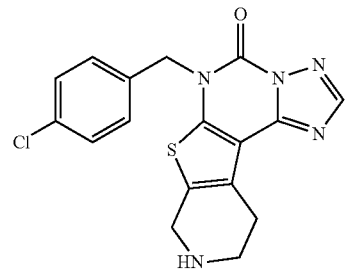

Step 10.1: 6-(4-chlorobenzyl)-8,9,10,11-tetrahydropyrido[4',3':4,5]thieno[3,2-e][1,2,4]triazolo[1,5-c]pyrimidin-5(6H)-one (10)

To a 100 mL flask containing tert-butyl 6-(4-chlorobenzyl)-5-oxo-5,6,10,11-tetrahydropyrido[4',3':4,5]thieno[3,2-e][1,2,4]triazolo[1,5-c]pyrimidine-9(8H)-carboxylate (0.55 g, 1.17 mmol) was added 4N hydrogen chloride in dioxane (10 mL). The resulting mixture was stirred at room temperature for four hours and it was concentrated under reduced pressure to yield 99 (0.47 g, 99%) as the hydrochloride salt.

Numerous compounds were made using the above general procedure, as exemplified in Table 10:

Preparative Example 101

6-(4-Chlorobenzyl)-9-methyl-8,9,10,11-tetrahydropyrido[4',3':4,5]thieno[3,2-e][1,2,4]triazolo[1,5-c]pyrimidin-5(6H)-one

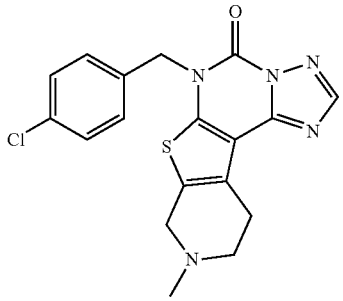

Step 11.1: 6-(4-chlorobenzyl)-8,9,10,11-tetrahydropyrido[4',3':4,5]thieno[3,2-e][1,2,4]triazolo[1,5-c]pyrimidin-5(6H)-one To a mixture of 6-(4-chlorobenzyl)-8,9,10,11-tetrahydropyrido[4',3':4,5]thieno[3,2-e][1,2,4]triazolo[1,5-c]pyrimidin-5(6H)-one hydrochloride (0.045 g, 0.121 mmol) and methyl iodide (0.019 g, 0.133 mmol) in DMF (1.5 mL) was added (0.025 g, 0.182 mmol). The resulting mixture was heated to 40 °C. After 16 hours the crude mixture was cooled to room temperature, filtered and purified via reverse-phase HPLC to yield 101 (0.037 g, 81%) as the trifluoroacetic acid salt.

TABLE 10

| Example | Structure | LC-MS (MH+) | 1H-NMR |
|---|---|---|---|
| 99 | $C_{17}H_{14}ClN_5OS$ | 372.1 | 1H NMR (400 MHz, DMSO-d6) δ 3.20-3.23 (m, 2H), 3.42-3.45 (m, 2H), 4.30-4.34 (m, 2H), 5.41 (s, 2H), 7.41-7.45 (m, 4H), 8.54 (s, 1H), 9.71 (br. s, 1H) |
| 100 | $C_{19}H_{19}N_5O_3S$ | 398.0 | 1H NMR (400 MHz, CDCl3) δ 1.84-1.95 (m, 2H), 2.93 (s, 2H), 3.19 (br s, 2H), 3.77 (s, 6H), 5.20 (s, 2H), 6.67-6.78 (m, 1H), 6.89-7.00 (m, 2H), 8.22-8.30 (m, 1H) |

Numerous compounds were made using the above general procedure, as exemplified in Table 11:

TABLE 11

| Example | Structure | LC-MS (MH+) | 1H-NMR |
|---|---|---|---|
| 101 | 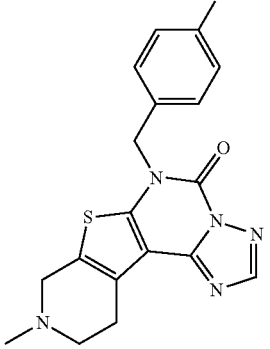<br>$C_{18}H_{16}ClN_5OS$ | 387.1 | 1H NMR (400 MHz, DMSO-d6) δ 2.93-2.99 (m, 2H), 3.18 (s, 3H), 3.35-3.37 (m, 2H), 3.74-3.77 (m, 2H), 5.41 (s, 2H), 7.41-7.47 (m, 4H), 8.55 (s, 1H) |

Preparative Example 102

6-(4-Chlorobenzyl)-9-benzyl-8,9,10,11-tetrahydropyrido[4',3':4,5]thieno[3,2-e][1,2,4]triazolo[1,5-c]pyrimidin-5(6H)-one

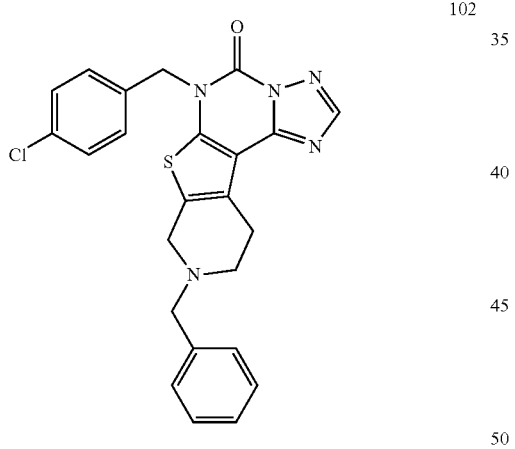

102

Step 12.1: 6-(4-chlorobenzyl)-9-benzyl-8,9,10,11-tetrahydropyrido[4',3':4,5]thieno[3,2-e][1,2,4]triazolo[1,5-c]pyrimidin-5(6H)-one (102)

6-(4-Chlorobenzyl)-8,9,10,11-tetrahydropyrido[4',3':4,5]thieno[3,2-e][1,2,4]triazolo[1,5-c]pyrimidin-5(6H)-one (80 mg, 0.22 mmol), sodium tri(acetoxy)borohydride (68 mg, 0.32 mmol), benzaldehyde (27 mg, 0.25 mmol) and THF (2 ml) were combined and stirred at room temperature for 18 hours. The mixture was concentrated, diluted with methanol, filtered and purified via reverse phase HPLC to yield 102 (50 mg, 40%) as the trifluoroacetic acid salt.

Numerous compounds were made using the above general procedure, as exemplified in Table 12:

TABLE 12
| Example | Structure | LC-MS (MH+) | 1H-NMR |
|---|---|---|---|
| 102 | 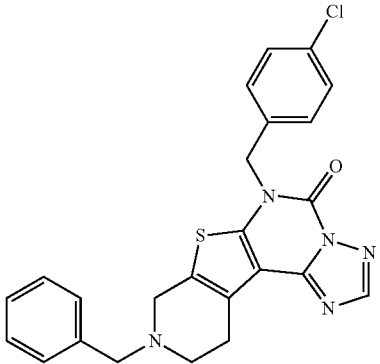<br>C₂₄H₂₀ClN₅OS | 462.1 | 1H NMR (400 MHz, DMSO-d6) δ 3.16-3.21 (m, 2H), 3.73-3.76 (m, 2H), 4.37-4.39 (m, 2H), 4.54 (s, 2H), 5.39 (s, 2H), 7.40-7.43 (m, 4H), 7.49-7.51 (m, 5H), 8.54 (s, 1H) |
| 103 | 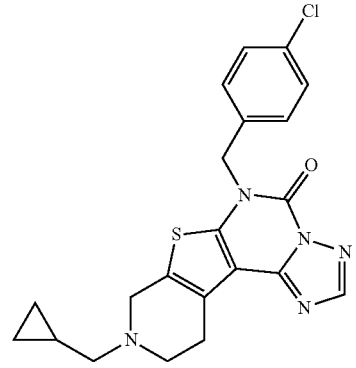<br>C₂₁H₂₀ClN₅OS | 426.2 | 1H NMR (400 MHz, DMSO-d6) δ 0.38-0.42 (m, 2H), 0.66-0.67 (m, 2H), 1.07-1.12 (m, 1H), 3.22-3.26 (m, 2H), 3.39-3.45 (m 2H), 3.81-3.85 (m, 2H), 4.37-4.39 (m, 1H), 4.73-4.76 (m, 1H), 5.42 (s, 2H), 7.43-7.45 (m, 4H), 8.55 (s, 1H) |
| 104 | 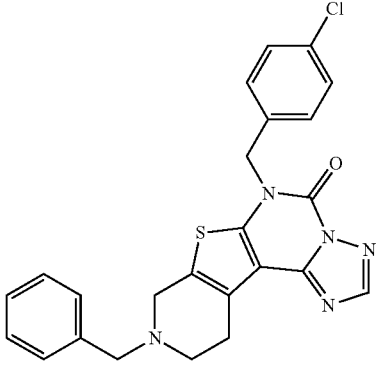<br>C₂₄H₂₀ClN₅OS | 462.1 | 1H NMR (400 MHz, DMSO-d6) δ 3.16-3.21 (m, 2H), 3.73-3.76 (m, 2H), 4.37-4.39 (m, 2H), 4.54 (s, 2H), 5.39 (s, 2H), 7.40-7.43 (m, 4H), 7.49-7.51 (m, 5H), 8.54 (s, 1H) |

TABLE 12-continued
| Example | Structure | LC-MS (MH+) | 1H-NMR |
|---|---|---|---|
| 105 | 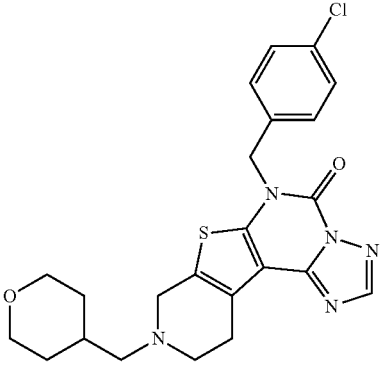 C₂₃H₂₄ClN₅O₂S | 470.2 | 1H NMR (400 MHz, DMSO-d6) δ 1.20-1.26 (m, 2H), 1.62-1.66 (m, 2H), 2.07-2.11 (m, 1H), 3.14-3.96 (m, 10H), 4.35-4.74 (m, 2H), 5.34-5.51 (m, 2H), 7.41-7.46 (m, 4H), 8.56 (s, 1H) |
| 106 | 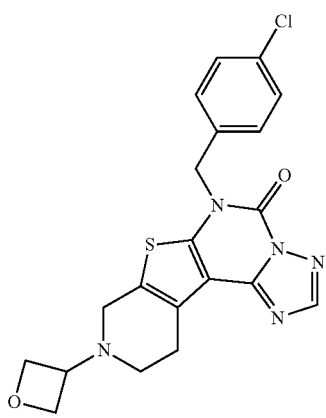 C₂₀H₁₈ClN₅O₂S | 428.1 | 1H NMR (400 MHz, CDCl3) δ 3.44-3.48 (m, 4H), 4.34-4.36 (m, 2H), 4.40-4.43 (m, 1H), 4.84-4.87 (m, 2H), 5.04-5.07 (m, 2H), 5.36 (s, 2H), 7.26-7.33 (d, J = 8 Hz, 2H), 7.37-7.39 (d, J = 8 Hz, 2H), 8.32 (s, 1H) |
| 107 | 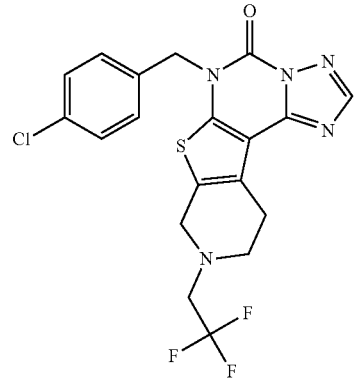 C₁₉H₁₅ClF₃N₅OS | 454.1 | 1H NMR (400 MHz, CD3OD) δ 3.09-3.13 (m, 4H), 3.31-3.35 (m, 2H), 3.92-3.94 (m, 2H), 5.43 (s, 2H), 7.35-7.37 (d, J = 8.0 Hz, 2H), 7.42-7.44 (d, J = 8.0 Hz, 2H), 8.39 (s, 1H) |

TABLE 12-continued

| Example | Structure | LC-MS (MH+) | 1H-NMR |
|---------|-----------|-------------|--------|
| 108 | C22H21N7O2S2 | 480.2 | 1H NMR (400 MHz, DMSO-d6) δ 2.72 (s, 3H), 3.08-3.12 (m, 2H), 3.13-3.17 (m, 2H), 3.71-3.74 (m, 5H), 4.39-4.42 (m, 2H), 5.30 (s, 2H), 6.89-6.91 (d, J = 9.2 Hz, 2H), 7.33-7.35 (d, J = 9.2 Hz, 2H), 8.51 (s, 1H) |
| 109 | C24H27N5O3S | 466.2 | 1H NMR (400 MHz, DMSO-d6) δ 1.08-1.20 (m, 2H), 1.62 (d, J = 12.30 Hz, 2H), 1.82 (ddd, J = 10.73, 7.22, 3.89 Hz, 1H), 2.35 (d, J = 7.15 Hz, 2H), 2.74-2.82 (m, 2H), 2.96 (br s, 2H), 3.29 (t, J = 11.29 Hz, 2H), 3.60 (s, 2H), 3.73 (s, 3H), 3.82 (dd, J = 11.11, 2.82 Hz, 2H), 5.30 (s, 2H), 6.91 (d, J = 8.53 Hz, 2H), 7.35 (d, J = 8.41 Hz, 2H), 8.49 (s, 1H) |
| 110 | C22H23N5O2S | 422.2 | 1H NMR (400 MHz, DMSO-d6) δ 0.40-0.41 (m, 2H), 0.66-0.68 (m, 2H), 1.08-1.11 (m, 1H) 3.21-3.25 (m, 2H), 3.38-3.38 (m, 2H), 3.72 (s, 3H), 3.83-3.86 (m, 2H), 4.37-4.76 (m, 2H), 5.34-5.36 (m, 2H), 6.90-6.92 (d, J = 6.8 Hz, 2H), 7.34-7.36 (d, J = 6.8 Hz, 2H), 8.55 (s, 1H) |

TABLE 12-continued

| Example | Structure | LC-MS (MH+) | 1H-NMR |
|---|---|---|---|
| 111 | C₂₃H₂₅N₅O₃S | 452.2 | 1H NMR (400 MHz, CDCl3) δ 1.63-1.65 (m, 2H), 3.48-3.55 (m, 5H), 3.78 (s, 3H), 3.96-3.98 (m, 2H), 4.35 (br. s, 2H), 4.47-4.50 (m, 4H), 5.34 (s, 2H), 6.86-6.88 (d, J = 6.8 Hz, 2H), 7.37-7.39 (d, J = 6.8 Hz, 2H), 8.30 (s, 1H) |
| 112 | C₂₂H₂₅N₅O₂S₂ | 456.1 | 1H NMR (400 MHz, DMSO-d6) δ 1.97-2.02 (m, 2H), 2.07 (s, 3H), 2.53-2.56 (m, 2H), 3.24-3.34 (m, 4H), 3.72 (s, 1H), 3.82-3.86 (m, 2H), 4.37-4.39 (m, 1H), 4.68-4.71 (m, 1H), 5.34-5.36 (m, 2H), 6.90-6.92 (d, J = 6.8 Hz, 2H), 7.34-7.36 (d, J = 6.8 Hz, 2H), 8.54 (s, 1H) |
| 113 | C₂₃H₂₅N₅O₃S | 452.2 | 1H NMR (400 MHz, DMSO-d6) δ 1.22-1.24 (m, 1H), 1.61-1.63 (m, 1H), 2.09-2.11 (m, 1H), 2.63-2.67 (m, 1H), 3.26-3.35 (m, 3H), 3.62-3.67 (m, 2H), 3.72 (s, 3H), 3.73-3.78 (m, 2H), 3.83-3.86 (m, 2H), 4.34-4.37 (m, 1H), 4.70-4.74 (m, 1H), 6.90-6.92 (d, J = 7.2 Hz, 2H), 7.34-7.36 (d, J = 7.2 Hz, 2H), 8.55 (s, 1H) |

TABLE 12-continued

| Example | Structure | LC-MS (MH+) | 1H-NMR |
|---|---|---|---|
| 114 | C$_{26}$H$_{21}$F$_2$N$_5$O$_4$S | 538.2 | 1H NMR (400 MHz, DMSO-d6) δ 3.17-3.21 (m, 2H), 3.50-3.55 (m, 2H), 3.72 (m, 3H), 4.33-4.65 (m, 4H), 5.32 (s, 2H), 6.88-6.90 (d, J = 7.2 Hz, 2H), 7.32-7.34 (d, J = 7.2 Hz, 2H), 7.35-7.37 (m, 1H), 7.52-7.54 (m, 2H), 8.54 (s, 1H) |
| 115 | C$_{23}$H$_{27}$N$_5$O$_2$S | 438.1 | 1H NMR (400 MHz, DMSO-d6) δ 1.06 (s, 9H), 3.01-3.03 (m, 2H), 3.23-3.26 (m, 2H), 3.54-3.57 (m, 2H), 3.72 (s, 3H), 4.43-4.46 (m, 1H), 4.67-4.70 (m, 1H), 5.29-5.41 (m, 2H), 6.90-6.92 (d, J = 6.8 Hz, 2H), 7.34-7.36 (d, J = 6.8 Hz, 2H), 8.56 (s, 1H) |
| 116 | C$_{23}$H$_{21}$N$_7$O$_2$S | 460.1 | 1H NMR (400 MHz, DMSO-d6) δ 3.33-3.35 (m, 2H), 3.57-3.59 (m, 2H), 3.72 (s, 3H), 4.57-4.60 (m, 2H), 4.76-4.78 (m, 2H), 5.33 (s, 2H), 6.90-6.91 (d, J = 6.8 Hz, 2H), 7.33-7.35 (d, J = 6.8 Hz, 2H), 7.60-7.62 (m, 1H), 8.54 (s, 1H), 8.93-8.94 (d, J = 3.6 Hz, 1H) |

TABLE 12-continued

| Example | Structure | LC-MS (MH+) | 1H-NMR |
|---|---|---|---|
| 117 | C₂₄H₂₇N₅O₃S | 466.2 | 1H NMR (400 MHz, DMSO-d6) δ 1.19-1.23 (m, 2H), 1.46-1.57 (m, 4H), 1.79-1.82 (m, 1H), 3.28-3.48 (m, 8H), 3.72 (s, 3H), 4.38-4.41 (m, 1H), 4.63-4.68 (m, 1H), 5.30-5.35 (m, 2H), 6.91-6.93 (d, J = 7.6 Hz, 2H), 7.35-7.37 (d, J = 7.6, 2H), 8.54 (s, 1H) |
| 118 | C₂₂H₂₅N₅O₄S₂ | 488.2 | 1H NMR (400 MHz, DMSO-d6) δ 1.97-2.06 (m, 2H), 2.14-2.18 (m, 2H), 3.00-3.02 (m, 2H), 3.02 (s, 3H), 3.15-3.26 (m, 4H), 3.72 (s, 3H), 4.36-4.39 (m, 1H), 4.69-4.72 (m, 1H), 5.33-5.35 (m, 2H), 6.90-6.92 (d, J = 6.8 Hz, 2H), 7.34-7.36 (d, J = 6.8 Hz, 2H), 8.55 (s, 1H) |
| 119 | C₂₃H₂₁N₇O₂S | 460.2 | 1H NMR (400 MHz, DMSO-d6) δ 3.19-3.24 (m, 2H), 3.38-3.42 (m, 2H), 3.72 (s, 3H), 4.19-4.45 (m, 4H), 5.32 (s, 2H), 6.90-6.92 (m, 2H), 7.34-7.36 (m, 2H), 7.63-7.65 (m, 1H), 8.52 (s, 1H), 8.85-8.87 (m, 1H), 9.25 (s, 1H) |

TABLE 12-continued
| Example | Structure | LC-MS (MH+) | 1H-NMR |
|---|---|---|---|
| 120 | 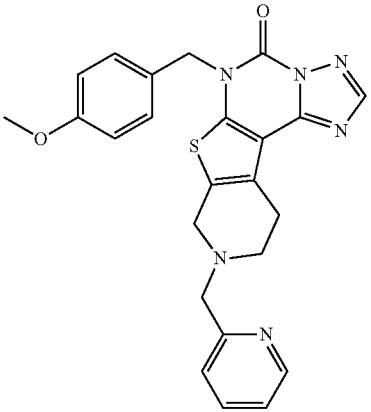 C₂₄H₂₂N₆O₂S | 459.2 | 1H NMR (400 MHz, DMSO-d6) δ 3.25-3.31 (m, 2H), 3.54-3.61 (m, 2H), 3.72 (s, 3H), 4.39-4.45 (m, 2H), 4.53 (s, 2H), 5.35 (s, 2H), 6.90-6.92 (m, 2H), 7.34-7.36 (m, 2H), 7.47-7.50 (m, 1H), 7.59-7.62 (m, 2H), 7.90-7.94 (m, 1H), 8.55 (s, 1H), 8.65-8.69 (m, 1H), |
| 121 | 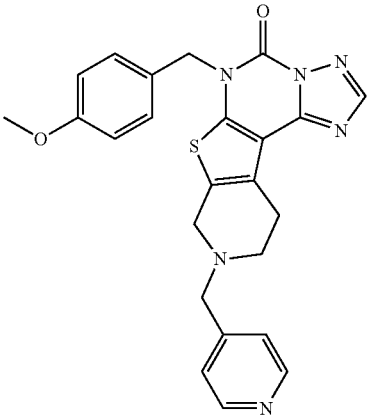 C₂₄H₂₂N₆O₂S | 459.2 | 1H NMR (400 MHz, DMSO-d6) δ 3.18-3.21 (m, 2H), 3.27-3.32 (m, 2H), 3.72 (s, 3H), 4.12-4.17 (m, 2H), 4.31 (s, 2H), 5.35 (s, 2H), 6.90-6.92 (m, 2H), 7.34-7.36 (m, 2H), 7.69-7.73 (m, 2H), 8.52 (s, 1H), 8.72-8.78 (m, 2H) |
| 122 | 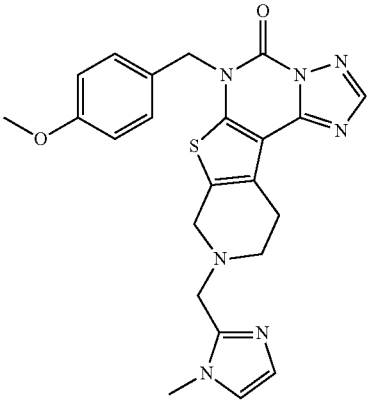 C₂₃H₂₃N₇O₂S | 462.1 | 1H NMR (400 MHz, DMSO-d6) δ 2.98-3.03 (m, 2H), 3.08-3.11 (m, 2H), 3.72 (s, 3H), 3.78-3.85 (m, 5H), 4.13 (s, 2H), 5.32 (m, 2H), 6.90-6.92 (m, 2H), 7.34-7.36 (m, 2H), 7.59 (s, 1H), 7.65 (s, 1H), 8.49 (s, 1H) |

TABLE 12-continued

| Example | Structure | LC-MS (MH+) | 1H-NMR |
|---------|-----------|-------------|--------|
| 123 | C₂₃H₂₂N₆O₂S₂ | 479.1 | 1H NMR (400 MHz, DMSO-d6) δ 2.45 (s, 3H), 3.15-3.55 (br. m, 5H), 3.72 (s, 3H), 4.05-4.15 (m, 2H), 4.35-4.58 (m, 2H), 5.35 (s, 2H), 6.90-6.92 (m, 2H), 7.34-7.36 (m, 2H), 8.55 (s, 1H), 9.08 (s, 1H), |
| 124 | C₂₁H₂₁N₅O₄S₂ | 472.2 | 1H NMR (400 MHz, DMSO-d6) δ 2.83-2.88 (m, 2H), 3.02-3.06 (m, 2H), 3.54-3.57 (m, 1H), 3.71-3.78 (m, 5H), 4.21-4.25 (m, 2H), 4.29-4.36 (m, 2H), 5.33 (s, 2H), 6.90-6.92 (m, 2H), 7.34-7.36 (m, 2H), 8.55 (s, 1H) |
| 125 | C₂₃H₂₅N₅O₄S | 468.2 | 1H NMR (400 MHz, DMSO-d6) δ 3.25-3.35 (m, 2H), 3.49-3.58 (m, 2H), 3.68-3.72 (m, 4H), 3.73-3.77 (m, 4H), 3.79-3.83 (m, 2H), 3.98-4.02 (m, 2H), 4.39-4.68 (m, 2H), 5.35 (s, 2H), 6.90-6.92 (m, 2H), 7.34-7.36 (m, 2H), 8.55 (s, 1H) |

TABLE 12-continued

| Example | Structure | LC-MS (MH+) | 1H-NMR |
|---------|-----------|-------------|--------|
| 126 | $C_{23}H_{23}N_5O_4S$ | 466.2 | 1H NMR (400 MHz, DMSO-d6) δ 1.89-1.95 (m, 1H), 2.32-2.39 (m, 2H), 3.19-3.28 (m, 2H), 3.42-3.62 (m, 4H), 3.77 (s, 3H), 4.28-4.56 (m, 4H), 5.32 (s, 2H), 6.90-6.92 (m, 2H), 7.34-7.36 (m, 2H), 8.55 (s, 1H) |
| 127 | $C_{25}H_{22}FN_5O_2S$ | 476.1 | 1H NMR (400 MHz, DMSO-d6) δ 3.74 (s, 3H), 4.15-4.74 (m, 7H), 5.34 (s, 2H), 6.88-6.95 (m, 2H), 7.30-7.39 (m, 4H), 7.55-7.64 (m, 2H), 8.56 (s, 1H) |
| 128 | $C_{25}H_{22}FN_5O_2S$ | 476.1 | 1H NMR (400 MHz, DMSO-d6) δ 3.29 (br s, 2H), 3.74 (s, 3H), 4.21-4.64 (m, 6H), 5.34 (s, 2H), 6.87-6.95 (m, 2H), 7.29-7.40 (m, 4H), 7.50-7.67 (m, 2H), 8.55 (s, 1H) |

TABLE 12-continued
| Example | Structure | LC-MS (MH+) | 1H-NMR |
|---|---|---|---|
| 129 | 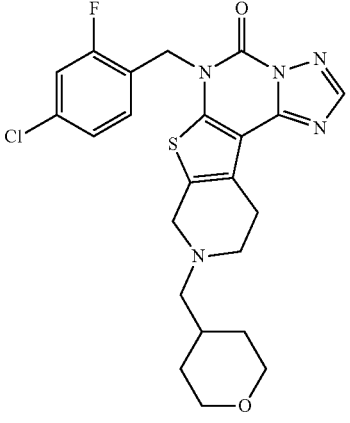<br>C$_{23}$H$_{23}$ClFN$_5$O$_2$S | 488.2 | 1H NMR (400 MHz, DMSO-d6) δ 1.26 (qd, J = 12.05, 4.14 Hz, 2H), 1.67 (d, J = 14.68 Hz, 2H), 2.12 (br s, 1H), 3.33 (br s, 7H), 3.76-3.93 (m, 4H), 4.30-4.46 (m, 1H), 4.69-4.85 (m, 1H), 5.35-5.58 (m, 2H), 7.25-7.32 (m, 1H), 7.43-7.52 (m, 1H), 7.53-7.61 (m, 1H), 8.58 (s, 1H), 9.87-10.04 (m, 1H) |
| 130 | 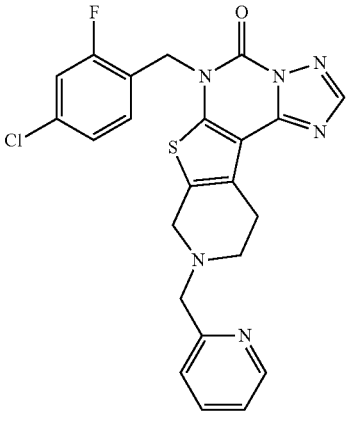<br>C$_{23}$H$_{18}$ClFN$_6$OS | 481.1 | 1H NMR (400 MHz, DMSO-d6) δ 3.27-3.39 (m, 2H), 3.58-3.73 (m, 2H), 4.43-4.52 (m, 2H), 4.56-4.68 (m, 2H), 5.38-5.47 (m, 2H), 7.23-7.30 (m, 1H), 7.43-7.49 (m, 1H), 7.50-7.61 (m, 3H), 7.94-8.01 (m, 1H), 8.57 (s, 1H), 8.69-8.73 (m, 1H) |
| 131 | 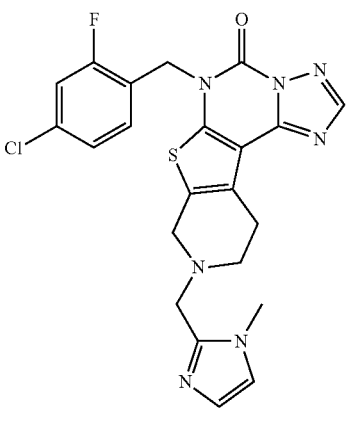<br>C$_{22}$H$_{19}$ClFN$_7$OS | 484.1 | 1H NMR (400 MHz, DMSO-d6) δ 2.93-3.01 (m, 2H), 3.08 (d, J = 5.27 Hz, 2H), 3.77-3.86 (m, 5H), 4.13 (s, 2H), 5.41 (s, 2H), 7.23-7.30 (m, 1H), 7.41-7.48 (m, 1H), 7.52-7.58 (m, 1H), 7.63 (d, J = 1.88 Hz, 1H), 7.70 (d, J = 1.88 Hz, 1H), 8.53 (s, 1H) |

TABLE 12-continued

| Example | Structure | LC-MS (MH+) | 1H-NMR |
|---|---|---|---|
| 132 | $C_{22}H_{17}ClFN_7OS$ | 482.1 | 1H NMR (400 MHz, DMSO-d6) δ 3.38 (br s, 2H), 3.78 (br s, 2H), 4.63 (br s, 2H), 4.81 (s, 2H), 5.43 (s, 2H), 7.27 (dd, J = 8.41, 1.88 Hz, 1H), 7.43-7.50 (m, 1H), 7.55 (dd, J = 10.16, 2.01 Hz, 1H), 7.60-7.66 (m, 1H), 8.57 (s, 1H), 8.96 (d, J = 4.89 Hz, 2H) |
| 133 | $C_{22}H_{21}ClN_5O_5S$ | 472.1 | 1H NMR (400 MHz, DMSO-d6) δ 1.58-1.74 (m, 1H), 2.07-2.20 (m, 1H), 2.61-2.76 (m, 1H), 3.19-3.39 (m, 3H), 3.40-3.56 (m, 2H), 3.67 (d, J = 8.28 Hz, 2H), 3.73-3.82 (m, 2H), 3.82-3.95 (m, 3H), 4.28-4.51 (m, 2H), 4.61-4.87 (m, 2H), 5.37-5.52 (m, 3H), 7.24-7.30 (m, 1H), 7.43-7.52 (m, 1H), 7.53-7.60 (m, 1H), 8.58 (s, 1H), 9.96-10.22 (m, 1H) |
| 134 | $C_{24}H_{27}N_5O_3S$ | 466.2 | 1H NMR (400 MHz, DMSO-d6) δ 1.28-1.42 (m, 1H), 1.44-1.67 (m, 2H), 1.80-1.95 (m, 1H), 2.03-2.18 (m, 1H), 3.05-3.54 (m, 7H), 3.74 (s, 4H), 3.79-3.90 (m, 2H), 4.24-4.48 (m, 1H), 4.60-4.87 (m, 2H), 5.24-5.49 (m, 2H), 6.94 (s, 2H), 7.32-7.42 (m, 2H), 8.56 (s, 1H), 9.89-10.22 (m, 1H) |

TABLE 12-continued

| Example | Structure | LC-MS (MH+) | 1H-NMR |
|---|---|---|---|
| 135 | C24H25F2N5O3S | 502.2 | 1H NMR (400 MHz, CDCl3) δ 1.25-1.39 (m, 2H), 1.69-1.78 (m, 2H), 1.80-1.94 (m, 1H), 2.58 (d, J = 7.28 Hz, 2H), 3.28 (t, J = 11.54 Hz, 2H), 3.38-3.47 (m, 2H), 3.82 (s, 5H), 3.96-4.04 (m, 2H), 5.40 (s, 2H), 6.91 (d, J = 8.66 Hz, 2H), 7.41 (d, J = 8.66 Hz, 2H), 8.42 (s, 1H) |
| 136 | C24H25F2N5O3S | 502.2 | 1H NMR (400 MHz, CDCl3) δ 1.23-1.38 (m, 1H), 1.60-1.73 (m, 2H), 1.85-1.93 (m, 1H), 1.94-2.04 (m, 1H), 2.63 (d, J = 7.15 Hz, 2H), 3.21-3.38 (m, 3H), 3.44-3.55 (m, 1H), 3.82 (s, 4H), 3.85-3.94 (m, 3H), 3.95-4.02 (m, 1H), 5.40 (s, 2H), 6.91 (d, J = 8.41 Hz, 2H), 7.41 (d, J = 8.41 Hz, 2H), 8.45 (s, 1H) |
| 137 | C23H20FN7O2S | 478.1 | 1H NMR (400 MHz, DMSO-d6) δ 3.30-3.42 (m, 4H), 3.73-3.81 (m, 5H), 4.55-4.66 (m, 2H), 4.75-4.83 (m, 2H), 5.38 (s, 2H), 6.76 (dd, J = 8.60, 2.45 Hz, 1H), 6.91 (dd, J = 12.49, 2.45 Hz, 1H), 7.34 (t, J = 8.91 Hz, 1H), 7.63 (t, J = 4.96 Hz, 1H), 8.57 (s, 1H), 8.96 (d, J = 4.89 Hz, 2H) |

TABLE 12-continued

| Example | Structure | LC-MS (MH+) | 1H-NMR |
|---|---|---|---|
| 138 | C₂₃H₂₂FN₇O₂S | 480.1 | 1H NMR (400 MHz, DMSO-d6) δ 2.93-3.00 (m, 2H), 3.04-3.12 (m, 2H), 3.75-3.84 (m, 8H), 4.11 (s, 2H), 5.36 (s, 2H), 6.75 (dd, J = 8.66, 2.51 Hz, 1H), 6.91 (dd, J = 12.49, 2.45 Hz, 1H), 7.32 (t, J = 8.78 Hz, 1H), 7.60-7.71 (m, 2H), 8.53 (s, 1H) |
| 139 | C₂₄H₂₁FN₆O₂S | 477.2 | 1H NMR (400 MHz, DMSO-d6) δ 3.30-3.36 (m, 2H), 3.64-3.70 (m, 2H), 3.77 (s, 3H), 4.49 (br s, 2H), 4.64 (s, 2H), 5.37 (s, 2H), 6.75 (dd, J = 8.60, 2.45 Hz, 1H), 6.91 (dd, J = 12.49, 2.45 Hz, 1H), 7.34 (t, J = 8.85 Hz, 1H), 7.53 (dd, J = 6.84, 5.08 Hz, 1H), 7.59 (d, J = 7.78 Hz, 1H), 7.98 (td, J = 7.72, 1.72 Hz, 1H), 8.57 (s, 1H), 8.71 (d, J = 4.89 Hz, 1H) |
| 140 | C₂₃H₂₄FN₅O₃S | 470.2 | 1H NMR (400 MHz, DMSO-d6) δ 1.59-1.71 (m, 1H), 2.07-2.19 (m, 1H), 2.63-2.73 (m, 1H), 3.19-3.47 (m, 7H), 3.63-3.70 (m, 3H), 3.77 (s, 3H), 3.82-3.90 (m, 2H), 5.36-5.49 (m, 2H), 6.76 (dd, J = 8.60, 2.45 Hz, 1H), 6.92 (dd, J = 12.49, 2.45 Hz, 1H), 7.35 (t, J = 8.91 Hz, 1H), 8.57 (s, 1H) |

TABLE 12-continued
| Example | Structure | LC-MS (MH+) | 1H-NMR |
|---|---|---|---|
| 141 | 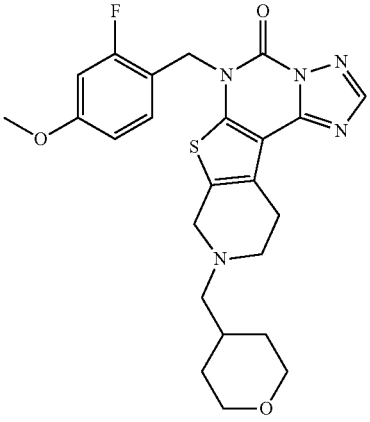<br>C₂₄H₂₆FN₅O₃S | 484.2 | 1H NMR (400 MHz, DMSO-d6) δ 1.04-1.24 (m, 2H), 1.55-1.67 (m, 2H), 1.75-1.90 (m, 1H), 2.32-2.39 (m, 2H), 2.74-2.83 (m, 2H), 2.91-3.00 (m, 2H), 3.24-3.33 (m, 2H), 3.57-3.63 (m, 2H), 3.76 (s, 3H), 3.79-3.87 (m, 2H), 5.33 (s, 2H), 6.74 (dd, J = 8.60, 2.32 Hz, 1H), 6.90 (dd, J = 12.42, 2.38 Hz, 1H), 7.30 (t, J = 8.85 Hz, 1H), 8.49 (s, 1H) |
| 142 | 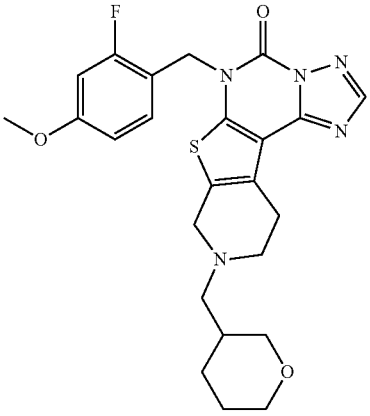<br>C₂₄H₂₆FN₅O₃S | 484.2 | 1H NMR (400 MHz, CDCl3) δ 1.53-1.81 (m, 3H), 2.03-2.33 (m, 2H), 3.11-3.28 (m, 2H), 3.39-3.61 (m, 6H), 3.78-3.87 (m, 5H), 3.95 (d, J = 10.29 Hz, 2H), 5.45 (s, 2H), 6.65-6.74 (m, 2H), 7.39 (t, J = 8.41 Hz, 1H), 8.34 (s, 1H) |
| 143 | 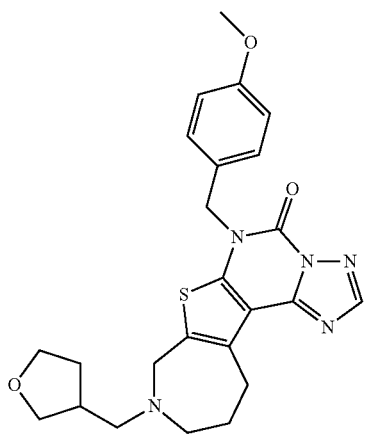<br>C₂₄H₂₇N₅O₃S | 466.2 | 1H NMR (400 MHz, DMSO-d6) δ 1.74-1.86 (m, 2H), 3.06-3.14 (m, 3H), 3.71-3.76 (m, 6H), 3.94-4.01 (m, 2H), 4.07-4.14 (m, 2H), 5.31 (s, 2H), 6.93 (d, J = 8.66 Hz, 2H), 7.37 (d, J = 8.66 Hz, 2H), 7.55-7.59 (m, 1H), 7.63-7.67 (m, 1H), 8.54 (s, 1H) |

TABLE 12-continued

| Example | Structure | LC-MS (MH+) | 1H-NMR |
|---|---|---|---|
| 144 | C₂₄H₂₅N₇O₂S | 476.2 | 1H NMR (400 MHz, DMSO-d6) δ 1.74-1.86 (m, 2H), 3.06-3.14 (m, 3H), 3.71-3.76 (m, 6H), 3.94-4.01 (m, 2H), 4.07-4.14 (m, 2H), 5.31 (s, 2H), 6.93 (d, J = 8.66 Hz, 2H), 7.37 (d, J = 8.66 Hz, 2H), 7.55-7.59 (m, 1H), 7.63-7.67 (m, 1H), 8.54 (s, 1H) |
| 145 | C₂₄H₂₃N₇O₂S | 474.2 | 1H NMR (400 MHz, DMSO-d6) δ 2.03-2.17 (m, 2H), 3.49-3.57 (m, 3H), 3.63-3.73 (m, 2H), 3.75 (s, 3H), 4.45-4.63 (m, 2H), 4.66-4.81 (m, 2H), 5.33 (br s, 2H), 6.94 (d, J = 8.53 Hz, 2H), 7.38 (d, J = 8.53 Hz, 2H), 7.60 (t, J = 4.96 Hz, 1H), 8.57 (s, 1H), 8.90 (d, J = 5.02 Hz, 1H) |
| 146 | C₂₅H₂₄N₆O₂S | 473.2 | 1H NMR (400 MHz, DMSO-d6) δ 2.02-2.15 (m, 2H), 3.57-3.68 (m, 4H), 3.76 (s, 3H), 4.40-4.49 (m, 2H), 4.66-4.75 (m, 2H), 5.34 (s, 2H), 6.95 (d, J = 8.53 Hz, 2H), 7.38 (d, J = 8.53 Hz, 2H), 7.46 (d, J = 7.78 Hz, 1H), 7.48-7.54 (m, 1H), 7.87-7.94 (m, 1H), 8.58 (s, 1H), 8.68 (d, J = 4.52 Hz, 1H) |

TABLE 12-continued

| Example | Structure | LC-MS (MH+) | 1H-NMR |
|---|---|---|---|
| 147 | C25H29N5O3S | 480.3 | 1H NMR (400 MHz, DMSO-d6) δ 1.07-1.26 (m, 2H), 1.39-1.52 (m, 1H), 1.61-1.73 (m, 1H), 1.90-2.20 (m, 3H), 2.92 (br s, 3H), 3.21-3.36 (m, 3H), 3.64-3.72 (m, 2H), 3.74 (s, 3H), 3.79-3.88 (m, 2H), 4.63-4.86 (m, 2H), 5.36 (d, J = 7.78 Hz, 2H), 6.93 (d, J = 8.66 Hz, 2H), 7.38 (d, J = 8.66 Hz, 2H), 8.57 (s, 1H) |
| 148 | C24H27N5O3S | 466.2 | 1H NMR (400 MHz, DMSO-d6) δ 1.13-1.27 (m, 2H), 1.51-1.62 (m, 2H), 1.84-1.99 (m, 3H), 2.89 (t, J = 6.21 Hz, 2H), 2.95 (d, J = 7.03 Hz, 2H), 3.17-3.32 (m, 4H), 3.74 (s, 3H), 3.81-3.90 (m, 2H), 5.25 (s, 2H), 6.92 (d, J = 8.66 Hz, 2H), 7.34 (d, J = 8.66 Hz, 2H), 8.45 (s, 1H) |
| 149 | C24H27N5O3S | 466.2 | 1H NMR (400 MHz, DMSO-d6) δ 1.18-1.33 (m, 1H), 1.40-1.54 (m, 1H), 1.54-1.64 (m, 1H), 1.71-1.82 (m, 1H), 1.87-1.99 (m, 3H), 2.85-2.97 (m, 4H), 3.16-3.23 (m, 2H), 3.68-3.79 (m, 7H), 5.26 (s, 2H), 6.93 (d, J = 8.66 Hz, 2H), 7.34 (d, J = 8.66 Hz, 2H), 8.45 (s, 1H) |

TABLE 12-continued

| Example | Structure | LC-MS (MH+) | 1H-NMR |
|---|---|---|---|
| 150 | C₂₃H₂₅N₅O₃S | 452.2 | 1H NMR (400 MHz, DMSO-d6) δ 1.50-1.61 (m, 1H), 1.90-1.99 (m, 2H), 2.86-2.93 (m, 2H), 3.01-3.07 (m, 2H), 3.17-3.25 (m, 2H), 3.39-3.44 (m, 2H), 3.69-3.79 (m, 7H), 5.26 (s, 2H), 6.92 (d, J = 8.78 Hz, 2H), 7.34 (d, J = 8.66 Hz, 2H), 8.46 (s, 1H) |
| 151 | C₂₁H₂₁F₂N₅O₂S | 446.2 | 1H NMR (400 MHz, METHANOL-d4) δ 1.47 (d, J = 6.90 Hz, 3H), 3.35-3.40 (m, 2H), 3.55-3.62 (m, 2H), 3.75-3.86 (m, 5H), 4.38-4.45 (m, 2H), 5.42 (s, 2H), 6.93 (d, J = 8.66 Hz, 2H), 7.42 (d, J = 8.66 Hz, 2H), 8.44 (s, 1H) |
| 152 | C₂₅H₂₂ClN₅O₂S | 492.0 | 1H NMR (400 MHz, CDCl3) δ 1.89-2.01 (m, 3H), 2.92 (t, J = 6.27 Hz, 2H), 3.03-3.15 (m, 2H), 3.71 (s, 3H), 4.13 (s, 2H), 5.16 (s, 2H), 6.69-6.82 (m, 2H), 7.13-7.32 (m, 8H), 8.14-8.25 (m, 1H) |

TABLE 12-continued

| Example | Structure | LC-MS (MH+) | 1H-NMR |
|---|---|---|---|
| 153 | C₂₆H₂₄ClN₅O₃S | 523.0 | 1H NMR (400 MHz, CDCl3) δ 1.95 (br s, 2H), 2.93 (s, 2H), 3.10 (br s, 2H), 3.76 (d, J = 18.57 Hz, 7H), 4.14 (s, 2H), 5.15 (s, 2H), 6.68-6.76 (m, 1H), 6.81-6.87 (m, 1H), 6.89-6.96 (m, 1H), 7.19-7.32 (m, 4H), 8.18-8.25 (m, 1H) |
| 154 | C₂₆H₂₅N₅O₃S | 488.0 | 1H NMR (400 MHz, CDCl3) δ 1.87-2.01 (m, 2H), 2.91 (t, J = 6.27 Hz, 2H), 3.11 (br s, 2H), 3.71-3.81 (m, 7H), 4.20 (s, 2H), 5.17 (s, 2H), 6.69-6.76 (m, 1H), 6.84-6.95 (m, 2H), 7.27 (d, J = 5.02 Hz, 5H), 8.24-8.30 (m, 1H) |
| 155 | C₂₆H₂₄ClN₅O₃S | 523.0 | 1H NMR (400 MHz, CDCl3) δ 1.89-2.01 (m, 2H), 2.92 (s, 2H), 3.12 (br s, 2H), 3.76 (d, J = 16.31 Hz, 6H), 4.16 (s, 2H), 5.17 (s, 2H), 6.68-6.75 (m, 1H), 6.84-6.94 (m, 2H), 7.18 (m, 3H), 8.23-8.29 (m, 1H) |

TABLE 12-continued

| Example | Structure | LC-MS (MH+) | 1H-NMR |
|---|---|---|---|
| 156 | $C_{24}H_{24}F_3N_5O_3S$ | 520.2 | 1H NMR (400 MHz, DMSO-d6) δ 1.06-1.22 (m, 2H), 1.55-1.66 (m, 2H), 1.78-1.94 (m, 1H), 2.44-2.49 (m, 2H), 3.21 (t, J = 11.86 Hz, 2H), 3.30 (t, J = 11.04 Hz, 2H), 3.77 (s, 3H), 3.79-3.87 (m, 4H), 5.39 (s, 2H), 6.75 (dd, J = 8.66, 2.51 Hz, 1H), 6.92 (dd, J = 12.55, 2.38 Hz, 1H), 7.36 (t, J = 8.85 Hz, 1H), 8.53 (s, 1H) |

Preparative Example 157

6-(4-Chlorobenzyl)-9-(pyrazine-2-carbonyl)-8,9,10,11-tetrahydropyrido[4',3': 4,5]thieno[3,2-e][1,2,4]triazolo[1,5-c]pyrimidin-5(6H)-one

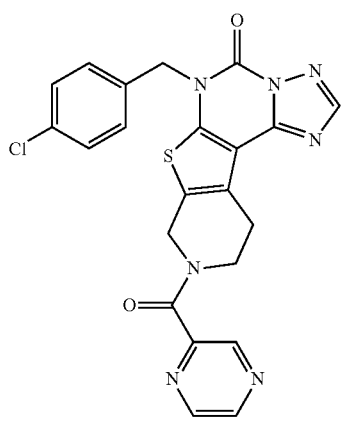

157

Step 13.1: 6-(4-chlorobenzyl)-9-(pyrazine-2-carbonyl)-8,9,10,11-tetrahydropyrido[4',3':4,5]thieno[3,2-e][1,2,4]triazolo[1,5-c]pyrimidin-5(6H)-one (13)

6-(4-Chlorobenzyl)-8,9,10,11-tetrahydropyrido[4',3':4,5]thieno[3,2-e][1,2,4]triazolo[1,5-c]pyrimidin-5(6H)-one (80 mg, 0.22 mmol), pyrazinecarboxylic acid (29 mg, 0.24 mmol), HATU (82 mg, 0.22 mmol) and triethylamine (0.090 mL, 0.65 mmol) were combined in DMF (2 mL) and stirred at room temperature for 18 hours. The mixture was filtered and purified by reverse phase HPLC to yield 157 (61 mg, 47%).

Numerous compounds were made using the above general procedure, as exemplified in Table 13:

TABLE 13
| Example | Structure | LC-MS (MH+) | 1H-NMR |
|---|---|---|---|
| 157 | 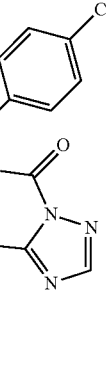 C22H16ClN7O2S | 478.1 | 1H NMR (400 MHz, DMSO-d6) δ 3.10-3.14 (m, 2H), 3.74-3.76 (m, 2H), 4.01-4.04 (m, 2H), 5.40 (s, 2H), 7.41-7.46 (m, 4H), 8.54 (s, 1H), 8.73-8.76 (m, 1H), 8.80 (m, 1H), 8.85-8.90 (m, 1H) |
| 158 | 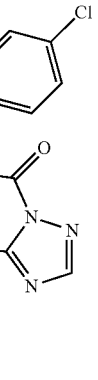 C21H18ClN5O2S | 440.1 | 1H NMR (400 MHz, DMSO-d6) δ 0.73-0.76 (m, 4H), 2.03-2.10 (m, 1H), 3.01-3.06 (m, 2H), 3.89-3.96 (m, 2H), 4.76-4.87 (m, 2H), 5.37 (s, 1H), 7.41-7.44 (m, 4H), 8.50 (s, 1H) |
| 159 |  C22H21N5O3S | 436.2 | 1H NMR (400 MHz, DMSO-d6) δ 0.74-0.75 (m, 4H), 1.95-1.98 (minor) 2.12-2.15 (major) (m, 1H), 2.94-2.96 (minor) 3.08-3.10 (major) (m, 2H), 3.79-3.81 (minor) 4.02-4.04 (major) (m, 2H), 4.66-4.68 (major) 4.95-4.97 (major) (m, 2H), 5.30 (s, 2H), 6.90-6.91 (d, J = 6.8 Hz, 2H), 7.33-7.35 (d, J = 6.8 Hz, 2H), 8.49 (s, 1H) |

TABLE 13-continued
| Example | Structure | LC-MS (MH+) | 1H-NMR |
|---|---|---|---|
| 160 | 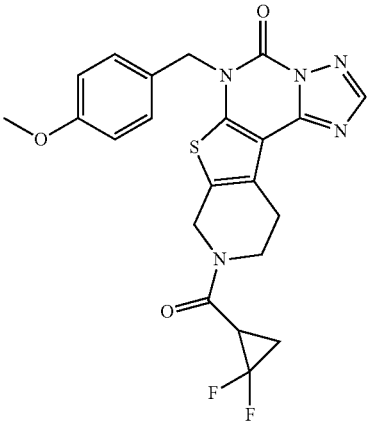<br>C₂₂H₁₉F₂N₅O₃S | 472.2 | 1H NMR (400 MHz, DMSO-d6) δ 1.86-1.96 (m, 2H), 2.97-3.05 (m, 2H), 3.31-3.34 (m, 1H), 3.72 (s, 3H), 3.82-4.00 (m, 2H), 4.69-4.82 (m, 2H), 5.30 (s, 2H), 6.89-6.91 (m, 2H), 7.33-7.35 (m, 2H), 8.50 (s, 1H) |
| 161 | 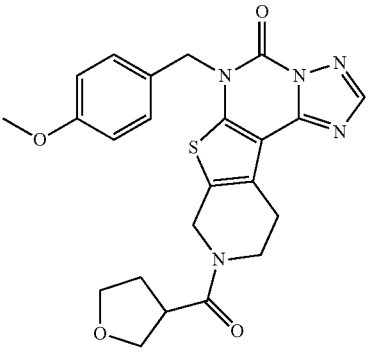<br>C₂₃H₂₃N₅O₄S | 466.1 | 1H NMR (400 MHz, DMSO-d6) δ 1.89-2.18 (m, 2H), 2.92-3.14 (m, 2H), 3.46-3.59 (m, 1H), 3.63-3.78 (m, 6H), 3.80-3.99 (m, 3H), 4.64-4.87 (m, 2H), 5.32 (s, 2H), 6.88-6.97 (m, 2H), 7.36 (d, J = 8.41 Hz, 2H), 8.51 (s, 1H) |
| 162 | 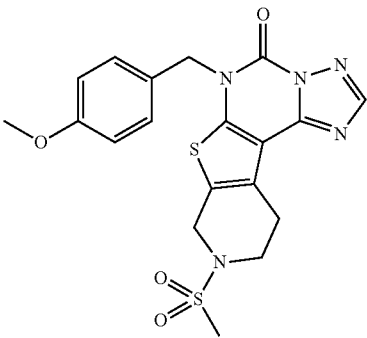<br>C₁₉H₁₉N₅O₄S₂ | 446.1 | 1H NMR (400 MHz, DMSO-d6) δ 2.96 (s, 3H), 3.09-3.12 (m, 2H), 3.54-3.57 (m, 2H), 3.72 (s, 2H), 4.46 (s, 2H), 5.31 (s, 2H), 6.90-6.92 (d, J = 7.2 Hz, 2H), 7.34-7.35 (d, J = 7.2 Hz, 2H), 8.50 (s, 1H) |

TABLE 13-continued
| Example | Structure | LC-MS (MH+) | 1H-NMR |
|---|---|---|---|
| 163 | 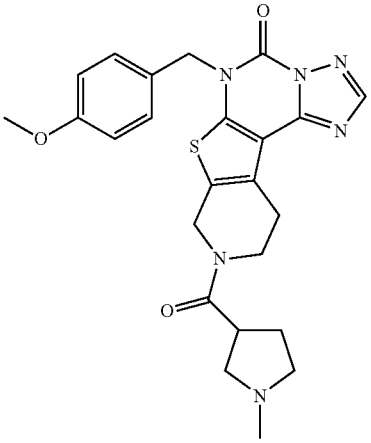 [SMILES: COc1ccc(Cn2c(=O)n3ncnc3c3c4c(sc32)CN(C(=O)[C@@H]2CCOC2)CC4)cc1 ; "C23H23N5O4S"] C24H26N6O3S | 479.2 | 1H NMR (400 MHz, DMSO-d6) δ 1.75-2.25 (m, 2H), 2.85-2.92 (m, 3H), 3.02-3.18 (m, 4H)3.20-3.38 (m, 1H), 3.52-3.61 (m, 2H), 3.72 (s, 3H), 3.81-3.90 (m, 2H), 4.65-4.85 (m, 2H), 5.29-5.35 (m, 2H), 6.90-6.92 (m, 2H), 7.34-7.36 (m, 2H), 8.55 (s, 1H) |
| 164 | 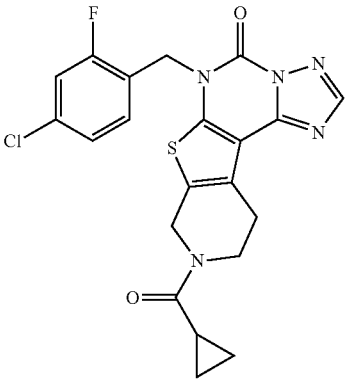 C21H17ClFN5O2S | 458.1 | 1H NMR (400 MHz, DMSO-d6) δ 0.77 (d, J = 5.52 Hz, 4H), 1.91-2.24 (m, 1H), 2.88-3.19 (m, 2H), 3.51-3.91 (m, 6H), 3.98-4.13 (m, 1H), 4.63-4.77 (m, 1H), 4.92-5.05 (m, 1H), 5.37-5.46 (m, 2H), 7.21-7.32 (m, 1H), 7.38-7.50 (m, 1H), 7.51-7.62 (m, 1H), 8.53 (s, 1H) |
| 165 | 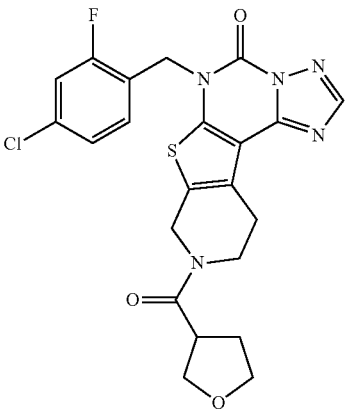 C22H19ClFN5O3S | 502.1 | 1H NMR (400 MHz, DMSO-d6) δ 1.90-2.18 (m, 2H), 2.95-3.03 (m, 1H), 3.06-3.13 (m, 1H), 3.34-3.57 (m, 2H), 3.72 (br s, 8H), 3.81-3.99 (m, 3H), 4.71 (d, J = 4.89 Hz, 1H), 4.82 (br s, 1H), 5.38-5.44 (m, 2H), 5.77 (s, 1H), 7.23-7.30 (m, 1H), 7.40-7.49 (m, 1H), 7.51-7.61 (m, 1H), 8.48-8.56 (m, 1H) |

TABLE 13-continued

| Example | Structure | LC-MS (MH+) | 1H-NMR |
|---|---|---|---|
| 166 | C₂₃H₂₁F₂N₅O₄S | 502.1 | 1H NMR (400 MHz, DMSO-d6) δ 1.89-2.18 (m, 2H), 3.53-3.63 (m, 1H), 3.65-3.73 (m, 2H), 3.75 (s, 3H), 3.84-3.98 (m, 1H), 4.21-4.34 (m, 1H), 4.41 (t, J = 11.23 Hz, 1H), 4.86 (br s, 1H), 4.99 (br s, 1H), 5.38 (d, J = 6.78 Hz, 2H), 5.77 (s, 1H), 6.94 (dd, J = 8.72, 3.33 Hz, 2H), 7.34-7.47 (m, 2H), 8.48-8.58 (m, 1H) |
| 167 | C₂₃H₂₂FN₅O₄S | 484.1 | 1H NMR (400 MHz, DMSO-d6) δ 1.91-2.17 (m, 2H), 2.94-3.02 (m, 1H), 3.05-3.12 (m, 1H), 3.47-3.56 (m, 1H), 3.65-3.75 (m, 3H), 3.77 (s, 3H), 3.81-3.97 (m, 3H), 4.68-4.85 (m, 2H), 5.36 (br s, 2H), 6.75 (dd, J = 8.53, 2.51 Hz, 1H), 6.91 (dd, J = 12.55, 2.51 Hz, 1H), 7.31 (t, J = 9.03 Hz, 1H), 8.52 (s, 1H) |
| 168 | C₂₂H₂₀FN₅O₃S | 454.1 | 1H NMR (400 MHz, DMSO-d6) δ 0.77 (d, J = 5.40 Hz, 4H), 1.96-2.21 (m, 1H), 3.07-3.16 (m, 2H), 3.77 (s, 3H), 3.80-4.09 (m, 2H), 4.66-5.03 (m, 2H), 5.36 (s, 2H), 6.75 (d, J = 8.16 Hz, 1H), 6.91 (d, J = 12.30 Hz, 1H), 7.27-7.37 (m, 1H), 8.52 (s, 1H) |

TABLE 13-continued
| Example | Structure | LC-MS (MH+) | 1H-NMR |
|---|---|---|---|
| 169 | 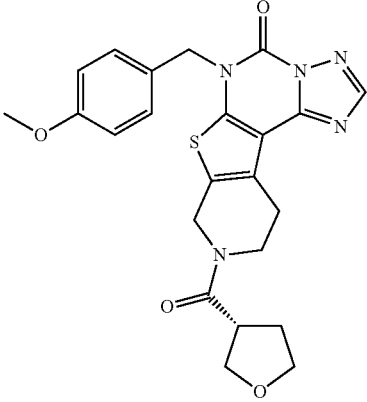<br>C₂₃H₂₃N₅O₄S | 466.1 | 1H NMR (400 MHz, DMSO-d6) δ 1.91-2.18 (m, 2H), 2.94-3.12 (m, 3H), 3.65-3.77 (m, 6H), 3.81-3.98 (m, 3H), 4.68-4.84 (m, 2H), 5.32 (s, 2H), 6.90-6.97 (m, 2H), 7.36 (d, J = 8.66 Hz, 2H), 8.52 (s, 1H) |
| 170 | 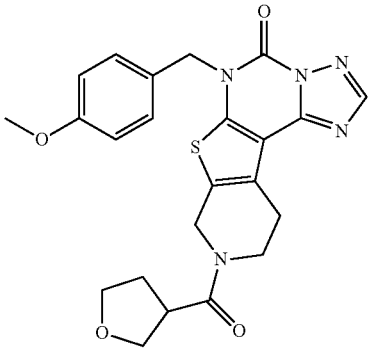<br>C₂₃H₂₃N₅O₄S | 466.1 | 1H NMR (400 MHz, DMSO-d6) δ 1.89-2.18 (m, 2H), 2.92-3.14 (m, 2H), 3.46-3.59 (m, 1H), 3.63-3.78 (m, 6H), 3.80-3.99 (m, 3H), 4.64-4.87 (m, 2H), 5.32 (s, 2H), 6.88-6.97 (m, 2H), 7.36 (d, J = 8.41 Hz, 2H), 8.51 (s, 1H) |
| 171 | 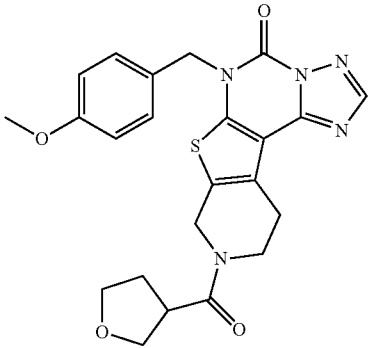<br>C₂₃H₂₃N₅O₄S | 466.1 | 1H NMR (400 MHz, DMSO-d6) δ 1.89-2.18 (m, 2H), 2.92-3.14 (m, 2H), 3.46-3.59 (m, 1H), 3.63-3.78 (m, 6H), 3.80-3.99 (m, 3H), 4.64-4.87 (m, 2H), 5.32 (s, 2H), 6.88-6.97 (m, 2H), 7.36 (d, J = 8.41 Hz, 2H), 8.51 (s, 1H) |

TABLE 13-continued
| Example | Structure | LC-MS (MH+) | 1H-NMR |
|---|---|---|---|
| 172 | 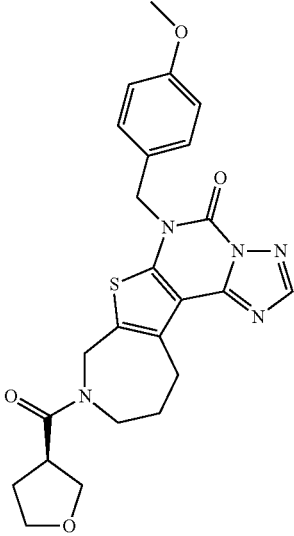<br>C₂₄H₂₅N₅O₄S | 481.2 | 1H NMR (400 MHz, DMSO-d6) δ 1.73-2.10 (m, 4H), 3.42 (br s, 3H), 3.57-3.70 (m, 3H), 3.71-3.93 (m, 6H), 4.58-4.65 (m, 1H), 4.80-4.86 (m, 1H), 5.29 (s, 2H), 6.93 (d, J = 8.28 Hz, 2H), 7.33-7.42 (m, 2H), 8.50 (s, 1H) |
| 173 | 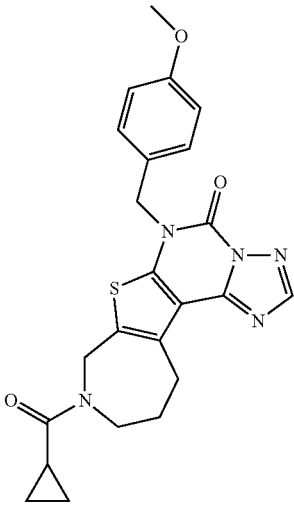<br>C₂₃H₂₃N₅O₃S | 451.2 | 1H NMR (400 MHz, DMSO-d6) δ 0.56-0.73 (m, 4H), 1.74-1.86 (m, 1H), 1.90-2.06 (m, 2H), 3.38-3.43 (m, 2H), 3.74 (s, 3H), 3.77-3.84 (m, 1H), 3.99-4.09 (m, 1H), 4.57-4.66 (m, 1H), 4.90-4.98 (m, 1H), 5.25-5.35 (m, 2H), 6.93 (d, J = 8.28 Hz, 2H), 7.38 (d, J = 8.28 Hz, 2H), 8.50 (s, 1H) |
| 174 | 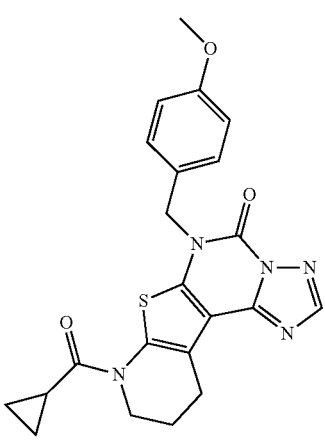<br>C₂₂H₂₁N₅O₃S | 436.2 | 1H NMR (400 MHz, DMSO-d6) δ 0.88-0.97 (m, 4H), 2.06-2.29 (m, 3H), 3.04-3.12 (m, 2H), 3.73 (s, 3H), 4.13-4.24 (m, 2H), 5.32 (s, 2H), 6.92 (d, J = 8.66 Hz, 2H), 7.32 (d, J = 8.66 Hz, 2H), 8.51 (s, 1H) |

TABLE 13-continued
| Example | Structure | LC-MS (MH+) | 1H-NMR |
|---|---|---|---|
| 175 | 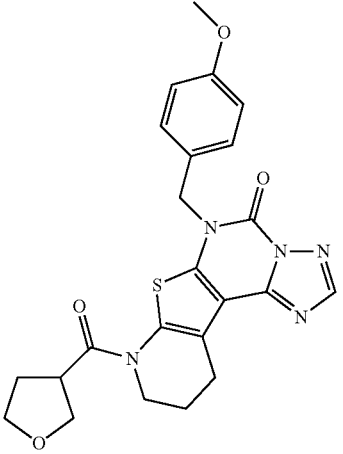<br>C₂₃H₂₃N₅O₄S | 466.2 | 1H NMR (400 MHz, DMSO-d6) δ 2.01-2.22 (m, 4H), 3.07 (t, J = 6.09 Hz, 2H), 3.61-3.86 (m, 7H), 3.90-4.08 (m, 3H), 5.34 (s, 2H), 6.93 (d, J = 8.66 Hz, 2H), 7.34 (d, J = 8.66 Hz, 2H), 8.51 (s, 1H) |
| 176 | 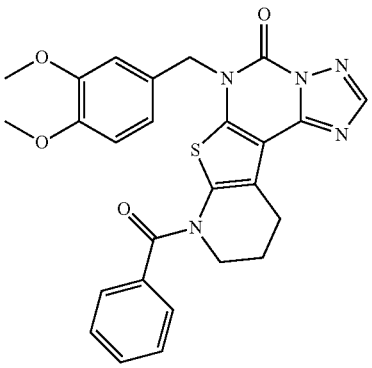<br>C₂₆H₃₃N₅O₄S | 502.0 | 1H NMR (400 MHz, CDCl3) δ 1.98-2.11 (m, 2H), 3.11 (s, 2H), 3.78 (d, J = 9.79 Hz, 6H), 3.86 (br s, 2H), 5.33 (s, 2H), 6.70-6.79 (m, 1H), 7.05-7.12 (m, 2H), 7.43 (s, 5H), 8.25-8.32 (m, 1H) |
| 177 | 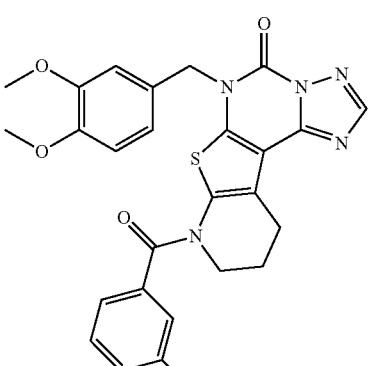<br>C₂₆H₂₂ClN₅O₄S | 537.0 | 1H NMR (400 MHz, CDCl3) δ 2.06 (d, J = 5.77 Hz, 2H), 3.13 (s, 2H), 3.72-3.83 (m, 8H), 5.32 (s, 2H), 6.75 (s, 2H), 7.07 (s, 1H), 7.27-7.33 (m, 1H), 7.33-7.41 (m, 1H), 7.42 (s, 2H), 8.21-8.28 (m, 1H) |

TABLE 13-continued

| Example | Structure | LC-MS (MH+) | 1H-NMR |
|---|---|---|---|
| 178 | 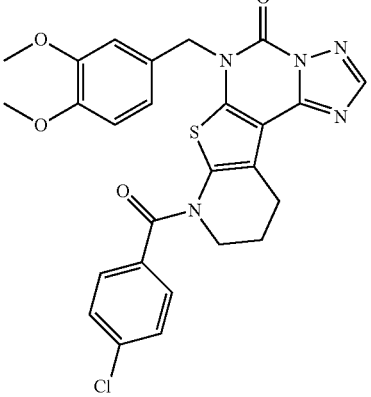<br>C26H22ClN5O4S | 537.0 | 1H NMR (400 MHz, CDCl3) δ 1.98-2.11 (m, 2H), 3.09-3.17 (m, 2H), 3.77 (d, J = 9.29 Hz, 8H), 5.32 (s, 2H), 6.70-6.77 (m, 1H), 7.04-7.11 (m, 2H), 7.34-7.45 (m, 4H), 8.24-8.31 (m, 1H) |

Preparative Example 179

6-(4-Methoxybenzyl)-9-(pyridin-2-yl)-8,9,10,11-tetrahydropyrido[4',3': 4,5]thieno[3,2-e][1,2,4]triazolo[1,5-c]pyrimidin-5(6H)-one

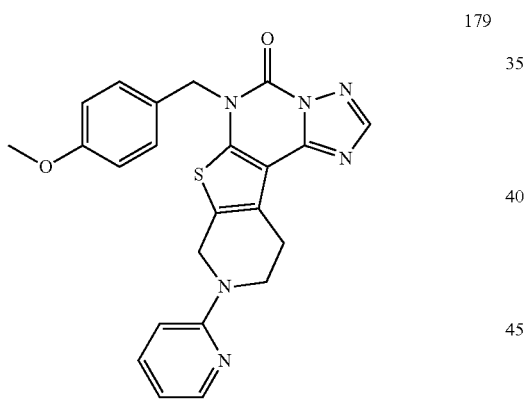

179

Step 14.1: 6-(4-methoxybenzyl)-9-(85mygdale-2-yl)-8,9,10,11-tetrahydropyrido[4',3':4,5]thieno[3,2-e][1,2,4]triazolo[1,5-c]pyrimidin-5(6H)-one (179)

6-(4-Methoxybenzyl)-8,9,10,11-tetrahydropyrido[4',3':4,5]thieno[3,2-e][1,2,4]triazolo[1,5-c]pyrimidin-5(6H)-one (50 mg, 0.14 mmol), 2-fluoropyridine (40 mg, 0.41 mmol) were combined DMF (2 mL) and heated at 160° C. by microwave for 1 h. The mixture was filtered and purified by reverse phase HPLC to yield 179 (30 mg, 39%).

Numerous compounds can be made using the above general procedure, including the following in Table 14:

TABLE 14

| Example | Structure | LC-MS (MH+) | 1H-NMR |
|---|---|---|---|
| 179 | $C_{23}H_{20}N_6O_2S$ | 445.1 | 1H NMR (400 MHz, DMSO-d6) δ 3.08-3.11 (m, 2H), 3.72 (s, 3H), 3.97-4.00 (m, 2H), 4.83 s, 2H), 5.31 (s, 2H), 6.74-6.76 (m, 1H), 6.90-6.91 (d, J = 5.2 Hz, 2H), 7.12-7.13 (m, 1H), 7.34-7.36 (d, J = 5.2 Hz, 2H), 7.69-7.72 (m, 1H), 8.10-8.11 (m, 1H), 8.49 (s, 1H) |

Preparative Example 180

6-(4-Methoxybenzyl)-9-(morpholin-2-ylmethyl)-8,9,10,11-tetrahydropyrido[4',3': 4,5]thieno[3,2-e][1,2,4]triazolo[1,5-c]pyrimidin-5(6H)-one

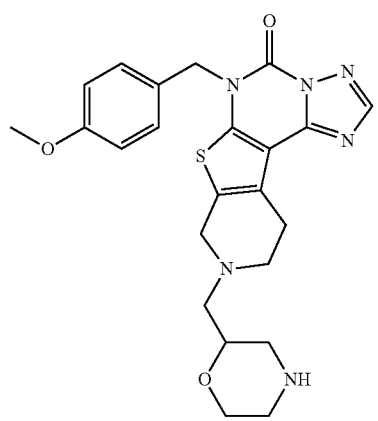

180

Step 15.1: 6-(4-methoxybenzyl)-9-(morpholin-2-ylmethyl)-8,9,10,11-tetrahydropyrido[4',3':4,5]thieno[3,2-e][1,2,4]triazolo[1,5-c]pyrimidin-5(6H)-one (180)

Tert-Butyl 2-((6-(4-methoxybenzyl)-5-oxo-5,6,10,11-tetrahydropyrido[4',3':4, 5]thieno[3,2-e][1,2,4]triazolo[1,5-c]pyrimidin-9(8H)-yl)methyl)morpholine-4-carboxylate (prepared according to Example 13, 75 mg, 0.13 mmol) was dissolved in 4M hydrogen chloride in dioxane (5 ml). The resulting mixture was stirred at room temperature for 4 hours. The crude mixture was concentrated, taken up methanol, filtered and purified by reverse-phase HPLC. The product was dissolved in methanol (1 mL) and passed through an ion exchange resin cartridge while washing with 10% methanolic ammonia solution. The collected solution was concentrated under reduced pressure to yield 33 mg (53%) of 180.

Numerous compounds were made using the above general procedure, as exemplified in Table 15:

TABLE 15

| Example | Structure | LC-MS (MH+) | 1H-NMR |
|---|---|---|---|
| 180 | $C_{23}H_{26}N_6O_3S$ | 467.2 | 1H NMR (500 MHz, DMSO-d6) δ 2.56-2.76 (m, 4H), 2.81-2.93 (m, 4H), 2.93-3.00 (m, 2H), 3.11-3.15 (m, 2H), 3.72 (s, 3H), 3.80-3.93 (m, 3H), 5.30 (s, 2H), 6.91 (d, J = 8.30 Hz, 2H), 7.34 (d, J = 8.82 Hz, 3H), 8.49 (s, 1H) |

TABLE 15-continued

| Example | Structure | LC-MS (MH+) | 1H-NMR |
|---|---|---|---|
| 181 | C₂₃H₂₄N₆O₃S | 465.1 | 1H NMR (400 MHz, DMSO-d6) δ 1.80-2.02 (m, 1H), 2.15-2.37 (m, 1H), 2.69 (d, J = 1.88 Hz, 1H), 3.01 (br s, 1H), 3.09-3.26 (m, 4H), 3.27-3.50 (m, 3H), 3.52-3.96 (m, 16H), 4.65-4.78 (m, 1H), 4.79-4.89 (m, 1H), 5.33 (s, 1H), 6.89-6.98 (m, 2H), 7.33-7.42 (m, 2H), 8.51-8.56 (m, 1H), 8.68-8.91 (m, 2H) |
| 182 | C₂₄H₂₈N₆O₂S | 465.2 | 1H NMR (400 MHz, DMSO-d6) δ 1.28-1.47 (m, 2H), 1.86-2.00 (m, 2H), 2.05-2.23 (m, 1H), 2.79-2.94 (m, 3H), 3.18 (br s, 3H), 3.24-3.37 (m, 5H), 3.40-3.59 (m, 2H), 3.75 (s, 4H), 4.25-4.52 (m, 2H), 4.57-4.87 (m, 1H), 5.36 (br s, 2H), 6.88-6.98 (m, 2H), 7.31-7.42 (m, 2H), 8.32-8.49 (m, 1H), 8.52-8.59 (m, 1H), 8.60-8.72 (m, 1H) |

Preparative Example 183

4-(4-Methoxybenzyl)-2-(morpholinomethyl)pyrazolo[1,5-c]thieno[3,2-e]pyrimidin-5(4H)-one

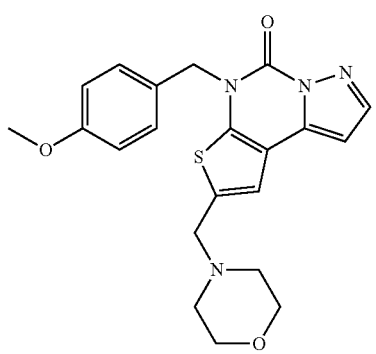

183

Step 16.1: 5-nitro-4-(1H-pyrazol-3-yl)thiophene-2-carbaldehyde

A flask containing 4-bromo-5-nitrothiophene-2-carbaldehyde (1.00 g, 4.24 mmol), (1H-pyrazol-5-yl)boronic acid (510 mg, 4.56 mmol), ethyleneglycol dimethyl ether (20 mL), triethylamine (1.80 mL), water (2.00 mL) and bis(diphenylphosphino)ferrocene]dichloropalladium(II) complex with dichloromethane (340 mg, 0.42 mmol) was evacuated and purged with nitrogen twice, then heated at 80 OC under nitrogen for 4 h. The reaction was cooled to room temperature, poured into a saturated solution of ammonium chloride (20 mL), extracted with ethyl acetate (3×10 mL), combined organics washed with a saturated solution of ammonium chloride (30 mL), dried ($Na_2SO_4$) and concentrated under reduced pressure. The crude product was purified by flash chromatography, eluting with ethyl acetate in hexanes, to yield 5-nitro-4-(1H-pyrazol-3-yl)thiophene-2-carbaldehyde as a yellow oil (950 mg, 28%). 1H NMR (400 MHZ, DMSO-d6) δ 6.99 (s, 1H), 7.94 (s, 1H), 8.42 (s, 1H), 10.07 (s, 1H).

Step 16.2: 5-amino-4-(1H-pyrazol-3-yl)thiophene-2-carbaldehyde

5-Nitro-4-(1H-pyrazol-5-yl)thiophene-2-carbaldehyde (40 mg, 0.18 mmol) was dissolved in absolute ethanol (4 mL). A saturated solution of sodium hydrosulfite in water was added dropwise until complete consumption of the starting material (10 minutes). Water (30 mL) added, the aqueous layer extracted with ethyl acetate (3×10 mL), and the resulting organics were dried (Na$_2$SO$_4$) and concentrated under reduced pressure. The crude product was purified by flash chromatography, eluting with ethyl acetate in hexanes, to yield 5-amino-4-(1H-pyrazol-3-yl)thiophene-2-carbaldehyde as a powder (11 mg, 42%). 1H NMR (400 MHZ, DMSO-d6) δ 6.60 (d, J 2.3 Hz, 1H), 7.80 (d, J 2.3 Hz, 1H), 8.02 (s, 1H), 9.49 (s, 1H).

Step 16.3: 5-oxo-4,5-dihydropyrazolo[1,5-c]thieno[3,2-e]pyrimidine-2-carbaldehyde 5-Amino-4-(1H-pyrazol-5-yl)thiophene-2-carbaldehyde (12 mg, 0.06 mmol) and bis(trichloromethyl) carbonate (55 mg, 0.19 mmol) were dissolved in toluene (3 mL) and THF (0.5 mL), and the reaction heated in a sealed tube at 100° C. for 3 h. The reaction was cooled to room temperature, hexanes (10 mL) added, suspension stirred at room temperature for 30 min, precipitate washed with additional hexanes (10 mL), dried under reduced pressure to yield 5-oxo-4,5-dihydropyrazolo[1,5-c]thieno[3,2-e]pyrimidine-2-carbaldehyde as a powder (11 mg, 81%). 1H NMR (400 MHZ, DMSO-d6) δ 6.99 (s, 1H), 8.12 (s, 1H), 8.45 (s, 1H), 9.93 (s, 1H), 13.06 (s, 1H).

Step 16.4: 4-(4-methoxybenzyl)-5-oxo-4,5-dihydropyrazolo[1,5-c]thieno[3,2-e]pyrimidine-2-carbaldehyde 5-Oxo-4,5-dihydropyrazolo[1,5-c]thieno[3,2-e]pyrimidine-2-carbaldehyde (30 mg, 0.14 mmol) was dissolved in N,N-dimethylformamide (3.0 mL), 1-(chloromethyl)-4-methoxybenzene (0.04 ml, 0.27 mmol) and potassium carbonate (57 mg, 0.41 mmol) were added and the reaction stirred at 60° C. for 5 h. Reaction poured into saturated ammonium chloride solution (20 mL), extracted with ethyl acetate (3×10 mL), organics washed with saturated ammonium chloride solution (20 mL), dried (Na$_2$SO$_4$) and concentrated under reduced pressure. The crude product was purified by flash chromatography, eluting with ethyl acetate in hexanes, to yield 4-(4-methoxybenzyl)-5-oxo-4,5-dihydropyrazolo[1,5-c]thieno[3,2-e]pyrimidine-2-carbaldehyde as a powder (16 mg, 89%). 1H NMR (400 MHz, acetone-d6) δ 3.80 (s, 3H), 5.46 (s, 2H), 6.92-7.00 (m, 3H), 7.51 (d, J=8.66 Hz, 2H), 8.08 (d, J=1.76 Hz, 1H), 8.37, (s, 1H), 9.94 (s, 1H).

Step 16.5: 4-(4-methoxybenzyl)-2-(morpholinomethyl)pyrazolo[1,5-c]thieno[3,2-e]pyrimidin-5(4H)-one 4-(4-Methoxybenzyl)-5-oxo-4,5-dihydropyrazolo[1,5-c]thieno[3,2-e]pyrimidine-2-carbaldehyde (16 mg, 0.05 mmol) was dissolved in dichloromethane (2 mL). Morpholine (0.020 mL, 0.24 mmol) and acetic acid (0.04 mL) were added and the mixture was stirred for 10 minutes before the addition of sodium cyanoborohydride (6 mg, 0.09 mmol). The reaction was stirred at room temperature for an additional 15 hours, poured into a saturated solution of aqueous sodium bicarbonate (20 mL), and extracted with ethyl acetate (3×10 mL). The combined extracts were dried (Na$_2$SO$_4$) and concentrated under reduced pressure. The residue was purified by HPLC to give 183 as a powder (11 mg, 45%).

Numerous compounds were made using the above general procedure, as exemplified in Table 16:

TABLE 16

| Example | Structure | LC-MS (MH+) | 1H-NMR |
|---|---|---|---|
| 183 | C$_{21}$H$_{22}$N$_4$O$_3$S | 411.1 | 1H NMR (400 MHz, Acetone) δ 3.42 (br s, 4H), 3.79 (s, 3H), 3.99 (br s, 4H), 4.70 (s, 2H), 5.32 (s, 2H), 6.77 (br s, 1H), 6.92 (d, J = 8.66 Hz, 2H), 7.44 (d, J = 8.53 Hz, 2H), 7.76 (s, 1H), 8.08 (br s, 1H) |
| 184 | C$_{23}$H$_{26}$N$_4$O$_3$S | 439.3 | 1H NMR (400 MHz, DMSO-d6) δ 1.03 (d, J = 6.27 Hz, 6H), 1.70 (t, J = 10.67 Hz, 2H), 2.75 (d, J = 10.42 Hz, 2H), 3.51-3.59 (m, 2H), 3.66 (s, 2H), 3.73 (s, 3H), 5.29 (s, 2H), 6.84 (d, J = 1.76 Hz, 1H), 6.93 (d, J = 8.66 Hz, 2H), 7.35 (d, J = 8.66 Hz, 2H), 7.40 (s, 1H), 8.05-8.14 (m, 1H) |

147

Compounds of Formula II

In a first embodiment, the invention provides a compound of Formula II:

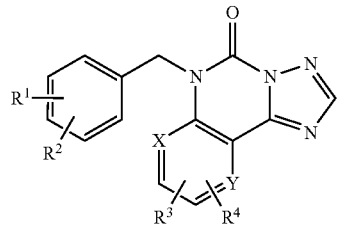

or a pharmaceutically acceptable salt thereof, wherein

X and Y are independently nitrogen or carbon, but at least one is nitrogen;

M=0-4;

each occurrence of $R^1$ and $R^2$ is independently selected from H, halo, aryl, heteroaryl, heterocycle, —CN, —($C_1$-$C_6$ alkyl) aryl, —($C_1$-$C_6$ alkyl) heteroaryl, —CN, $C_1$-$C_6$ alkyl, $C_1$-$C_6$ thioalkyl, $C_1$-$C_6$ thiohaloalkyl, $C_1$-$C_6$ haloalkyl, $C_2$-$C_6$ alkenyl, $C_2$-$C_6$ alkynyl, —OH, $C_1$-$C_6$ alkoxy, $C_1$-$C_6$ haloalkoxy, —$NO_2$, —$SO_2C_1$-$C_6$ alkyl, —$SOC_1$-$C_6$ alkyl, —$SO_2NH(C_1$-$C_6$ alkyl), —$SO_2N(C_1$-$C_6$ alkyl)$_2$, —CONH($C_1$-$C_6$ alkyl), —CON($C_1$-$C_6$ alkyl)$_2$, —C(O)O($C_1$-$C_6$ alkyl), —C(O)O($C_1$-$C_6$ alkyl)aryl, —OC(O)($C_1$-$C_6$ alkyl), —OC(O)($C_1$-$C_6$ alkyl)aryl, —$SO_2NH_2$, —$CONH_2$, —$CO_2H$, —COH, —$NH_2$, $C_1$-$C_6$ alkylamino, di-$C_1$-$C_6$ alkylamino, —$N_3$, cyanate, isocyanate, thiocyanate, isothiocyanate, —($C_2$-$C_6$ alkenyl)O($C_1$-$C_6$ alkyl), —($C_1$-$C_6$ alkyl)O($C_1$-$C_6$ alkyl), —($C_1$-$C_6$ alkyl)O($C_1$-$C_6$ alkyl)O($C_1$-$C_6$ alkyl), aryloxy, arylthio, —CO($C_1$-$C_6$ alkyl), —CO(aryl), —CO(heteroaryl), and —CO(heterocycle);

or $R^1$ and $R^2$ are on adjacent carbons and taken together with the carbons to which they are attached form a 5-6 member saturated or unsaturated monocylic ring system comprising one or more oxygen or nitrogen atoms, preferably 1-2 oxygens, wherein the ring system is optionally substituted with one or more groups selected from halo, $C_1$-$C_6$ alkyl; $C_1$-$C_6$ alkoxy; and $C_1$-$C_6$ haloalkoxy;

$R^3$ and $R^4$ are independently selected from H, halo, —CN, $C_1$-$C_6$ alkyl, $C_1$-$C_6$ haloalkyl, —OH, $C_1$-$C_6$ alkoxy, $C_1$-$C_6$ haloalkoxy, aryl, heteroaryl, —($C_1$-$C_6$ alkyl) aryl, —($C_1$-$C_6$ alkyl) heteroaryl, —$NO_2$, —$SO_2C_1$-$C_6$ alkyl, —$SO_2N(C_1$-$C_6$ alkyl)$_2$, —CONH($C_1$-$C_6$ alkyl), —CON($C_1$-$C_6$ alkyl)$_2$; —($CR^7R^8$)$_{0-3}NR^5R^6$ in which $R^5$ and $R^6$ and the nitrogen to which they are attached may form a ring taken from azetidine, pyrollidine, piperidine, homopiperidine, morpholine, morpholinone, homomorpholine, homomorpholinone, piperazine, piperazinone, homopiperazine and homopiperazinone with the ring optionally substituted with up to three independent occurrences of $R^1$, and more specifically with aryl or heteroaryl, either optionally substituted with one or more halo, —CN, $C_1$-$C_6$ alkyl, OH, $C_1$-$C_6$ alkoxy, $C_1$-$C_6$ haloalkoxy, —$NO_2$, —$SO_2C_1$-$C_6$ alkyl;

or $R^3$ and $R^4$ taken together with the carbons to which they are attached form a 5-6 member monocylic ring system comprising one or more oxygen atoms;

$R^5$, $R^6$, $R^7$, and $R^8$ are independently selected from H, F, $C_1$-$C_6$ alkyl, $C_1$-$C_6$ haloalkyl, OH, $C_1$-$C_6$ alkoxy, —$C_1$-$C_6$ haloalkoxy, —$SO_2C_1$-$C_6$ alkyl, —$SO_2N(C_1$-$C_6$ alkyl)$_2$, —$CO_2(C_1$-$C_6$ alkyl), —$CO_2CH_2C_6H_5$, —CONH($C_1$-$C_6$ alkyl), and —CON($C_1$-$C_6$ alkyl)$_2$;

148 or any two of $R^5$, $R^6$, $R^7$, and $R^8$ taken together with the atoms to which they are attached form a 3-7 member monocyclic ring containing up to two heteroatoms selected from nitrogen, oxygen, and sulfur.

In a specific aspect, a compound of Formula II corresponding to the first embodiment may include one or more of the following: M=1 or 2; one or more of $R^1$, $R^2$, $R^3$, and $R^4$ is halo, more particularly, halomethyl; X is N and Y is CH; one or more of $R^1$, $R^2$, $R^3$, and $R^4$ is halo, more particularly, halomethyl; $R^1$ is H and $R^2$ is —$C_1$-$C_6$ alkoxy, more specifically —$OCH_3$; $R^1$ is halo, more specifically F, Cl, or Br, and $R^2$ is $C_1$-$C_6$ alkoxy; $R^1$ is F, Cl, or Br and $R^2$ is —$CF_3$ or —$CHF_2$; $R^3$ is $C_1$-$C_6$ alkyl, more specifically methyl, and $R^4$ is H.

In second embodiment, the invention provides a compound of Formula II, or a pharmaceutically acceptable salt thereof, wherein:

X and Y are independently nitrogen or carbon, but at least one is nitrogen;

M=0-4;

each occurrence of $R^1$ and $R^2$ is independently selected from H, halo, —CN, $C_1$-$C_3$ alkyl, $C_1$-$C_3$ haloalkyl, OH, $C_1$-$C_3$ alkoxy, $C_1$-$C_3$ haloalkoxy, —$NO_2$, —$SO_2C_1$-$C_3$ alkyl, —$SO_2N(C_1$-$C_3$ alkyl)$_2$, —CONH($C_1$-$C_3$ alkyl), —CON($C_1$-$C_3$ alkyl)$_2$, aryl, and heteroaryl;

or $R^1$ and $R^2$ are on adjacent carbons and taken together with the carbons to which they are attached form a 5-6 member monocylic ring system comprising one or more oxygen atoms, preferably 1-2 oxygens, wherein the ring system is optionally substituted with one or more groups selected from halo, preferably F; $C_1$-$C_3$ alkyl; $C_1$-$C_3$ alkoxy; and $C_1$-$C_3$ haloalkoxy;

$R^3$ and $R^4$ are independently selected from H, halo, —CN, $C_1$-$C_3$ alkyl, $C_1$-$C_3$ haloalkyl, OH, $C_1$-$C_3$ alkoxy, $C_1$-$C_3$ haloalkoxy, —$NO_2$, —$SO_2C_1$-$C_3$ alkyl, —$SO_2N(C_1$-$C_3$ alkyl)$_2$, —CONH($C_1$-$C_3$ alkyl), —CON($C_1$-$C_3$ alkyl)$_2$, —($CR^7R^8$)$_{0-3}NR^5R^6$; and aryl or heteroaryl, either optionally substituted with one or more groups selected from halo, CN, $C_1$-$C_3$ alkyl, OH, $C_1$-$C_3$ alkoxy, —$C_1$-$C_3$ haloalkoxy, —$NO_2$, and —$SO_2C_1$-$C_3$ alkyl;

or $R^3$ and $R^4$ taken together with the carbons to which they are attached form a 5-6 member monocylic ring system comprising one or more oxygen atoms;

$R^5$, $R^6$, $R^7$, and $R^8$ are independently selected from H, F, $C_1$-$C_3$ alkyl, $C_1$-$C_3$ haloalkyl, OH, $C_1$-$C_3$ alkoxy, $C_1$-$C_3$ haloalkoxy, —$SO_2C_1$-$C_3$ alkyl, —$SO_2N(C_1$-$C_3$ alkyl)$_2$, —CONH($C_1$-$C_3$ alkyl), and —CON($C_1$-$C_3$ alkyl)$_2$;

or any two of $R^5$, $R^6$, $R^7$, and $R^8$ taken together with the atoms to which they are attached form a 3-7 member monocyclic ring containing up to two heteroatoms selected from nitrogen, oxygen, and sulfur.

In a specific aspect, a compound of Formula II, corresponding to the second embodiment, may include one or more of the following: M=1 or 2; one or more of $R^1$, $R^2$, $R^3$, and $R^4$ is halo, more particularly, halomethyl; X is N and Y is CH; one or more of $R^1$, $R^2$, $R^3$, and $R^4$ is halo, more particularly, halomethyl; $R^1$ is H and $R^2$ is $C_1$-$C_3$ alkoxy; $R^1$ is halo, more specifically F, Cl, or Br, and $R^2$ is $C_1$-$C_3$ alkoxy; $R^1$ is F, Cl, or Br and $R^2$ is —$CF_3$ or —$CHF_2$; $R^3$ is $C_1$-$C_3$ alkyl, more specifically methyl, and $R^4$ is H.

In other embodiments, the invention provides a compound of Formula II (or pharmaceutical composition thereof) wherein any of $R^1$ through $R^{11}$ is independently selected from H, halo, aryl, heteroaryl, heterocycle, —CN, $C_1$-$C_6$ alkyl, $C_1$-$C_6$ thioalkyl, $C_1$-$C_6$ thiohaloalkyl, $C_1$-$C_6$ haloalkyl, $C_2$-$C_6$ alkenyl, $C_2$-$C_6$ alkynyl, —OH, $C_1$-$C_6$ alkoxy, $C_1$-$C_6$ haloalkoxy, —$NO_2$, —$SO_2C_1$-$C_6$ alkyl, —$SOC_1$-$C_6$ alkyl, —$SO_2NH(C_1$-$C_6$ alkyl), —$SO_2N(C_1$-$C_6$ alkyl)$_2$, —CONH(C$_1$-C$_6$ alkyl), —CON(C$_1$-C$_6$ alkyl)$_2$, —C(O)O(C$_1$-C$_6$ alkyl), —C(O)O(C$_1$-C$_6$ alkyl)aryl, —OC(O)(C$_1$-C$_6$ alkyl), —OC(O)(C$_1$-C$_6$ alkyl)aryl, —SO$_2$NH$_2$, —CONH$_2$, —CO$_2$H, —COH, —NH$_2$, C$_1$-C$_6$ alkylamino, di-C$_1$-C$_6$ alkylamino, —N$_3$, cyanate, isocyanate, thiocyanate, isothiocyanate, —(C$_2$-C$_6$ alkenyl)O(C$_1$-C$_6$ alkyl), —(C$_1$-C$_6$ alkyl)O(C$_1$-C$_6$ alkyl), —(C$_1$-C$_6$ alkyl)O(C$_1$-C$_6$ alkyl)O(C$_1$-C$_6$ alkyl), aryloxy, arylthio, —CO(C$_1$-C$_6$ alkyl), —CO(aryl), —CO(heteroaryl), and —CO(heterocycle).

More particularly, the invention provides a compound of Formula II (or pharmaceutical compositions thereof) wherein any of R$^1$ through R$^{11}$ is independently selected from H, halo, aryl, heteroaryl, heterocycle, —CN, C$_1$-C$_3$ alkyl, C$_1$-C$_6$ thioalkyl, C$_1$-C$_{63}$ thiohaloalkyl, C$_1$-C$_3$ haloalkyl, C$_2$-C$_6$ alkenyl, C$_2$-C$_6$ alkynyl, —OH, C$_1$-C$_3$ alkoxy, C$_1$-C$_3$ haloalkoxy, —NO$_2$, —SO$_2$C$_1$-C$_3$ alkyl, —SOC$_1$-C$_3$ alkyl, —SO$_2$NH(C$_1$-C$_3$ alkyl), —SO$_2$N(C$_1$-C$_3$ alkyl)$_2$, —CONH(C$_1$-C$_3$ alkyl), —CON(C$_1$-C$_3$ alkyl)$_2$, —C(O)O(C$_1$-C$_3$ alkyl), —C(O)O(C$_1$-C$_3$ alkyl)aryl, —OC(O)(C$_1$-C$_3$ alkyl), —OC(O)(C$_1$-C$_3$ alkyl)aryl, —SO$_2$NH$_2$, —CONH$_2$, —CO$_2$H, —COH, —NH$_2$, C$_1$-C$_3$ alkylamino, di-C$_1$-C$_3$ alkylamino, —N$_3$, cyanate, isocyanate, thiocyanate, isothiocyanate, —(C$_2$-C$_6$ alkenyl)O(C$_1$-C$_3$ alkyl), —(C$_1$-C$_3$alkyl)O(C$_1$-C$_3$ alkyl), —(C$_1$-C$_3$ alkyl)O(C$_1$-C$_3$ alkyl)O(C$_1$-C$_3$ alkyl), aryloxy, arylthio, —CO(C$_1$-C$_3$ alkyl), —CO(aryl), —CO(heteroaryl), and —CO(heterocycle).

Synthetic Examples

Compounds of Formula II can be prepared using the general synthetic schemes illustrated below. Amino-cyanoazines XXVII can be alkoxyformylated with ethyl or methyl chloroformate and the resulting carbonate, when heated with formylhydrazine affords the triazolopyrimidinone (Scheme 7). This compound can be treated with a suitable benzylic electrophile XXX, in which L is a leaving group such as chloride, bromide, methanesulfonate, etc. to afford target compounds.

Scheme 7

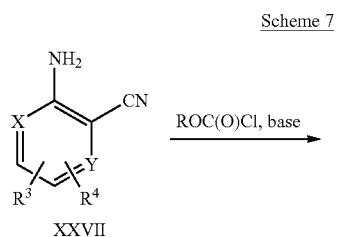

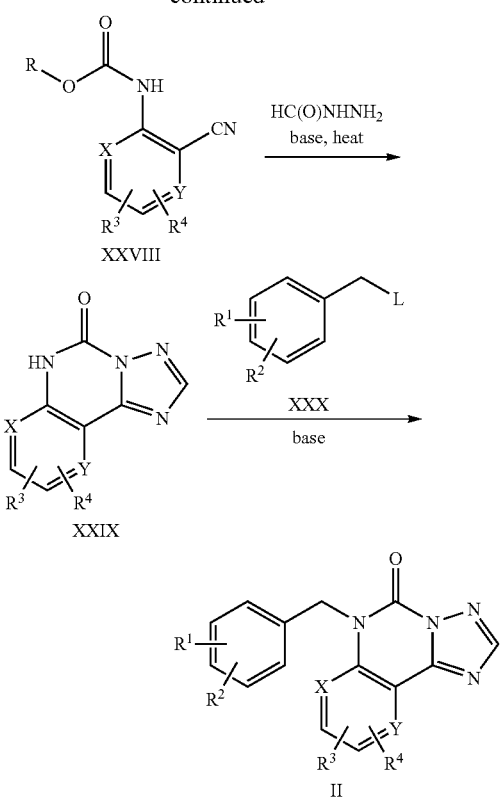

When R$^3$ or R$^4$ is bromine, this group can be converted to an aliphatic, aromatic or amino-based side chain via palladium or copper catalyzed couplings according to Scheme 8. Reaction with an organometallic reagent R3-M, in which M represents a metal or metalloid and encompassing ligands, allows introduction of aromatic, vinylogous and aliphatic groups. A subclass of this transformation is the reaction of aminomethyl(trifluoroborates) with XXXI to provide amines XXXIII. Heating XXXI with amines in the presence of a suitable catalyst affords compound XXXII. Similarly, the transformations depicted in Scheme 2 can be performed on intermediates XXVII, XXVII or XXIX of Scheme 7, when they are substituted with bromine, and the resulting products carried through the sequence as described.

Scheme 8

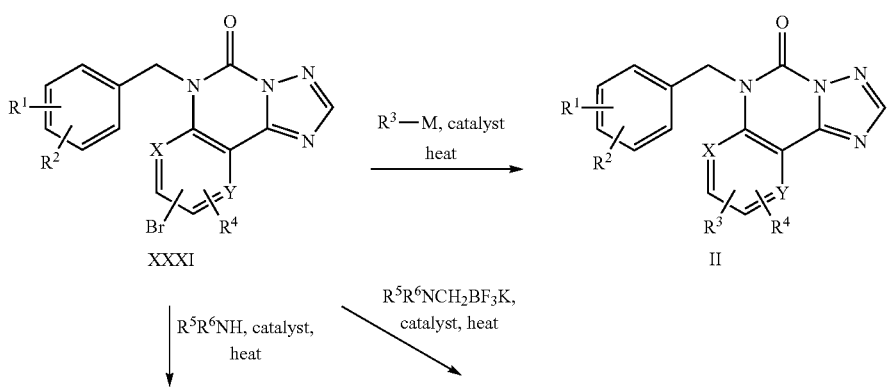

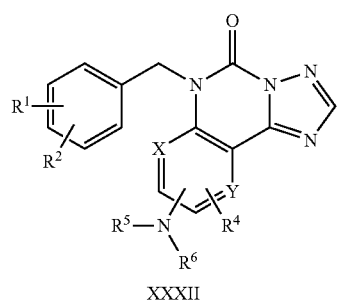

XXXII

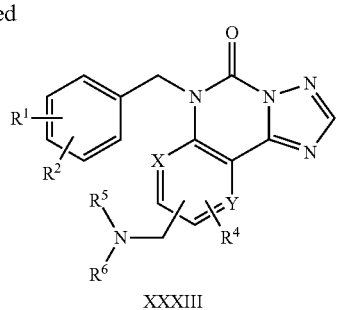

XXXIII

Bromide XXXI can be converted to an aldehyde directly by heating with carbon monoxide and heat under pressure, or in a two step procedure by a palladium catalyzed coupling reaction with potassium trifluoro(vinyl)boronate and oxidative cleavage of the resulting double bond (Scheme 9). Reductive amination with a primary or secondary amine and a reducing agent such as sodium triacetoxyborohydride affords compound XXXII.

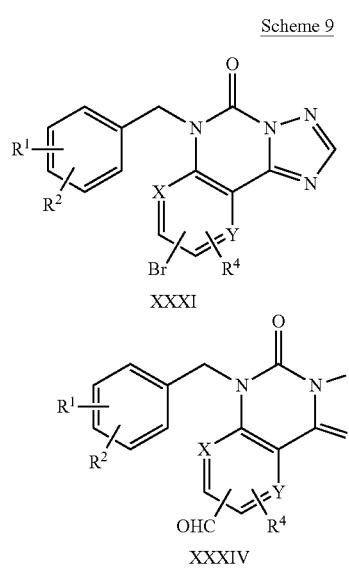

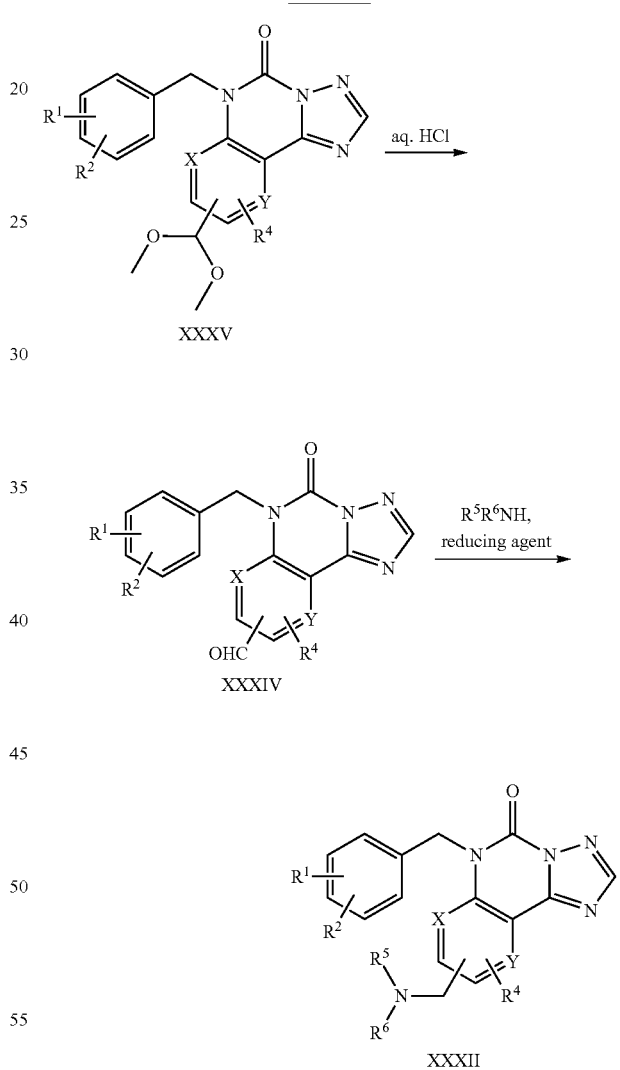

Aldehydes XXXIV can also be prepared by utilizing an acetal starting material in Scheme 7. The resulting product of this sequence XXXV can then be heated with aqueous acid to provide aldyhde XXXIV which can reductively aminated with a primary or secondary amine and a reducing agent such as sodium triacetoxyborohydride to afford compound XXXII (Scheme 10).

Bromide XXXI can also be converted to a ketone by reaction with a tin-substituted enol ether and acid catalyzed hydrolysis of the coupling product (Scheme 11). Reductive amination of the resulting ketone with a primary or secondary amine and a reducing agent such as sodium triacetoxyborohydride affords compound XXXVIII.

Scheme 11

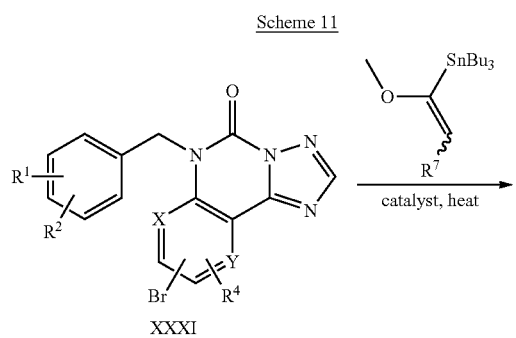

XXXI

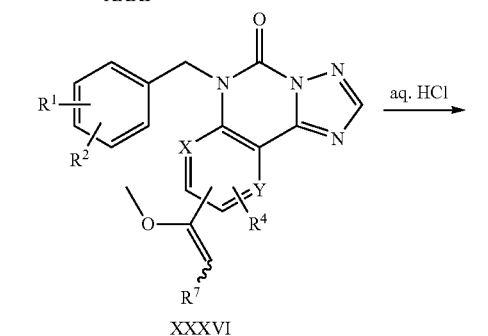

XXXVI

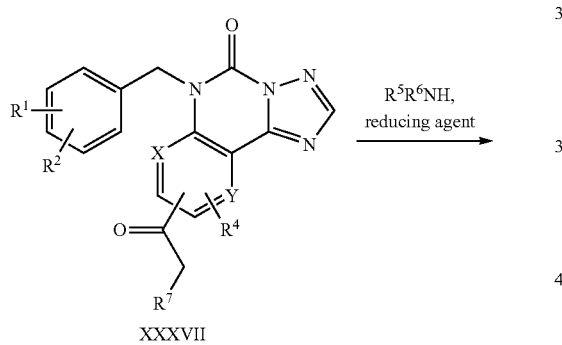

XXXVII

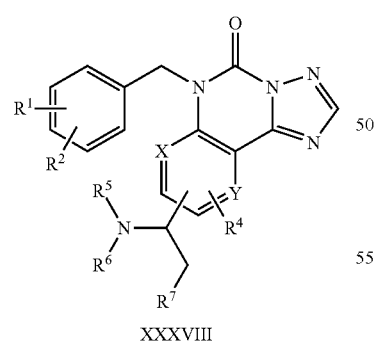

XXXVIII

Scheme 12

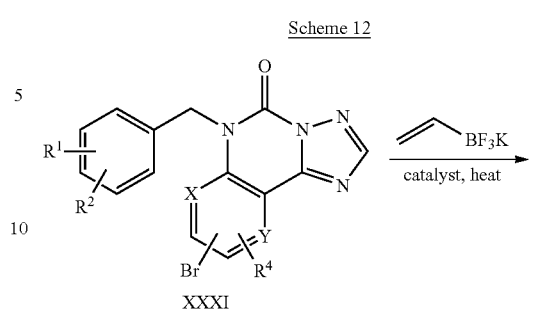

XXXI

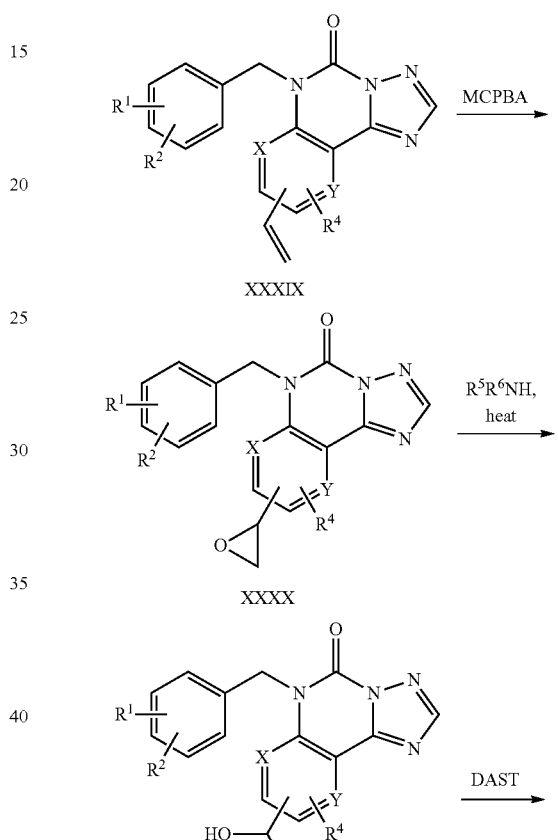

XXXIX

XXXX

XXXXI

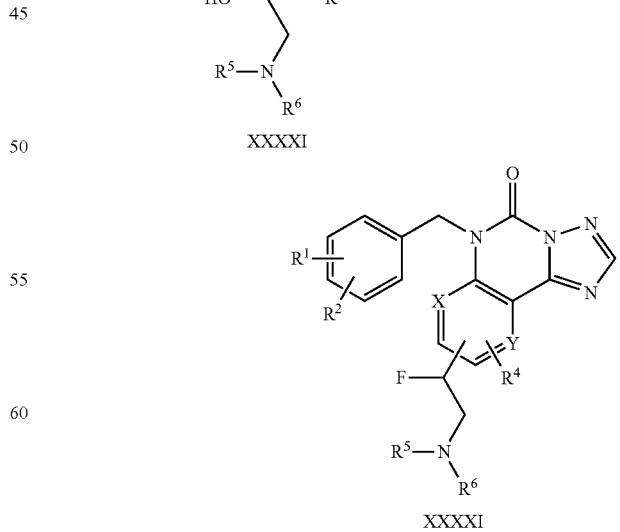

XXXXII

Bromide XXXI can be converted to an epoxide by a two step process involving vinylation and epoxidation by MCPBA (Scheme 12). Heating the product of this process with a primary or secondary amine provides a hydroxyl amine XXXXI. The alcohol can be converted to a fluorinated product XXXXII by treatment with a suitable fluorinating agent.

Preparative Examples

Instrumentation

1H NMR spectra were obtained on a Bruker Ultrashield 400 Plus instrument at 400 MHz and referenced relative to residual protonated material in the deuterated solvent. Preparative HPLC was performed on a Shimadzu Prominence system using a Waters SunFire OBD 30 mm×100 mm×2.5 µm (particle size) C18 column with a 15 minute gradient of 10-100% acetonitrile in water and 0.05% trifluoroacetic acid added as a modifier to both phases. Elution profiles were monitored by UV at 254 and 220 nm. LC-MS analyses were performed on an Agilent LC-1200 system employing a Waters SunFire 2.1 mm×50 mm×2.5 m (particle size) C18 column with a 4.5 minute gradient of 0-100% acetonitrile in water and 0.1% formic acid added as a modifier to both phases. Elution profiles were monitored by UV at 254 and 220 nm. TIC chromatograms were monitored using APCI in positive mode.

Preparative Example 185

9-Bromo-6-(4-methoxybenzyl)pyrido[3,2-e][1,2,4]triazolo[1,5-c]pyrimidin-5(6H)-one

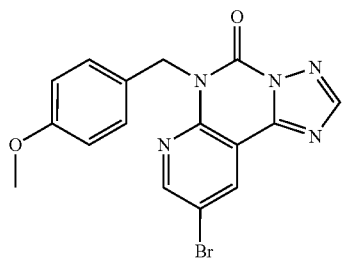

185

Step 17.1: methyl 5-bromo-3-cyanopyridin-2-ylcarbamate

Lithium bis(trimethylsilyl)amide in THF (1.0 N, 22 mL, 22 mmol) was added to a stirred solution of 2-amino-5-bromopyridine-3-carbonitrile (2.0 g, 10 mmol) in THF (30 mL) at −78° C. and the mixture was stirred at this temperature for 30 minutes. Methyl chloroformate (1.06 g, 11.1 mmol) was added and the mixture was warmed to room temperature and stirred for 2 hours. It was cooled in ice bath and quenched with saturated aqueous ammonium chloride (50 mL). The aqueous layer was extracted with ethyl acetate (3×50 mL) and the combined organic fractions were washed with brine (2×50 mL), dried over anhydrous sodium sulfate and concentrated under vacuum. The residue was purified by LC (elution with 10% ethyl acetate in petroleum ether) to afford the carbamate (1.43 g, 63%). 1H NMR (400 MHz, CDCl3) δ 3.85 (s, 3H), 7.45 (br s, 1H), 8.05 (s, 1H), 8.65 (s, 1H). LCMS (M-1, 254.0).

Step 17.2: 9-bromopyrido[3,2-e][1,2,4]triazolo[1,5-c]pyrimidin-5(6H)-one

Formyl hydrazine (60 mg, 1.0 mmol) was added to a solution of methyl 5-bromo-3-cyanopyridin-2-ylcarbamate (255 mg, 1.0 mmol) in 1-methylpyrrolidinone (5 mL) and the resulting mixture was stirred at 120° C. for 3 hours. The mixture was cooled to room temperature and poured into ice-water (20 mL). The resulting solid was separated by filtration, washed with water and hexanes and dried under vacuum to afford the title compound (160 mg, 60%). 1H NMR (400 MHz, DMSO-d6) δ 8.60 (s, 1H), 8.70 (s, 1H), 8.80 (s, 1H), 13.00 (br s, 1H). LCMS (MH+, 266.3).

Step 17.3: 9-bromo-6-(4-methoxybenzyl)pyrido[3,2-e][1,2,4]triazolo[1,5-c]pyrimidin-5(6H)-one (1)

1-(Chloromethyl)-4-methoxybenzene (3.10 ml, 22.9 mmol) was added to a stirred solution of 9-bromopyrido[3,2-e][1,2,4]triazolo[1,5-c]pyrimidin-5(6H)-one (3.02 g, 11.35 mmol) and potassium carbonate (4.71 g, 34.1 mmol) in 1-methylpyrrolidinone (60 ml) and the mixture was heated at 40° C. for 14 hours. The mixture was filtered, and the resulting solid was washed liberally with dichloromethane. The combined organics were concentrated under vacuum and the residue was triturated with ethyl acetate (40 mL) to afford 3.07 g (70%) of the benzylated product as a brown powder.

Numerous compounds were made using the above general procedure, as exemplified in Table 17:

TABLE 17

| Example | Structure | LC-MS (MH+) | 1H-NMR |
|---|---|---|---|
| 185 | C16H12BrN5O2 | 386.1 | 1H NMR (400 MHz, CDCl3) δ 3.77 (s, 3H), 5.72 (s, 2H), 6.83 (d, J = 8.66 Hz, 2H), 7.58 (d, J = 8.66 Hz, 2H), 8.37 (s, 1H), 8.76 (d, J = 2.38 Hz, 1H), 8.82 (d, J = 2.38 Hz, 1H) |

TABLE 17-continued
| Example | Structure | LC-MS (MH+) | 1H-NMR |
|---|---|---|---|
| 186 | 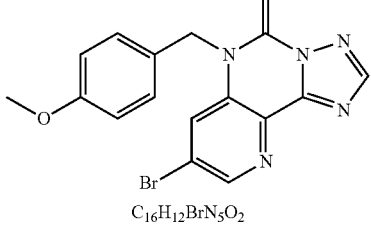<br>C₁₆H₁₂BrN₅O₂ | 386 | 1H NMR (400 MHz, CDCl3) δ 3.80 (br s, 3H), 5.52 (br s, 2H), 6.91 (d, J = 8.16 Hz, 2H), 7.27-7.30 (m, 2H), 7.95 (br s, 1H), 8.50 (br s, 1H), 8.77 (br s, 1H) |
| 187 | 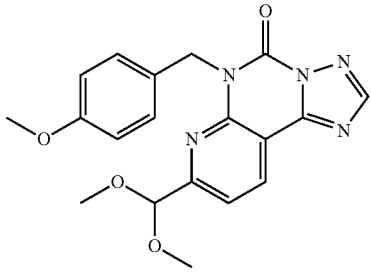<br>C₁₉H₁₉N₅O₄ | 382.2 | 1H NMR (400 MHz, CDCl3) δ 3.46 (s, 6H), 3.76 (s, 3H), 5.50 (s, 1H), 5.76 (s, 2H), 6.78-6.88 (m, 2H), 7.68 (d, J = 2.01 Hz, 3H), 8.35 (s, 1H), 8.66 (d, J = 8.03 Hz, 1H) |
| 188 | 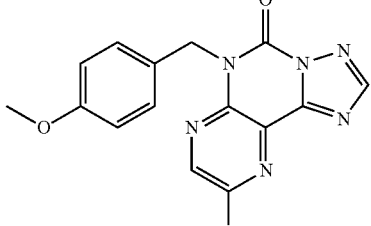<br>C₁₅H₁₁BrN₆O₂ | 387 | 1H NMR (400 MHz, CDCl3) δ 3.77 (s, 3H), 5.68 (s, 2H), 6.83 (d, J = 8.53 Hz, 2H), 7.54 (d, J = 8.66 Hz, 2H), 8.50 (s, 1H), 8.81 (s, 1H) |
Preparative Example 189
9-(3,4-Dimethoxyphenyl)-6-(4-methoxybenzyl) pyrido[3,2-e][1,2,4]triazolo[1,5-c]pyrimidin-5(6H)-one
189
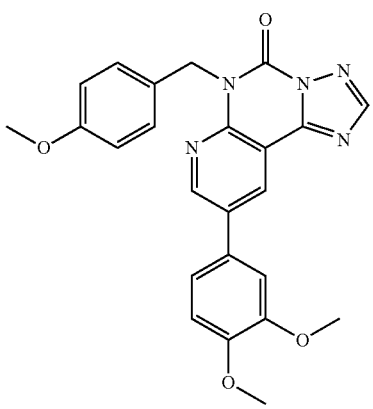

Step 18.1: 6-(4-methoxybenzyl)-9-vinylpyrido[3,2-e][1,2,4]triazolo[1,5-c]pyrimidin-5(6H)-one (189)

9-Bromo-6-(4-methoxybenzyl)pyrido[3,2-e][1,2,4]triazolo[1,5-c]pyrimidin-5(6H)-one (75 mg, 0.19 mmol), 3,4-dimethoxyphenylboronic acid (75 mg, 0.41 mmol), potassium phosphate (104 mg, 0.49 mmol) and ethyleneglycol dimethyl ether (3 ml) were combined and nitrogen was bubbled through for 10 minutes. Tris(dibenzylideneacetone)dipalladium(0) (13 mg, 0.01 mmol) was added and the mixture was heated for 2 hours at 120° C. in the microwave. The mixture was filtered and purified by HPLC to afford 6 mg (7%) of the title compound as a white solid.

Numerous compounds were made using the above general procedure, as exemplified in Table 18:

TABLE 18

| Example | Structure | LC-MS (MH+) | 1H-NMR |
|---|---|---|---|
| 189 | 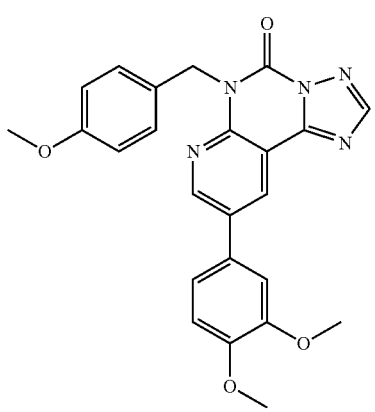 $C_{24}H_{21}N_5O_4$ | 444.2 | 1H NMR (400 MHz, CDCl3) δ 3.76 (s, 3H), 3.96 (s, 3H), 3.99 (s, 3H), 5.78 (s, 2H), 6.83-6.84 (m, 2H), 7.02 (d, J = 6.7 Hz, 1H), 7.15 (d, J = 1.6 Hz, 1H), 7.24 (dd, J = 6.7, 1.5 Hz, 1H), 7.62-7.64 (m, 2H), 8.37 (s, 1H), 8.76 (d, J = 1.9 Hz, 1H), 8.99 (d, J = 1.9 Hz, 1H) |
| 190 | 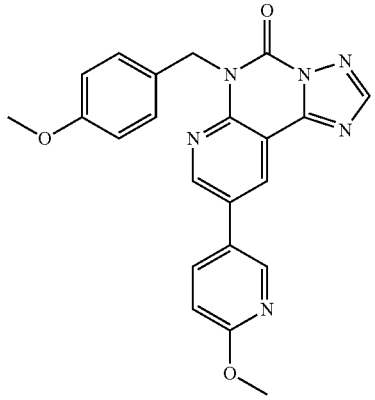 $C_{22}H_{18}N_6O_3$ | 415.1 | 1H NMR (DMSO-d6) δ 3.70 (s, 3H), 3.92 (s, 3H), 5.63 (s, 2H), 6.86 (d, J = 7.0 Hz, 2H), 6.98 (d, J = 7.0 Hz, 1H), 7.38 (d, J = 7.0 Hz, 2H), 8.26 (dd, J = 7.0, 2.1 Hz, 1H), 8.65 (s, 1H), 8.70 (d, J = 1.9 Hz, 1H), 8.87 (d, J = 1.9 Hz, 1H), 9.14 (d, J = 1.9 Hz, 1H) |
| 191 | 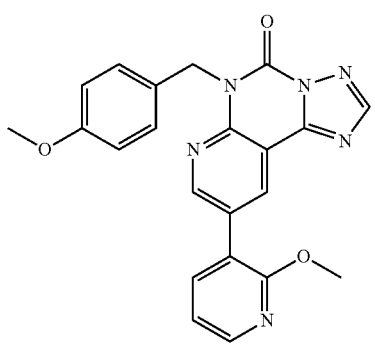 $C_{22}H_{18}N_6O_3$ | 415.1 | 1H NMR (DMSO-d6) δ 3.71 (s, 3H), 3.94 (s, 3H), 5.62 (s, 2H), 6.86 (d, J = 7.0 Hz, 2H), 7.18 (dd, J = 5.9, 4.0 Hz, 1H), 7.39 (d, J = 7.0 Hz, 2H), 8.02 (dd, J = 5.9, 1.5 Hz, 1H), 8.28 (dd, J = 4.0, 1.5 Hz, 1H), 8.62 (s, 1H), 8.82 (d, J = 1.8 Hz, 1H), 8.99 (d, J = 1.9 Hz, 1H) |

Preparative Example 192

6-(4-Methoxybenzyl)-9-(3-methyl-6-oxopyridazin-1(6H)-yl)pyrido[3,2-e][1,2,4]triazolo[1,5-c]pyrimidin-5(6H)-one

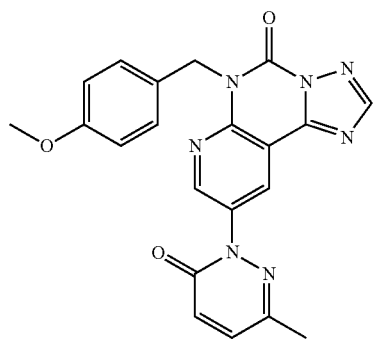

Step 19.1: 6-(4-methoxybenzyl)-9-(3-methyl-6-oxopyridazin-1(6H)-yl)pyrido[3,2-e][1,2,4]triazolo[1,5-c]pyrimidin-5(6H)-one (192)

9-Bromo-6-(4-methoxybenzyl)pyrido[3,2-e][1,2,4]triazolo[1,5-c]pyrimidin-5(6H)-one (75 mg, 0.19 mmol), 6-methylpyridazin-3(2H)-one (43 mg, 0.39 mmol), copper (I) iodide (44 mg, 0.23 mmol), dioxane (3 ml), trans-1,2-diaminocyclohexane (0.030 ml, 0.25 mmol) and cesium carbonate (152 mg, 0.47 mmol) were combined and heated at 120° C. for 12 hours in the microwave. The mixture was filtered and the residue was purified by HPLC to afford 9 mg (11%) of the title compound as a white solid.

Numerous compounds were made using the above general procedure, as exemplified in Table 19:

Preparative Example 193

9-(4-Cyclopropylpiperazin-1-yl)-6-(4-methoxybenzyl)pyrido[3,2-e][1,2,4]triazolo[1,5-c]pyrimidin-5(6H)-one

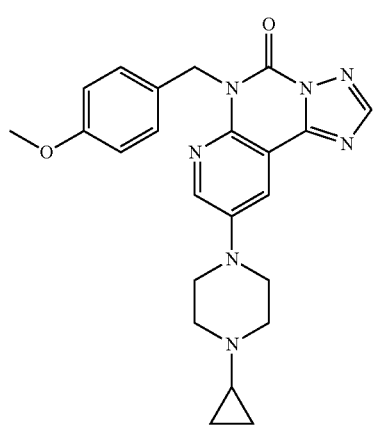

Step 20.1: 9-(4-cyclopropylpiperazin-1-yl)-6-(4-methoxybenzyl)pyrido[3,2-e][1,2,4]triazolo[1,5-c]pyrimidin-5(6H)-one (193)

9-Bromo-6-(4-methoxybenzyl)pyrido[3,2-e][1,2,4]triazolo[1,5-c]pyrimidin-5(6H)-one (63 mg, 0.16 mmol) and 1-cyclopropylpiperazine (103 mg, 0.82 mmol) were dissolved in toluene (2 ml) and nitrogen was bubbled through the mixture while 2,2'-bis(diphenylphosphino)-1,1'-binaphthyl (41 mg, 0.07 mmol), cesium carbonate (159 mg, 0.49 mmol) and palladium(II) acetate (7 mg, 0.03 mmol) were added. The mixture was heated at 100° C. for 16 hours. It was concentrated under a stream of nitrogen and the residue was taken up in DMF, filtered and purified by preparative HPLC to afford 25 mg (27%) of the title compound as a yellow solid.

Numerous compounds were made using the above general procedure, as exemplified in Table 20:

TABLE 19

| Example | Structure | LC-MS (MH+) | 1H-NMR |
|---------|-----------|-------------|--------|
| 192 | $C_{21}H_{17}N_7O_3$ | 416.1 | 1H NMR (400 MHz, CDCl3) δ 2.44 (s, 3H), 3.76 (s, 3H), 5.77 (s, 2H), 6.81-6.83 (m, 2H), 7.03 (d, J = 7.7 Hz, 1H), 7.60-7.61 (m, 2H), 8.36 (s, 1H), 8.99 (d, J = 2.1 Hz, 1H), 9.25 (d, J = 2.1 Hz, 1H) |

TABLE 20
| Example | Structure | LC-MS (MH+) | 1H-NMR |
|---|---|---|---|
| 193 | 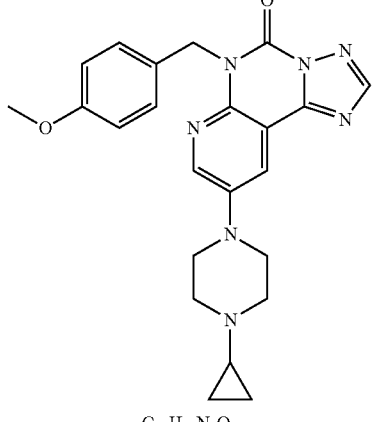 C23H25N7O2 | 432.2 | 1H NMR (400 MHz, CDCl3) δ 0.84-1.00 (m, 2H), 1.38 (d, J = 3.01 Hz, 2H), 2.01 (s, 2H), 2.35-2.51 (m, 1H), 3.50 (s, 4H), 3.61 (br s, 4H), 3.76 (s, 3H), 5.70 (s, 2H), 6.82 (d, J = 8.53 Hz, 2H), 7.57 (d, J = 8.41 Hz, 2H), 8.07 (d, J = 2.89 Hz, 1H), 8.33 (s, 1H), 8.47 (d, J = 2.89 Hz, 1H) |
| 194 | 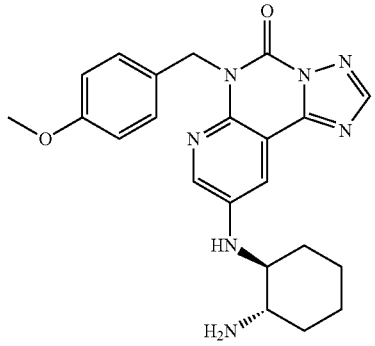 C22H25N7O2 | 420.2 | 1H NMR (400 MHz, CDCl3) δ 1.20-1.45 (m, 4H), 1.68-1.77 (m, 2H), 1.98-2.06 (m, 2H), 2.93-2.97 (m, 2H), 3.70 (s, 3H), 5.53 (s, 2H), 6.15 (d, J = 8.1 Hz, 1H), 6.83-6.86 (m, 2H), 7.31-7.34 (m, 2H), 7.82 (d, J = 2.3 Hz, 1H), 7.88 (br s, 3H), 8.29 (d, J = 2.3 Hz, 1H), 8.57 (s, 1H) |
| 195 | 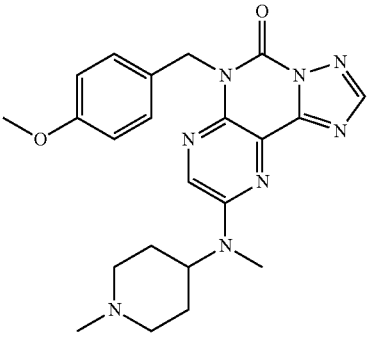 C22H26N8O2 | 435.3 | 1H NMR (400 MHz, CDCl3) δ 1.92 (d, J = 13.30 Hz, 2H), 2.40-2.58 (m, 2H), 2.84 (s, 3H), 3.03 (br s, 2H), 3.11 (s, 3H), 3.67 (d, J = 11.80 Hz, 2H), 3.77 (s, 3H), 5.18 (tt, J = 12.25, 3.75 Hz, 1H), 5.66 (s, 2H), 6.83 (d, J = 8.78 Hz, 2H), 7.56 (d, J = 8.66 Hz, 2H), 8.27 (s, 1H), 8.43 (s, 1H) |

TABLE 20-continued
| Example | Structure | LC-MS (MH+) | 1H-NMR |
|---|---|---|---|
| 196 | 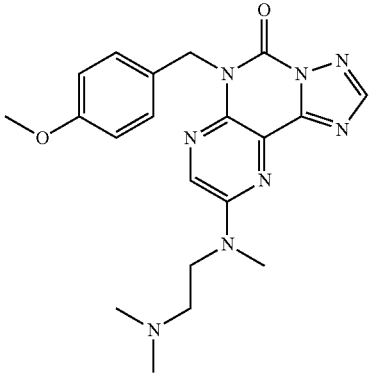 C$_{20}$H$_{24}$N$_8$O$_2$ | 409.2 | 1H NMR (400 MHz, CDCl3) δ 3.02 (s, 6H), 3.29 (s, 3H), 3.40 (t, J = 6.15 Hz, 2H), 3.76 (s, 3H), 4.18 (t, J = 6.15 Hz, 2H), 5.65 (s, 2H), 6.83 (d, J = 8.66 Hz, 2H), 7.56 (d, J = 8.66 Hz, 2H), 8.27 (s, 1H), 8.37 (s, 1H), 12.76 (br s, 1H) |
| 197 | 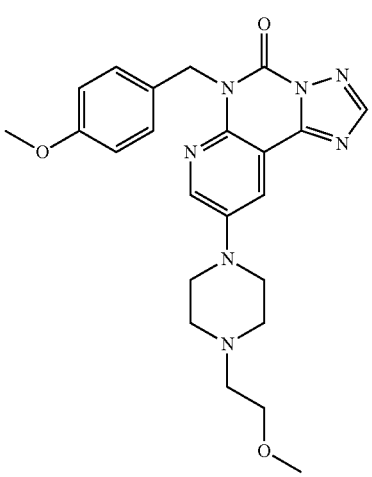 C$_{23}$H$_{27}$N$_7$O$_3$ | 450.3 | 1H NMR (400 MHz, CDCl3-d) δ 3.29-3.35 (m, 2H), 3.40 (s, 3H), 3.64 (br s, 8H), 3.77 (s, 3H), 3.81-3.87 (m, 2H), 5.71 (s, 2H), 6.83 (d, J = 8.53 Hz, 2H), 7.57 (d, J = 8.41 Hz, 2H), 8.08 (d, J = 2.89 Hz, 1H), 8.34 (s, 1H), 8.49 (d, J = 2.76 Hz, 1H) |
| 198 | 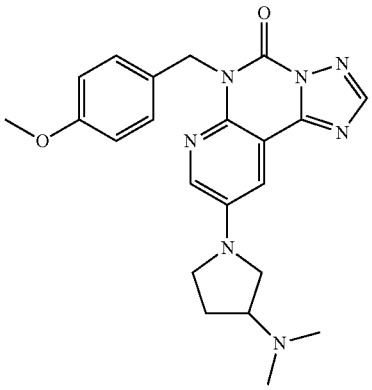 C$_{22}$H$_{25}$N$_7$O$_2$ | 420.2 | 1H NMR (400 MHz, CDCl3-d) δ 2.58 (d, J = 8.03 Hz, 2H), 2.91 (s, 6H), 3.45-3.59 (m, 3H), 3.76 (s, 3H), 3.78-3.95 (m, 3H), 5.71 (s, 2H), 6.82 (d, J = 8.41 Hz, 2H), 7.58 (d, J = 8.78 Hz, 2H), 7.70 (d, J = 3.01 Hz, 1H), 8.22 (d, J = 2.63 Hz, 1H), 8.33 (s, 1H) |

TABLE 20-continued

| Example | Structure | LC-MS (MH+) | 1H-NMR |
|---|---|---|---|
| 199 | C₂₃H₂₇N₇O₂ | 434.3 | 1H NMR (400 MHz, CDCl3) δ 1.90-2.08 (m, 2H), 2.27 (d, J = 9.91 Hz, 2H), 2.85 (s, 6H), 2.96 (t, J = 12.11 Hz, 2H), 3.25-3.38 (m, 1H), 3.77 (s, 3H), 3.94 (d, J = 11.92 Hz, 2H), 5.71 (s, 2H), 6.83 (d, J = 8.53 Hz, 2H), 7.58 (d, J = 8.53 Hz, 2H), 8.05 (d, J = 2.89 Hz, 1H), 8.34 (s, 1H), 8.51 (d, J = 2.89 Hz, 1H) |
| 200 | C₂₂H₂₄N₆O₃ | 421.1 | 1H NMR (400 MHz, DMSO-d6) δ 1.54 (d, J = 11.67 Hz, 2H), 1.64-1.81(m, 2H), 2.80 (s, 3H), 3.40-3.48 (m, 2H), 3.63 (s, 3H), 3.86 (dd, J = 11.04, 4.02 Hz, 2H), 4.03 (t, J = 11.42 Hz, 1H), 5.47 (s, 2H), 6.78 (d, J = 8.66 Hz, 2H), 7.27 (d, J = 8.53 Hz, 2H), 7.78 (d, J = 3.01 Hz, 1H), 8.47 (d, J = 3.14 Hz, 1H), 8.50 (s, 1H) |
| 201 | C₂₂H₂₄N₆O₃ | 421.1 | 1H NMR (400 MHz, DMSO-d6) δ 1.11 (d, J = 6.15 Hz, 6H), 2.33 (t, J = 10.98 Hz, 2H), 3.63 (s, 3H), 3.64-3.69 (m, 2H), 3.73 (d, J = 11.80 Hz, 2H), 5.48 (s, 2H), 6.77 (d, J = 8.53 Hz, 2H), 7.27 (d, J = 8.41 Hz, 2H), 7.93 (d, J = 2.76 Hz, 1H), 8.51 (s, 1H), 8.54 (d, J = 2.76 Hz, 1H) |
| 202 | C₂₂H₂₇N₇O₂ | 422.2 | 1H NMR (400 MHz, DMSO-d6) δ 1.93 (dt, J = 15.12, 7.37 Hz, 2H), 2.79 (d, J = 4.14 Hz, 6H), 3.05 (s, 3H), 3.10-3.19 (m, 2H), 3.51-3.56 (m, 2H), 3.71 (s, 3H), 5.56 (s, 2H), 6.86 (d, J = 8.53 Hz, 2H), 7.34 (d, J = 8.41 Hz, 2H), 7.78 (d, J = 2.89 Hz, 1H), 8.44 (d, J = 2.89 Hz, 1H), 8.59 (s, 1H), 9.43 (br s, 1H) |

TABLE 20-continued

| Example | Structure | LC-MS (MH+) | 1H-NMR |
|---|---|---|---|
| 203 | C₂₁H₂₃N₇O₄S | 470.1 | 1H NMR (400 MHz, DMSO-d6) δ 2.88 (s, 3H), 3.23 (d, J = 5.27 Hz, 4H), 3.34-3.43 (m, 4H), 3.63 (s, 3H), 5.48 (s, 2H), 6.78 (d, J = 8.53 Hz, 2H), 7.27 (d, J = 8.41 Hz, 2H), 8.00 (d, J = 2.89 Hz, 1H), 8.52 (s, 1H), 8.57 (d, J = 2.89 Hz, 1H) |

Preparative Example 204

Benzyl 2-(6-(4-Methoxybenzyl)-5-oxo-5,6-dihydro-pyrido[3,2-e][1,2,4]triazolo[1,5-c]pyrimidin-9-yl)ethylcarbamate

204

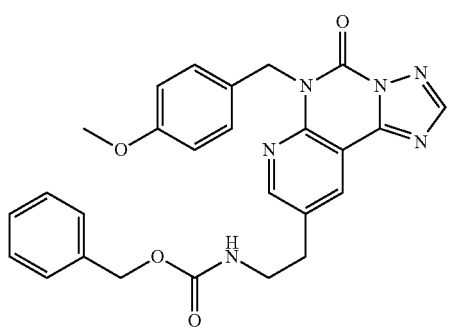

Step 21.1: benzyl 2-(6-(4-methoxybenzyl)-5-oxo-5,6-dihydropyrido[3,2-e][1,2,4]triazolo[1,5-c]pyrimidin-9-yl)ethylcarbamate (204)

9-Bromo-6-(4-methoxybenzyl)pyrido[3,2-e][1,2,4]triazolo[1,5-c]pyrimidin-5(6H)-one (30 mg, 0.078 mol), potassium (2-(benzyloxycarbonylamino)ethyl)trifluoroborate (30 mg, 0.11 mol), cesium carbonate (122 mg, 0.38 mmol), [1,1'-bis(diphenylphosphino)ferrocene]-dichloropalladium (II) DCM complex (5 mg, 0.01 mol), toluene (0.75 ml) and degassed water (0.25 ml) were added in order. The mixture was heated at 80° C. for 16 hours, concentrated under a stream of nitrogen, diluted with DMF (1.5 mL), filtered and purified by HPLC to afford 6 mg (12%) of 204 as a white solid.

Numerous compounds were made using the above general procedure, as exemplified in Table 21:

TABLE 21

| Example | Structure | LC-MS (MH+) | 1H-NMR |
|---|---|---|---|
| 204 | C₂₆H₂₄N₆O₄ | 485.2 | 1H NMR (400 MHz, DMSO-d6) δ 2.92 (t, J = 5.4 Hz, 2H), 3.35-3.36 (m, 2H), 3.69 (s, 3H), 4.94 (s, 2H), 5.58 (s, 2H), 6.83-6.85 (m, 2H), 7.24-7.26 (m, 2H), 7.35-7.37 (m, 2H), 7.40 (dd, J = 4.4, 4.4 Hz, 1H), 8.51 (d, J = 1.5 Hz, 1H), 8.61 (s, 1H), 8.65 (d, J = 1.6 Hz, 1H) |

TABLE 21-continued
| Example | Structure | LC-MS (MH+) | 1H-NMR |
|---|---|---|---|
| 205 | 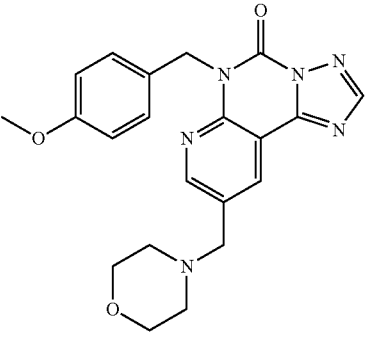<br>$C_{21}H_{22}N_6O_3$ | 407.2 | 1H NMR (DMSO-d6) δ 3.62-3.20 (m, 6H), 3.71 (s, 3H), 4.05-3.90 (m, 2H), 4.56 (s, 2H), 5.60 (s, 2H), 6.87-6.84 (m, 2H), 7.38 (d, J = 7.0 Hz, 2H), 8.67 (s, 1H), 8.86-8.40 (m, 2H), 10.15 (br s, 1H) |
| 206 | 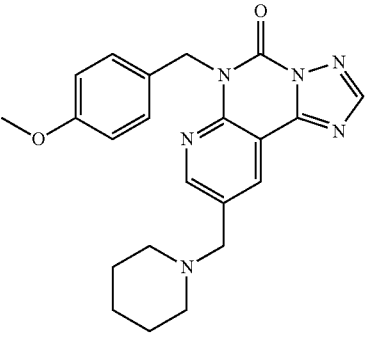<br>$C_{22}H_{24}N_6O_2$ | 405.3 | 1H NMR (400 MHz, CDCl3) δ 1.98 (br s, 6H), 2.57-2.93 (m, 2H), 3.56-3.72 (m, 2H), 3.78 (s, 3H), 4.38 (s, 2H), 5.76 (s, 2H), 6.85 (d, J = 8.66 Hz, 2H), 7.60 (d, J = 8.66 Hz, 2H), 8.37 (s, 1H), 8.73 (s, 1H), 8.97 (s, 1H) |
| 207 | 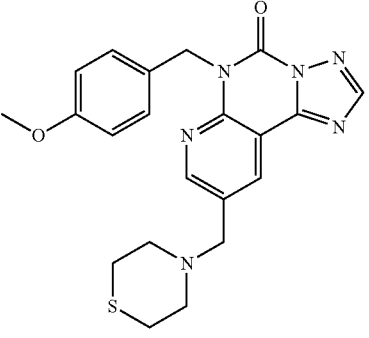 [SMILES: COc1ccc(Cn2c(=O)n3ncnc3c3cc(CN4CCN(C)CC4)cnc32)cc1]<br>$C_{21}H_{22}N_6O_2S$ | 423.2 | 1H NMR (400 MHz, CDCl3) δ 3.03 (br s, 4H), 3.47 (br s, 4H), 3.78 (s, 3H), 4.38 (s, 2H), 5.75 (s, 2H), 6.84 (d, J = 8.66 Hz, 2H), 7.59 (d, J = 8.66 Hz, 2H), 8.37 (s, 1H), 8.74 (d, J = 2.01 Hz, 1H), 8.93 (d, J = 2.13 Hz, 1H) |
| 208 | 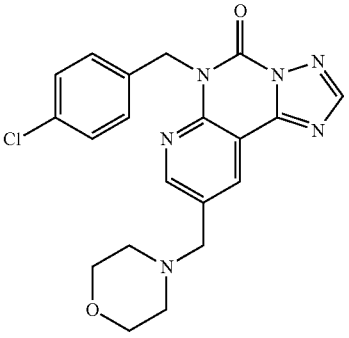<br>$C_{20}H_{19}ClN_6O_2$ | 411.1 | 1H NMR (400 MHz, CDCl3) δ 3.54 (br s, 3H), 4.04 (t, J = 4.45 Hz, 4H), 4.41 (s, 2H), 5.78 (s, 2H), 7.30 (d, J = 8.78 Hz, 5H), 7.54-7.68 (m, 2H), 8.43 (s, 1H), 8.82 (s, 1H), 8.97 (s, 1H) |

TABLE 21-continued

| Example | Structure | LC-MS (MH+) | 1H-NMR |
|---|---|---|---|
| 209 | 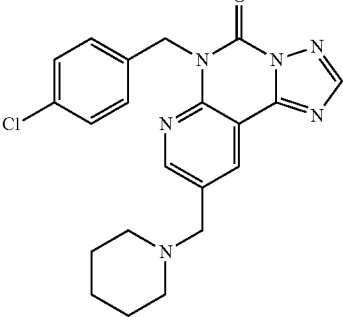<br>$C_{21}H_{21}ClN_6O$ | 409.1 | 1H NMR (400 MHz, CDCl3) δ 1.96 (br s, 3H), 2.01-2.24 (m, 2H), 2.75 (t, J = 11.73 Hz, 2H), 3.55 (br s, 3H), 3.68 (d, J = 11.04 Hz, 3H), 4.38 (s, 2H), 5.78 (s, 2H), 7.31 (d, J = 8.41 Hz, 2H), 7.60 (d, J = 8.41 Hz, 2H), 8.42 (s, 1H), 8.82 (d, J = 1.88 Hz, 1H), 9.04 (d, J = 1.76 Hz, 1H) |
| 210 | 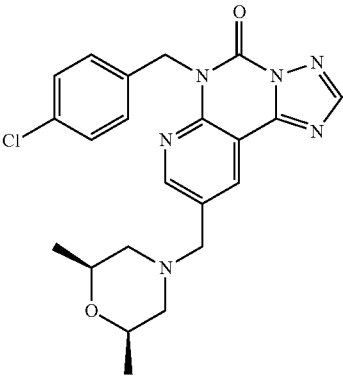<br>$C_{22}H_{23}ClN_6O_2$ | 439.2 | 1H NMR (400 MHz, CDCl3) δ 1.26 (d, J = 6.27 Hz, 6H), 2.50 (t, J = 11.11 Hz, 2H), 3.48 (d, J = 11.29 Hz, 2H), 4.14 (dd, J = 10.16, 5.90 Hz, 2H), 4.36 (s, 2H), 5.78 (s, 2H), 7.31 (d, J = 8.53 Hz, 2H), 7.60 (d, J = 8.53 Hz, 2H), 8.44 (s, 1H), 8.83 (d, J = 1.63 Hz, 1H), 9.04 (s, 1H) |

Preparative Example 211

9-(2-Aminoethyl)-6-(4-methoxybenzyl)pyrido[3,2-e][1,2,4]triazolo[1,5-c]pyrimidin-5(6H)-one Step 22.1: tert-butyl 2-(6-(4-methoxybenzyl)-5-oxo-5,6-dihydropyrido[3,2-e][1,2,4]triazolo[1,5-c]pyrimidin-9-yl)ethylcarbamate The title compound was prepared as described in Step 21.1 and used in the next step without further characterization.

Step 22.2: 9-(2-aminoethyl)-6-(4-methoxybenzyl)pyrido[3,2-e][1,2,4]triazolo[1,5-c]pyrimidin-5(6H)-one (211)

tert-Butyl 2-(6-(4-methoxybenzyl)-5-oxo-5,6-dihydropyrido[3,2-e][1,2,4]triazolo[1,5-c]pyrimidin-9-yl)ethylcarbamate (6 mg, 0.011 mmol) was treated with dichloromethane (2 ml) and 2,2,2-trifluoroacetic acid (2 ml), stirred for 1 hour and concentrated under vacuum. The residue was suspended in chloroform (3 mL) and concentrated and dissolved in methanol (3 mL) and concentrated again to afford 4 mg (12%) of the trifluoroacetic acid salt of 6 as a white solid.

Numerous compounds were made using the above general procedure, as exemplified in Table 22:

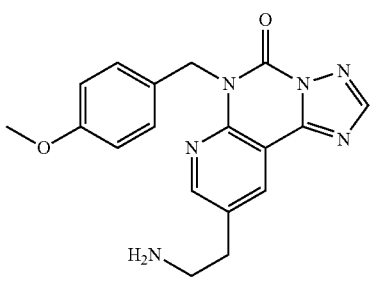

TABLE 22

| Example | Structure | LC-MS (MH+) | 1H-NMR |
|---|---|---|---|
| 211 | 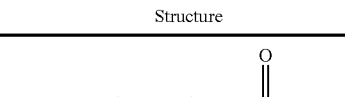 $C_{18}H_{18}N_6O_2$ | 351.2 | 1H NMR (400 MHz, DMSO-d6) δ 3.05 (t, J = 6.0 Hz, 2H), 3.21 (t, J = 5.9 Hz, 2H), 3.70 (s, 3H), 5.59 (s, 2H), 6.84-6.87 (m, 2H), 7.35-7.37 (m, 2H), 7.83-7.86 (m, 3H), 8.62 (d, J = 1.8 Hz, 1H), 8.63 (s, 1H), 8.71 (d, J = 1.9 Hz, 1H) |

Preparative Example 212

6-(4-Methoxybenzyl)-9-(2-(tetrahydro-2H-pyran-4-ylamino)ethyl)pyrido[3,2-e][1,2,4]triazolo[1,5-c]pyrimidin-5(6H)-one

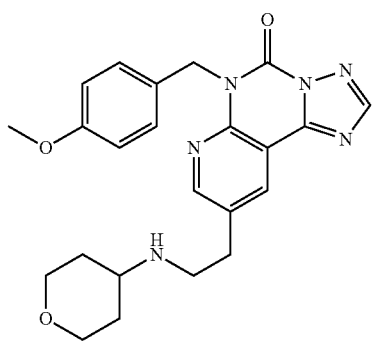

212

Step 23.1: 6-(4-methoxybenzyl)-9-(2-(tetrahydro-2H-pyran-4-ylamino)ethyl)pyrido[3,2-e][1,2,4]triazolo[1,5-c]pyrimidin-5(6H)-one (212)

9-(2-Aminoethyl)-6-(4-methoxybenzyl)pyrido[3,2-e][1,2,4]triazolo[1,5-c]pyrimidin-5(6H)-one (38 mg, 0.11 mmol), dichloromethane (1 ml), methanol (0.5 ml), tetrahydro-4H-pyran-4-one (65 mg, 0.65 mmol), and triethylamine (18 µl, 0.13 mmol) were combined and stirred for 20 minutes. Sodium cyanoborohydride (24 mg, 0.38 mmol) was added and the mixture was stirred for 18 hours. Water (0.1 mL) was added, the mixture was stirred for 1 h, and then it was concentrated under a stream of nitrogen. The residue was taken up in DMF, filtered and purified by HPLC to afford 24 mg (40%) of the trifluoroacetic acid salt of 212 as a white solid.

Numerous compounds were made using the above general procedure, as exemplified in Table 23:

TABLE 23

| Example | Structure | LC-MS (MH+) | 1H-NMR |
|---|---|---|---|
| 212 | 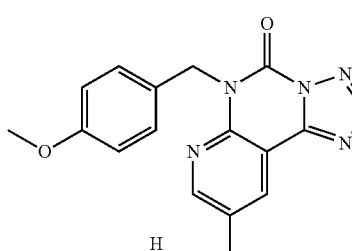 $C_{23}H_{26}N_6O_3$ | 435.3 | 1H NMR (DMSO-d6) δ 1.54 (qd, J = 9.8, 6.1 Hz, 2H), 1.97 (dd, J = 9.9, 3.5 Hz, 2H), 3.13-3.10 (m, 2H), 3.39-3.29 (m, 5H), 3.70 (s, 3H), 3.92 (dd, J = 9.1, 3.2 Hz, 2H), 5.59 (s, 2H), 6.85 (d, J = 7.0 Hz, 2H), 7.36 (d, J = 7.0 Hz, 2H), 8.64 (s, 1H), 8.67 (d, J = 1.9 Hz, 1H), 8.71 (br s, 2H), 8.73 (d, J = 1.8 Hz, 1H) |

TABLE 23-continued

| Example | Structure | LC-MS (MH+) | 1H-NMR |
|---|---|---|---|
| 213 | 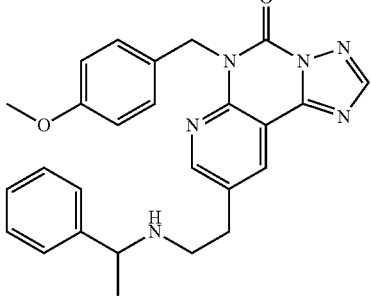 C26H26N6O2 | 455.2 | 1H NMR (DMSO-d6) δ 1.58 (d, J = 5.5 Hz, 3H), 3.31-3.06 (m, 4H), 3.70 (s, 3H), 4.43 (q, J = 5.1 Hz, 1H), 5.57 (s, 2H), 6.85 (d, J = 7.0 Hz, 2H), 7.35 (d, J = 7.0 Hz, 2H), 7.51-7.40 (m, 5H), 8.59 (d, J = 1.8 Hz, 1H), 8.63 (s, 1H), 8.66 (d, J = 1.8 Hz, 1H), 8.97 (br s, 1H), 9.11 (br s, 1H) |

Preparative Example 214
6-(4-Methoxybenzyl)-9-vinylpyrido[3,2-e][1,2,4]triazolo[1,5-c]pyrimidin-5(6H)-one

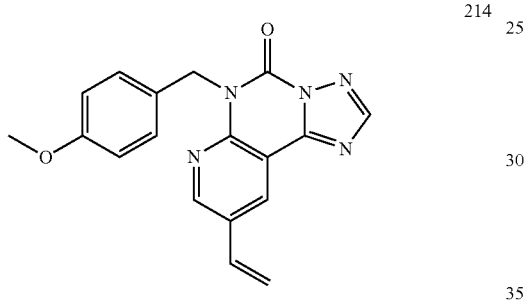

214

Step 24.1: 6-(4-methoxybenzyl)-9-vinylpyrido[3,2-e][1,2,4]triazolo[1,5-c]pyrimidin-5(6H)-one (214)

9-Bromo-6-(4-methoxybenzyl)pyrido[3,2-e][1,2,4]triazolo[1,5-c]pyrimidin-5(6H)-one (500 mg, 1.29 mmol), tributyl(vinyl)stannane (0.45 ml, 1.6 mmol), toluene (5 ml) and tetrakis(triphenylphosphoranyl)-palladium (33 mg, 0.03 mmol) were combined and heated at 100° C. for 16 hours. The mixture was filtered through Celite with DCM washing, concentrated under vacuum and the residue was purified by flash chromatography (elution with 10-100% ethyl acetate in hexanes) to afford 398 mg (92%) of 214 as a white solid.

Numerous compounds were made using the above general procedure, as exemplified in Table 24.

TABLE 24

| Example | Structure | LC-MS (MH+) | 1H-NMR |
|---|---|---|---|
| 214 | 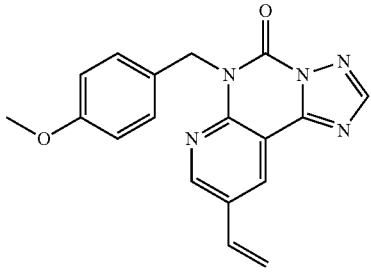 C18H15N5O2 | 334.1 | 1H NMR (400 MHz, CDCl3) δ 3.76 (s, 3H), 5.52 (d, J = 11.04 Hz, 1H), 5.75 (s, 2H), 5.98 (d, J = 17.69 Hz, 1H), 6.77-6.86 (m, 3H), 7.56-7.67 (m, 2H), 8.36 (s, 1H), 8.66 (d, J = 2.38 Hz, 1H), 8.79 (d, J = 2.38 Hz, 1H) |

TABLE 24-continued

| Example | Structure | LC-MS (MH+) | 1H-NMR |
|---|---|---|---|
| 215 | C₁₉H₁₉N₅O₄ | 382.1 | 1H NMR (400 MHz, CDCl3) δ ppm 3.45 (s, 3H), 3.76 (s, 3H), 4.75 (s, 2H), 4.78 (s, 2H), 5.76 (s, 2H), 6.78-6.87 (m, 2H), 7.57-7.67 (m, 2 H) 8.36 (s, 1 H) 8.65 (d, J = 2.26 Hz, 1 H) 8.78 (d, J = 2.26 Hz, 1 H) |
| 216 | C₂₀H₁₉N₅O₃ | 378.2 | 1H NMR (400 MHz, CDCl3) δ 1.48 (t, J = 6.96 Hz, 3H), 3.77 (s, 3H), 4.00 (q, J = 6.94 Hz, 2H), 4.41 (d, J = 3.14 Hz, 1H), 4.84 (d, J = 3.14 Hz, 1H), 5.76 (s, 2H), 6.83 (d, J = 8.53 Hz, 2H), 7.60 (d, J = 8.53 Hz, 2H), 8.36 (s, 1H), 8.83 (d, J = 2.13 Hz, 1H), 9.04 (d, J = 2.01 Hz, 1H) |

Preparative Example 217

9-(Hydroxymethyl)-6-(4-methoxybenzyl)pyrido[3,2-e][1,2,4]triazolo[1,5-c]pyrimidin-5(6H)-one

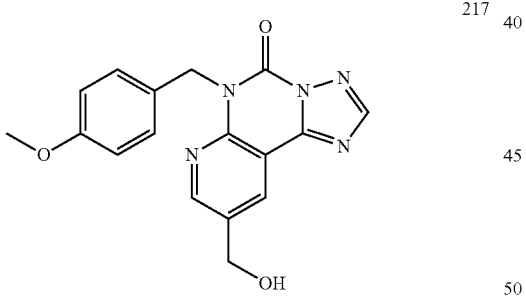

217

Step 25.1: 9-(hydroxymethyl)-6-(4-methoxybenzyl)pyrido[3,2-e][1,2,4]triazolo[1,5-c]pyrimidin-5(6H)-one (217)

A suspension of 6-(4-methoxybenzyl)-9-((methoxymethoxy)methyl)pyrido[3,2-e][1,2,4]triazolo[1,5-c]pyrimidin-5(6H)-one (40 mg, 0.10 mmol), methanol (0.80 ml) and 5 N hydrochloric acid (0.40 ml) was stirred at 50° C. for 16 hours. The mixture was extracted with DCM (1 mL), basified to pH 14 with 15% aqueous sodium hydroxide and extracted with DCM (2 mL). The combined DCM extracts were concentrated and the residue was taken up in DMF and purified by HPLC to afford 21 mg (59%) of 217 as a white powder.

Numerous compounds were made using the above general procedure, as exemplified in Table 25.

TABLE 25

| Example | Structure | LC-MS (MH+) | 1H-NMR |
|---|---|---|---|
| 217 | 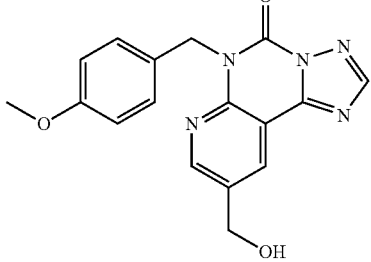<br>C₁₇H₁₅N₅O₃ | 338.1 | 1H NMR (DMSO-d6) δ 3.69 (s, 3H), 4.69 (d, J = 4.6 Hz, 2H), 5.54 (t, J = 4.6 Hz, 1H), 5.59 (s, 2H), 6.84 (d, J = 6.9 Hz, 2H), 7.36 (d, J = 6.9 Hz, 2H), 8.58 (d, J = 1.6 Hz, 1H), 8.60 (s, 1H), 8.72 (d, J = 1.6 Hz, 1H) |

Preparative Example 218

9-(2-Oxa-5-azabicyclo[2.2.1]heptan-5-ylmethyl)-6-(4-methoxybenzyl)pyrido[3,2-e][1,2,4]triazolo[1,5-c]pyrimidin-5(6H)-one

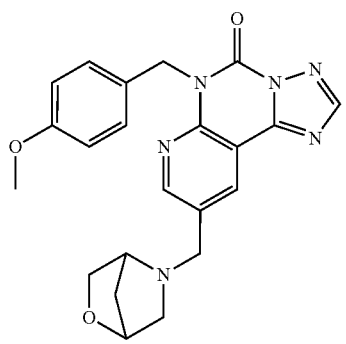

218

Step 26.1: 6-(4-methoxybenzyl)-9-vinylpyrido[3,2-e][1,2,4]triazolo[1,5-c]pyrimidin-5(6H)-one 9-Bromo-6-(4-methoxybenzyl)pyrido[3,2-e][1,2,4]triazolo[1,5-c]pyrimidin-5(6H)-one (2.00 g, 5.18 mmol), potassium trifluoro(vinyl)borate (1.51 g, 11.3 mmol), butan-1-ol (20 ml), triethylamine (1.05 ml, 7.53 mmol) and [1,1'-bis(diphenylphosphino)ferrocene]dichloropalladium(II)-dichloromethane complex (0.31 g, 0.38 mmol) were combined and heated at 100° C. for 20 hours. The mixture was cooled, concentrated under vacuum and taken up in dichloromethane (120 mL). It was washed with water (50 mL) and brine (50 mL), dried (MgSO₄) and concentrated under vacuum. The residue was triturated with ethyl acetate (15 mL) for 20 hours, filtered, washed with cold ethyl acetate and suction dried to afford 1.09 g (63%) of the title compound as a yellow powder. 1H NMR (400 MHz, CDCl3) δ 3.76 (s, 3H), 5.52 (d, J=10.92 Hz, 1H), 5.75 (s, 2H), 5.98 (d, J=17.57 Hz, 1H), 6.75-6.88 (m, 3H), 7.60 (d, J=8.66 Hz, 2H), 8.36 (s, 1H), 8.66 (d, J=2.13 Hz, 1H), 8.79 (d, J=2.26 Hz, 1H). LCMS (MH+, 334.1).

Step 26.2: 6-(4-methoxybenzyl)-5-oxo-5,6-dihydro-pyrido[3,2-e][1,2,4]triazolo[1,5-c]pyrimidine-9-carbaldehyde 6-(4-Methoxybenzyl)-9-vinylpyrido[3,2-e][1,2,4]triazolo[1,5-c]pyrimidin-5(6H)-one (3.96 g, 11.9 mmol) was suspended in tetrahydrofuran (80 ml) and heated with a heat gun to effect dissolution. Similarly sodium periodate (5.84 g, 27.3 mmol) was heated in water (40 ml) to effect dissolution. The above solutions were combined with vigorous stirring. While the stirred mixture was still at 40° C., osmium(VIII) oxide in tert-butanol (2.90 ml, 2.5%, 0.30 mmol) was added and the mixture was stirred vigorously for 4 hours. It was diluted with water (300 mL) and extracted with ethyl acetate (3×150 mL) and DCM (3×150 mL). The combined extracts were dried (MgSO₄) and concentrated to afford 4.13 g (99%) of the title compound as a black solid which was used without further purification. 1H NMR (400 MHz, CDCl3) δ 3.77 (s, 3H), 5.80 (s, 2H), 6.83 (d, J=8.66 Hz, 2H), 7.61 (d, J=8.66 Hz, 2H), 8.41 (s, 1H), 9.10 (d, J=2.13 Hz, 1H), 9.26 (d, J=2.13 Hz, 1H), 10.21 (s, 1H). LCMS (MH+, 336.2).

Step 26.3: 9-(2-oxa-5-azabicyclo[2.2.1]heptan-5-ylmethyl)-6-(4-methoxybenzyl)pyrido[3,2-e][1,2,4]triazolo[1,5-c]pyrimidin-5(6H)-one (218)

6-(4-Methoxybenzyl)-5-oxo-5,6-dihydropyrido[3,2-e][1,2,4]triazolo[1,5-c]pyrimidine-9-carbaldehyde (49 mg, 0.15 mmol), 2-oxa-5-azabicyclo[2.2.1]heptane (49 mg, 0.36 mmol), acetonitrile (1 ml), triethylamine (0.051 mL, 0.37 mmol) and acetic acid (0.040 ml, 0.69 mmol) were combined and stirred for 10 minutes. Sodium cyanoborohydride (18 mg, 0.29 mmol) was added and the mixture was stirred for 18 hours at room temperature. The mixture was diluted with methanol, filtered, and purified by preparative HPLC to afford 35 mg (45%) of the trifluoroacetic acid salt of 218 as a white solid.

Numerous compounds were made using the above general procedure, as exemplified in Table 26:

TABLE 26

| Example | Structure | LC-MS (MH+) | 1H-NMR |
|---|---|---|---|
| 218 | C₂₂H₂₂N₆O₃ | 419.2 | 1H NMR (400 MHz, CDCl3) δ 2.25 (d, J = 11.42 Hz, 1H), 2.43 (br s, 1H), 3.44-3.63 (m, 2H), 3.76 (s, 3H), 3.91 (d, J = 10.42 Hz, 1H), 4.37-4.53 (m, 3H), 4.56-4.65 (m, 1H), 4.73 (s, 1H), 5.74 (s, 2H), 6.76-6.91 (m, 2H), 7.60 (d, J = 8.78 Hz, 2H), 8.38 (s, 1H), 8.83 (s, 1H), 9.08 (s, 1H) |
| 219 | C₁₉H₂₀N₆O₂ | 365.2 | 1H NMR (DMSO-d6) δ 2.80 (s, 6H), 3.70 (s, 3H), 4.50 (s, 2H), 5.60 (s, 2H), 6.86 (d, J = 7.0 Hz, 2H), 7.38 (d, J = 7.0 Hz, 2H), 8.66 (s, 1H), 8.84 (d, J = 1.8 Hz, 1H), 8.89 (d, J = 1.8 Hz, 1H), 9.89 (br s, 1H) |
| 220 | C₂₃H₂₆N₆O₃ | 435.3 | 1H NMR (400 MHz, CDCl3) δ 1.23 (d, J = 6.27 Hz, 6H), 2.39-2.52 (m, 2H), 3.35 (d, J = 11.42 Hz, 2H), 3.77 (s, 3H), 4.31 (br s, 2H), 4.34-4.45 (m, 2H), 5.74 (s, 2H), 6.83 (d, J = 8.53 Hz, 2H), 7.62 (d, J = 8.53 Hz, 2H), 8.38 (s, 1H), 8.90 (d, J = 2.26 Hz, 1H), 9.34 (d, J = 2.13 Hz, 1H), 13.90 (br s, 1H) |
| 221 | C₂₂H₂₅N₇O₂ | 420.2 | 1H NMR (400 MHz, CDCl3) δ 2.89 (s, 2H), 3.11 (br s, 3H), 3.40 (br s, 2H), 3.78 (s, 2H), 3.95 (s, 1H), 5.76 (s, 1H), 6.85 (d, J = 8.53 Hz, 1H), 7.60 (d, J = 8.41 Hz, 1H), 8.38 (s, 1H), 8.72 (s, 1H), 8.76 (s, 1H) |

TABLE 26-continued

| Example | Structure | LC-MS (MH+) | 1H-NMR |
|---|---|---|---|
| 222 | C₂₃H₂₆N₆O₃ | 435.3 | 1H NMR (400 MHz, CDCl3) δ 1.65 (s, 6H), 3.12 (br s, 2H), 3.23-3.73 (m, 4H), 3.76 (s, 3H), 4.00 (br s, 2H), 5.73 (s, 2H), 6.75-6.90 (m, 2H), 7.59 (d, J = 8.66 Hz, 2H), 8.37 (s, 1H), 8.81 (d, J = 1.88 Hz, 1H), 9.03 (d, J = 2.01 Hz, 1H) |
| 223 | C₂₃H₂₆N₆O₃ | 435.2 | 1H NMR (400 MHz, CDCl3) δ 1.40 (br s, 6H), 3.22-3.68 (m, 4H), 3.77 (s, 3H), 3.93-4.18 (m, 2H), 4.41 (br s, 2H), 5.74 (s, 2H), 6.74-6.91 (m, 2H), 7.61 (d, J = 8.66 Hz, 2H), 8.39 (s, 1H), 8.79 (d, J = 2.13 Hz, 1H), 9.05 (d, J = 2.01 Hz, 1H) |
| 224 | C₂₃H₂₆N₆O₃ | 435.2 | 1H NMR (400 MHz, CDCl3) δ 0.97 (t, J = 7.47 Hz, 3H), 1.42-1.63 (m, 2H), 2.58 (t, J = 11.17 Hz, 1H), 2.80-3.02 (m, 1H), 3.50 (dd, J = 19.95, 11.04 Hz, 2H), 3.77 (s, 3H), 3.81-3.95 (m, 1H), 3.99-4.16 (m, 2H), 4.37 (s, 2H), 5.74 (s, 2H), 6.76-6.91 (m, 2H), 7.51-7.68 (m, 2H), 8.39 (s, 1H), 8.80 (d, J = 2.26 Hz, 1H), 9.05 (d, J = 2.26 Hz, 1H) |
| 225 | C₂₃H₂₆N₆O₃ | 435.2 | 1H NMR (400 MHz, CDCl3) δ 1.25 (d, J = 6.27 Hz, 3H), 1.55 (d, J = 6.65 Hz, 3H), 2.80 (t, J = 10.98 Hz, 1H), 3.26 (d, J = 12.05 Hz, 1H), 3.59 (d, J = 6.40 Hz, 1H), 3.78 (d, J = 14.56 Hz, 1H), 3.74-3.83 (m, 4H), 4.05-4.18 (m, 1H), 4.23-4.36 (m, 2H), 5.74 (s, 2H), 6.78-6.92 (m, 2H), 7.55-7.70 (m, 2H), 8.32-8.46 (m, 1H), 8.85 (d, J = 2.13 Hz, 1H), 9.13 (d, J = 2.01 Hz, 1H) |

TABLE 26-continued
| Example | Structure | LC-MS (MH+) | 1H-NMR |
|---|---|---|---|
| 226 | 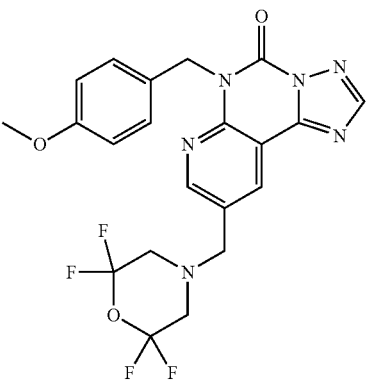 [SMILES: COc1ccc(Cn2c(=O)n3ncnc3c3cc(CN4CC(F)(F)OC(F)(F)C4)cnc32)cc1]<br>C₂₁H₁₈F₄N₆O₃ | 479.1 | 1NMR (400 MHz, CDCl3) δ 3.08 (t, J = 8.16 Hz, 4H), 3.77 (s, 3H), 3.95 (s, 2H), 5.76 (s, 2H), 6.79-6.89 (m, 2H), 7.57-7.67 (m, 2H), 8.38 (s, 1H), 8.62 (d, J = 2.26 Hz, 1H), 8.78 (d, J = 2.26 Hz, 1H) |
| 227 | 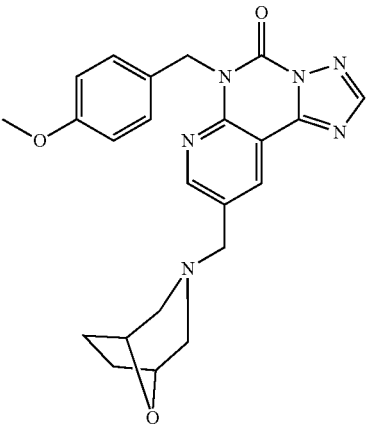 [SMILES: COc1ccc(Cn2c(=O)n3ncnc3c3cc(CN4CC5CCC(C4)O5)cnc32)cc1]<br>C₂₃H₂₄N₆O₃ | 433.3 | 1H NMR (400 MHz, CDCl3) δ 2.07-2.14 (m, 2H), 2.34-2.39 (m, 2H), 3.09 (dd, J = 11.98, 2.70 Hz, 2H), 3.48 (d, J = 11.67 Hz, 2H), 3.77 (s, 3H), 4.37 (s, 2H), 4.53 (br s, 2H), 5.74 ( s, 2H), 6.83 (d, J = 8.66 Hz, 2H), 7.60 (d, J = 8.66 Hz, 2H), 8.39 (s, 1H), 8.78 (d, J = 2.13 Hz, 1H), 9.01 (s, 1H) |
| 228 | 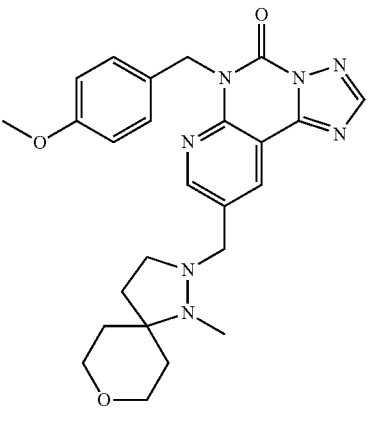 [SMILES: COc1ccc(Cn2c(=O)n3ncnc3c3cc(CN4CCC5(CCOCC5)N4C)cnc32)cc1]<br>C₂₅H₂₉N₇O₃ | 476.3 | 1H NMR (400 MHz, CDCl3) δ 1.93 (br s, 2H), 2.06 (td, J = 12.36, 4.89 Hz, 2H), 2.39 (t, J = 7.34 Hz, 2H), 3.00 (s, 3H), 3.34 (t, J = 7.47 Hz, 2H), 3.42-3.53 (m, 2H), 3.77 (s, 3H), 4.10 (dd, J = 11.61, 4.71 Hz, 2H), 4.60 (s, 2H), 5.75 (s, 2H), 6.76-6.90 (m, 2H), 7.61 (d, J = 8.66 Hz, 2H), 8.39 (s, 1H), 8.68 (d, J = 2.13 Hz, 1H), 8.81 (d, J = 2.13 Hz, 1H) |

TABLE 26-continued

| Example | Structure | LC-MS (MH+) | 1H-NMR |
|---|---|---|---|
| 229 | C$_{22}$H$_{24}$N$_6$O$_3$ | 421.2 | 1H NMR (400 MHz, CDCl3) δ 1.24 (d, J = 6.27 Hz, 3H), 2.55 (t, J = 11.11 Hz, 1H), 2.90 (td, J = 11.26, 4.58 Hz, 1H), 3.41-3.57 (m, 2H), 3.77 (s, 3H), 3.97-4.14 (m, 3H), 4.28-4.44 (m, 2H), 5.74 (s, 2H), 6.83 (d, J = 8.66 Hz, 2H), 7.60 (d, J = 8.66 Hz, 2H), 8.39 (s, 1H), 8.78 (s, 1H), 9.01 (s, 1H) |
| 230 | C$_{22}$H$_{24}$N$_6$O$_3$ | 421.3 | 1H NMR (400 MHz, CDCl3) δ 1.63 (d, J = 6.53 Hz, 3H), 3.28 (d, J = 11.80 Hz, 2H), 3.77 (s, 3H), 3.82-4.20 (m, 6H), 5.74 (s, 2H), 6.83 (d, J = 8.66 Hz, 2H), 7.60 (d, J = 8.66 Hz, 2H), 8.39 (s, 1H), 8.81 (d, J = 1.76 Hz, 1H), 9.03 (s, 1H) |
| 231 | C$_{22}$H$_{25}$N$_7$O$_3$ | 436.2 | 1H NMR (400 MHz, CDCl3) δ 1.24 (d, J = 6.15 Hz, 6H), 2.68 (t, J = 10.98 Hz, 2H), 3.57 (d, J = 11.42 Hz, 2H), 3.75 (s, 3H), 4.00 (dd, J = 9.85, 6.09 Hz, 2H), 4.53 (br s, 2H), 5.69 (s, 2H), 6.81 (d, J = 8.41 Hz, 2H), 7.57 (d, J = 8.41 Hz, 2H), 8.50 (s, 1H), 9.11 (s, 1H) |
| 232 | 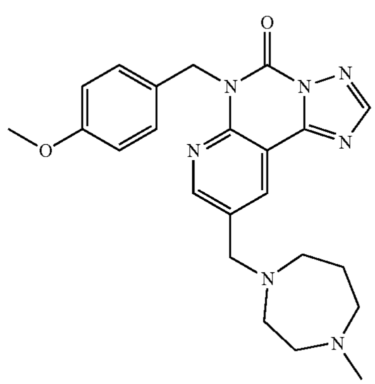 | 434.2 | 1H NMR (400 MHz, DMSO-d6) δ 1.92-2.20 (m, 2H), 2.85 (s, 3H), 2.85-3.75 (m, 11H), 4.11-4.46 (m, 2H), 5.61 (s, 2H), 6.87 (d, J = 8.66 Hz, 2H), 7.40 (d, J = 8.41 Hz, 2H), 8.66 (s, 1H), 8.72-8.88 (m, 2H) |

TABLE 26-continued

| Example | Structure | LC-MS (MH+) | 1H-NMR |
|---|---|---|---|
| | $C_{23}H_{27}N_7O_2$ | | |
| 233 | 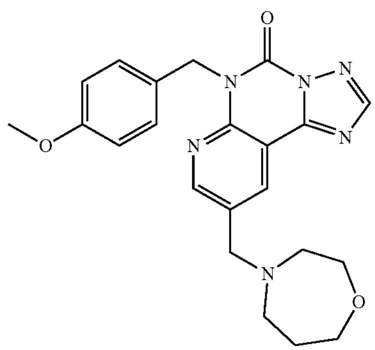 | 421.2 | 1H NMR (400 MHz, DMSO-d6) δ 2.02-2.19 (m, 2H), 3.21-3.49 (m, 4H), 3.51-3.79 (m, 13H), 4.58-4.72 (m, 2H), 5.61 (s, 2H), 6.88 (d, J = 8.66 Hz, 2H), 7.40 (d, J = 8.66 Hz, 2H), 8.68 (s, 1H), 8.89 (s, 1H), 8.94 (s, 1H) |
| | $C_{22}H_{24}N_6O_3$ | | |
| 234 | 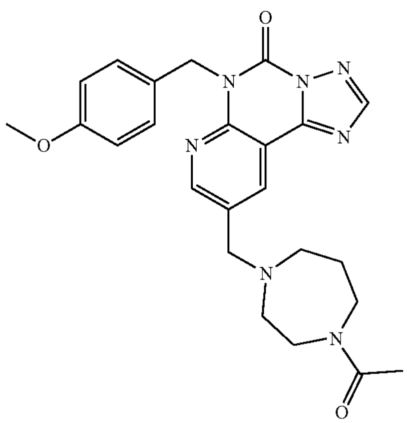 | 462.3 | 1H NMR (400 MHz, DMSO-d6) δ 2.00-2.22 (m, 5H), 3.05-3.67 (m, 8H), 3.72 (s, 3H), 4.53-4.72 (m, 2H), 5.61 (s, 2H), 6.88 (d, J = 8.41 Hz, 2H), 7.41 (d, J = 8.41 Hz, 2H), 8.68 (s, 1H), 8.87 (s, 1H), 8.91 (s, 1H) |
| | $C_{24}H_{27}N_7O_3$ | | |
| 235 | 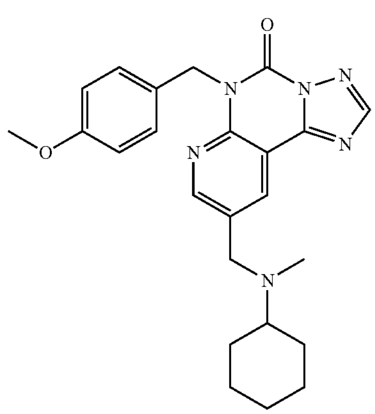 | 433.3 | 1H NMR (400 MHz, DMSO-d6) δ 1.10-1.72 (m, 6H), 1.81-1.96 (m, 2H), 1.99-2.21 (m, 2H), 2.61-2.67 (m, 3H), 3.33-3.41 (m, 1H), 3.72 (s, 3H), 4.38-4.73 (m, 2H), 5.62 (s, 2H), 6.87 (d, J = 8.66 Hz, 2H), 7.40 (d, J = 8.53 Hz, 2H), 8.68 (s, 1H), 8.90 (s, 1H), 8.94 (s, 1H) |
| | $C_{24}H_{28}N_6O_2$ | | |

TABLE 26-continued

| Example | Structure | LC-MS (MH+) | 1H-NMR |
| --- | --- | --- | --- |
| 236 | C₂₃H₂₆N₆O₃ | 435.2 | 1H NMR (400 MHz, DMSO-d6) δ 1.42-1.59 (m, 1H), 1.72-1.86 (m, 1H), 1.98-2.09 (m, 1H), 2.15-2.25 (m, 1H), 2.99-3.21 (m, 2H), 3.23-3.30 (m, 3H), 3.35-3.52 (m, 2H), 3.53-3.61 (m, 1H), 3.72 (s, 3H), 4.50-4.61 (m, 2H), 5.61 (s, 2H), 6.87 (d, J = 8.53 Hz, 2H), 7.40 (d, J = 8.66 Hz, 2H), 8.68 (s, 1H), 8.83-8.92 (m, 2H) |
| 237 | C₂₃H₂₆N₆O₃ | 435.2 | 1H NMR (400 MHz, DMSO-d6) δ 1.74-1.92 (m, 2H), 1.98-2.12 (m, 2H), 2.64-2.71 (m, 3H), 3.32-3.44 (m, 2H), 3.59-3.81 (m, 4H), 3.99-4.10 (m, 2H), 4.37-4.49 (m, 1H), 4.69-4.79 (m, 1H), 5.62 (s, 2H), 6.87 (d, J = 8.66 Hz, 2H), 7.40 (d, J = 8.53 Hz, 2H), 8.68 (s, 1H), 8.90 (s, 1H), 8.95 (s, 1H) |
| 238 | C₂₄H₂₉N₇O₃ | 464.3 | 1H NMR (400 MHz, DMSO-d6) δ 2.54-2.75 (m, 2H), 2.86-3.21 (m, 4H), 3.26-3.33 (m, 5H), 3.35-3.55 (m, 2H), 3.65 (t, J = 4.71 Hz, 2H), 3.72 (s, 3H), 3.85-3.94 (m, 2H), 5.60 (s, 2H), 6.87 (d, J = 8.53 Hz, 2H), 7.39 (d, J = 8.41 Hz, 2H), 8.64 (s, 1H), 8.64-8.67 (m, 1H), 8.75-8.78 (m, 1H) |

TABLE 26-continued

| Example | Structure | LC-MS (MH+) | 1H-NMR |
|---|---|---|---|
| 239 | C₂₃H₂₈N₆O₃ | 437.2 | 1H NMR (400 MHz, DMSO-d6) δ 1.27-1.47 (m, 6H), 3.14-3.20 (m, 1H), 3.22 (s, 3H), 3.41-3.56 (m, 4H), 3.72 (s, 4H), 4.48-4.67 (m, 2H), 5.61 (s, 2H), 6.87 (d, J = 8.53 Hz, 2H), 7.40 (d, J = 8.66 Hz, 2H), 8.68 (s, 1H), 8.91 (s, 1H), 8.97 (s, 1H) |
| 240 | C₂₂H₂₅N₇O₂ | 420.2 | 1H NMR (400 MHz, DMSO-d6) δ 2.79 (s, 5H), 2.93 (br s, 3H), 3.55 (d, J = 10.29 Hz, 30H), 3.75 (s, 6H), 3.78 (s, 5H), 3.99 (s, 2H), 5.55 (s, 2H), 6.92 (d, J = 8.78 Hz, 2H), 7.37 (d, J = 8.66 Hz, 2H), 7.92 (s, 1H), 8.64 (s, 1H) |
| 241 | C₂₁H₂₂N₆O₃ | 407.2 | 1H NMR (400 MHz, DMSO-d6) δ 2.99 (br s, 4H), 3.74 (s, 4H), 3.76-4.06 (m, 12H), 4.41 (br s, 2H), 5.57 (s, 2H), 6.90 (d, J = 8.66 Hz, 2H), 7.39 (d, J = 8.66 Hz, 2H), 8.22 (br s, 1H), 8.68 (s, 1H), 8.77 (s, 1H) |
| 242 | C₂₂H₂₄N₆O₂ | 405.2 | 1H NMR (400 MHz, CDCl3) δ 1.91 (br s, 2H), 2.14 (br s, 2H), 2.65 (br s, 2H), 2.77-3.00 (m, 2H), 3.50 (br s, 2H), 3.79 (s, 3H), 4.28 (s, 2H), 5.73 (s, 2H), 6.89 (d, J = 8.53 Hz, 2H), 7.47 (d, J = 8.16 Hz, 2H), 8.55 (s, 1H), 8.60 (s, 1H), 8.80 (br s, 1H) |

TABLE 26-continued

| Example | Structure | LC-MS (MH+) | 1H-NMR |
|---|---|---|---|
| 243 | C₂₁H₂₂N₆O₂S | 423.2 | 1H NMR (400 MHz, CDCl3) δ 2.91 (br s, 4H), 3.20 (br s, 4H), 3.67 (s, 3H), 4.21 (s, 2H), 5.57 (s, 2H), 6.77 (d, J = 8.66 Hz, 2H), 7.27 (d, J = 8.53 Hz, 2H), 8.41 (br s, 1H), 8.44 (s, 1H), 8.52 (s, 1H) |
| 244 | C₂₃H₂₆N₆O₃ | 435.3 | 1H NMR (400 MHz, CDCl3) δ 1.10 (d, J = 6.27 Hz, 6H), 2.28 (t, J = 11.23 Hz, 2H), 3.16 (d, J = 11.42 Hz, 2H), 3.67 (s, 3H), 3.85-4.02 (m, 2H), 4.20 (s, 2H), 5.51 (s, 2H), 6.76 (d, J = 8.66 Hz, 2H), 7.25 (d, J = 8.53 Hz, 2H), 8.31 (s, 1H), 8.42 (s, 1H), 8.53 (s, 1H) |
| 245 | C₂₁H₂₄N₆O₃ | 409.2 | 1H NMR (400 MHz, DMSO-d6) δ 2.79 (s, 3H), 3.33 (s, 5H), 3.72 (s, 5H), 4.44-4.71 (m, 2H), 5.61 (s, 2H), 6.87 (d, J = 8.66 Hz, 2H), 7.40 (d, J = 8.66 Hz, 2H), 8.68 (s, 1H), 8.85-8.90 (m, 1H), 8.91-8.96 (m, 1H) |

TABLE 26-continued

| Example | Structure | LC-MS (MH+) | 1H-NMR |
|---|---|---|---|
| 246 | C₂₃H₂₃N₇O₄ | 462.2 | 1H NMR (400 MHz, DMSO-d6) δ 2.90-3.44 (m, 4H), 3.65-3.82 (m, 5H), 3.91-4.49 (m, 5H), 5.61 (s, 2H), 6.87 (d, J = 8.66 Hz, 2H), 7.40 (d, J = 8.53 Hz, 2H), 8.66 (s, 1H), 8.70-8.88 (m, 2H) |
| 247 | C₂₃H₂₆N₆O₃ | 435.3 | 1H NMR (400 MHz, CDCl3) δ 1.16 (m, 6H), 2.36 (br s, 2H), 2.84 (br s, 1H), 3.61-3.74 (m, 3H), 3.77 (s, 3H), 3.82 (br s, 1H), 5.75 (s, 2H), 6.83 (d, J = 8.66 Hz, 2H), 7.62 (d, J = 8.53 Hz, 2H), 8.36 (s, 1H), 8.63 (br s, 1H), 8.75 (br s, 1H) |
| 248 | C₂₃H₂₆N₆O₃ | 435.3 | 1H NMR (400 MHz, CDCl3) δ 1.15 (m, 6H), 2.36 (br s, 2H), 2.83 (br s, 1H), 3.60-3.74 (m, 3H), 3.77 (s, 4H), 3.83 (d, J = 9.41 Hz, 1H), 5.75 (s, 2H), 6.83 (d, J = 8.66 Hz, 2H), 7.62 (d, J = 8.53 Hz, 2H), 8.36 (s, 1H), 8.63 (br s, 1H), 8.74 (br s, 1H) |

Preparative Example 249

6-(4-Methoxybenzyl)-9-(piperazin-1-ylmethyl)pyrido[3,2-e][1,2,4]triazolo[1,5-c]pyrimidin-5(6H)-one

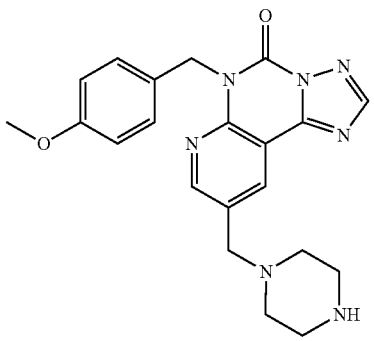

Step 27.1: tert-butyl 2-(6-(4-methoxybenzyl)-5-oxo-5,6-dihydropyrido[3,2-e][1,2,4]triazolo[1,5-c]pyrimidin-9-yl)ethylcarbamate The title compound was prepared as described in Step 21.1 and used in the next step without further characterization.

Step 27.2: 6-(4-methoxybenzyl)-9-(piperazin-1-ylmethyl)pyrido[3,2-e][1,2,4]triazolo[1,5-c]pyrimidin-5(6H)-one (249)

The title compound was prepared as described in Step 21.2.

Numerous compounds were made using the above general procedure, as exemplified in Table 27:

TABLE 27

| Example | Structure | LC-MS (MH+) | 1H-NMR |
|---|---|---|---|
| 249 | $C_{21}H_{23}N_7O_2$ | 406.2 | 1H NMR (400 MHz, CDCl3 and DMSO-d6) δ 2.74 (br s, 4H), 3.11 (br s, 4H), 3.65 (d, J = 2.01 Hz, 3H), 3.96 (br s, 2H), 5.62 (s, 2H), 6.71 (dd, J = 8.72, 1.95 Hz, 2H), 7.47 (dd, J = 8.66, 1.88 Hz, 2H), 8.25 (d, J = 2.01 Hz, 1H), 8.51 (s, 1H), 8.58-8.71 (m, 1H), 9.84 (br s, 1H) |
| 250 | $C_{23}H_{27}N_7O_2$ | 434.2 | 1H NMR (400 MHz, DMSO-d6) δ 1.18 (d, J = 6.53 Hz, 6H), 2.12 (t, J = 11.80 Hz, 2H), 3.03 (d, J = 10.29 Hz, 2H), 3.34 (br s, 2H), 3.72 (s, 3H), 3.81 (br s, 2H), 5.60 (s, 2H), 6.87 (d, J = 8.66 Hz, 2H), 7.39 (d, J = 8.66 Hz, 2H), 8.21 (d, J = 8.53 Hz, 1H), 8.62 (d, J = 2.13 Hz, 1H), 8.64 (s, 1H), 8.76 (d, J = 2.13 Hz, 1H), 8.95 (br s, 1H) |

Preparative Example 251

6-(4-Methoxybenzyl)-9-((4-((tetrahydrofuran-3-yl)methyl)piperazin-1-yl)methyl)pyrido[3,2-e][1,2,4]triazolo[1,5-c]pyrimidin-5(6H)-one

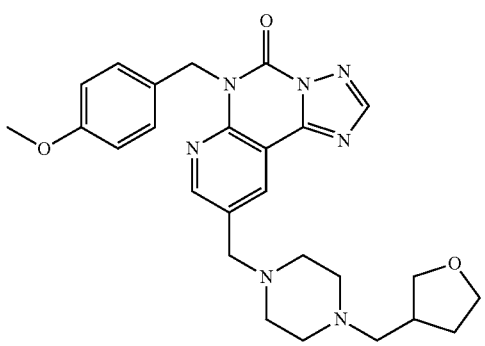

251

Step 28.1: 6-(4-methoxybenzyl)-9-((4-((tetrahydrofuran-3-yl)methyl)piperazin-1-yl)methyl)pyrido[3,2-e][1,2,4]triazolo[1,5-c]pyrimidin-5(6H)-one (251)

The title compound was prepared as described in Step 26.3.

Numerous compounds were made using the above general procedure, as exemplified in Table 28.

Preparative Example 252

6-(4-Methoxybenzyl)-9-((4-(methylsulfonyl)piperazin-1-yl)methyl)pyrido[3,2-e][1,2,4]triazolo[1,5-c]pyrimidin-5(6H)-one

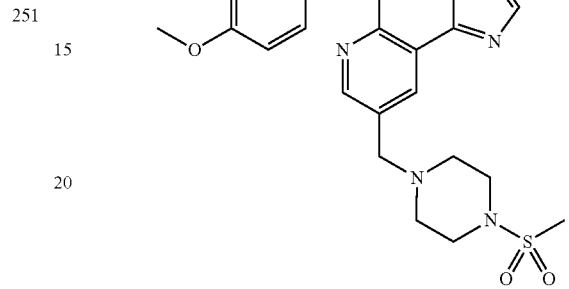

252

Step 29.1: 6-(4-methoxybenzyl)-9-((4-(methylsulfonyl)piperazin-1-yl)methyl)pyrido[3,2-e][1,2,4]triazolo[1,5-c]pyrimidin-5(6H)-one (252)

6-(4-Methoxybenzyl)-9-(piperazin-1-ylmethyl)pyrido[3,2-e][1,2,4]triazolo[1,5-c]pyrimidin-5 (6H)-one (34 mg, 0.09 mmol), acetonitrile (1 ml), triethylamine (75 µl, 0.53 mmol), and methane sulfonyl chloride (50 mg, 0.44 mmol) were combined and the mixture was stirred for 4 hours, filtered through a plug of C18 and purified by preparative HPLC to afford 17 mg (33%) of the sulfonamide as a white solid.

The following compounds were prepared using the above procedures.

TABLE 28

| Example | Structure | LC-MS (MH+) | 1H-NMR |
|---|---|---|---|
| 251 | $C_{26}H_{31}N_7O_3$ | 490.3 | 1H NMR (400 MHz, CDCl3 and DMSO-d6) δ 5 1.68 (dd, J = 12.49, 6.96 Hz, 1H), 2.13 (d, J = 6.02 Hz, 1H), 2.69 (d, J = 6.27 Hz, 1H), 2.80-3.07 (m, 6H), 3.19-3.52 (m, 2H), 3.57-3.73 (m, 3H), 3.59-3.70 (m, 2H), 3.70-3.82 (m, 2H), 3.88 (t, J = 7.47 Hz, 1H), 3.99-4.67 (m, 7H), 5.63 (s, 2H), 6.72 (d, J = 8.66 Hz, 2H), 7.48 (d, J = 8.41 Hz, 2H), 8.15-8.31 (m, 1H), 8.55 (br s, 1H), 8.63 (br s, 1H) |

TABLE 29

| Example | Structure | LC-MS (MH+) | 1H-NMR |
|---|---|---|---|
| 252 | C₂₂H₂₅N₇O₄S | 484.2 | 1H NMR (400 MHz, CDCl3 and DMSO-d6) δ 2.48 (d, J = 1.63 Hz, 2H), 2.76 (d, J = 2.26 Hz, 3H), 3.09 (br s, 4H), 3.54 (br s, 4H), 3.65 (d, J = 2.51 Hz, 3H), 4.21 (br s, 2H), 5.63 (d, J = 1.76 Hz, 2H), 6.72 (dd, J = 8.78, 2.26 Hz, 2H), 7.47 (dd, J = 8.66, 2.38 Hz, 2H), 8.26 (d, J = 2.38 Hz, 1H), 8.85 (br s, 1H), 9.00 (br s, 1H) |
| 253 | C₂₃H₂₈N₈O₄S | 513.2 | 1H NMR (400 MHz, CDCl3 and DMSO-d6) δ 2.70 (d, J = 2.64 Hz, 6H), 3.13 (br s, 4H), 3.40-3.59 (m, 4H), 3.63 (d, J = 2.76 Hz, 3H), 4.32 (br s, 2H), 5.60 (s, 2H), 6.69 (dd, J = 8.72, 2.45 Hz, 2H), 7.39-7.59 (m, 2H), 8.24 (d, J = 2.89 Hz, 1H), 8.93 (br s, 1H), 9.08 (br s, 1H) |
| 254 | C₂₃H₂₂F₃N₇O₃ | 502.2 | 1H NMR (400 MHz, CDCl3 and DMSO-d6) δ 2.94 (br s, 4H), 3.64 (s, 3H), 3.80 (br s, 4H), 4.07 (br s, 2H), 5.61 (s, 2H), 6.61-6.78 (m, 2H), 7.45 (d, J = 8.66 Hz, 2H), 8.24 (s, 1H), 8.76 (br s, 1H), 8.90 (br s, 1H) |

TABLE 29-continued

| Example | Structure | LC-MS (MH+) | 1H-NMR |
|---|---|---|---|
| 255 | 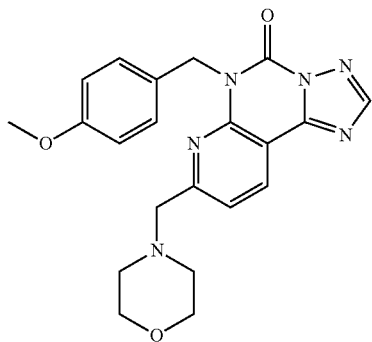<br>$C_{26}H_{29}N_7O_4$ | 504.3 | 1H NMR (400 MHz, CDCl3 and DMSO-d6) δ 1.89-2.20 (m, 2H), 2.88-3.25 (m, 5H), 3.36-3.64 (m, 4H), 3.68 (d, J = 0.88 Hz, 3H), 3.72-3.95 (m, 4H), 4.26 (br s, 2H), 5.65 (br s, 2H), 6.74 (d, J = 7.78 Hz, 2H), 7.50 (d, = 7.65 Hz, 2H), 8.28 (d, J = 1.00 Hz, 1H), 8.88 (br s, 1H), 9.09 (br s, 1H) |

Preparative Example 256

6-(4-Methoxybenzyl)-8-(morpholinomethyl)pyrido[3,2-e][1,2,4]triazolo[1,5-c]pyrimidin-5(6H)-one

256

Step 30.1: 6-(4-methoxybenzyl)-5-oxo-5,6-dihydropyrido[3,2-e][1,2,4]triazolo[1,5-c]pyrimidine-8-carbaldehyde 8-(Dimethoxymethyl)-6-(4-methoxybenzyl)pyrido[3,2-e][1,2,4]triazolo[1,5-c]pyrimidin-5(6H)-one (682 mg, 1.79 mmol), tetrahydrofuran (20 ml), water (5 ml) and 12 N hydrochloric acid (3 ml) were combined and stirred at room temperature for 20 hours. The mixture was neutralized slowly with powdered sodium bicarbonate to pH 8. The mixture was diluted with water (20 mL) and extracted with ethyl acetate (3×20 mL). The combined extracts were dried (MgSO₄) and concentrated to afford 516 mg (77%) of the aldehyde as a yellow foam, which was used without further purification. 1H NMR (400 MHz, CDCl3) δ 3.73-3.81 (m, 3H), 5.83, (s, 2H), 6.85 (d, J=8.66 Hz, 2H), 7.64 (d, J=8.53 Hz, 2H), 8.03 (d, J=7.78 Hz, 1H), 8.42 (s, 1H), 8.83 (d, J=7.91 Hz, 1H), 10.22 (s, 1H). LCMS (MH+, 336.1).

Step 30.2: 6-(4-methoxybenzyl)-8-(morpholinomethyl)pyrido[3,2-e][1,2,4]triazolo[1,5-c]pyrimidin-5(6H)-one (14)

The title compound was prepared as described in Step 26.3.

Numerous compounds were made using the above general procedure, as exemplified in Table 30.

TABLE 30

| Example | Structure | LC-MS (MH+) | 1H-NMR |
|---|---|---|---|
| 256 | 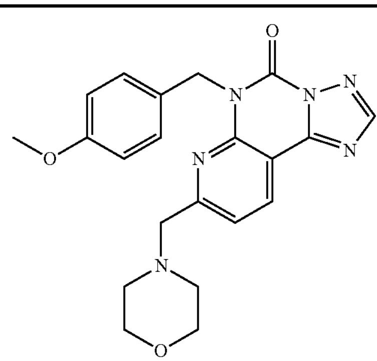 | 407.2 | 1H NMR (400 MHz, CDCl3) δ 3.47 (br s, 2H), 3.76 (s, 3H), 3.79-3.82 (m,2H), 3.87 (br s, 4H), 4.41 (s, 2H), 5.78 (s, 2H), 6.82 (d, J = 8.66 Hz, 2H), 7.30 (d, J = 9.29 Hz, 2H), 7.72 (d, J = 7.91 Hz, 1H), 8.44 (s, 1H), 8.76 (d, J = 7.91 Hz, 1H) |

TABLE 30-continued

| Example | Structure | LC-MS (MH+) | 1H-NMR |
|---|---|---|---|
| | C₂₁H₂₂N₆O₃ | | |
| 257 | C₂₃H₂₆N₆O₃ | 435.3 | 1H NMR (400 MHz, CDCl3) δ 1.12 (d, J = 6.27 Hz, 6H), 2.43 (t, J = 11.04 Hz, 2H), 3.38 (d, J = 11.67 Hz, 2H), 3.75 (s, 3H), 4.02 (dd, J = 10.23, 6.34 Hz, 2H), 4.44 (s, 2H), 5.76 (s, 2H), 6.83 (d, J = 8.66 Hz, 2H), 7.36 (d, J = 8.66 Hz, 2H), 7.70 (d, J = 7.78 Hz, 1H), 8.43 (s, 1H), 8.76 (d, J = 7.91 Hz, 1H) |
| 258 | C₂₂H₂₄N₆O₃ | 421.2 | 1H NMR (400 MHz, CDCl3) δ 1.31 (s, 3H), 3.11 (s, 2H), 3.74 (s, 3H), 4.32-4.40 (m, 4H), 4.56 (s, 3H), 5.81 (s, 2H), 6.80 (d, J = 8.53 Hz, 2H), 7.30 (d, J = 8.66 Hz, 2H), 7.60 (d, J = 7.91 Hz, 1H), 8.42 (s, 1H), 8.76 (d, J = 7.91 Hz, 1H) |
| 259 | C₂₃H₂₆N₆O₃ | 435.3 | 1H NMR (400 MHz, CDCl3) δ 1.54-1.69 (m, 1H), 2.06-2.30 (m, 2H), 2.69 (dt, J = 14.09, 6.95 Hz, 2H), 2.80 (s, 3H), 3.10 (br s, 2H), 3.39 (dd, J = 8.91, 6.15 Hz, 1H), 3.70-3.75 (m, 1H), 3.76 (s, 3H), 3.81-3.87 (m, 1H), 3.90 (dd, J = 8.85, 7.22 Hz, 1H), 4.51 (s, 2H), 5.76 (s, 2H), 6.83 (d, J = 8.53 Hz, 2H), 7.32 (d, J = 8.66 Hz, 2H), 7.76 (d, J = 7.91 Hz, 1H), 8.43 (s, 1H), 8.79 (d, J = 7.91 Hz, 1H) |

TABLE 30-continued

| Example | Structure | LC-MS (MH+) | 1H-NMR |
|---|---|---|---|
| 260 | C₂₁H₂₂N₆O₂ | 391.2 | 1H NMR (400 MHz, CDCl3) δ 0.67 (d, J = 6.53 Hz, 2H), 1.23 (d, J = 3.01 Hz, 2H), 2.42 (tt, J = 7.29, 3.75 Hz, 1H), 2.84 (s, 3H), 3.76 (s, 3H), 4.55 (s, 2H), 5.74 (s, 2H), 6.81 (d, J = 8.53 Hz, 2H), 7.36 (d, J = 8.66 Hz, 2H), 7.74 (d, J = 7.78 Hz, 1H), 8.43 (s, 1H), 8.76 (d, J = 7.91 Hz, 1H) |
| 261 | C₂₂H₂₅N₇O₄S | 484.2 | 1H NMR (400 MHz, CDCl3) δ 2.87 (s, 3H), 3.15 (br s, 4H), 3.53 (br s, 4H), 3.78 (s, 3H), 4.37 (s, 2H), 5.76 (s, 2H), 6.85 (d, J = 8.66 Hz, 2H), 7.30 (d, J = 8.66 Hz, 2H), 7.70 (d, J = 8.03 Hz, 1H), 8.44 (s, 1H), 8.77 (d, J = 7.91 Hz, 1H) |
| 262 | C₂₄H₂₂N₆O₂ | 427.3 | 1H NMR (400 MHz, CDCl3) d 3.62 (s, 3H), 4.03 (s, 2H), 4.26 (s, 2H), 5.71 (s, 2H), 6.67 (d, J = 8.53 Hz, 2H), 7.19-7.38 (m, 10H), 8.24-8.35 (m, 1H), 8.57-8.65 (m, 1H) |
| 263 | C₂₃H₂₀N₆O₂ | 413.2 | 1H NMR (400 MHz, CDCl3) d 3.67 (s, 3H), 4.60 (s, 2H), 5.67 (s, 2H), 6.63 (d, J = 8.03 Hz, 2H), 6.73 (d, J = 8.53 Hz, 3H), 6.75-6.82 (m, 1H), 7.12 (s, 2H), 7.33-7.40 (m, 1H), 7.41-7.48 (m, 2H), 8.22-8.34 (m, 1H), 8.45-8.57 (m, 1H) |

TABLE 30-continued

| Example | Structure | LC-MS (MH+) | 1H-NMR |
|---|---|---|---|
| 264 | 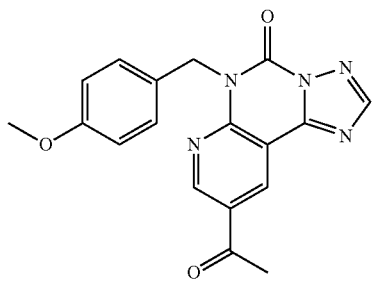 $C_{25}H_{22}N_6O_2$ | 439.2 | 1H NMR (400 MHz, CDCl3) d 3.68 (s, 3H), 4.46 (br s, 3H), 4.64 (s, 2H), 5.69 (s, 2H), 6.73 (d, J = 8.53 Hz, 2H), 7.03-7.13 (m, 2H), 7.18 (s, 4H), 7.24-7.33 (m, 2H), 7.47-7.56 (m, 1H), 8.28-8.41 (m, 1H), 8.60-8.71 (m, 1H) |

Preparative Example 265

9-Acetyl-6-(4-methoxybenzyl)pyrido[3,2-e][1,2,4]triazolo[1,5-c]pyrimidin-5(6H)-one Step 31.1: 9-acetyl-6-(4-methoxybenzyl)pyrido[3,2-e][1,2,4]triazolo[1,5-c]pyrimidin-5(6H)-one (265)

6-(4-Methoxybenzyl)-9-(1-ethoxyvinyl)pyrido[3,2-e][1,2,4]triazolo[1,5-c]pyrimidin-5(6H)-one (147 mg, 0.39 mmol) was suspended in dioxane (6 ml) and 6 N hydrochloric acid (3 ml) and stirred for 4 hours. The mixture was basified to pH 11 with 1 N sodium hydroxide and extracted with DCM (3×15 mL). The combined extracts were dried (MgSO₄) and concentrated to afford 122 mg (90%) of the ketone as a yellow solid.

Numerous compounds were made using the above general procedure, as exemplified in Table 31:

TABLE 31

| Example | Structure | LC-MS (MH+) | 1H-NMR |
|---|---|---|---|
| 265 | $C_{18}H_{15}N_5O_3$ | 350.2 | 1H NMR (400 MHz, CDCl3) δ 2.73 (s, 3H), 3.76 (s, 3H), 5.79 (s, 2H), 6.78-6.89 (m, 2H), 7.56-7.66 (m, 2H), 8.39 (s, 1H), 9.13 (d, J = 2.26 Hz, 1H), 9.35 (d, J = 2.26 Hz, 1H) |

Preparative Example 266

9-(1-((2S,6R)-2,6-Dimethylmorpholino)ethyl)-6-(4-methoxybenzyl)pyrido[3,2-e][1,2,4]triazolo[1,5-c]pyrimidin-5(6H)-one

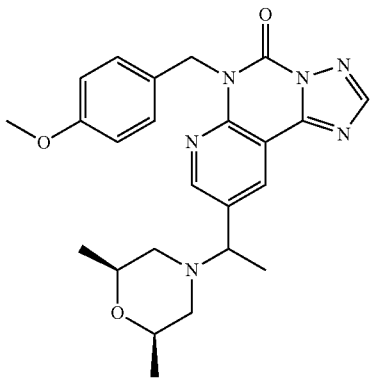 [SMILES: COc1ccc(Cn2c(=O)n3ncnc3c3cc(C(C)N4C[C@@H](C)O[C@@H](C)C4)cnc32)cc1]

266

Step 32.1: 9-(1-((2S,6R)-2,6-dimethylmorpholino)ethyl)-6-(4-methoxybenzyl)pyrido[3,2-e][1,2,4]triazolo[1,5-c]pyrimidin-5(6H)-one (266)

9-Acetyl-6-(4-methoxybenzyl)pyrido[3,2-e][1,2,4]triazolo[1,5-c]pyrimidin-5(6H)-one (67 mg, 0.19 mmol), (2S,6R)-2,6-dimethylmorpholine (0.060 ml, 0.49 mmol), acetonitrile (1 ml) and acetic acid (0.020 mL, 0.35 mmol) were combined and stirred for 10 minutes. Sodium cyanoborohydride (18 mg, 0.29 mmol) was added and the mixture was stirred for 3 days at 50° C. The mixture was filtered and purified by preparative HPLC to afford 26 mg (23%) of 266 as a white solid.

Numerous compounds were made using the above general procedure, as exemplified in Table 32:

Preparative Example 267

9-(1-Hydroxy-2-morpholinoethyl)-6-(4-methoxybenzyl)pyrido[3,2-e][1,2,4]triazolo[1,5-c]pyrimidin-5(6H)-one

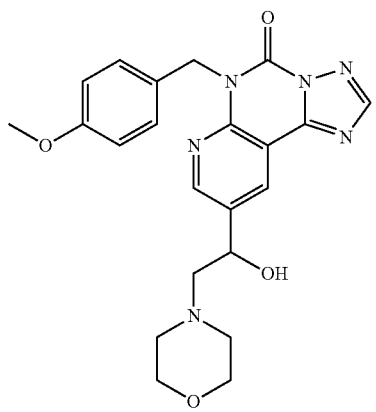

267

Step 33.1: 9-(1-hydroxy-2-morpholinoethyl)-6-(4-methoxybenzyl)pyrido[3,2-e][1,2,4]triazolo[1,5-c]pyrimidin-5(6H)-one (267)

3-Chloroperbenzoic acid (139 mg, 0.62 mmol) was added to a stirred solution of 6-(4-methoxybenzyl)-9-vinylpyrido[3,2-e][1,2,4]triazolo[1,5-c]pyrimidin-5(6H)-one (138 mg, 0.41 mmol) in dichloromethane (1.3 ml) and the mixture was stirred for 18 hours. Saturated sodium bicarbonate (3 mL) was added and the mixture was stirred for 2 hours and diluted with dichloromethane (5 mL). The organic layer was separated, dried ($MgSO_4$) and concentrated under vacuum to afford 118 mg of the crude epoxide as a yellow semi-solid. This material was treated with morpholine (0.50 ml) and stirred for 16 hours at room temperature. The mixture was concentrated under vacuum and the residue was taken up in DMSO, filtered and purified by HPLC to afford 63 mg (26%) of the trifluoroacetic acid salt of 267 as a white powder.

TABLE 32

| Example | Structure | LC-MS (MH+) | 1H-NMR |
|---|---|---|---|
| 266 | $C_{24}H_{28}N_6O_3$ | 449.3 | 1H NMR (400 MHz, CDCl3) δ 1.19 (d, J = 6.27 Hz, 3H), 1.23 (d, J = 6.27 Hz, 3H), 1.92 (d, J = 7.03 Hz, 3H), 2.34 (td, J = 11.01, 2.32 Hz, 2H), 3.32 (d, J = 11.42 Hz, 1H), 3.57 (d, J = 11.42 Hz, 1H), 3.77 (s, 3H), 4.12 (d, J = 7.03 Hz, 2H), 4.54 (q, J = 6.86 Hz, 1H), 5.75 (s, 2H), 6.85 (d, J = 8.66 Hz, 2H), 7.62 (d, J = 8.66 Hz, 2H), 8.40 (s, 1H), 8.74 (s, 1H), 8.95 (s, 1H) |

Numerous compounds were made using the above general procedure, as exemplified in Table 33:

TABLE 33

| Example | Structure | LC-MS (MH+) | 1H-NMR |
|---|---|---|---|
| 267 | 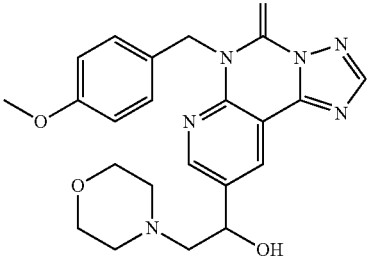<br>$C_{22}H_{24}N_6O_4$ | 437.2 | 1H NMR (400 MHz, CDCl3) δ 3.11 (br s, 4H), 3.26 (dd, J = 13.30, 2.89 Hz, 1H), 3.35 (dd, J = 13.30, 10.67 Hz, 1H), 3.76 (s, 3H), 4.12 (br s, 4H), 5.65-5.71 (m, 1H), 5.73 (s, 2H), 6.82 (d, J = 8.78 Hz, 2H), 7.58 (d, J = 8.66 Hz, 2H), 8.35 (s, 1H), 8.69 (d, J = 2.26 Hz, 1H), 8.90 (d, J = 2.26 Hz, 1H) |
| 268 | 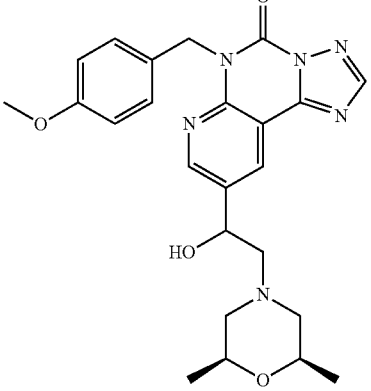<br>$C_{24}H_{28}N_6O_4$ | 465.3 | 1H NMR (400 MHz, CDCl3) δ 1.29 (d, J = 6.40 Hz, 2H), 1.31 (d, J = 6.27 Hz, 2H), 2.57 (d, J = 11.92 Hz, 2H), 3.21 (d, J = 13.30 Hz, 2H), 3.25-3.39 (m, 2H), 3.66 (d, J = 11.29 Hz, 1H), 3.76 (s, 3H), 3.80-3.89 (m, 1H), 4.19 (d, J = 16.06 Hz, 2H), 5.60 (d, J = 10.16 Hz, 1H), 5.74 (s, 2H), 6.78-6.87 (m, 2H), 7.59 (d, J = 8.66 Hz, 2H), 8.36 (s, 1H), 8.67 (s, 1H), 8.90 (s, 1H) |

Preparative Example 269

9-(1-Fluoro-2-morpholinoethyl)-6-(4-methoxybenzyl)pyrido[3,2-e][1,2,4]triazolo[1,5-c]pyrimidin-5(6H)-one

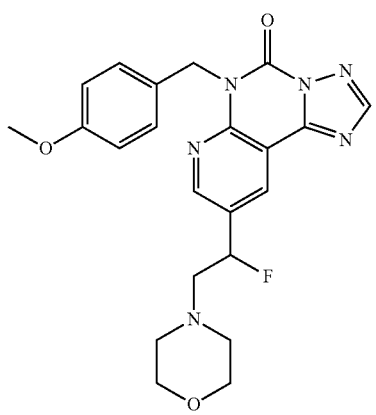

269

Step 34.1: 9-(1-fluoro-2-morpholinoethyl)-6-(4-methoxybenzyl)pyrido[3,2-e][1,2,4]triazolo[1,5-c]pyrimidin-5(6H)-one (269)

(Dimethylamino)sulfur trifluoride (0.010 ml, 0.18 mmol) was added to a stirred solution of 9-(1-hydroxy-2-morpholinoethyl)-6-(4-methoxybenzyl)pyrido[3,2-e][1,2,4]triazolo[1,5-c]pyrimidin-5(6H)-one (49 mg, 0.090 mmol) in acetonitrile (1 ml). After 4 hours, additional (dimethylamino)sulfur trifluoride (0.035 ml, 0.36 mmol) was added and the mixture was stirred at 60° C. for 20 hours, cooled to room temperature, diluted with aqueous sodium bicarbonate (3 mL) and extracted with DCM (2×3 mL). The combined extracts were concentrated under a stream of nitrogen and the residue was taken up in methanol, filtered and purified by preparative HPLC. The resulting material retained some impurities so it was diluted with aqueous sodium bicarbonate (3 mL) and extracted with DCM (2×3 mL). The combined extracts were concentrated under a stream of nitrogen and the residue was purified by flash chromatography (elution with 0-40% IPA in ethyl acetate) to afford 9 mg (21%) of 269 as a white powder.

Numerous compounds were made using the above general procedure, as exemplified in Table 34:

TABLE 34

| Example | Structure | LC-MS (MH+) | 1H-NMR |
|---|---|---|---|
| 269 | 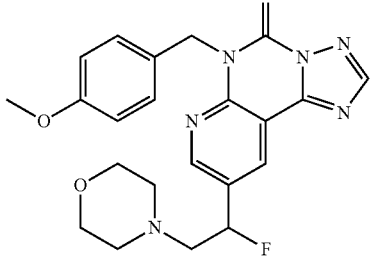<br>$C_{22}H_{23}FN_6O_3$ | 439.1 | 1H NMR (400 MHz, CDCl3) δ 2.58-2.72 (m, 4H), 2.82 (ddd, J = 27.98, 13.93, 3.39 Hz, 1H), 3.01 (ddd, J = 18.85, 14.15, 7.53 Hz, 1H), 3.72-3.76 (m, 4H), 3.76 (s, 3H), 5.75 (s, 2H), 5.84 (d, J = 47.93 Hz, 1H), 6.76-6.88 (m, 2H), 7.60 (d, J = 8.66 Hz, 2H), 8.36 (s, 1H), 8.64 (d, J = 1.88 Hz, 1H), 8.80 (s, 1H) |
| 270 | 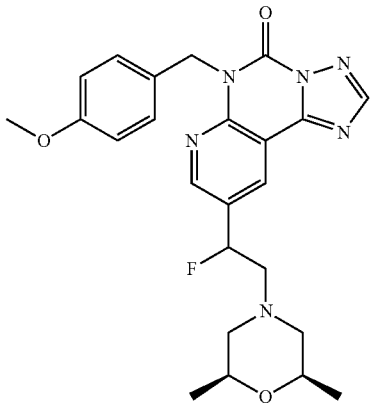 [SMILES: COc1ccc(Cn2c(=O)n3ncnc3c3cc(C(F)CN4C[C@@H](C)O[C@@H](C)C4)cnc32)cc1]<br>$C_{24}H_{27}FN_6O_3$ | 467.3 | 1H NMR (400 MHz, CDCl3) δ 1.28 (d, J = 6.27 Hz, 3H), 1.33 (d, J = 6.40 Hz, 3H), 2.46-2.70 (m, 2H), 3.35 (d, J = 8.41 Hz, 1H), 3.44 (d, J = 11.80 Hz, 1H), 3.56-3.73 (m, 2H), 3.77 (s, 2H), 3.80-3.90 (m, 1H), 4.12-4.28 (m, 2H), 5.75 (s, 2H), 6.61 (dd, J = 48.19, 9.41 Hz, 1H), 6.83 (d, J = 8.66 Hz, 2H), 7.60 (d, J = 8.66 Hz, 2H), 8.39 (s, 1H), 8.72 (s, 1H), 8.88 (s, 1H) |

Preparative Example 271

6-(4-Methoxybenzyl)-9-(2,2,2-trifluoro-1-hydroxyethyl)pyrido[3,2-e][1,2,4]triazolo[1,5-c]pyrimidin-5(6H)-one

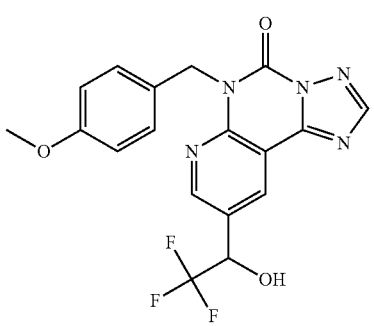

271

Step 35.1: 6-(4-methoxybenzyl)-9-(2,2,2-trifluoro-1-hydroxyethyl)pyrido[3,2-e][1,2,4]triazolo[1,5-c]pyrimidin-5(6H)-one (271)

9-Acetyl-6-(4-methoxybenzyl)pyrido[3,2-e][1,2,4]triazolo[1,5-c]pyrimidin-5(6H)-one (254 mg, 0.76 mmol), tetrahydrofuran (1.3 ml) and 2 M trimethyl(trifluoromethyl)silane in THF (0.45 ml, 0.91 mmol) were combined and stirred for 10 minutes. A 2 M solution of tetrabutylammonium fluoride in THF (75 µl, 0.08 mmol) was added and stirring was continued for 3 days. Some starting material persisted so additional trimethyl(trifluoromethyl)silane (0.45 ml, 0.91 mmol) and tetrabutylammonium fluoride (75 µl, 0.08 mmol) were added and the mixture was stirred for 4 hours. It was diluted with aqueous sodium bicarbonate (5 mL) and extracted with ethyl acetate (2×10 mL). The combined extracts were concentrated under vacuum and the residue was purified by flash chromatography (elution with 10-100% ethyl acetate in hexanes) to afford 154 mg (48%) of 271 as a white powder.

Compounds were made using the above general procedure, as exemplified in Table 35:

TABLE 35

| Example | Structure | LC-MS (MH+) | 1H-NMR |
|---|---|---|---|
| 271 | 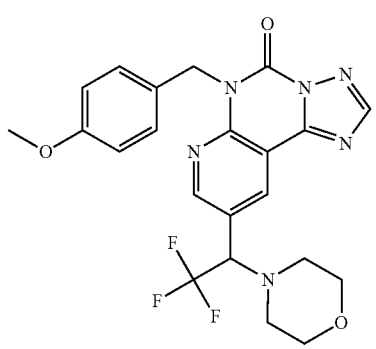 $C_{18}H_{14}F_3N_5O_3$ | 406.1 | 1H NMR (400 MHz, CDCl3 + DMSO-d6) δ 3.27 (s, 3H), 4.80 (q, J = 6.90 Hz, 1H), 5.24 (s, 2H), 6.33 (d, J = 8.66 Hz, 2H), 7.05 (d, J = 8.53 Hz, 2H), 7.91 (s, 1H), 8.32 (s, 1H), 8.39 (s, 1H) |

Preparative Example 272

6-(4-Methoxybenzyl)-9-(2,2,2-trifluoro-1-morpholinoethyl)pyrido[3,2-e][1,2,4]triazolo[1,5-c]pyrimidin-5(6H)-one

Step 36.1: 6-(4-methoxybenzyl)-9-(2,2,2-trifluoro-1-morpholinoethyl)pyrido[3,2-e][1,2,4]triazolo[1,5-c]pyrimidin-5(6H)-one (272)

Methane sulfonyl chloride (49 µl, 0.63 mmol) was added to a stirred solution of 6-(4-methoxybenzyl)-9-(2,2,2-trifluoro-1-hydroxyethyl)pyrido[3,2-e][1,2,4]triazolo[1,5-c]pyrimidin-5(6H)-one (127 mg, 0.31 mmol) and triethylamine (131 µl, 0.94 mmol) in DCM (1.3 ml) and the mixture was stirred for 2 hours. It was diluted with DCM (10 mL), washed with aqueous sodium bicarbonate (5 mL), dried (MgSO₄) and concentrated under vacuum to afford the crude mesylate as a brown gum. This material was taken up in DMF (1 ml) and treated with morpholine (0.10 ml, 1.06 mmol) and heated at 70° C. for 20 hours. Additional morpholine (0.10 ml, 1.06 mmol) was added and heating was continued for 3 days. The mixture was concentrated under a stream of nitrogen and the residue was taken up in DMF, filtered and purified by preparative HPLC to afford 39 mg (20%) of 272 as a white powder.

Compounds were made using the above general procedure, as exemplified in Table 36.

TABLE 36

| Example | Structure | LC-MS (MH+) | 1H-NMR |
|---|---|---|---|
| 272 | $C_{22}H_{21}F_3N_6O_3$ | 475.2 | 1H NMR (400 MHz, CDCl3) δ 2.72 (br s, 4H), 3.74 (q, J = 4.02 Hz, 4H), 3.78 (s, 3H), 4.23 (q, J = 8.03 Hz, 1H), 5.76 (s, 2H), 6.85 (d, J = 8.66 Hz, 2H), 7.62 (d, J = 8.66 Hz, 2H), 8.40 (s, 1H), 8.72 (d, J = 2.26 Hz, 1H), 8.82 (d, J = 2.26 Hz, 1H) |

Preparative Example 273

9-(((2S,6R)-2,6-Dimethylmorpholino)methyl)-6-(4-(trifluoromethoxy)benzyl)pyrido[3,2-e][1,2,4]triazolo[1,5-c]pyrimidin-5(6H)-one

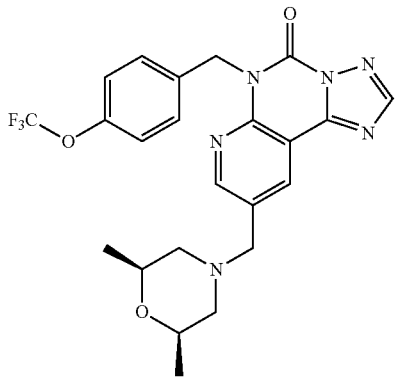

273

Step 37.1: 2-amino-5-(((2S,6R)-2,6-dimethylmorpholino)methyl)nicotinonitrile A suspension of 2-amino-5-bromonicotinonitrile (50 mg, 0.25 mmol), potassium (((2S,6R)-2,6-dimethylmorpholino)methyl)-trifluoroborate (219 mg, 0.51 mmol), cesium carbonate (247 mg, 0.76 mmol), dicyclohexyl(2',4',6'-triisopropylbiphenyl-2-yl)phosphine (36 mg, 0.076 mmol) and palladium(II) acetate (8.5 mg, 0.038 mmol) in dioxane (1 mL) and water (0.1 mL) was purged with nitrogen for 10 minutes, then sealed and heated at 80° C. for 15 hours. The reaction was filtered through Celite while still hot, cooled to room temperature, and diluted with water (10 mL). The resulting precipitate was filtered, washed with water (10 mL) and hexanes (10 mL), and dried under vacuum to give the title compound as a solid (57 mg, 92%). 1H NMR (400 MHz, DMSO-d6) δ 1.03 (d, J=6.3 Hz, 6H), 1.61 (t, J=10.7 Hz, 2H), 2.64 (d, J=10.7 Hz, 2H), 3.45-3.61 (m, 2H), 6.83 (s, 2H), 7.74 (d, J=2.3 Hz, 1H), 8.03-8.19 (m, 1H).

Step 37.2: ethyl 3-cyano-5-(((2S,6R)-2,6-dimethylmorpholino)methyl)pyridin-2-ylcarbamate Sodium hydride in mineral oil (60%, 25 mg, 0.61 mmol) was added to 2-amino-5-(((2S,6R)-2,6-dimethylmorpholino)methyl)nicotinonitrile (100 mg, 0.41 mmol) in THF (2 mL) and the mixture was stirred for 5 minutes. Ethyl chloroformate (0.05 ml, 0.48 mmol) was added followed by additional sodium hydride (16 mg, 0.41 mmol) and the reaction stirred at room temperature for 3 hours. The reaction was poured into a saturated solution of sodium bicarbonate (10 mL), extracted with ethyl acetate (3×5 mL), dried ($Na_2SO_4$) and concentrated under reduced pressure. The residue was taken up in methanol (10 mL) and stirred with potassium carbonate (170 mg) for 10 minutes. It was then poured into saturated sodium bicarbonate (10 mL) and extracted with ethyl acetate (3×5 mL). The extracts were dried ($Na_2SO_4$) and concentrated under reduced pressure. The residue was purified by flash chromatography, eluting with ethyl acetate in hexanes gave the title compound as a white powder (104 mg, 80%). 1H NMR (400 MHz, DMSO-d6) δ 1.04 (d, J=6.27 Hz, 6H), 1.26 (t, J=7.03 Hz, 3H), 1.69 (t, J=10.60 Hz, 2H), 2.67 (d, J=10.67 Hz, 2H), 3.51 (s, 2H), 3.54-3.62 (m, 2H), 4.17 (q, J=7.11 Hz, 2H), 8.12-8.24 (m, 1H), 8.56 (d, J=2.01 Hz, 1H), 10.37 (s, 1H).

Step 37.3: 9-(((2S,6R)-2,6-dimethylmorpholino)methyl)pyrido[3,2-e][1,2,4]triazolo[1,5-c]pyrimidin-5(6H)-one The above carbamate (35 mg, 0.11 mmol), formyl hydrazine (8 mg, 0.13 mmol) and N-ethyl N-isopropylpropan-2-amine (0.01 mL, 0.055 mmol) were heated in N,N-dimethylacetamide (1 mL) at 125° C. for 15 hours. The reaction was cooled to room temperature and purified directly by HPLC to yield the title compound as a solid (29 mg, 84%). 1H NMR (400 MHz, DMSO-d6) δ 1.04 (d, J=6.15 Hz, 6H), 1.73 (t, J=10.67 Hz, 2H), 2.72 (d, J=10.79 Hz, 2H), 3.53-3.66 (m, 4H), 8.45 (s, 1H), 8.57 (s, 1H), 8.62 (s, 1H), 12.82 (br s, 1H).

Step 37.4: 9-(((2S,6R)-2,6-dimethylmorpholino)methyl)-6-(4-(trifluoromethoxy)benzyl)pyrido[3,2-e][1,2,4]triazolo[1,5-c]pyrimidin-5(6H)-one (273)

To a mixture of 9-(((2S,6R)-2,6-dimethylmorpholino)methyl)pyrido[3,2-e][1,2,4]triazolo[1,5-c]pyrimidin-5(6H)-one (50 mg, 0.16 mmol) and 4-(trifluoromethoxy)benzyl bromide (49 mg, 0.19 mmol) in N,N-dimethylformamide (2 ml) was added potassium carbonate (44 mg, 0.32 mmol). The resulting mixture was heated at 55° C. overnight. The crude mixture was filtered then purified directly via reverse phase HPLC to yield 273 (58 mg, 61%) as a white solid.

Numerous compounds were made using the above general procedure, as exemplified in Table 37:

TABLE 37

| Example | Structure | LC-MS (MH+) | 1H-NMR |
|---|---|---|---|
| 273 | 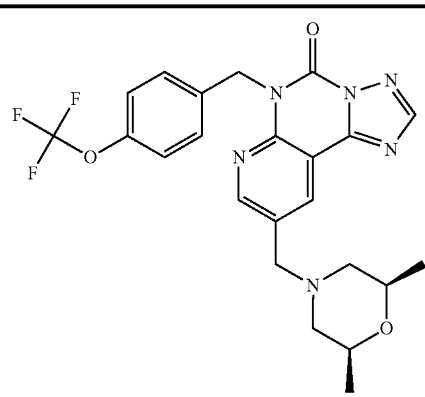 | 489.2 | 1H NMR (400 MHz, DMSO-d6) δ 1.14 (d, J = 6.15 Hz, 6H), 2.63-2.85 (m, 2H), 3.26-3.45 (m, 2H), 3.72-3.86 (m, 2H), 4.40-4.62 (m, 2H), 5.70 (s, 2H), 7.32 (d, J = 8.28 Hz, 2H), 7.59 (d, J = 8.66 Hz, 2H), 8.69 (s, 1H), 8.84 (s, 1H), 8.89 (br s, 1H) |

TABLE 37-continued

| Example | Structure | LC-MS (MH+) | 1H-NMR |
|---|---|---|---|
| 274 | C₂₃H₂₃F₃N₆O₃ | 437.2 | 1H NMR (400 MHz, DMSO-d6) δ 1.13 (d, J = 6.02 Hz, 6H), 2.19 (s, 3H), 2.59-2.85 (m, 2H), 3.16-3.51 (m, 2H), 3.71-3.85 (m, 2H), 4.38-4.68 (m, 2H), 5.62 (s, 2H), 7.07 (t, J = 9.16 Hz, 1H), 7.26-7.32 (m, 1H), 7.34-7.40 (m, 1H), 8.69 (s, 1H), 8.77-8.92 (m, 2H) |
| 275 | C₂₃H₂₅FN₆O₂ | 423.2 | 1H NMR (400 MHz, DMSO-d6) δ 1.14 (d, J = 6.27 Hz, 6H), 2.65-2.86 (m, 2H), 3.29-3.47 (m, 2H), 3.72-3.86 (m, 2H), 4.47-4.63 (m, 2H), 5.66 (s, 2H), 7.15 (t, J = 8.85 Hz, 2H), 7.51 (dd, J = 8.47, 5.58 Hz, 2H), 8.69 (s, 1H), 8.81-8.86 (m, 1H), 8.87-8.92 (m, 1H) |
| 276 | C₂₂H₂₃FN₆O₂ | 453.2 | 1H NMR (400 MHz, DMSO-d6) δ 1.14 (d, J = 6.27 Hz, 6H), 2.68-2.83 (m, 2H), 3.31-3.43 (m, 2H), 3.74-3.84 (m, 5H), 4.49-4.61 (m, 2H), 5.61 (s, 2H), 7.11 (t, J = 8.72 Hz, 1H), 7.21-7.36 (m, 2H), 8.69 (s, 1H), 8.83-8.86 (m, 1H), 8.87-8.91 (m, 1H) |
| | C₂₃H₂₅FN₆O₃ | | |

TABLE 37-continued

| Example | Structure | LC-MS (MH+) | 1H-NMR |
|---|---|---|---|
| 277 | C₂₃H₂₅FN₆O₃ | 453.2 | 1H NMR (400 MHz, DMSO-d6) δ 1.14 (d, J = 6.27 Hz, 6H), 2.67-2.84 (m, 2H), 3.30-3.43 (m, 2H), 3.75 (s, 3H), 3.76-3.84 (m, 2H), 4.47-4.59 (m, 2H), 5.64 (s, 2H), 6.65 (dd, J = 8.66, 2.38 Hz, 1H), 6.88 (dd, J = 12.36, 2.45 Hz, 1H), 7.23 (t, J = 8.91 Hz, 1H), 8.70 (s, 1H), 8.80-8.85 (m, 1H), 8.87-8.93 (m, 1H) |
| 278 | C₂₂H₂₂BrFN₆O₂ | 501.1 | 1H NMR (400 MHz, CDCl3) δ 1.24 (d, J = 6.27 Hz, 6H), 2.46 (t, J = 11.11 Hz, 2H), 3.47 (d, J = 11.54 Hz, 2H), 3.91-4.08 (m, 2H), 4.33 (s, 2H), 5.73 (s, 2H), 7.06 (t, J = 8.41 Hz, 1H), 7.54-7.65 (m, 1H), 7.86 (d, J = 6.40 Hz, 1H), 8.41 (s, 1H), 8.72 (s, 1H), 8.89 (d, J = 1.63 Hz, 1H) |
| 279 | C₂₃H₂₃N₇O₂ | 430.2 | 1H NMR (400 MHz, CDCl3) δ 1.25 (d, J = 6.15 Hz, 6H), 2.47 (t, J = 11.17 Hz, 2H), 3.48 (d, J = 11.29 Hz, 2H), 3.99 (dd, J = 10.35, 6.09 Hz, 2H), 4.33 (s, 2H), 5.85 (s, 2H), 7.67 (d, J = 7.91 Hz, 1H), 8.12 (d, J = 8.78 Hz, 1H), 8.42 (s, 1H), 8.76 (s, 1H), 8.86 (s, 1H), 9.01 (s, 1H) |

TABLE 37-continued

| Example | Structure | LC-MS (MH+) | 1H-NMR |
|---|---|---|---|
| 280 | C<sub>26</sub>H<sub>32</sub>N<sub>6</sub>O<sub>2</sub> | 461.3 | 1H NMR (400 MHz, CDCl3) δ 1.24 (d, J = 6.40 Hz, 6H), 1.28 (s, 9H), 2.43 (t, J = 11.11 Hz, 3H), 3.44 (d, J = 11.04 Hz, 2H), 3.94-4.08 (m, 2H), 4.31 (s, 2H), 5.78 (s, 2H), 7.31-7.39 (m, 2H), 7.57 (d, J = 8.41 Hz, 2H), 8.39 (s, 1H), 8.68 (d, J = 2.26 Hz, 1H), 8.89 (d, J = 2.26 Hz, 1H) |
| 281 | C<sub>23</sub>H<sub>23</sub>N<sub>7</sub>O<sub>2</sub> | 430.2 | 1H NMR (400 MHz, CDCl3) 5 1.25 (d, J = 6.27 Hz, 6H), 2.52 (t, J = 11.23 Hz, 2H), 3.54 (d, J = 11.42 Hz, 2H), 3.93-4.04 (m, 2H), 4.38 (s, 2H), 4.77 (s, 1H), 5.31 (s, 1H), 7.43-7.50 (m, 1H), 7.57-7.61 (m, 2H), 7.89 (d, J = 1.38 Hz, 1H), 8.43 (s, 1H), 8.79 (d, J = 2.38 Hz, 1H), 8.87 (d, J = 2.38 Hz, 1H) |
| 282 | C<sub>23</sub>H<sub>26</sub>N<sub>6</sub>O<sub>4</sub>S | 483.2 | 1H NMR (400 MHz, CDCl3) δ 1.26 (d, J = 6.40 Hz, 6H), 2.50 (t, J = 11.17 Hz, 2H), 3.04 (s, 3H), 3.51 (d, J = 11.04 Hz, 2H), 3.96-4.07 (m, 2H), 4.35 (s, 2H), 5.88 (s, 2H), 7.80 (d, J = 8.41 Hz, 2H), 7.91 (d, J = 8.53 Hz, 2H), 8.44 (s, 1H), 8.76 (d, J = 2.38 Hz, 1H), 8.88 (d, J = 2.38 Hz, 1H) |

TABLE 37-continued

| Example | Structure | LC-MS (MH+) | 1H-NMR |
|---|---|---|---|
| 283 | C₂₃H₂₆N₆O₂ | 419.8 | H NMR (400 MHz, CDCl3) δ 1.15 (d, J = 6.40 Hz, 6H), 1.84 (t, J = 10.67 Hz, 2H), 2.60 (s, 3H), 2.69 (d, J = 10.29 Hz, 2H), 3.60 (s, 2H), 3.65-3.74 (m, 2H), 5.80 (s, 2H), 6.93 (d, J = 7.65 Hz, 1H), 7.04 (t, J = 7.59 Hz, 1H), 7.13-7.18 (m, 1H), 7.20-7.24 (m, 1H), 8.40 (s, 1H), 8.64 (dd, J = 10.35, 2.20 Hz, 2H) |
| 284 | C₂₂H₂₃IN₆O₂ | 531.0 | 1H NMR (400 MHz, CDCl3) d = 8.86 (d, J = 2.4 Hz, 1H), 8.75 (d, J = 2.3 Hz, 1H), 8.41 (s, 1H), 7.95 (t, J = 1.6 Hz, 1H), 7.64-7.55 m, 2H), 7.05 (t, J = 7.8 Hz, 1H), 5.73 (s, 2H), 4.37 (s, 2H), 4.04-3.93 (m, 2H), 3.52 (d, J = 11.2 Hz, 2H), 2.48 (t, J = 11.2 Hz, 2H), 1.25 (d, J = 6.4 Hz, 6H) |
| 285 | C₂₂H₂₂F₂N₆O₂ | 441.2 | 1H NMR (400 MHz, CDCl3), δ 1.27 (d, J = 6.40 Hz, 6H), 2.48 (t, J = 11.23 Hz, 2H), 3.49 (d, J = 11.04 Hz, 2H), 3.97-4.09 (m, 2H), 4.35 (s, 2H), 5.77 (s, 2H), 6.71-6.81 1H), 7.09-7.18 (m, 2H), 8.44 (s, 1H), 8.76 (d, J = 2.38 Hz, 1H), 8.88 (d, J = 2.26 Hz, 1H) |

TABLE 37-continued

| Example | Structure | LC-MS (MH+) | 1H-NMR |
|---|---|---|---|
| 286 | C₂₃H₂₅BrN₆O₃ | 514.1 | 1H NMR (400 MHz, CDCl3) δ 1.25 (d, J = 6.27 Hz, 6H), 2.42 (t, J = 11.11 Hz, 2H), 3.42 (d, J = 11.04 Hz, 2H), 3.79 (s, 3H), 3.99-4.08 (m, 2H), 4.28 (s, 2H), 5.84 (s, 2H), 6.70-6.77 (m, 1H), 6.89 (d, J = 8.66 Hz, 1H), 7.20 (d, J = 2.51 Hz, 1H), 8.46 (s, 1H), 8.74-8.81 (m, 2H) |
| 287 | C₂₃H₂₄F₂N₆O₃ | 471.2 | 1H NMR (400 MHz, CDCl3) δ 1.24 (d, J = 6.27 Hz, 6H), 2.39 (t, J = 11.11 Hz, 2H), 3.07-3.15 (m, 1H), 3.36 (d, J = 11.29 Hz, 2H), 3.52 (s, 1H), 3.77 (s, 3H), 3.90 (s, 1H), 3.95-4.07 (m, 2H), 4.24 (s, 2H), 5.84 (s, 2H), 6.36-6.47 (m, 2H), 6.62-6.70 (m, 1H), 8.40 (s, 1H), 8.71 (d, J = 2.26 Hz, 1H), 8.79 (d, J = 2.26 Hz, 1H) |
| 288 | C₂₄H₂₆N₈O₂ | 459.2 | 1H NMR (400 MHz, CDCl3) δ 8.93 (d, J = 2.4 Hz, 1H), 8.68 (d, J = 2.3 Hz, 1H), 8.41 (s, 1H), 7.94 (d, J = 0.8 Hz, 1H), 7.72 (s, 1H), 7.66 (d, J = 8.8 Hz, 1H), 7.45 (dd, J = 1.3, 8.4 Hz, 1H), 5.95 (s, 2H), 4.30 (s, 2H), 4.07 (s, 3H), 4.01 (dd, J = 6.4, 8.9 Hz, 2H), 3.43 (d, J = 11.3 Hz, 2H), 2.42 (t, J = 11.2 Hz, 2H), 1.23 (d, J = 6.3 Hz, 6H) |

TABLE 37-continued

| Example | Structure | LC-MS (MH+) | 1H-NMR |
|---|---|---|---|
| 289 | C$_{25}$H$_{26}$N$_8$O$_2$ | 471.2 | 1H NMR (400 MHz, CDCl3) δ 8.92 (d, J = 2.4 Hz, 1H), 8.72 (d, J = 2.4 Hz, 1H), 8.43 (s, 1H), 7.91 (d, J = 2.3 Hz, 1H), 7.78-7.74 (m, 2H), 7.73 (d, J = 1.5 Hz, 1H), 7.68-7.60 (m, 2H), 6.50-6.44 (m, 1H), 5.84 (s, 2H), 4.33 (s, 2H), 4.13-3.92 (m, 2H), 3.46 (d, J = 11.0 Hz, 3H), 2.45 (t, J = 11.2 Hz, 3H), 1.25 (d, J = 6.3 Hz, 6H) |
| 290 | C$_{23}$H$_{23}$F$_3$N$_6$O$_3$ | 489.2 | 1H NMR (400 MHz, CDCl3) δ 8.70-8.62 (m, 2H), 8.39 (s, 1H), 7.33-7.28 (m, 1H), 6.89 (dd, J = 2.3, 10.5 Hz, 1H), 6.85-6.78 (m, 1H), 6.47 (t, J = 72.9 Hz, 1H), 5.85 (s, 2H), 3.77-3.64 (m, 2H), 3.62 (s, 2H), 2.70 (d, J = 10.7 Hz, 2H), 1.86 (t, J = 10.7 Hz, 2H), 1.30-1.23 (m, 3H), 1.15 (d, J = 6.3 Hz, 6H) |
| 291 | C$_{23}$H$_{24}$F$_2$N$_6$O$_3$ | 471.1 | 1H NMR (400 MHz, CDCl3) δ 8.81 (d, J = 1.8 Hz, 1H), 8.71 (s, 1H), 8.40 (s, 1H), 7.24-7.15 (m, 2H), 5.69 (s, 2H), 3.99 (br s., 1H), 3.95 (s, 3H), 3.93-3.83 (m, 2H), 3.71 (s, 1H), 2.23-2.13 (m, 1H), 1.44 (s, 1H), 1.20 (d, J = 6.3 Hz, 6H) |

TABLE 37-continued

| Example | Structure | LC-MS (MH+) | 1H-NMR |
|---|---|---|---|
| 292 | C₂₃H₂₄F₂N₆O₃ | 471.2 | 1H NMR (400 MHz, methanol-d4) δ 1.20 (d, J = 6.27 Hz, 6H), 2.25-2.54 (m, 2H), 3.10-3.22 (m, 2H), 3.74-3.83 (m, 2H), 3.86 (s, 3H), 4.05-4.30 (m, 2H), 5.83 (s, 2H), 6.77-6.86 (m, 1H), 7.03-7.12 (m, 1H), 8.55 (s, 1H), 8.82 (s, 2H) |
| 293 | C₂₃H₂₃F₃N₆O₂S | 505.1 | 1H NMR (400 MHz, CDCl3) δ 8.56 (d, J = 2.1 Hz, 1H), 8.52 (d, J = 2.1 Hz, 1H), 8.32 (s, 1H), 7.69 (d, J = 7.3 Hz, 1H), 7.30-7.21 (m, 2H), 7.14 (dd, J = 1.6, 7.5 Hz, 1H), 6.03 (s, 2H), 3.67-3.55 (m, 2H), 3.50 (s, 2H), 2.59 (d, J = 10.4 Hz, 2H), 1.75 (t, J = 10.7 Hz, 2H), 1.06 (d, J = 6.3 Hz, 6H) |
| 294 | C₂₂H₂₂ClFN₆O₂ | 457.1 | 1H NMR (400 MHz, CDCl3) δ 8.64 (d, J = 2.3 Hz, 1H), 8.56 (d, J = 2.1 Hz, 1H), 8.29 (s, 1H), 7.63 (dd, J = 2.1, 7.0 Hz, 1H), 7.47 (ddd, J = 2.3, 4.6, 8.5 Hz, 1H), 6.99 (t, J = 8.7 Hz, 1H), 5.65 (s, 2H), 3.66-3.57 (m, 2H), 3.54 (s, 2H), 2.61 (d, J = 10.3 Hz, 2H), 1.78 (t, J = 10.7 Hz, 2H), 1.07 (d, J = 6.3 Hz, 6H) |

TABLE 37-continued

| Example | Structure | LC-MS (MH+) | 1H-NMR |
|---|---|---|---|
| 295 | C₂₂H₂₂Cl₂N₆O₂ | 473.0 | 1H NMR (400 MHz, CDCl3) δ 8.63 (d, J = 2.1 Hz, 1H), 8.56 (d, J = 2.1 Hz, 1H), 8.30 (s, 1H), 7.64 (d, J = 2.0 Hz, 1H), 7.41 (dd, J = 2.0, 8.3 Hz, 1H), 7.30 (d, J = 8.3 Hz, 1H), 5.65 (s, 2H), 3.66-3.57 (m, 2H), 3.54 (s, 2H), 2.61 (d, J = 10.4 Hz, 2H), 1.78 (t, J = 10.6 Hz, 2H), 1.07 (d, J = 6.3 Hz, 6H) |
| 296 | C₂₃H₂₅ClN₆O₃ | 469.2 | 1H NMR (400 MHz, CDCl3) δ 1.26 (d, J = 6.27 Hz, 6H), 2.45 (t, J = 11.23 Hz, 2H), 3.47 (d, J = 11.17 Hz, 2H), 3.79 (s, 3H), 4.00-4.08 (m, 2H), 4.32 (s, 2H), 5.86 (s, 2H), 6.70 (dd, J = 8.72, 2.57 Hz, 1H), 6.95-7.01 (m, 2H), 8.45 (s, 1H), 8.77 (d, J = 1.63 Hz, 2H) |
| 297 | C₂₃H₂₄F₂N₆O₃ | 471.2 | 1H NMR (400 MHz, CDCl3) δ 8.59-8.52 (m, 2H), 8.30 (s, 1H), 7.21 (s, 1H), 7.09 (d, J = 7.9 Hz, 2H), 7.03-6.97 (m, 1H), 6.82-6.39 (m, 1H), 5.80 (s, 2H), 3.64-3.56 (m, 2H), 3.52 (s, 2H), 2.60 (d, J = 10.5 Hz, 2H), 1.76 (t, J = 10.7 Hz, 2H), 1.06 (d, J = 6.3 Hz, 6H) |

TABLE 37-continued

| Example | Structure | LC-MS (MH+) | 1H-NMR |
|---|---|---|---|
| 298 | C₂₂H₂₂ClFN₆O₂ | 457.1 | 1H NMR (400 MHz, CDCl3) δ 8.72 (d, J = 2.3 Hz, 1H), 8.65 (d, J = 2.1 Hz, 1H), 8.38 (s, 1H), 7.46-7.31 (m, 3H), 5.76 (s, 2H), 3.76-3.67 (m, 2H), 3.63 (s, 2H), 2.70 (d, J = 10.3 Hz, 2H), 1.87 (t, J = 10.7 Hz, 2H), 1.15 (d, J = 6.4 Hz, 6H) |
| 299 | C₂₂H₂₂ClFN₆O₂ | 457.1 | 1H NMR (400 MHz, CDCl3) δ 8.72 (d, J = 2.3 Hz, 1H), 8.66 (d, J = 2.1 Hz, 1H), 8.39 (s, 1H), 7.40 (s, 1H), 7.26-7.21(m, 1H), 7.04-6.99 (m, 1H), 5.75 (s, 2H), 3.75-3.67 (m, 2H), 3.64 (s, 2H), 2.71 (d, J = 10.4 Hz, 2H), 1.87 (t, J = 10.7 Hz, 2H), 1.16 (d, J = 6.3 Hz, 6H) |
| 300 | C₂₆H₂₉N₇O₃ | 488.2 | 1H NMR (400 MHz, CDCl3) δ 8.86 (d, J = 2.1 Hz, 1H), 8.72 (d, J = 2.1 Hz, 1H), 8.37 (s, 1H), 7.61 (d, J = 8.7 Hz, 2H), 7.50 (d, J = 8.8 Hz, 2H), 5.75 (s, 2H), 4.35 (s, 2H), 3.99 (dd, J = 6.3, 9.2 Hz, 2H), 3.83 (t, J = 7.1 Hz, 2H), 3.47 (d, J = 11.3 Hz, 2H), 2.60 (t, J = 8.1 Hz, 2H), 2.49 (t, J = 11.2 Hz, 2H), 2.15 (quin, J = 7.6 Hz, 2H), 1.23 (d, J = 6.3 Hz, 6H) |

TABLE 37-continued

| Example | Structure | LC-MS (MH+) | 1H-NMR |
|---|---|---|---|
| 301 | C₂₄H₂₈N₆O₃ | 449.2 | 1H NMR (400 MHz, CDCl3) δ 8.90 (d, J = 2.3 Hz, 1H), 8.67 (d, J = 2.4 Hz, 1H), 8.37 (s, 1H), 7.59 (d, J = 8.7 Hz, 2H), 6.87-6.77 (m, 2H), 5.73 (s, 2H), 4.28 (s, 2H), 4.06-3.93 (m, 4H), 3.40 (d, J = 11.2 Hz, 2H), 2.40 (t, J = 11.2 Hz, 2H), 1.37 (t, J = 7.0 Hz, 3H), 1.23 (d, J = 6.4 Hz, 6H)2H), 3.83 (t, J = 7.1 Hz, 2H), 3.47 (d, J = 11.3 Hz, 2H), 2.60 (t, J = 8.1 Hz, 2H), 2.49 (t, J = 11.2 Hz, 2H), 2.15 (quin, J = 7.6 Hz, 2H), 1.23 (d, J = 6.3 Hz, 6H) |
| 302 | C₂₂H₂₂F₂NO₂ | 441.4 | 1H NMR (400 MHz, CDCl3) δ 8.79 (s, 1H), 8.67 (s, 1H), 8.39 (s, 1H), 7.54-7.45 (m, 1H), 7.41 (d, J = 6.3 Hz, 1H), 7.14-7.05 (m, 1H), 5.74 (s, 2H), 3.93-3.77 (m, 4H), 2.99 (d, J = 8.9 Hz, 2H), 2.15-2.03 (m, 2H), 1.19 (d, J = 6.1 Hz, 6H) |
| 303 | C₂₃H₂₆N₆O₂S | 451.1 | 1H NMR (400 MHz, CDCl3) δ 8.72 (s, 1H), 8.62 (s, 1H), 8.37 (s, 1H), 7.57 (d, J = 8.0 Hz, 2H), 7.19 (d, J = 8.0 Hz, 2H), 5.76 (s, 2H), 3.75-3.67 (m, 2H), 3.63 (s, 2H), 2.71 (d, J = 10.9 Hz, 2H), 2.44 (s, 3H), 1.87 (t, J = 10.5 Hz, 2H), 1.15 (d, J = 6.3 Hz, 6H) |

TABLE 37-continued

| Example | Structure | LC-MS (MH+) | 1H-NMR |
|---|---|---|---|
| 304 | 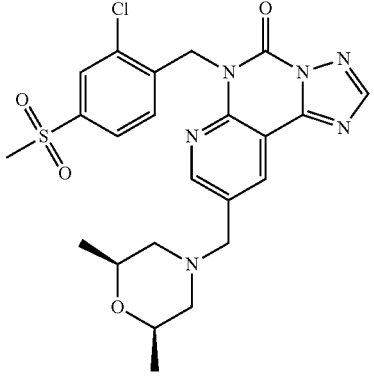 [SMILES: C[C@@H]1CN(Cc2cnc3c(c2)c2ncnn2c(=O)n3Cc2ccc(S(C)(=O)=O)cc2Cl)C[C@H](C)O1] $C_{23}H_{25}ClN_6O_4S$ | 417.1 | 1H NMR (400 MHz, CDCl3) δ 1.25 (d, J = 6.15 Hz, 6H), 2.46 (t, J = 11.17 Hz, 2H), 3.06 (s, 3H), 3.44-3.49 (m, 2H), 3.93-4.05 (m, 3H), 4.30 (s, 2H), 5.94 (s, 2H), 7.14 (d, J = 8.28 Hz, 1H), 7.70 (d, J = 8.16 Hz, 1H), 8.05 (s, 1H), 8.47 (s, 1H), 8.73 (s, 1H), 8.82 (s, 1H) |

PDE1B Inhibitory Assay

Assay Conditions

PDE1B inhibition was determined by an IMAP TR-FRET assay. The IMAP TR-FRET PDE assay was optimized for concentration of enzyme, Calmodulin, cAMP or cGMP substrate, DMSO tolerance, and incubation time.

Into each well of a solid white 1536 well plate (Corning) was dispensed 250 pg full-length recombinant NH-terminal GST tagged human PDE1B enzyme (BPS Bioscience Cat #60011, San Diego, Calif.) in 2.5 µL IMAP BSA reaction buffer (Molecular Devices, Sunnyvale, Calif.) containing 10 U/ml Calmodulin and 2.5 mM $CaCl_2$ (Sigma Aldrich.) After a brief centrifugation, 30 nl compound was added by transfer from 1 mM stock in DMSO using a Kalypsys 1536 Pintool. Plates were incubated for 5 minutes at room temperature before dispensing 1.5 µL of 533 nM 5-carboxy fluorescein (FAM)-labeled cAMP (Molecular Devices, Sunnyvale, Calif.) for a final concentration of 200 nM. After a brief centrifugation, the plates were incubated for 30 minutes at room temperature. The assay was terminated by adding 5 µL IMAP binding reagent/Tb complex (Molecular Devices, Sunnyvale, Calif.) to each well.

Plates were incubated 1 hour at room temperature and read on a Viewlux multimode plate reader (Perkin Elmer). The instrument was set to excite using the DUG11 filter and measure using 490/10 nm and 520/10 nm filters. Ratios of acceptor and donor were then calculated.

Data Analysis

For $IC_{50}$ calculations, the values of % efficacy versus a series of compound concentrations were then plotted using non-linear regression analysis of sigmoidal dose-response curves generated with the equation $Y=B+(T-B)/1+10((Log\ EC50-X)\times Hill\ Slope)$, where Y=percent activity, B=minimum percent efficacy, T=maximum percent efficacy, X=logarithm of compound and Hill Slope=slope factor or Hill coefficient. The $IC_{50}$ value was determined by the concentration causing a half-maximal percent efficacy.

Results

Table 38 presents the negative log of the half-maximal molar inhibitory concentration ($pIC_{50}$), with respect to PDE1B activity, for Formula I and II compounds.

TABLE 38

| PDE1B $pIC_{50}$ | Preparative Example Numbers |
|---|---|
| >7 | 29, 31, 33, 34, 35, 36, 37, 38, 39, 40, 41, 44, 45, 46, 47, 48, 50, 51, 52, 53, 54, 55, 56, 57, 58, 59, 60, 61, 62, 63, 64, 65, 66, 67, 68, 69, 70, 71, 73, 74, 75, 80, 90, 103, 105, 106, 108, 109, 110, 111, 112, 113, 115, 116, 117, 118, 119, 120, 121, 122, 123, 125, 126, 127, 128, 129, 130, 131, 132, 133, 134, 135, 136, 137, 138, 139, 140, 141, 142, 143, 144, 145, 146, 147, 148, 149, 150, 156, 157, 158, 159, 160, 161, 162, 164, 165, 166, 167, 168, 169, 170, 171, 172, 173, 174, 175, 179, 184, 189, 191, 220, 224, 225, 228, 229, 246, 247, 253, 266, 268, 270, 272, 277, 287 |
| 6-7 | 3, 5, 6, 8, 9, 11, 15, 17, 22, 23, 25, 26, 27, 28, 30, 32, 42, 43, 49, 72, 76, 77, 78, 79, 82, 83, 84, 85, 87, 88, 91, 93, 94, 95, 101, 102, 104, 107, 114, 124, 151, 152, 163, 180, 181, 182, 183, 185, 188, 190, 192, 193, 197, 198, 199, 200, 201, 203, 204, 205, 206, 207, 208, 210, 213, 214, 215, 216, 217, 218, 221, 222, 223, 226, 227, 230, 231, 233, 234, 236, 239, 245, 248, 252, 254, 255, 257, 259, 260, 261, 262, 263, 264, 265, 267, 269, 271, 273, 274, 275, 276, 278, 284, 290, 291, 292, 294, 295, 296, 298, 301, 302, 303 |
| 5-6 | 1, 2, 10, 12, 13, 16, 18, 19, 20, 24, 81, 86, 89, 92, 96, 97, 99, 100, 153, 155, 176, 186, 187, 194, 195, 196, 202, 209, 211, 212, 219, 232, 235, 237, 238, 240, 241, 242, 243, 244, 249, 250, 251, 256, 258, 273, 283, 285, 286, 299 |
| <5 | 4, 7, 14, 21, 98, 177, 178, 279, 280, 281, 282, 288, 289, 293, 297, 300, 304 |

PDE1 Selectivity of Compounds
Assay Conditions

The selectivity of compounds of the present invention was determined using a panel of recombinant human PDEs and an in vitro enzymatic assay (BPS Bioscience). Series of dilutions of each test compound were prepared with 10% DMSO in assay buffer and 5 µl of the dilution was added to a 50 µl reaction so that the final concentration of DMSO is 1% in all of reactions.

The enzymatic reactions were conducted at room temperature for 60 minutes in a 50 µl mixture containing PDE assay buffer, 100 nM FAM-cAMP, or 100 nM FAM-cGMP, a recombinant PDE enzyme and the test compound.

After the enzymatic reaction, 100 µl of a binding solution (1:100 dilution of the binding agent with the binding agent diluent) was added to each reaction and the reaction was performed at room temperature for 60 minutes.

Fluorescence intensity was measured at an excitation of 485 nm and an emission of 528 nm using a Tecan Infinite M1000 microplate reader.

Data Analysis

PDE activity assays were performed in duplicate at each concentration. Fluorescence intensity is converted to fluorescence polarization using the Tecan Magellan6 software. The fluorescence polarization data were analyzed using the computer software, Graphpad Prism. The fluorescence polarization (FPt) in absence of the compound in each data set was defined as 100% activity. In the absence of PDE and the compound, the value of fluorescent polarization (FPb) in each data set was defined as 0% activity. The percent activity in the presence of the compound was calculated according to the following equation: % activity=(FP−FPb)/(FPt−FPb)×100%, where FP=the fluorescence polarization in the presence of the compound.

For $IC_{50}$ calculations, the values of % activity versus a series of compound concentrations were then plotted using non-linear regression analysis of Sigmoidal dose-response curve generated with the equation Y=B+(T−B)/1+10((Log EC50−X)×Hill Slope), where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity.

Results

Exemplary compounds of the present invention displayed selectivity for PDE1 enzymes versus isoforms from many, if not all, other PDE families. In addition, exemplary compounds showed greater specificity for PDE1B compared to PDE1A and PDE1C.

COMPOSITIONS

Definitions

The following definitions, although presented in this section, are applicable to the entire specification.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I or Formula II and pharmaceutically acceptable excipients.

As used herein, the phrase "pharmaceutically acceptable" refers to molecular entities and compositions that are generally regarded as "safe," e.g., that are physiologically tolerable and do not typically produce an allergic or similar untoward reaction, such as gastric upset, dizziness and the like, or other significant adverse events, when administered to a human. Preferably, as used herein, the term "pharmaceutically acceptable" means approved by a regulatory agency of the Federal or a state government of listed in the U.S. Pharmacopeia or other generally recognized pharmacopeia for use in animals, and more particularly in humans.

In particular, the term "pharmaceutically acceptable salts" refers to salts prepared from pharmaceutically acceptable non-toxic bases or acids including inorganic bases or acids and organic bases or acids. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. See Stahl and Wermuth (eds), Pharmaceutical Salts; Properties, Selection, and Use: $2^{nd}$ Revised Edition, Wiley-VCS, Zurich, Switzerland (2011).

The term "carrier" refers to an adjuvant, vehicle, or excipients, with which the compound is administered. In preferred embodiments of this invention, the carrier is a solid carrier. Suitable pharmaceutical carriers include those described in Remington: The Science and Practice of Pharmacy, $21^{st}$ Ed., Lippincott Williams & Wilkins (2005).

The term "dosage form," as used herein, is the form in which the dose is to be administered to the subject or patient. The drug or supplement is generally administered as part of a formulation that includes nonmedical agents. The dosage form has unique physical and pharmaceutical characteristics. Dosage forms, for example, may be solid, liquid or gaseous. "Dosage forms," may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the terms "inactive" and "inert" refer to any compound that is an inactive ingredient of a described composition. The definition of "inactive ingredient" as used herein follows that of the U.S. Food and Drug Administration, as defined in 21 C.F.R. 201.3(b)(8), which is any component of a drug product other than the active ingredient Formulations Compounds in accordance with the present invention can be administered alone, or alternatively, in the form of pharmaceutical composition. Thus, the present invention includes pharmaceutical compositions comprising a compound of Formula I or II and a pharmaceutically acceptable carrier.

The compounds (as well as compositions and processes) of the present invention may also be used in the manufacture of a medicament for the therapeutic applications described herein Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Any suitable route of administration may be employed for providing a mammal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I or Formula II as an active ingredient or a pharmaceutically acceptable salt thereof, and may also contain a pharmaceutically acceptable carrier and optionally other therapeutic ingredients.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable and appropriate dosage of the drug.

The pharmaceutical compositions also include solvates and hydrates of the compounds of Formula I or Formula II.

The term "solvate" refers to a molecular complex of a compound represented by Formula I or II (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The crystalline forms may also exist as complexes with other innocuous small molecules, such as L-phenylalanine, L-proline, L-pyroglutamic acid and the like, as co-crystals or solvates or hydrates of the co-crystalline material. The solvates, hydrates and co-crystalline compounds may be prepared using procedures described in PCT Publication No. WO 08/002,824, incorporated herein by reference, or other procedures well-known to those of skill in the art.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with various of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula I and Formula II can be determined by comparing their in vitro activity, and in vivo activity in animal models. Methods for the extrapolation of effective dosages in mice, and other animals, to humans are known to the art.

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range of from about 0.01 to about 100 mg/kg, more specifically from about 0.1 to about 100/mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing 1 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu M$, preferably, about 1 to 50 $\mu M$ most preferably, about 2 to about 30 $\mu M$. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present invention.

Methods and Uses

Definitions

The following definitions, although presented in this section, are applicable to the entire specification.

The term "animal" or "subject" may be a vertebrate, in particular, a mammal, and more particularly, a human, and includes a laboratory animal in the context of a clinical trial or screening or activity experiment. Thus, as can be readily appreciated by one of ordinary skill in the art, the compositions and methods of the present invention are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

As used herein, the term "disease" may be used interchangeably with "condition" or "disorder".

As used in the present disclosure, the term "effective amount" or "therapeutically effective amount" means an amount or dose of a compound or composition of the present invention effective in treating the particular disease, condition, or disorder disclosed herein and thus producing the desired preventative, inhibitory, or ameliorative effect.

The term "treat," as used herein, is interchangeable with "treatment" and "treating" and includes:

(i) prevention of the disease, disorder, or condition, i.e., reducing the incidence of and/or ameliorating the effect and/or duration of a disease, disorder, or condition from occurring in subjects that may get, be exposed to and/or be predisposed to the disease, disorder or condition, but may not yet have been diagnosed as having it; or are diagnosed as having the disease, disease, or condition; or are at risk of developing such disease, disorder, or condition;

(ii) inhibition of the disease, disorder, or condition, i.e., preventing or delaying the onset of a disease, disorder, or condition; arresting further development or progression of a disease, disorder, or condition in a subject already suffering from or having one or more symptoms of the disease, disorder, or condition; or reducing the risk of a disease, disorder, or condition worsening;

(iii) amelioration of the disease, disorder, or condition, i.e., attenuating, relieving, reversing or eliminating the disease, disorder, or condition, or one or more of symptoms thereof.

The compounds of the present invention may be administered as a mono-therapy or administered as part of a combination therapy. For example, one or more of the compounds of the present invention may be co-administered or used in combination with one or more additional therapies known in the art.

By "enhancing" or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal. As a result, long term memory acquisition is faster or better retained. Enhancing performance of a cognitive task refers to the ability to potentiate or improve performance of a specified cognitive task by an animal relative to the normal performance of the cognitive task by the animal.

Indications

Generally

The present invention provides methods of treating a disease, condition, or disorder in an animal by inhibiting PDE1, and more specifically, PDE1B. The methods generally comprise the step of administering a therapeutically effective amount of a compound of the present invention, or a pharmaceutically salt thereof, to a patient in need thereof to treat the disorder or disease. In certain embodiments, the present invention provides a use of a compound as described herein in the manufacture of a medicament for treating a disease, condition, or disorder by inhibiting PDE1, and PDE1B specifically.

PDE1-related indications that can be treated by compounds and compositions of the present invention include, but are not limited to, nervous system disorders, cardiovascular disorders, metabolic diseases, gastrointestinal and liver diseases, cancer disorders, hematological disorders, pulmonary and vascular diseases, neurological disorders and urological disorders.

PDE1-related indications also encompass diseases (e.g., Parkinson's disease or cocaine addiction) that include aberrant or dysregulated signaling pathways mediated by PDE1 (e.g., Parkinson's disease or cocaine addiction), and more specifically, PDE1B. Such PDE1-related signaling pathways, preferably in the nervous system, include, but are not limited to, those involving nitric oxide, natriuretic peptides (e.g., ANP, BNP, CNP), dopamine, noradrenalin, neurotensin, cholecystokinin (CCK), vasoactive intestinal peptide (VIP), serotonin, glutamate (e.g., NMDA receptor, AMPA receptor), GABA, acetylcholine, adenosine (e.g., A2A receptor), cannabinoids, natriuretic peptides (e.g., ANP, BNP, CNP), and endorphins. Accordingly, compounds of the present invention are useful in treating disorders that include an aberrant or dysregulated signaling pathway mediated by PDE1, and specifically, PDE1B. In a specific aspect, they are useful in treating disorders characterized by alterations in dopamine signaling. See, e.g., Nishi and Snyder, 2010, J Pharmacol. Sci. 114, 6-16.

CNS Disorders

The present invention includes the use of a compound or composition herein in a method of treating a CNS disorder, comprising administration of an effective amount of the compound or composition to a patient in need thereof. More specifically, a compound or composition of the present invention can be used in a method to treat a cognitive impairment associated with a CNS disorder.

CNS disorders within the scope of the present invention include, but are not limited to, Alzheimer's disease, Parkinson's disease, Huntington's disease, attention deficit disorder (ADD), attention deficit hyperactivity disorder (ADHD), neurodegenerative disorders, Tourette's syndrome, tic disorders, Lesch-Nyan disease, pain, dystonias, substance or drug abuse, fetal alcohol syndrome, schizophrenia, schizoaffective disorder, depression, affective disorder, manic-depressive disorder, obsessive-compulsive disorder, eating disorder, panic-disorder, anxiety disorder, migraine, myoclonus, premenstrual syndrome, post-traumatic stress syndrome, carcinoid syndrome, stroke, epilepsy, sleep or circadian rhythm disorder, sexual disorder, stress disorder, hypertension, and nervous system cancers.

In specific embodiments, the CNS disorder is Huntington's disease, schizophrenia, Parkinson's disease, Alzheimer's disease, schizophrenia, mild-cognitive impairment, and ADHD.

In other embodiments, the CNS disorder is substance or drug abuse, or fetal alcohol syndrome.

In one aspect, the compounds of the present invention are useful in improving neuronal plasticity—an essential property of the brain that is impaired in numerous CNS disorders. By inhibiting PDE1 activity, compounds of the present invention can enhance levels of $Ca^{2+}$ and cAMP/cGMP, triggering a signaling cascade that ultimately activates transcription factors, including the cAMP responsive element binding protein (CREB). CREB activation can then increase expression of neuronal plasticity-related genes, neurotrophic factors, and neuroprotective molecules—which in turn can promote the functional and morphological changes necessary for neuronal plasticity to occur. (See e.g., Tully et al., 2003, Nat. Rev. Drug. Discov. 2, 267-277; Alberini, 2009, Physiol. Rev. 89, 121-145.

More generally, cyclic nucleotide signaling pathways, including those involving PDE1, are critical regulators of neural function and plasticity, and alterations in these pathways have been implicated in various disorders of the brain. For example, In Alzheimer's disease, there is evidence that accumulation of amyloid-β protein decreases CREB phosphorylation, resulting in cognitive deficits. Vitolo et al., 2002, Proc. Natl. Acad. Sci. USA. 99, 13217-13221. Indeed, pharmacological methods to increase cAMP levels can restore neuronal plasticity and LTP in Alzheimer's models. Vitolo et al., 2002, Proc. Natl. Acad. Sci. USA. 99, 13217-13221. Similarly, intra-cellular signaling of dopamine D1 and various serotonin receptors, which signal through cyclic nucleotides, is known to be defective in various disorders, including depression, schizophrenia and cognitive disorders. In addition, altered cAMP/cGMP levels are associated with Parkinson's disease, and PDE1B activity is increased in a Parkinson's model. Sancesario et al., 2004, Eur. J. Neurosci. 20, 989-1000). Moreover, chronic elevation in calcium levels (which has been linked to cell death) is implicated in Alzheimer's disease, as well as other neurodegenerative diseases, such as Parkinson's and Huntington's. Because calcium signaling can regulate PDE1 function, inhibitors of the present invention are useful in treating such disorders.

Cognitive Impairments

In certain embodiments, compounds and compositions of the present invention are used in methods for treating a cognitive impairment associated with a neurological disorder. For the purposes of the present invention, the term "cognitive impairment" is used interchangeably with "cognitive disorder," "cognitive dysfunction," "cognitive deficit," and "cognitive disability" throughout this application, and all are deemed to cover similar therapeutic indications.

In specific embodiments, the invention provides various methods relying on the use of compounds and compositions of the present invention to treat a cognitive deficit associated with a CNS disorder, such as a cognitive impairment affecting memory formation. In another aspect, a compound or composition of the present invention is administered with a cognitive training protocol to treat a cognitive disorder. In a specific aspect, the cognitive deficit is associated with a CNS disorder selected from one or more of the group comprising dementias and neurodegenerative disorders, progressive CNS diseases, psychiatric disorders, developmental and genetic conditions, age-associated memory impairments, and learning disabilities.

Cognitive disorders can significantly impair social and occupational functioning, adversely impacting the autonomy and quality of life of the affected individual. An estimated four to five million Americans (about 2% of all ages and 15% of those older than 65) have some form and degree of cognitive impairment. Abrams et al., Merck Manual of Geriatrics, Whitehouse Station (NJ), Medical Services (1995).

Cognitive disorders reflect problems in cognition, i.e., the general processes by which knowledge is acquired, retained and used. Accordingly, cognitive disorders can encompass impairments in cognitive functions such as concentration, perception, attention, information processing, learning, memory, and/or language. Cognitive disorders can also encompass impairments in psychomotor learning, which include physical skills, such as movement and coordination; disruptions in fine motor skills, such as the ability to use precision instruments or tools; and deficits in gross motor skills, such as those elicited in dance, musical, or athletic performance.

Cognitive disorders can also encompass impairments in executive functions, which include abilities underlying the planning and execution of goal-oriented behaviors. Such abilities include flexibility, i.e., the capacity for quickly switching to the appropriate mental mode; anticipation and prediction based on pattern recognition; reasoning and problem-solving; decision making; working memory, i.e., the capacity to hold and manipulate internally (or externally) derived information in real time; emotional self-regulation, including the ability to recognize and manage one's emotions for good performance; sequencing, such as the ability to dissect complex actions into manageable units and prioritize them in the right order; and self-inhibition, i.e., the ability to withstand distraction and internal urges.

Cognitive disorders commonly occur in association with CNS disorders (also referred to as CNS conditions or CNS diseases). Such CNS disorders include, but are not limited to, the following categories (which are not mutually exclusive):

(1) dementias, such as those associated with Alzheimer's disease, Parkinson's disease; Huntington's disease, Pick's disease, Creutzfeldt-Jakob, ALS, AIDS Dementia, and other neurodegenerative disorders; as well as cognitive disabilities associated with progressive diseases involving the nervous system, such as multiple sclerosis.

(2) psychiatric disorders, which include affective disorders (mood disorders), such as depression and bipolar disorder; psychotic disorders, such as schizophrenia and delusional disorder; and neurotic and anxiety disorders, such as phobias, panic disorders, obsessive-compulsive disorder, generalized anxiety disorder, eating disorders, and posttraumatic stress disorder;

(3) developmental and genetic conditions affecting cognitive function, such as autism spectrum disorders; fetal alcohol spectrum disorders (FASD); Rubinstein-Taybi syndrome, down syndrome, and other forms of mental retardation; and progressive disorders involving the nervous system, such as multiple sclerosis;

(4) trauma-dependent losses of cognitive functions, such as impairments in memory, language, or motor skills resulting from brain trauma; head injury; cerebrovascular disorders, such as stroke, ischemia, hypoxia, and viral infection (e.g., encephalitis); excitotoxicity; seizures; and alcohol abuse;

(5) age-associated memory impairments, including those affecting patients in early stages of cognitive decline, as in Mild Cognitive Impairment (MCI); and (6) learning disabilities, such as perceptual handicaps, dyslexia, and attention deficit disorders.

In some cases, cognitive impairments can be a direct result of a CNS disorder. For example, impairments in speech and language may be a direct result of a stroke or head-injury that damages the brain regions controlling speech and language, as in aphasia.

In other cases, cognitive impairments may be associated with a complex developmental syndrome, CNS disorder, or genetic syndrome. For example, such impairments include cognitive deficits associated with schizophrenia or Parkinson's disease, or deficits in executive control that accompany autism or mental retardation.

In still other cases, such impairments can result from progressive diseases that impact CNS function, such as multiple sclerosis (MS). About one-half of MS patients will experience problems with cognitive function, such as slowed thinking, decreased concentration, and impaired memory. Such problems typically occur later in the course of MS, although in some cases they occur much earlier—if not at the onset of disease.

Augmented Cognitive Training

In some embodiments, the compounds and compositions of the instant invention are administered in conjunction with cognitive training to improve the efficiency of such training. The phrase "in conjunction" means that a compound or composition of the present invention enhances CREB pathway function during cognitive training. As used herein, the term "cognitive training" is interchangeable with "training protocol," "training," and "cognitive training protocol."

Training Protocols

Cognitive training protocols and the underlying principles are well known in the art. See, e.g., U.S. Pat. No. 7,868,015 (and references cited therein); Klingberg et al., 2005, J. Am. Acad. Child. Adolesc. Psychiatry 44, 177-186; Belleville et al., 2006, Dement. Geriatr. Cogn. Disord. 22, 486-499; Jaeggi et al., 2008, Proc. Natl. Acad. Sci. USA 105, 6829-6833; Lustig et al., 2009, Neuropsychol. Rev. 19, 504-522; Park and Reuter-Lorenz, 2009, Ann. Rev. Psych. 60, 173-196; Chein et al., 2010, Psychon. Bull. Rev. 17, 193-199; Klingberg, 2010, Trends Cogn. Sci. 14, 317-324; Owen et al., 2010, Nature 465, 775-778; Jaeggi et al., 2011, Proc. Natl. Acad. Sci. USA 108, 10081-10086.

Cognitive training protocols are directed to numerous cognitive dimensions, including memory, concentration and attention, perception, learning, planning, sequencing, and judgment. One or more protocols (or modules) underling a cognitive training program can be provided to a subject.

In some embodiments, the protocols can be used to treat, or rehabilitate, cognitive impairments in afflicted subjects. Such protocols may be restorative or remedial, intended to reestablish prior skills and cognitive functions, or they may be focused on delaying or slowing cognitive decline due to neurological disease. Other protocols may be compensatory, providing a means to adapt to a cognitive deficit by enhancing function of related and uninvolved cognitive domains. In other embodiments, the protocols can be used to improve particular skills or cognitive functions in otherwise healthy individuals. For example, a cognitive training program might include modules focused on delaying or preventing cognitive decline that normally accompanies aging; here the program is designed to maintain or improve cognitive health.

In general, a cognitive training protocol (or module) comprises a set of distinct exercises that can be process-specific or skill-based:

Process-specific training focuses on improving a particular cognitive domain such as attention, memory, language, or executive functions. Here the goal of cognitive training is to obtain a general improvement that transfers from the trained activities to untrained activities associated with the same cognitive function or domain. For example, an auditory cognitive training protocol can be used to treat a student with impaired auditory attention. At the end of training, the student should show a generalized improvement in auditory attention, manifested by an increased ability to attend to and concentrate on verbal information presented in class- and therefore to remember to write down and complete homework assignments. Similarly, a cognitive training protocol may be directed to impaired executive function in an autistic subject, preventing the subject from carrying out instructions to complete an activity, such as making a meal, cleaning one's room, or preparing for school in the morning. Cognitive training allows the subject to focus his attention and concentration and as a result, complete the sequence of tasks required for such activities.

Skill-based cognitive training is aimed at improving performance of a particular activity or ability. Here the goal of cognitive training is to obtain a general improvement in the skill or ability. For example, a training protocol may focus on learning a new language, performing a musical instrument, or improving memory. The different exercises within such a protocol will focus on core components underlying skill. Modules for increasing memory, for example, may include tasks directed to the recognition and use of fact, and the acquisition and comprehension of explicit knowledge rules.

Some cognitive rehabilitation programs may rely on a single strategy (such as computer-assisted cognitive training) targeting either an isolated cognitive function or multiple functions concurrently. For example, the CogState testing method comprises a customizable range of computerized cognitive tasks able to measure baseline and change in cognitive domains underlying attention, memory, executive function, as well as language and social-emotional cognition. See, e.g., Yoshida et al., 2011, PloS ONE 6, e20469; Frederickson et al., 2010, Neuroepidemiology 34, 65-75. Other cognitive rehabilitation programs may use an integrated or interdisciplinary approach. Cognitive training programs may involve computer games, handheld game devices, interactive exercises, and may employ feedback and adaptive models.

Augmenting Agents

Cognitive training generally requires multiple training sessions to attain the desired benefits. This can be costly and time-consuming, deterring subject compliance and the realization of real world benefits that endure over time.

The efficiency of cognitive training can be improved by administering certain agents (known as augmenting agents) in conjunction with cognitive training. Such augmenting agents have the ability to enhance CREB pathway function. More particularly, this method (known as augmented cognitive training or ACT) can decrease the number of training sessions required to improve performance of a cognitive function, relative to the improvement observed by cognitive training alone. See, e.g., U.S. Pat. No. 7,868,015; U.S. Pat. No. 7,947,731; U.S. 2008/0051437.

In a particular embodiment, the method comprises the steps of: (a) providing cognitive training to a subject in need of treatment of a cognitive deficit under conditions sufficient to produce an improvement in performance by said animal of a cognitive function whose impairment is associated with said cognitive deficit; (b) administering a compound or composition of the present invention to the animal in conjunction with said cognitive training; repeating steps (a) and (b) one or more times; and (d) reducing the number of training sessions sufficient to produce the improvement in performance, relative to the improvement in performance produced by cognitive training alone.

More generally, compounds and compositions of the present invention can be used in conjunction with any psychotherapeutic approach that is intended to modulate cognitive function in the brain, thereby enhancing the efficacy of the such therapy by reducing the number of sessions—and hence time—necessary to attain benefits.

In a specific aspect, the cognitive deficit treated by these methods is or includes memory impairment, and more particularly, a defect in long-term memory. Long-term memory (LTM) generally comprises two main biological properties. First, formation of long-term memory requires synthesis of new proteins. Second, it involves cAMP-responsive transcription and is mediated through the cAMP-response element binding protein (CREB) family transcription factors. Accordingly, in some embodiments, compounds of the present invention are useful in enhancing memory formation in an animal, and more particularly, transcription-dependent memory.

Behavioral Assays

Numerous behavioral assays are available to assess the ability of a candidate compound to enhance memory formation, including the contextual conditioning, temporal conditioning, and object recognition assays. (See Biological Examples) Other, non-limiting examples of appropriate training protocols to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The training protocols can also be used in accordance with the present invention as will be understood by those of ordinary skill in the art. These training protocols can be directed towards the evaluation of, without limitation, hippocampus-, cortex-, and/or amygdale-dependent memory formation or cognitive performance.

Cardiovascular Disorders

PDE1 enzymes and cyclic nucleotides are emerging as key mediators of pathological processes that underlie many vascular disorders, including hypertension and myocardial infarction. For example, PDE1 appears to play a role in regulating cardiomyocyte hypertrophy via a mechanism involving cross-talk between Ca2+ and cyclic nucleotide signaling. See, e.g., Miller et al., 2011, Basic Res. Cardiol. 106, 1023-1039; Miller et al, 2009, Circ. Res. 105, 956-964. Moreover, PDE1 enzymes constitute the majority of cAMP- and cGMP-hydrolytic activity in human myocardium, implicating them in regulating signaling pathways involved in heart failure Accordingly, the present invention includes the use of a compound or composition herein in a method of treating a cardiovascular disorder, comprising administration of an effective amount of the compound or composition to a patient in need thereof.

Cardiovascular diseases within the scope of the present invention encompass, but are not limited to, angina pectoris, coronary artery disease, hypertension, congestive heart failure, myocardial infarction, ischemic diseases of the heart, atrial and ventricular arrhythmias, hypertensive vascular diseases, peripheral vascular diseases, and atherosclerosis.

In some embodiments, methods of treating a cardiovascular disorder in accord with the present invention comprise increasing cGMP concentration, cAMP concentration, or both, in any part of the heart muscle of a subject, the method comprising administering to the subject a compound or composition described herein.

In other embodiments, compounds of the present invention may be useful in lowering the heart rate or blood pressure in an animal.

Renal Disorders

PDE1 inhibitors are emerging therapeutic agents for progressive renal disease. See, e.g., Cheng et al., 2007, Soc. Exp. Biol. Med. 232, 38-51. Consistent with these findings, recent studies indicate that cAMP and cGMP regulate a variety of signaling pathways involved in the development and progression of renal disease, including pathways that modulate mitogenesis, inflammation, and extracellular matrix synthesis. See e.g., Wang et al., 2010, Kidney Int. 77. 129-140.

Accordingly, the present invention provides compound or compositions in methods for treating a renal disorder, comprising administering an effective amount of the compound or composition to a patient in need thereof. In a particular aspect, the renal disorder is selected from one or more of the group comprising renal artery stenosis, pyelonephritis, glomerulonephritis, kidney tumors, polycystic kidney disease, injury to the kidney, and damage resulting from radiation of the kidney.

Hematological Disorders

PDE1B is highly expressed in the hematological system, including leukocytes (peripheral blood), bone marrow stromal cells, bone marrow CD33+ cells, cord blood CD34+ cells, neutrophils cord blood, neutrophils peripheral blood, spleen, spleen liver cirrhosis. Accordingly, the present invention includes methods to treat a hematological disorder, comprising administering a compound or composition herein to a patient in need thereof. Hematological diseases within the scope of the present invention comprises disorders of the blood and all its constituents, including, but not limited to anemias, myeloproliferative disorders, hemorrhagic disorders, leukopenia, eosinophilic disorders, leukemias, lymphomas, plasma cell dyscrasias, and disorders of the spleen.

Gastrointestinal and Liver Diseases

PDE1B shows differential expression between diseased (e.g., cancerous) and healthy stomach tissue, diseased (e.g., cancerous) versus healthy ileum tissue, diseased (cirrhotic) versus and healthy liver. Accordingly, the present invention includes methods to treat a gastrointestinal disorder, comprising administering a compound or composition herein to a patient in need thereof. Gastrointestinal diseases within the scope of the present invention comprise, but are not limited to, disorders of the esophagus, stomach, duodenum, pancreas, bowel, and liver.

Cancer Disorders

PDE1B shows high expression in numerous cancer tissues, including tumors of the stomach, ileum, ovary, breast, and kidney, as well as differential expression between cancerous and healthy stomach, ileum, lung, ovary, breast, and kidney. Accordingly, the present invention includes methods to treat a cancer disorder, comprising administering a compound or composition herein to a patient in need thereof. Cancer disorders within the scope of the present invention comprise, but are not limited to, neoplasms, dysplasias, hyperplasias, and neoplasms, including cancers of the stomach, ileum, ovary, breast, and kidney.

Neurodegenerative Disorders

The present invention provides a method for treating the effects of injuries or diseases that result in neuronal degeneration or a method for promoting neurogenesis or neurite outgrowth These methods involve administering to a patient in need thereof an effective amount of a compound or composition of the present invention. It has been found that the PDE1 inhibitors of the present invention promote neurite outgrowth and neurogenesis.

Alternatively, at least one compound of the present invention is used to treat stem cells or neuronal progenitor cells prior to the cells being administered to the patient by implantation at the site of neuronal degeneration. In some embodiments, methods described herein involve modulating neurogenesis or neurite outgrowth ex vivo with a compound such that a composition containing neural stem cells, neural progenitor cells and/or differentiated neural cells can be subsequently administered to an individual to treat a disease or condition. In some embodiments, the method of treatment comprises the steps of contacting a neural stem cell or neural progenitor cell with one or more compounds of the invention to modulate neurite outgrowth and transplanting the cells into a patient in need or treatment. Methods of transplanting stem and progenitor cells are known in the art. In some embodiments, methods described herein allow treatment of diseases or conditions by directly replacing or replenishing damaged or dysfunctional neurons.

The method of the present invention which promotes neurogenesis is involved in cell renewal in the central nervous system (CNS) and includes all types of CNS cells.

In one embodiment, methods of the present invention are used to treat primary nervous system injury, e.g. closed head injuries and blunt trauma, such as those caused by participation in dangerous sports, penetrating trauma, such as gunshot wounds, hemorrhagic stroke, ischemic stroke, glaucoma, cerebral ischemia, or damages caused by surgery such as tumor excision or may even promote nerve regeneration in order to enhance or accelerate the healing of such injuries or of neurodegenerative diseases such as those discussed below. In addition, the method may be used to treat a disease or disorder resulting in a degenerative process.

In another embodiment, methods of the present invention are used to inhibit secondary degeneration which may otherwise follow primary nervous system injury.

The compounds of the invention may be used to treat various diseases or disorders of the central or peripheral nervous system, including diabetic neuropathy, amyotrophic lateral sclerosis (ALS). Peripheral nerve injuries and peripheral or localized neuropathies including, but not limited to, porphyria, acute sensory neuropathy, chronic ataxic neuropathy, complications of various drugs and toxins, amyloid polyneuropathies, adrenomyeloneuropathy, giant axonal neuropathy may be treated by this method.

In addition the compounds can be used for post-operative treatments such as for tumor removal from CNS and other forms of surgery on the CNS. The compounds can also be used for treatment of spinal cord trauma.

BIOLOGICAL EXAMPLES

The present disclosure will be further illustrated by the following biological examples. These examples are understood to be exemplary only, and not to limit the scope of the invention disclosed herein.

Biological Example 1

Effect of siRNA Mediated Knockdown of PDE1B on Memory Formation

The role of pde1b in memory formation in animals was evaluated by RNA interference. See, e.g., Peters et al., 2009, Genes Brain Behav. 8, 320-329. The results showed that siRNA-mediated inhibition of pde1b in animals enhanced several forms of long-term memory, including contextual and temporal (trace) memory.
Procedures
siRNA Initially, several non-modified siRNAs were tested for pde1a and pde1b knockdown in vitro using Neuro 2a cells. The siRNAs were specific to the Pde1 isoforms as identified by BLAST search. Several siRNAs showed efficacy in reducing pde1b mRNA levels and were chosen for further in vivo characterization. The behavioral studies used in vivo grade siSTABLE siRNA, which was chemically modified to enhance stability (Dharmacon Inc., Lafayette, USA). The sequence of the pde1b-6 siRNA sense strand was: 5'-GC-UACAUGGUGAAGCAGUU-3'. The sequence of the non-targeting, control siRNA sense strand was: 5'-UAGCGAC-UAAACACAUCAAUU-3'.
Subjects Young-adult (12-16 weeks old) C57BL/6Jax (Jackson Laboratories) male mice were utilized for contextual conditioning and C57Bl/6NTac (Taconic Farms) mice for trace fear conditioning. Upon arrival, mice were group-housed (5 mice) in standard laboratory cages and maintained on a 12:12 hours light-dark cycle. Experiments were always conducted during the light phase of the cycle.

After surgery for hippocampal cannulation, mice were housed in individual cages for the duration of the experiment. Mice received food and water ad libitum except when being trained or tested. They were maintained and bred under standard conditions, consistent with National Institutes of Health (NIH) guidelines and approved by the Institutional Animal Care and Use Committee.
Animal Surgery For both contextual and trace conditioning, mice were infused with non-targeting or Pde1b siRNA into the hippocampus. For the injection of siRNA, mice were anesthetized with 20 mg/kg Avertin and implanted with a 33-gauge guide cannula bilateraly into the dorsal hippocampus (coordinates: A=−1.8 mm, L=+/−1.5 mm to a depth of 1.2 mm) or into amygdala (coordinates: A=−1.58 mm, L=+/−2.8 mm to a depth of 4.0 mm) (Franklin and Paxinos, The Mouse Brain in Stereotaxic Coordinates. Academic Press, San Diego 2003). Five to nine days after recovery from surgery, animals were injected with siRNA diluted to 0.5 μg/μl in 5% glucose and mixed with 6 equivalents of a 22 kDa linear polyethyleneimine (Fermentas). After 10 min of incubation at room temperature, 2 μl were injected into each hippocampus through an infusion cannula that was connected to a micro-syringe by a polyethylene tube. Animals were handled gently to minimize stress.

A total of 3 infusions of siRNA were given over a period of 3 days (1 g siRNA per hippocampus per day). Mice were trained 3 days after the last siRNA injection and tested 24 hours later. Behavioral testing was initiated 3 days later. This design was chosen based on pilot experiments on siRNA knockdown in hippocampus, and because previous studies have indicated that gene-knockdown by siRNA duplexes takes several days to develop in CNS. See, e.g., Salahpour et al., 2007, Biol. Psychiatry 61, 65-69; Tan et al., 2005, Gene Therapy 12, 59-66; Thakker et al., 2004, Proc. Natl. Acad. Sci. USA 101, 17270-17275.
Fear Conditioning
Rationale Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. See, e.g., Fanselow, 1984, Behav. Neurosci. 98, 269-277; Fanselow, 1984, Behav. Neurosci. 98, 79-95; Phillips and LeDoux, 1992, Behav. Neurosci. 106, 274-285.

Contextual conditioning has been used to investigate the neural substrates mediating fear-motivated learning. See, e.g., Phillips and LeDoux, 1992, Behav. Neurosci. 106, 274-285; Kim et al., 1993, Behav. Neurosci. 107, 1093-1098. Recent studies in mice and rats provided evidence for functional interaction between hippocampal and non-hippocampal systems during contextual conditioning training. See, e.g., Maren et al., 1997, Behav. Brain Res. 88, 261-274; Maren et al., 1997, Neurobiol. Learn. Mem. 67, 142-149; Frankland et al., 1998, Behav. Neurosci. 112, 863-874. Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning and memory and strain differences in mice. See, e.g., Bourtchouladze et al., 1994, Cell 79, 59-68; Bourtchouladze et al., 1998, Learn Mem. 5, 365-374; Kogan et al., 1997, Current Biology 7, 1-11; Silva et al., 1996, Current Biology 6, 1509-1518; Abel et al., 1997, Cell 88, 615-626; Giese et al., 1998, Science 279, 870-873; Logue et al., 1997, Neuroscience 80, 1075-1086; Chen et al., 1996, Behav. Neurosci. 110, 1177-1180; Nguyen et al., 2000, Learn Mem. 7, 170-179.

Because robust learning can be triggered with a few minutes training session, contextual conditioning has been especially useful to study the biology of temporally distinct processes of short- and long-term memory. See, e.g., Kim et al., 1993, Behav. Neurosci. 107, 1093-1098; Abel et al., 1997, Cell 88, 615-626; Bourtchouladze et al., 1994, Cell 79, 59-68; Bourtchouladze et al., 1998, Learn. Mem. 5, 365-374. As such, contextual conditioning provides an excellent model to evaluate the role of various novel genes in hippocampal-dependent memory formation.

Protocol

Previous investigations had established that training with 1× or 2×CS-US pairings induces sub-maximal (weak) memory in wild-type mice. See, e.g., U.S.2009/0053140; Tully et al., 2003, Nat. Rev. Drug Discov. 2, 267-77; Bourtchouladze et al. 1998, Learn. Mem. 5, 365-374. Accordingly, contextual conditioning in this study was performed as described by Bourtchouladze et al., 1994, Cell 79, 59-68.

An automated fear conditioning system (Colburn Instruments) was used for contextual conditioning and a manual setup (Med Associates) for trace fear conditioning. Mice were placed in the conditioning chamber and allowed to explore for 2 min. A total of two foot-shocks were delivered (0.6 mA, 2 s duration) with an inter-trial interval of 1 min. Freezing was scored for 30 s after the last foot-shock (immediate freezing). Mice were then returned to their home-cage. Memory was tested after 24 h (LTM). To assess contextual memory, freezing behavior was scored for 3 min intervals of 1 s in the chamber in which the mice were trained Trace Conditioning Rationale Trace fear conditioning is a form of Pavlovian conditioning, in which an interval of time passes between CS termination and UCS onset. Thus, the CS and US are separated in time by a trace interval, and the memory of this temporal relationship requires the hippocampus and prefrontal cortex. See Knight et al., 2004, J. Neurosci. 24, 218-228.

Trace conditioning becomes increasingly difficult as the time interval between CS and US increases. For example, C57BL/6 mice show poor memory if the trace interval between CS and US is 60 seconds or longer. See, e.g., U.S.2009/0053140. Moreover, previous studies have demonstrated that this memory impairment can be overcome if mice are treated with siRNA against PP1, a negative regulator of plasticity in the hippocampus. Peters et al., 2009, Genes Brain Behav. 8, 320-329. Consequently, the trace conditioning assay provides a method to test the ability of a compound to facilitate hippocampal-dependent memory.

Protocol

Facilitation of temporal memory in this study was assessed using a single CS-US pairing with a 60 s trace interval. For this study, standardized mouse contextual fear conditioning equipment was used (Med Associates, Inc., VA; Bourtchouladze et al., 1994, Cell 79, 59-68; (Bourtchouladze et al., 1998 Learn Mem. 5, 365-374). On the training day, the mouse was placed into the conditioning chamber for 2 minutes before the onset of the conditioned stimulus (CS), a 2800 Hz tone, which lasted for 20 seconds at 75 dB. Sixty seconds after the end of the tone, a 0.5 mA shock unconditioned stimulus (US) was delivered to the animal for two seconds. Following an additional 30 s in the chamber, the mouse was returned to its home cage.

Mice were tested at 24 h after training in a novel chamber located in another procedural room to avoid confounding effects of contextual conditioning. The internal conditioning chamber was removed and replaced with a mouse cage. Different colored tape was placed on the backside of each cage to differentiate one from another. Three different cages were used in rotation in order to decrease the possibility of scent contamination from subject to subject. A 30-watt lamp was placed inside the chamber to insure difference in illumination between training and testing. The cages were cleaned using a soapy solution instead of ethanol.

Each test began with two minutes of light only (pre-CS), then 20 seconds of tone presentation (CS), followed by an additional 30 seconds of light only (post-CS). In the same manner as during training, the mice were scored one at a time for "freezing" in five-second intervals, as for contextual conditioning described above. The proceeding of each experiment was filmed. The proportion of the freezing response specific to the auditory memory was determined by subtraction of preCS freezing (non-specific) from CS freezing (CS-preCS).

Statistical Analyses

All behavioral experiments were designed and performed in a balanced fashion: First, for each experimental condition (e.g., a specific dose effect) an equal number of experimental and control mice were used. Second, each experimental condition was replicated several times and replicate days were added to generate final number of subjects. Third, each session was video recorded and the experimenter was unaware (blind) to the treatment the subjects during training and testing.

Data were analyzed by ANOVA using JMP software. Except where indicated, all values in the text and figures are expressed as mean+SEM.

Results

Contextual Memory

When tested in contextual fear conditioning with 2 CS-US pairings to induce weak (sub-maximal) contextual memory, pde1b siRNA-injected mice showed significantly enhanced freezing 24 hours after training, compared to non-targeting siRNA-injected mice (FIG. 1).

Trace Memory

Figure 2:
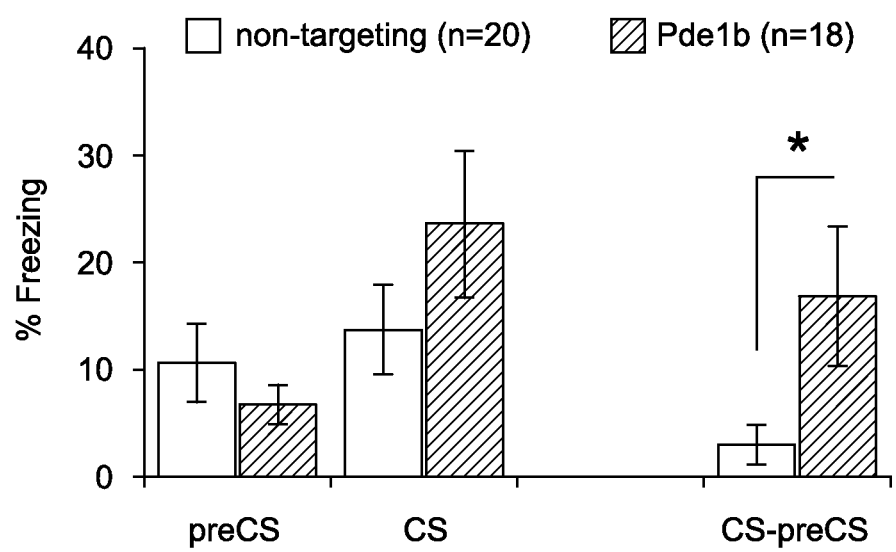
FIG. 2 is a bar graph showing the effect of siRNA-mediated knockdown of PDE1b in mouse hippocampal tissue on one-day memory in a trace-conditioning assay.

Similarly, when tested in trace conditioning with one CS/US pairing and a 60-s trace interval, pde1b siRNA-injected mice showed enhanced trace memory (FIG. 2). Repeated measures ANOVA revealed a significant treatment-by-trial interaction ($p<0.05$). Contrast analysis revealed that pde1b siRNA and control mice froze an equal proportion of time to tone (CS: $p=0.13$, preCS: $p=0.54$). However, only pde1b siRNA-treated mice formed a memory for the CS, while mice treated with control siRNA did not (effect of tone CS: $p<0.05$ and $p=0.62$ for pde1b and control siRNA, respectively). Moreover, pde1b treated mice showed significantly higher freezing if the nonspecific freezing in the alternate testing context was subtracted from the response to tone CS (CS-preCS: $p<0.05$). Thus, siRNA-mediated knockdown of hippocampal pde1b enhanced memory formation after trace fear conditioning as observed for contextual fear conditioning.

Taken together these results show that Pde1b is a negative regulator of memory formation in the hippocampus, a temporal lobe structure that is critical to memory formation in mice as well as in humans. Importantly, Pde1b siRNA induced a 'gain of function' (that is, enhancement of contextual and temporal memory formation). Hence these results show that Pde1b is a valid target for enhancing cognition, and memory specifically.

Biological Example 2

Effect of siRNA Mediated Knockdown of PDE1 on Neurite Growth

In the mouse, pde1b is highly expressed in the dentate gyrus and olfactory bulb, the two areas where neurogenesis occurs in the adult nervous system. Neurogenesis is the process by which new neurons are born and undergo dendritic and synaptic differentiation to integrate with functional circuitry. Neurogenesis in the hippocampus has been implicated in memory formation. See, e.g., Shors et al., 2001, Nature 410, 372-376; Shors et al., 2004, Trends Neurosci. 27, 250-256. The studies here evaluated the effect of pde1b inhibition of neurite outgrowth in the PC12 subclone NS1 (Cellomics). Neurite outgrowth (NOG) in PC12 cells (and primary neurons) occurs upon activation of signaling pathways that act through CREB. See, e.g., Greene and Tischler, 1976, Proc. Natl. Acad. Sci. USA 73, 2424-2428; Cheng et al., 2002, J. Biol. Chem. 277, 33930-33942.

This study evaluated the effect on neurite outgrowth (NOG) of drugs known to enhance cAMP-mediated activation of CREB, i.e., the PDE4 inhibitor rolipram—and compared these effects with those induced by siRNA-mediated inhibition of pde1b.

Methods

Cell Culture

Neuroscreen 1 (NS1) Cells (Cellomics Inc.) were cultured on collagen type I coated 75 cm2 plastic flasks (Biocoat, Becton Dickinson) in a humidified incubator at 37° C. in 5% $CO_2$. Cells were cultured in RPMI complete cell culture medium (Cambrex) supplemented with 10% heat-inactivated horse serum (Invitrogen), 5% heat-inactivated fetal bovine serum (Cellgro), and 2 mM L-glutamine (Cambrex). For expansion, the cells were trypsinized and split at 80% confluence. Cell culture media was changed every 2 to 3 days.

NS1 cells were harvested and counted using a Coulter counter (Becton Dickinson Coulter Z1). Cells were seeded in 96-well collagen I coated plates at a density of 2000 cells per well in volume of 200 µl. RPMI media was supplemented with 200 ng/ml nerve growth factor (NGF, Sigma). NS1 cells were incubated for 72 hours to allow differentiation to a neuronal phenotype. NGF as then diluted to 50 ng/ml and the cells were treated with siRNA or compound at the indicated doses in FIG. 2A.

Neurite Outgrowth Assay

Neurite outgrowth (NOG) assays were performed using the Cellomics Arrayscan II Vti HCS scanner. Cells were stained using the HitKit™ HCS reagent kit (Cellomics) according to the manufacturer's instructions (which were previously validated for specific labeling of both neurites and neuronal cell bodies. Briefly, cells were fixed in 3.7% formaldehyde and stained with Hoechst dye to label the nuclei. The cells were then washed in neurite outgrowth buffer, incubated for one hour with the primary antibody for neurite outgrowth (anti-tubulin III), washed again, and incubated with fluorescently labeled secondary antibody solution for 1 hr.

Antibody-stained 96-well plates were stored at 4° C. in the dark until scanning. Plates were scanned using Cellomics ArrayScan II Vti HCS scanner. The neurite outgrowth assay is based on two channels to scanning: (1) Channel 1, which detects the Hoechst Dye and is used by the software to identify cells and for automated focusing; and (2) Channel 2, which detects the FITC fluorescence of the secondary antibody and is used by the software to calculate all data generated in reference to neurites.

siRNA and Drug Administration

Pde1b-specific siRNAs were the same as those described in Biological Example 1. The adenylyl cyclase stimulator forskolin and the selective PDE4 small molecule inhibitor Rolipram were administered at the doses indicated in FIG. 3A.

Results

Figure 3A:
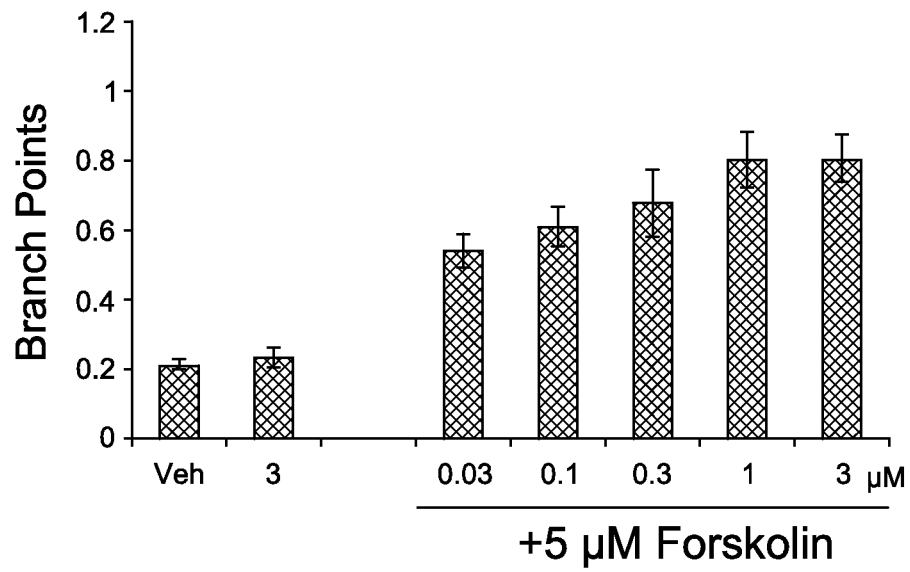
FIG. 3A is a bar graph showing the effect on neurite outgrowth of rolipram-mediated inhibition of PDE4. Bars represent the mean±SEM of neurite length and branching of at least 100 NS1 cells; n=8 wells/bar.
Figure 3B:
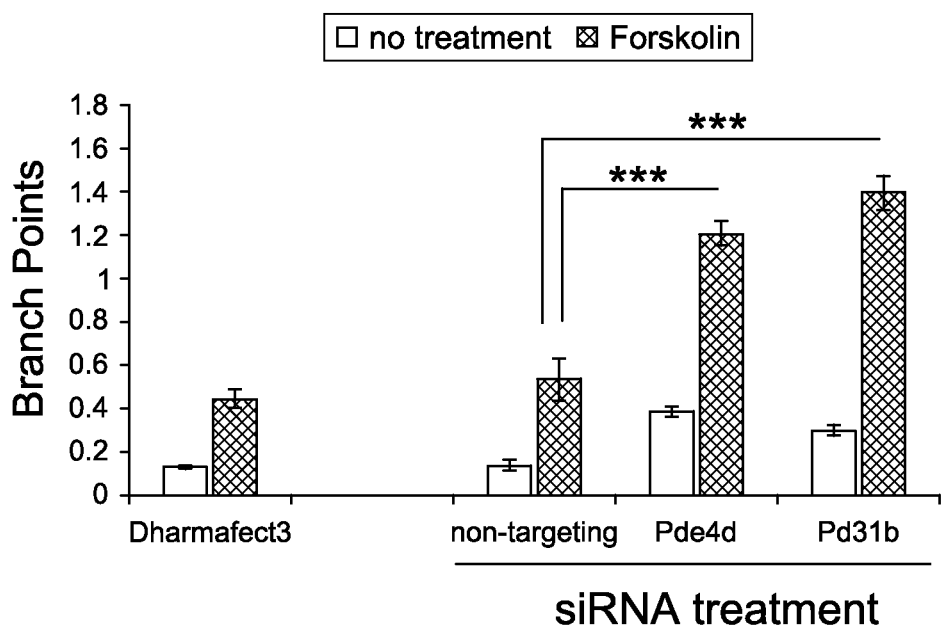
FIG. 3B is a bar graph showing the effect on neurite outgrowth of siRNA-mediated inhibition of Pde4d or Pde1b. Bars represent the mean±SEM of neurite length and branching of at least 100 NS1 cells; n=8 wells/bar.

As shown in FIG. 3A, neurite length and branching in NS1 cells was enhanced in dose-dependent manner by acute treatment with Rolipram and forskolin—but was not affected by treatment with Rolipram alone. Similarly, FIG. 3B shows that neurite outgrowth in NS1 cells was enhanced by siRNA-mediated knockdown of pde4d (the target of Rolipram) or pde1b in combination with forskolin. In contrast to Rolipram (which likely only inhibits PDE4 for several hours), pde4d and pde1b siRNA administration (>48 h) each had a small effect on NOG without the addition of Forskolin.

These results demonstrate that Pde1b inhibition leads to a functional enhancement of neurite growth in NS1 cells. Accordingly, the NOG assay also offers a suitable secondary (cellular/phenotypic) assay to test Pde1b inhibitors identified from a high throughput screening campaign.

Biological Example 3

Effect of Exemplary Compounds on Memory

The studies here evaluated the effect of exemplary compounds of the present invention on memory and haloperidol induced catalepsy mice and rats
Methods
Subjects Three month old B6129F1/J hybrid male mice (Jackson Laboratories, Bar Harbor, Me.) male mice were utilized for contextual conditioning fear conditioning and novel object recognition studies and C57BL/6J males (Jackson Laboratories) were used for catalepsy studies. Outbred hooded Long Evans rats (200 g average weight, Harlan) were used for rat object recognition and fear conditioning. Upon arrival, mice were group-housed (4 mice/cage) in Inovive IVC racks and maintained on a 12:12 hours light-dark cycle. Rats were house in standard cages in groups of two. Experiments were always conducted during the light phase of the cycle. The animals received food and water ad libitum except during training and testing. All procedures were consistent with National Institutes of Health (NIH) guidelines and approved by the DNS/Helicon Institutional Animal Care and Use Committee.
Drug Administration Pde1 inhibitors and positive control were dosed in a Vehicle containing 10% DMSO, 30% PEG (MW400) and 60% PBS, unless specified otherwise. For subcutaneous dosing (s.c.), all drugs were administered at a volume of 10 ml per kg 30 min prior to behavior training unless specified otherwise. For oral dosing (p.o.), animals were dosed at the indicated amount 30 minutes prior to training.
Contextual Conditioning
Protocol Contextual conditioning was essentially carried out as described in Biological Example 1. An automated fear conditioning system (Colburn Instruments) was used for contextual conditioning and a manual setup (Med Associates) for trace fear conditioning. Mice were placed in the conditioning chamber and allowed to explore for 2 min. A total of two foot-shocks were delivered (0.2 mA, 2 s duration) with an inter-trial interval of 1 min. As previously noted, these training conditions generate sub-maximal, or weak, memory in control mice, thereby allowing one to evaluate whether a Pde1b compound of the present invention can enhance memory formation.

Freezing was scored for 30 s after the last foot-shock (immediate freezing). The mice were then returned to their home-cage. Memory was tested after 24 h (LTM) for 3 min by scoring freezing behavior in intervals of is in the chamber in which the mice were trained.
Object Recognition Memory
Rationale Novel Object Recognition (NOR) is an assay of recognition learning and memory retrieval, which takes advantage of the spontaneous preference of rodents to investigate a novel object compared with a familiar one.

The NOR test has been employed extensively to assess the potential cognitive-enhancing properties of novel compounds derived from high-throughput screening. Object recognition is an ethologically relevant task that does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one. See Bourtchouladze et. al., 2003, Proc. Natl. Acad. Sci. USA 100, 10518-10522).

Studies indicate that the NOR procedure involves several brain regions, including the cortex and the hippocampus. Recent neuroimaging studies in humans demonstrated that memory in object recognition depends on prefrontal cortex (PFC). See Delbert et al., 1999, Neurology 52, 1413-1417. Consistent with these findings, rats with the PFC lesions show poor working memory when they are required to discriminate between familiar and novel objects. See Mitchell, 1998, Behav. Brain Res. 97, 107-113. Other studies on monkeys and rodents suggest that the hippocampus is important for novel object recognition. See, e.g., Teng et al., 2000, J. Neurosci 20, 3853-3863; Mumby, 2001, Brain Res. 127, 159-181. Hence, object recognition provides an excellent behavioral model to evaluate drug-compound effects on cognitive task associated with function of the hippocampus and cortex.
Protocol The novel object recognition task was performed as described by Bevins and Besheer, 2006 (Nat. Protocol. 1, 1306-1311) using a standard novel object recognition system for rats (Stoelting). Objects were placed in the center of the box, testing was carried out in low light, and time exploring objects was assessed using Ethovision Software. All videos were reviewed by trained observers.

For two consecutive days, rats were habituated to the chamber for 5 min with 5 min of handling immediately following exposure to the apparatus. The next day, rats treated with 10% DMSO, 30% PEG400, 60% Saline vehicle or drug 30 min before training were exposed to either two white blocks or two grey balls (~4 cm in width/diameter) for 3 min. A performance control group was treated with vehicle and exposed to object for 15 min. Approximately 24 h after training, rats were exposed to one familiar object and one novel object (grey ball is replaced with a white block and vice versa) and the time exploring each object was measured. Memory was scored by calculation of a discrimination index $((T_N-T_F)/(T_N+T_F))*100$; between group comparison) and by comparison of the time exploring the novel versus familiar object on the test day (within group comparison).

Statistical Analyses

All behavioral experiments were designed and performed in a balanced fashion: (i) For each experimental condition (e.g. a specific dose-effect) an equal number of experimental and control mice were used; (ii) Each experimental condition was replicated several times, and (iii) Replicate days were added to generate final number of subjects. The proceeding of each session was filmed. In each experiment, the experimenter was unaware (blind) to the treatment of the subjects during training and testing. Data were analyzed by ANOVA using JMP software, followed by contrast analysis.

Data were transformed using box-cox transformation, and the results of contrast analysis comparing treatment groups to vehicle are shown (LS means students-t). Except were indicated, all values in the text and figures are expressed as Mean±SEM.

Results

Exemplary compounds of Formula I and II were found to significantly enhance 24 hour memory, and where tested, to enhance 48 hour memory, in the object recognition assay. Control experiments showed that compound administration did not significantly affect the cumulative distance traveled or amount of time spent exploring the left and right halves of the box. Significant effects were seen at several concentrations, depending on the compound, including concentrations of 0.1 mg/kg and 1 mg/kg.

Exemplary compounds were also found to enhance contextual memory in the fear conditioning assay. Significant effects were seen at several concentrations, depending on the compound, including 0.01 mg/kg, 0.03 mg/kg, and 1.0 mg/kg.

Biological Example 4

Effect of Exemplary Compounds on Cardiac Function

Exemplary compounds of the present invention were also evaluated in several models of cardiovascular function, in both guinea pigs and in telemeterized male rats. Each test compound (or vehicle) was administered by oral gavage, and animals were evaluated after each dose for any abnormal clinical signs. Systemic blood pressure (systolic, diastolic, and mean arterial pressure), HR and pulse pressure were recorded following dosing.

The results showed no notable effects of vehicle administration on systemic blood pressure, heart rate, or arterial pulse pressure in these studies. All parameters were within expected range during the entire monitoring period. In contrast, however, administration of several test compounds let to a reduction in blood pressure, and in some cases, prolongation of the QTc interval.

It will be understood by one skilled in the art that the described embodiments herein do not limit the scope of the invention. The specification, including the examples, is intended to be exemplary only, and it will be apparent to those skilled in the art that various modifications and variations can be made in the present invention without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:
1. A compound of Formula I:

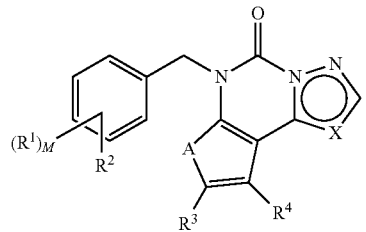

or a pharmaceutically acceptable salt thereof, wherein
A is O (oxygen) or S (sulfur);
X is CH or N (nitrogen);
M=1 or 2;
each occurrence of $R^1$ and $R^2$ is independently selected from H, halo, aryl, heteroaryl, —($C_1$-$C_6$ alkyl) aryl, —($C_1$-$C_6$ alkyl) heteroaryl, heterocycle, —CN, $C_1$-$C_6$ alkyl, $C_1$-$C_6$ thioalkyl, $C_1$-$C_6$ thiohaloalkyl, $C_1$-$C_6$ haloalkyl, $C_2$-$C_6$ alkenyl, $C_2$-$C_6$ alkynyl, —OH, $C_1$-$C_6$ alkoxy, $C_1$-$C_6$ haloalkoxy, —$NO_2$, —$SO_2C_1$-$C_6$ alkyl, —$SOC_1$-$C_6$ alkyl, —$SO_2NH(C_1$-$C_6$ alkyl), —$SO_2N(C_1$-$C_6$ alkyl)$_2$, —CONH($C_1$-$C_6$ alkyl), —CON($C_1$-$C_6$ alkyl)$_2$, —C(O)O($C_1$-$C_6$ alkyl), —C(O)O($C_1$-$C_6$ alkyl) aryl, —OC(O)($C_1$-$C_6$ alkyl), —OC(O)($C_1$-$C_6$ alkyl) aryl, —$SO_2NH_2$, —$CONH_2$, —$CO_2H$, —COH, —$NH_2$, $C_1$-$C_6$ alkylamino, di-$C_1$-$C_6$ alkylamino, —$N_3$, cyanate, isocyanate, thiocyanate, isothiocyanate, —($C_2$-$C_6$ alkenyl)O($C_1$-$C_6$ alkyl), —($C_1$-$C_6$ alkyl)O($C_1$-$C_6$ alkyl), —($C_1$-$C_6$ alkyl)O($C_1$-$C_6$ alkyl)O($C_1$-$C_6$ alkyl), aryloxy, arylthio, —CO($C_1$-$C_6$ alkyl), —CO(aryl), —CO(heteroaryl), and —CO(heterocycle);
or $R^1$ and $R^2$ are on adjacent carbons and are taken together with the carbons to which they are attached to form an optionally substituted 5-6 member saturated or unsaturated monocylic ring system, optionally comprising one or more oxygen, sulfur, or nitrogen atoms;
$R^3$ and $R^4$ are independently selected from H, halo, —CN, $C_1$-$C_6$ alkyl, $C_1$-$C_6$ haloalkyl, —OH, $C_1$-$C_6$ alkoxy, $C_1$-$C_6$ haloalkoxy, aryl, heteroaryl, —($C_1$-$C_6$ alkyl) aryl, —($C_1$-$C_6$ alkyl) heteroaryl, heterocycle, —$NO_2$, —$SO_2C_1$-$C_6$ alkyl, —$SO_2N(C_1$-$C_6$ alkyl)$_2$, —CONH($C_1$-$C_6$ alkyl), —CON($C_1$-$C_6$ alkyl)$_2$, and —$(CR^{10}R^{11})_{0-3}NR^{12}R^{13}$;
or $R^3$ and $R^4$ taken together with the carbons to which they are attached form a saturated or unsaturated monocylic ring system, having the following structure:

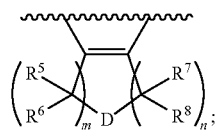

D is O (oxygen), S (sulfur), —SO—, —$SO_2$—, or —N—$R^9$—;
m and n are independently 0-4, with the proviso that the sum of m and n is 1-5 when D is O (oxygen), S (sulfur), —SO—, —$SO_2$—, —N—$R^9$—;
$R^5$, $R^6$, $R^7$, $R^8$, $R^{10}$ and $R^{11}$ are independently selected from —H, —F, —$C_1$-$C_6$ alkyl, —$C_1$-$C_6$ haloalkyl, —OH, —$C_1$-$C_6$ alkoxy, —$C_1$-$C_6$ haloalkoxy, —$SO_2C_1$-

$C_6$ alkyl, —$SO_2N(C_1$-$C_6$ alkyl)$_2$, —$CO_2(C_1$-$C_6$ alkyl), —$CONH(C_1$-$C_6$ alkyl), and —$CON(C_1$-$C_6$ alkyl)$_2$; and $R^9$, $R^{12}$, and $R^{13}$ are independently selected from —H, —$C_1$-$C_6$ alkyl, aryl, heteroaryl, —$SO_2C_1$-$C_6$ alkyl, —$SO_2N(C_1$-$C_6$ alkyl)$_2$, —$CONH(C_1$-$C_6$ alkyl), —$CON(C_1$-$C_6$ alkyl)$_2$, —$CO(C_1$-$C_6$ alkyl), —CO(aryl), —CO(heteroaryl), and —CO(heterocycle); or $R^{12}$ and $R^{13}$ taken together with the nitrogen to which they are attached form an optionally substituted heterocycle.

2. The compound of claim 1, wherein one or more of $R^1$, $R^2$, $R^3$, and $R^4$ is halomethyl.

3. The compound of claim 1, wherein $R^1$ is H, and $R^2$ is $C_1$-$C_6$ alkoxy; or $R^1$ is F, Cl, or Br, and $R^2$ is —$CF_3$ or —$CHF_2$.

4. The compound of claim 1, wherein A is S (sulfur); and X is N (nitrogen).

5. The compound of claim 1, wherein $R^3$ is $C_1$-$C_6$ alkyl; and $R^4$ is H, or $R^3$ is $C_1$-$C_6$ alkyl; and $R^4$ is —$(CR^{10}R^{11})_{0-3}NR^{12}R^{13}$.

6. A compound of Formula I:

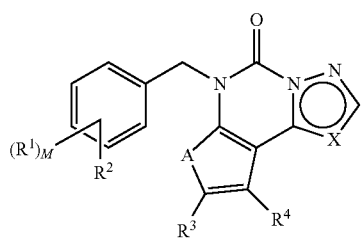

or a pharmaceutically acceptable salt thereof, wherein

A is O (oxygen) or S (sulfur);

X is CH or N (nitrogen);

M=1 or 2;

each occurrence of $R^1$ and $R^2$ is independently selected from —H, halo, —CN, —$C_1$-$C_3$ alkyl, —$C_1$-$C_3$ haloalkyl, —OH, —$C_1$-$C_3$ haloalkoxy, —$NO_2$, —$SO_2C_1$-$C_3$ alkyl, —$SO_2N(C_1$-$C_3$ alkyl)$_2$, —CONH($C_1$-$C_3$ alkyl), and —CON($C_1$-$C_3$ alkyl)$_2$;

or $R^1$ and $R^2$ are on adjacent carbons and taken together with the carbons to which they are attached form a 5-6 member monocylic ring system comprising one or more oxygen atoms, wherein the ring system is optionally substituted with one or more F;

$R^3$ and $R^4$ are independently selected from H, F, Cl, Br, —CN, —$C_1$-$C_3$ alkyl, —$C_1$-$C_6$, —$CF_3$, —$CHF_2$, —OH, —$C_1$-$C_3$ alkoxy, —$OCF_3$, —$NO_2$, —$SO_2C_1$-$C_3$ alkyl, —$SO_2N(C_1$-$C_3$ alkyl)$_2$, —CONH($C_1$-$C_3$ alkyl), —CON($C_1$-$C_3$ alkyl)$_2$, and —$(CR^{10}R^{11})_{0-3}NR^{12}R^{13}$; and $R^{12}$, and $R^{13}$ are independently selected from H, —$C_1$-$C_6$ alkyl, aryl, heteroaryl, —$SO_2C_1$-$C_6$ alkyl, —$SO_2N(C_1$-$C_6$ alkyl)$_2$, —$CONH(C_1$-$C_6$ alkyl), and —$CON(C_1$-$C_6$ alkyl)$_2$.

7. The compound of claim 6, wherein one or more of $R^1$, $R^2$, $R^3$, and $R^4$ is halomethyl.

8. The compound of claim 6, wherein $R^1$ is H, and $R^2$ is —$C_1$-$C_3$ alkoxy; or $R^1$ is F, Cl, or Br, and $R^2$ is —$CF_3$ or —$CHF_2$.

9. The compound of claim 6, wherein A is S (sulfur); X is N (nitrogen); $R^1$ is F, Cl, or Br; and $R^2$ is —$C_1$-$C_3$ alkoxy.

10. The compound of claim 6, wherein $R^3$ is —$C_1$-$C_3$ alkyl; and $R^4$ is H, or $R^3$ is —$C_1$-$C_3$ alkyl; and $R^4$ is —$(CR^{10}R^{11})_{0-3}NR^{12}R^{13}$.

11. A compound of Formula I:

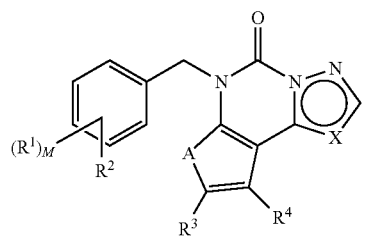

or a pharmaceutically acceptable salt thereof, wherein

A is O (oxygen) or S (sulfur);

X is CH or N (nitrogen);

M=1 or 2;

each occurrence of $R^1$ and $R^2$ is independently selected from H, halo, —CN, $C_1$-$C_6$ alkyl, $C_1$-$C_6$ haloalkyl, —OH, $C_1$-$C_6$ alkoxy, $C_1$-$C_6$ haloalkoxy, —$NO_2$, —$SO_2C_1$-$C_6$ alkyl, —$SO_2N(C_1$-$C_6$ alkyl)$_2$, —CONH($C_1$-$C_6$ alkyl), and —CON($C_1$-$C_6$ alkyl)$_2$; or $R^1$ and $R^2$ are on adjacent carbons and taken together with the carbons to which they are attached form a 5-6 member monocylic ring system comprising one or two oxygen atoms, wherein the ring system is optionally substituted with one or more F;

$R^3$ and $R^4$ taken together with the carbons to which they are attached form a monocylic ring system, having the following structure:

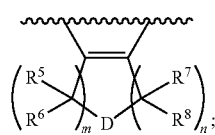

D is O (oxygen), S (sulfur), —SO—, —$SO_2$—, or —N—$R^9$—;

m and n are independently 0-4, with the proviso that the sum of m and n is 1-5 when D is O (oxygen), S (sulfur), —SO, —$SO_2$, —N—$R^9$;

$R^5$, $R^6$, $R^7$, $R^8$, $R^{10}$ and $R^{11}$ are independently selected from H, F, —$C_1$-$C_6$ alkyl, —$C_1$-$C_6$ haloalkyl, —OH, —$C_1$-$C_6$ alkoxy, —$C_1$-$C_6$ haloalkoxy, —$SO_2C_1$-$C_6$ alkyl, —$SO_2N(C_1$-$C_6$ alkyl)$_2$, —$CONH(C_1$-$C_6$ alkyl), and —$CON(C_1$-$C_6$ alkyl)$_2$; and $R^9$, $R^{12}$, and $R^{13}$ are independently selected from H, —$C_1$-$C_6$ alkyl, aryl, heteroaryl, —$SO_2C_1$-$C_6$ alkyl, —$SO_2N(C_1$-$C_6$ alkyl)$_2$, —$CONH(C_1$-$C_6$ alkyl), and —$CON(C_1$-$C_6$ alkyl)$_2$.

12. The compound of claim 11, wherein $R^1$ is H, and $R^2$ is $C_1$-$C_6$ alkoxy; or $R^1$ is F, Cl, or Br, and $R^2$ is —$CF_3$ or —$CHF_2$.

13. The compound of claim 12, wherein A is S (sulfur); and X is N (nitrogen).

14. The compound of claim 12, wherein $R^3$ is —$C_1$-$C_6$ alkyl; and $R^4$ is —$(CR^{10}R^{11})_{0-3}NR^{12}R^{13}$.

15. A compound of Formula I:

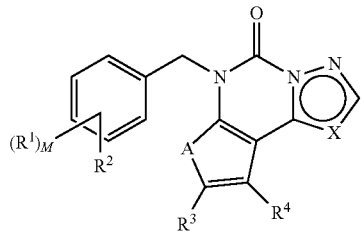

or a pharmaceutically acceptable salt thereof, wherein
A is O (oxygen) or S (sulfur);
X is CH or N (nitrogen);
M=1 or 2;
each occurrence of $R^1$ and $R^2$ is independently selected from H, halo, aryl, heteroaryl, —($C_1$-$C_3$ alkyl) aryl, —($C_1$-$C_3$ alkyl) heteroaryl, heterocycle, —CN, $C_1$-$C_3$ alkyl, $C_1$-$C_3$ thioalkyl, $C_1$-$C_3$ thiohaloalkyl, $C_1$-$C_3$ haloalkyl, $C_2$-$C_6$ alkenyl, $C_2$-$C_6$ alkynyl, —OH, $C_1$-$C_3$ alkoxy, $C_1$-$C_3$ haloalkoxy, —$NO_2$, —$SO_2C_1$-$C_6$ alkyl, —$SOC_1$-$C_3$ alkyl, —$SO_2NH(C_1$-$C_3$ alkyl), —$SO_2N(C_1$-$C_3$ alkyl$)_2$, —CONH($C_1$-$C_3$ alkyl), —CON($C_1$-$C_3$ alkyl$)_2$, —C(O)O($C_1$-$C_3$ alkyl), —C(O)O($C_1$-$C_3$ alkyl) aryl, —OC(O)($C_1$-$C_3$ alkyl), —OC(O)($C_1$-$C_3$ alkyl) aryl, —$SO_2NH_2$, —$CONH_2$, —$CO_2H$, —COH, —$NH_2$, $C_1$-$C_3$ alkylamino, di-$C_1$-$C_3$ alkylamino, —$N_3$, cyanate, isocyanate, thiocyanate, isothiocyanate, —($C_2$-$C_6$ alkenyl)O($C_1$-$C_3$ alkyl), —($C_1$-$C_3$ alkyl)O($C_1$-$C_3$ alkyl), —($C_1$-$C_3$ alkyl)O($C_1$-$C_3$ alkyl)O($C_1$-$C_3$ alkyl), aryloxy, arylthio, —CO($C_1$-$C_3$ alkyl), —CO(aryl), —CO(heteroaryl), and —CO(heterocycle);
or $R^1$ and $R^2$ are on adjacent carbons and taken together with the carbons to which they are attached form a 5-6 member saturated or unsaturated monocylic ring system comprising one or two oxygen atoms, wherein the ring system is optionally substituted with one or more F;
$R^3$ and $R^4$ taken together with the carbons to which they are attached form a monocylic ring system, having the following structure:

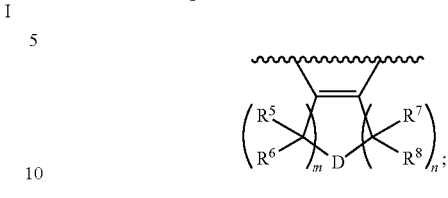

D is O (oxygen), S (sulfur), —SO—, —$SO_2$—, or —N—$R^9$—;
m and n are independently 0-4, with the proviso that the sum of m and n is 1-5 when D is O (oxygen), S (sulfur), —SO—, —$SO_2$—, —N—$R^9$;
$R^5$, $R^6$, $R^7$, $R^8$, $R^{10}$ and $R^{11}$ are independently selected from H, F, $C_1$-$C_3$ alkyl, $C_1$-$C_3$ haloalkyl, —OH, $C_1$-$C_3$ alkoxy, $C_1$-$C_3$ haloalkoxy, —$SO_2C_1$-$C_6$ alkyl, —$SO_2N(C_1$-$C_3$ alkyl$)_2$, —CONH($C_1$-$C_3$ alkyl), and —CON($C_1$-$C_3$ alkyl$)_2$; and
$R^9$, $R^{12}$, and $R^{13}$ are independently selected from H, $C_1$-$C_3$ alkyl, aryl, heteroaryl, —$SO_2C_1$-$C_3$ alkyl, —$SO_2N(C_1$-$C_3$ alkyl$)_2$, —CONH($C_1$-$C_3$ alkyl), and —CON($C_1$-$C_3$ alkyl$)_2$.

16. The compound of claim 15, wherein $R^1$ is H, and $R^2$ is $C_1$-$C_3$ alkoxy; or $R^1$ is F, Cl, or Br, and $R^2$ is —$CF_3$ or —$CHF_2$.

17. The compound of claim 16, wherein A is S (sulfur); and X is N (nitrogen).

18. The compound of claim 16, wherein $R^3$ is $C_1$-$C_3$ alkyl; and $R^4$ is —($CR^{10}R^{11})_{0-3}NR^{12}R^{13}$.

19. A compound selected from the group consisting of Examples 31, 33, 34, 35, 36, 38, 39, 44, 51, 55, 61, 62, 63, 69, 105, 109, 135 and 141, or a pharmaceutically acceptable salt thereof.

20. A pharmaceutical composition comprising a compound of claim 1; and a pharmaceutically acceptable carrier.

* * * * *